US009885049B2

(12) United States Patent
Lutz et al.

(10) Patent No.: US 9,885,049 B2
(45) Date of Patent: Feb. 6, 2018

(54) MODULATION OF PRE-MRNA USING SPLICE MODULATING OLIGONUCLEOTIDES AS THERAPEUTIC AGENTS IN THE TREATMENT OF DISEASE

(71) Applicant: Drexel University, Philadelphia, PA (US)

(72) Inventors: Gordon J. Lutz, Kennett Square, PA (US); Melanie K. Tallent, Kennett Square, PA (US); Nicole Michele Lykens, Woodbury, NJ (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 15/160,438

(22) Filed: May 20, 2016

(65) Prior Publication Data
US 2017/0037411 A1 Feb. 9, 2017

Related U.S. Application Data

(62) Division of application No. 14/188,168, filed on Feb. 24, 2014, now Pat. No. 9,359,603, which is a division of application No. 13/144,409, filed as application No. PCT/US2010/021078 on Jan. 14, 2010, now Pat. No. 8,680,254.

(60) Provisional application No. 61/144,543, filed on Jan. 14, 2009.

(51) Int. Cl.
*A61K 31/7115* (2006.01)
*C12N 15/113* (2010.01)
*A61K 48/00* (2006.01)
*C12N 15/11* (2006.01)

(52) U.S. Cl.
CPC ........ *C12N 15/1138* (2013.01); *A61K 48/005* (2013.01); *C12N 15/11* (2013.01); *C12N 15/111* (2013.01); *C12N 15/113* (2013.01); *C12N 15/1135* (2013.01); *C12N 15/1137* (2013.01); *C12N 2310/11* (2013.01); *C12N 2320/33* (2013.01)

(58) Field of Classification Search
None
See application file for complete search history.

(56) References Cited

U.S. PATENT DOCUMENTS

| 5,166,320 | A | 11/1992 | Wu |
| 5,876,930 | A | 3/1999 | Livak |
| 6,110,676 | A | 8/2000 | Coull |
| 6,582,908 | B2 | 6/2003 | Fodor |
| 6,965,025 | B2 | 11/2005 | Gaarde |
| 8,680,254 | B2 | 3/2014 | Lutz et al. |
| 9,359,603 | B2 | 6/2016 | Lutz et al. |
| 2003/0082571 | A1 | 5/2003 | Kachab |
| 2003/0170654 | A1 | 9/2003 | Crocetti |
| 2004/0192626 | A1 | 9/2004 | McSwiggen |
| 2005/0026164 | A1 | 2/2005 | Zhou |
| 2005/0287648 | A1 | 12/2005 | Smith |
| 2007/0032441 | A1 | 2/2007 | McSwiggen |
| 2009/0105139 | A1* | 4/2009 | Kole ...................... C07K 14/71 514/1.1 |

FOREIGN PATENT DOCUMENTS

| EP | 1752536 | 2/2007 |
| EP | 1013361 B1 | 1/2012 |
| WO | WO 88/09810 | 12/1988 |
| WO | WO 89/10134 | 11/1989 |
| WO | WO 98/39352 | 9/1998 |
| WO | WO 99/14226 | 3/1999 |
| WO | WO 2008/153933 A2 | 12/2008 |

OTHER PUBLICATIONS

Office Action dated Dec. 23, 2015 in corresponding Canadian Application No. 2,750,379, filed Jan. 14, 2010.
Response dated Jun. 23, 2016 in corresponding Canadian Application No. 2,750,379, filed Jan. 14, 2010.
Office Action dated Apr. 5, 2016 in corresponding Canadian Application No. 2,750,379, filed Jan. 14, 2010.
Extended European Search Report dated Sep. 13, 2013 in corresponding European Application No. 10732104.4, filed Jan. 14, 2010.
Supplementary European Search Report dated Oct. 1, 2013 in corresponding European Application No. 10732104.4, filed Jan. 14, 2010.
Response dated Apr. 11, 2014 in corresponding European Application No. 10732104.4, filed Jan. 14, 2010.
Examination Report dated Jul. 9, 2015 in corresponding European Application No. 10732104.4, filed Jan. 14, 2010.
Response dated Jan. 19, 2016 in corresponding European Application No. 10732104.4, filed Jan. 14, 2010.
Examination Report dated Nov. 9, 2016 in corresponding European Application No. 10732104.4, filed Jan. 14, 2010.
Response dated Mar. 6, 2017 in corresponding European Application No. 10732104.4, filed Jan. 14, 2010.
Examination Report dated Aug. 5, 2013 in corresponding Australian Application No. 2010204639, filed Jan. 14, 2010.
Response dated Jul. 31, 2014 in corresponding Australian Application No. 2010204639, filed Jan. 14, 2010.
Examination Report dated Aug. 15, 2014 in corresponding Australian Application No. 2010204639, filed Jan. 14, 2010.
Response dated Oct. 29, 2014 in corresponding Australian Application No. 2010204639, filed Jan. 14, 2010.

(Continued)

*Primary Examiner* — Richard A Schnizer
(74) *Attorney, Agent, or Firm* — Howson & Howson LLP

(57) ABSTRACT

The present invention encompasses a class of compounds known as splice modulating oligonucleotides (SMOs) that modulate pre-mRNA splicing, thereby affecting expression and functionality of a specific protein in a cell. The present invention further provides compositions and methods for modulating pre-mRNA splicing using a SMO of the invention to abrogate disease-causing mutations in a protein. Accordingly, the present invention provides compositions and methods of treating a subject at risk of, susceptible to, or having a disease, disorder, or condition associated with aberrant or unwanted target pre-mRNA expression or activity.

8 Claims, 8 Drawing Sheets

(56) References Cited

OTHER PUBLICATIONS

Akopian, "Reliable long-lasting depression interacts with variable short-term facilitation to determine corticostriatal paired-pulse plasticity in young rats", Journal of Physiology, 580:225-240 (2007).
Albo, F. et.al., "Modulation of AMPA receptors in spinal motor neurons by the neuroprotective agent riluzole", J.Neurosci.Res., Oct. 2004, 78(2): 200-207.
Altschul, "Gapped BLAST and PSI-BLAST: a new generation of protein database search programs", Nucleic Acids Research, 25(17):3389-3402 (1997).
Bagdy, "Serotonin and epilepsy", Journal of Neurochemistry, 100: 857-873 (2007).
Beers, "Parvalbumin overexpression alters immune-mediated increases in intracellular calcium, and delays disease onset in a transgenic model of familial amyotrophic lateral sclerosis", Journal of Neurochemistry, 79:499-509 (2001).
Bensimon, G. et.al., "A controlled trial of riluzole in amyotrophic lateral sclerosis. ALS/Riluzole Study Group", N.Engl.J.Med., Mar. 1994, 330(9): 585-591.
Bowe, "O—GlcNAc integrates the proteasome and transcriptome to regulate nuclear hormone receptors", Molecular and Cell Biology, 26:8539-8550 (Nov. 2006).
Brorson, "AMPA receptor desensitization predicts the selective vulnerability of cerebellar purkinje cells to excitotoxicity", Journal of Neuroscience, 15:4515-4524 (Jun. 1995).
Carriedo, "AMPA exposures induce mitochondrial Ca2+ overload and ROS generation in spinal motor neurons in vitro", Journal of Neuroscience, 20:240-250 (Jan. 1, 2000).
Cartegni, "ESEfinder: a web resource to identify exonic splicing enhancers", Nucleic Acids Research, 31: 3568-3571 (2003).
Cartegni, "Correction of disease-associated exon skilling by synthetic exon-specific activators," Nature Structural Biology, published online Jan. 13, 2003, pp. 120-125, vol. 10, No. 2.
Cashman, "Neuroblastoma x spinal cord (NSC) hybrid cell lines resemble developing motor neurons" Developmental Dynamics, 194:209-221 (1992).
Cheah, B.C. et.al., "Riluzole, neuroprotection and amyotrophic lateral sclerosis", Curr.Med.Chem., Mar. 2010, 17(18): 1942-1959.
Chen, "Contributions of receptor desensitization and saturation to plasticity at the retinogeniculate synapse", Neuron, 33:779-788 (Feb. 28, 2002).
Clippinger, "Hepatitis B Virus X Protein Modulates Apoptosis in Primary Ray Hepatocytes by Regulating both NF-κB and the Mitochondrial Permeability Transition Pore", J. Virol., 83(10):4718-4731 (May 2009).
Coleman, "Isoform-specific early trafficking of AMPA receptor flip and flop variants", Journal of Neuroscience, 25:11220-11229 (Oct. 25, 2006).
Cristiano, "Hepatic gene therapy: adenovirus enhancement of receptor-mediated gene delivery and expression in primary hepatocytes", Proceedings of the National Academy of Sciences, USA, 90:2122-2126 (Mar. 1993).
Curiel, "Adenovirus enhancement of transferrin-polylysine mediated gene delivery", Proceedings of the National Academy of Sciences, USA, 88:8850 (Oct. 1991).
Demeule, "Identification and design of peptides a s a new drug delivery system for the brain", Journal of Pharmacology and Experimental Therapeutics, 324(3):1064-1072 (2008).
Doble, A. "The pharmacology and mechanism of action of riluzole", Neurology, Dec. 1996, 47 (6 Suppl 4): S233-S241.
Dorfmueller, "GlcNAcstatins are nanomolar inhibitors of human O-GlcNAcase inducing cellular hyper-O-GlcNAcylation", Biochemical Journal, 420:221-227 (2009).
Du, "Cyclophilin D deficiency attenuates mitochondrial and neuronal perturbation and ameliorates learning and memory in Alzheimer's disease", Nature Medicine, 14(10):1097-1105 (Oct. 2008).
Du, "Mitochondrial permeability transition pore in Alzheimer's disease: Cyclophilin D and amyloid beta", Biochimica et Biophysica Acta, 1802:198-204 (2010—available online Jul. 16, 2009).
EBI Accession No. BM116830, Nov. 27, 2001, Database EMBL [Online].
EBI Accession No. BV729971, Oct. 10, 2008, Database EMBL [Online].
Finn, "Synthesis and properties of DNA-PNA chimeric oligomers", Nucleic Acids Research, 24 (17):3357-63 (1996).
Foran, et al., "Glutamate Transporters and the Excitotoxic Path to Motor Neuron Degeneration in Amyotrophic Lateral Sclerosis," Antioxidants & Redox Signaling, Jul. 2009, 11(7): 1587-1602.
Frank, "Sleep and sleep homeostasis in mice lacking the 5-HT2c receptor", Neuropsychopharmacology, 27:869-873 (Nov. 2002).
Funk, "Modulation of neural network activity in vitro by cyclothiazide, a drug that blocks desensitization of AMPA receptors", Journal of Neuroscience, 15:4046-4056 (May 1995).
Garcia-Blanco, Alternative splicing in disease and therapy, Nature Biotechnology, May 2004, pp. 535-546, vol. 22, No. 5.
Gardner, "Correlation of AMPA receptor subunit composition with synaptic input in the mammalian cochlear nuclei", Journal of Neuroscience, 21: 7428-7437 (Sep. 15, 2001).
Gautier, "α-DNA IV: α-anomeric and β-anomeric tetrathymidylates covalently linked to intercalating oxazolopyridocarbazole. Synthesis, physiochemical properties and poly (rA) binding", Nucleic Acids Res., 15(16):6625-6641 (1987).
Giorgio, "Cyclophilin D in mitochondrial pathophysiology", Biochimica et Biophysica Acta, 1-6 (2010).
Goforth, Enhancement of AMPA-mediated current after Journal of Neuroscience, 19:7367-7374 (Sep. 1, 1999).
Herlitze, Argiotoxin Detects Molecular Differences in AMPA Receptor Channels, Neuron, Jun. 1993, pp. 1131-1140, vol. 10.
Hjelmstad, "Lack of AMPA receptor desensitization during basal synaptic transmission in the hippocampal slice", Journal of Neurophysiology, 81:3096-3099 (1999).
Hua, "Enhancement of SMN2 exon 7 inclusion by antisense oligonucleotides targeting the exon", Public Library of Science Biology, 5(4):e73 (Apr. 2007).
Inoue, "Synthesis and hybridization studies on two complementary nona(2'-O-methyl)ribonucleotides", Nucleic Acids Research, 15:6131-6148 (1987).
Jayakar, AMPA Receptor Regulation Mechanisms: Future Target for Safer Neuroprotective Drugs, Int. J. Neurosci., Jun. 2004, pp. 695-734, vol. 114, No. 6.
Kalin, "Increased levels of the FoxM1 transcription factor accelerate development and progression of prostate carcinomas in both TRAMP and LADY transgenic mice", Cancer Research, 66(3):1712-20 (Feb. 1, 2006).
Kanekiyo, "Receptor-associated protein interacts with amyloid-β peptide and promotes its cellular uptake", Journal of Biological Chemistry, 284:33352-33359 (Oct. 13, 2009).
Karlin, "Applicants and statistics for multiple high-scoring segments in molecular sequences", Proceedings of the National Academy of Sciences, USA, 90:5873-77 (Jun. 1993).
Karlin, "Methods for assessing the statistical significance of molecular sequence features by using general scoring schemes", Proceedings of the National Academy of Sciiences, USA, 87:2264-68 (Mar. 1990).
Karras, "Deletion of individual exons and induction of soluble murine interleukin-5 receptor-α chain expression through antisense oligonucleotide-mediated redirection of pre-mRNA splicing", Molecular Pharmacology, 58:380-387 (2000).
Kato, "The targeting of cyclophilin D by RNAi as a novel cardioprotective therapy: evidence from two-photon imaging", Cardiovascular Research, 83:335-344 (2009).
Kawahara, Excitotoxicity and ALS: What is unique about the AMPA receptors expressed on spinal motor neurons?, Amyotrophic Lateral Sclerosis, Sep. 2005, pp. 131-144, vol. 6, No. 3.
Kim, "The forkhead box m1 transcription factor stimulates the proliferation of tumor cells during development of lung cancer", Cancer Research, 66(4):2153-61 (Feb. 15, 2006).

(56) References Cited

OTHER PUBLICATIONS

Kishore, "The snoRNA HBII-52 Regulates Alternative Splicing of the Serotonin Receptor 2C", Science, 311: 230-232 and online 'supporting materials' (Jan. 13, 2006—published online Dec. 15, 2005).
Koike-Tani, "Mechanisms Underlying Developmental Speeding in AMPA-EPSC decay time at the calys of held", Journal of Neuroscience, 25(1):199-207 (Jan. 5, 2005).
Kole, RNA modulation, repair and modeling by splice switching oligonucleotides, Acta Biochimica Polonica, presented lecture beginning Jun. 26, 2004, pp. 373-378, vol. 51, No. Feb. 2004.
Lacomblez, L. et.al., "Dose-ranging study of riluzole in amyotrophic lateral sclerosis. Amyotrophic Lateral Sclerosis/Riluzole Study Group II", Lancet, May 1996, 347: 1425-1431.
Lazarus, "O—GlcNAc cycling: Implications for neurodegenerative disorders", International Journal of Biochemistry and Cell Biology, 41(11):2134-2146 (Nov. 2009).
Le, "SMNΔ7, the major product of the centromeric survival motor neuron (SMN2) gene, extends survival in mice with spinal muscular atrophy and associates with full-length SMN", Human Molecular Genetics, 14(6): 845-857 (2005).
Lee, "A conserved GXXXG motif in APH-1 is critical for assembly and activity of the γ-secretase complex", Journal of Biological Chemistry, 279(6):4144-4152 (Feb. 6, 2004).
Lemaitre, "Specific antiviral activity of a poly(L-lysine)-conjugated oligodeoxyribonucleotide sequence complementary to vesicular stomatitis virus N protein mRNA initiation site", Proceedings of the National Academy of Sciences, USA, 84:648-652 (Feb. 1987).
Letsinger, "Cholesteryl-conjugated oligonucleotides: synthesis, properties, and activity as inhibitors of replication of human immunodeficiency virus in cell culture", Proceedings of the National Academy of Sciiences, USA, 86:6553-6556 (Sep. 1989).
Liang, "Hepatitis B: The Virus and Disease", Hepatology, S13-S21 (May 2009).
Liu, "FoxM1B is overexpressed in human glioblastomas and critically regulates the tumorigenicity of glioma cells", Cancer Research, 66(7): 3593-602 (Apr. 1, 2006).
Lykens, Antiepileptic activity in mice of a novel oligonucleotide that directs GluR1 splicing, Neuroscience 2010, Nov. 13, 2010, Program#/Poster# 35.16/E36 (Presentation Abstract).
Lykens, Development of Splice Modulating Oligomers Targeting AMPA Receptor Alternative Splicing as Therapeutics for Neurological Diseases, Dissertation Presented to the Faculty of the Drexel University College of Medicine, Jun. 2011, 165 pp.
Mag, "Synthesis and selective cleavage of oligodeoxyribonucleotides containing non-chiral internucleotide phosphoramidate linkages", Nucleic Acids Research 17(15):5973-88 (1989).
Martin, "DNA labeling in living cells", Cytometry Part A, 67A:45-52 (2005).
Martin, "The mitochondrial permeability transition pore: A molecular target for amyotrophic lateral sclerosis therapy", Biochimica et Biophysica Acta, 1802:186-197 (2010—available online Aug. 3, 2009).
Mathews, "Incorporating chemical modification constraints into a dynamic programming algorithm for prediction of RNA secondary structure", Proceedings of the National Academy of Sciences, USA, 101(19):7287-7292 (May 11, 2004).
Matveeva, "Thermodynamic criteria for high hit rate antisense oligonucleotide design", Nucleic Acids Research, 31(17): 4989-4994 (2003).
Niu, "Protection against lipopolysacharide-induced myocardial dysfunction in mice by cardiac-specific expression of soluble Fas", J. Molecular and Cellular Cardiology, 44:160-169 (2008—online Oct. 4, 2007).
Palecek, "Calcium dynamics and buffering in motoneurones of the mouse spinal cord", Journal of Physiology, 520, pt. 2:485-502 (1999).
Perry-O'Keefe, "Peptide nucleic acid pre-gel hybridization: an alternative to southern hybridization", Proceedings of the National Academy of Sciences, USA, 93:14670-675 (Dec. 1996).
Qiu, "Somatostatin receptor subtype 4 couples to the M-current to regulate seizures", Journal of Neuroscience, 28:3567-3576 (Apr. 2, 2008).
Roca, "Determinants of the inherent strength of human 5' splice sites", RNA, 11: 683-698 (2005).
Sazani, Therapeutic potential of antisense oligonucleotides as modulators of alternative splicing, The Journal of Clinical Investigation, Aug. 2003, pp. 481-486, vol. 112, No. 4.
Scott, S. et al., Design, power, and interpretation of studies in the standard murine model of ALS, Amyotrophic Lateral Sclerosis, Dec. 2007, 9(1): 4-15.
Seifert, "Enhanced relative expression of glutamate receptor 1 flip AMPA receptor subunits in hippocampal astrocytes of epilepsy patients with ammon's horn sclerosis", Journal of Neuroscience 24: 1996-2003 (Feb. 25, 2004).
Sekiguchi, "Pharmacological detection of AMPA receptor heterogeneity by use of two allosteric potentiators in rat hippocampal cultures", British Journal of Pharmacology, 123: 1294-1303 (1998).
Serneels, "γ-Secretase heterogeneity in the Aph1 subunit: relevance for Alzheimer's disease", Science, 324:639-642 (May 1, 2009).
Shirotani, "Identification of distinct γ-secretase complexes with different APH-1 variants", Journal of Biological Chemistry, 279(40):41340-41345 (Oct. 1, 2004).
Singh, "Splicing of a critical exon of human survival motor neuron is regulated by a unique silencer element located in the last intron", Molecular and Cell Biology, 26(4):1333-1346 (Feb. 2006).
Smith, "Antisense oligonucleotide therapy for neurodegenerative disease", Journal of Clinical Investigations, 116(8): 2290-2296 (Aug. 2006).
Sukma, "Chronic treatment with imipramine inhibits cell growth and enhances serotonin 2C receptor mRNA expression in NG 108-15 cells", Journal of Pharmacological Science, 92: 433-436 (2003).
Tallent, "Somatostatin acts in CA1 and CA3 to reduce hippocampal epileptiform activity", Journal of Neurophysiology, 81: 1626-1635 (1999).
Tan, "Involvement of mitochondrial permeability transition in hepatitis B virus replication", Virus Research, 145:307-311 (Aug. 12, 2009).
Tecott, "Perturbed dentate gyrus function in serotonin 5-HT2C receptor mutant mice", Proceedings of the National Academy of Sciences, USA, 95:15026-15031 (Dec. 1998).
Teh, "FOXM1 is a downstream target of Gli1 in basal cell carcinomas", Cancer Research, 62:4773-80 (Aug. 15, 2002).
Tohda, "RNA editing and short variant of serotonin 2C receptor mRNA in neuronally differentiated NG108-15 cells", Journal of Pharmacological Science, 96:164-169 (2004).
Tohda, "The mRNA expression of serotonin 2C subtype receptors uncoupled with inositol hydrolysis in NG108-15 cells", Japanese Journal of Pharmacology, 90:138-144 (2002).
Tomiyama, Flip and Flop Splice Variants of AMPA Receptor Subunits in the Spinal Cord of Amyotrophic Lateral Sclerosis, Synapse, Sep. 15, 2002, pp. 245-249, vol. 45, No. 4.
Van Damme, "GluR2-dependent properties of AMPA receptors determine the selective vulnerability of motor neurons to excitotoxicity", Journal of Neurophysiology, 88: 1279-1287 (2002).
Van Den Bosch, L. et.al., "The role of excitotoxicity in the pathogenesis of amyotrophic lateral sclerosis", Biochim.Biophys.Acta, May 2006, 1762:1068-1082.
Vinogradov, "Nanogels for oligonucleotide delivery to the brain", Bioconjugate Chemistry, 5:50-60 (2004).
Wade, "Synergistic impairment of glucose homeostasis in ob/ob mice lacking functional serotonin 2C receptors", Endocrinology, 149: 955-961 (Mar. 2008; e-publication: Nov. 26, 2007).
Wang, "Down-regulation of forkhead box M1 transcription factor leads to the inhibition of invasion and angiogenesis of pancreatic cancer cells", Cancer Research, 67 (17): 8293-300 (Sep. 1, 2007).
Whisenhunt, "Disrupting the enzyme complex regulating O-GlcNAcylation blocks signaling and development", Glycobiology, 16:551-563 (2006).

(56) References Cited

OTHER PUBLICATIONS

Williams, "Induction of Dystrophin Expression by Exon Skipping in mdx Mice Following Intramuscular Injection of Antisense Oligonucleotides Complexed with PEG-PEI Copolymers", Molecular Therapy, 14(1):88-96 (Jul. 2006).

Williams, "Oligonucleotide Mediated Survival of Motor Neuron Protein Expression in CNS Improves Phenotype in a Mouse Model of Spinal Muscular Atrophy", J. Neuroscience, 29(24):7633-7638 (Jun. 17, 2009).

Wilson, "Hepatocyte-directed gene transfer in vivo leads to transient improvement of hypercholesterolemia in low density lipoprotein receptor-deficient rabbits", Journal of Biological Chemistry, 267:963-967 (Jan. 15, 1992).

Wonsey, "Loss of the forkhead transcription factor FoxM1 causes centrosome amplification and mitotic catastrophe", Cancer Research, 65 (12):5181-9 (Jun. 15, 2005).

Wood, "Modulating the Expression of Disease Genes with RNA-Based Therapy", PLoS Genetics, 3(6)(e109):845-854 (Jun. 2007).

Wu, "Receptor-mediated gene delivery and expression in vivo", Journal of Biological Chemistry, 263: 14621-14624 (Oct. 15, 1988).

Xia, "Positive α-amino-3-hydroxy-5-methyl-4-isoxazolepropionic acid (AMPA) receptor modulators have different impact on synaptic transmission in the thalamus and hippocampus", Journal of Pharmacology and Experimental Therapeutics, 313(1):277-285 (2005).

Yeo, "Discovery and analysis of evolutionarily conserved intronic splicing regulatory elements", PLoS Genetics, 3:e85 (May 2007).

Yeo, "Identification and analysis of alternative splicing events conserved in human and mouse", Proceedings of the National Academy of Sciences, USA, 102(8): 2850-2855 (Feb. 22, 2005).

Zhang, "Computational definition of sequence motifs governing constitutive exon splicing", Genes Development, 18:1241-1250 (2004).

International Search Report of International Stage of priority U.S. Appl. No. 13/144,409 (PCT/US2010/021078).

International Preliminary Report on Patentability (incorporating Written Opinion) of International Stage of priority U.S. Appl. No. 13/144,409 (PCT/US2010/021078).

\* cited by examiner

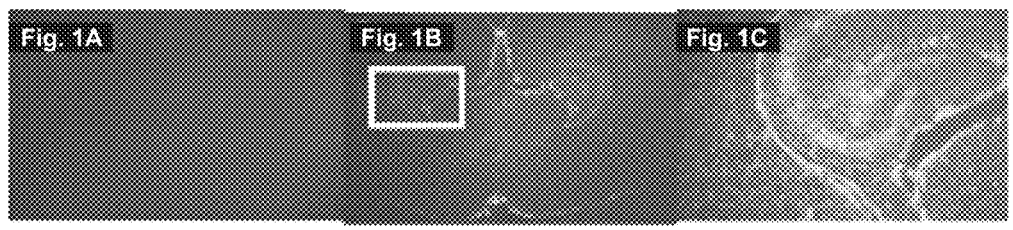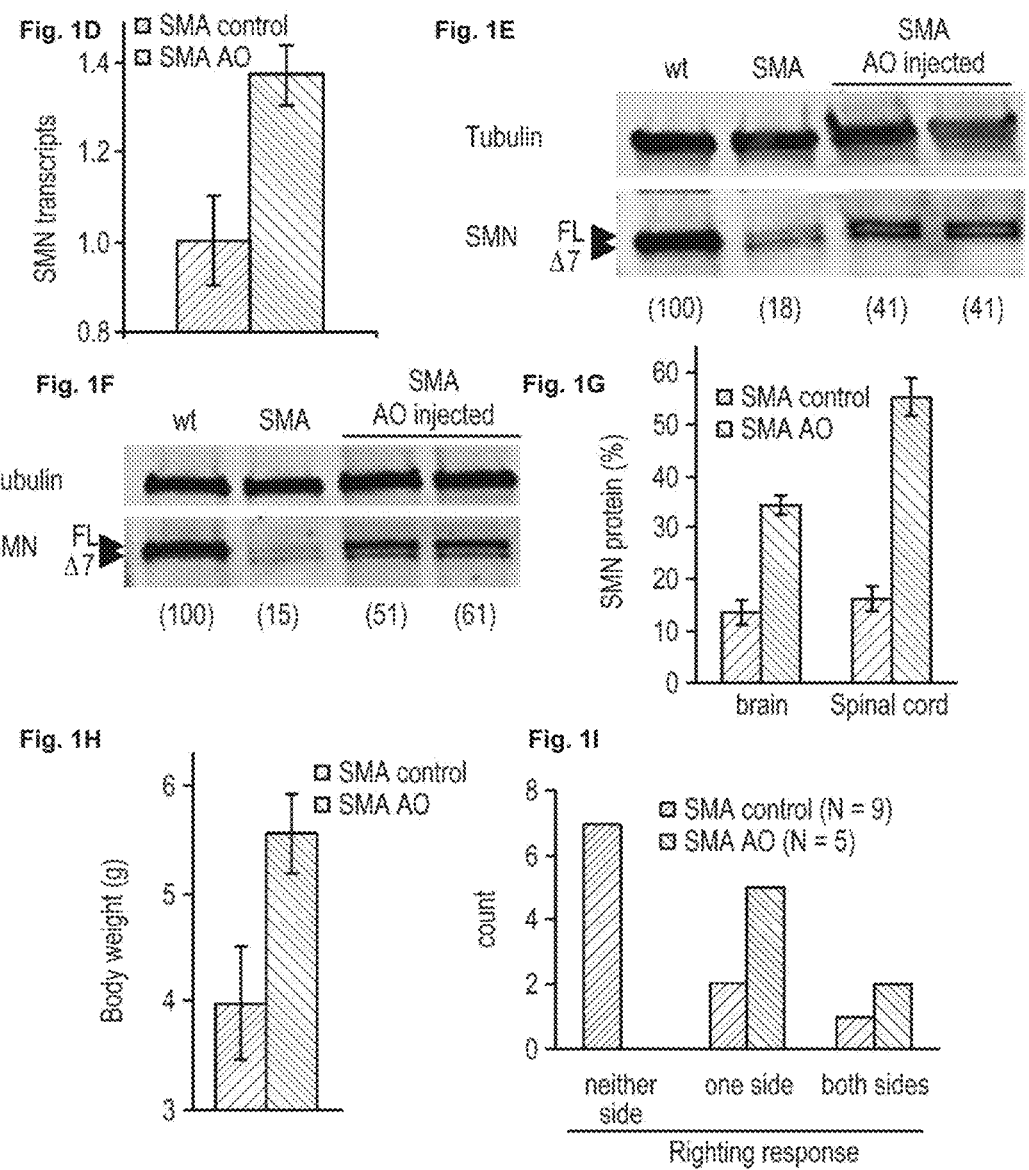

```
                            10        20        30        40
mGluR1-flop exon   AAATCCAGTAAACCTGGCAGTGTTAAAACTGAACGAGCAG
mGluR2-flop exon   AAATGCGGTTAACCTCGCAGTACTAAAACTGAATGAACAA
mGluR3-flop exon   AAATGCTGTTAACCTGGCAGTATTAAAACTGAATGAGCAA
mGluR4-flop exon   AAATGCTGTTAACCTCGCAGTTTTAAAACTGAATGAACAA
mGluR1-flip exon   AGGTCCCGTAAACCTAGCGGTTTTGAAACTCAGTGAGCAA
mGluR2-flip exon   AACCCCAGTAAATCTTGCAGTATTGAAACTCAGTGAGCAA
mGluR3-flip exon   AACGCCTGTAAACCTTGCAGTATTGAAACTCAGTGAACAA
mGluR4-flip exon   AACTCCTGTAAACCTTGCCGTTTTGAAACTCAGTGAGGCA 50        60        70        80
mGluR1-flop exon   GGCTTTTGGACAAATTGAAAAACAAATGGTGGTACGACAG
mGluR2-flop exon   GGCCTGTTGGACAAATTGAAAAACAAATGGTGGTACGACA
mGluR3-flop exon   GGCCTCTTGGACAAATTGAAAAACAAATGGTGGTACGACA
mGluR4-flop exon   GGCCTCTTGGACAAATTGAAAAACAAATGGTGGTACGACA
mGluR1-flip exon   GGCGTCTTAGACAAGCTGAAAAGCAAATGGTGGTACGATA
mGluR2-flip exon   GGCGTCTTAGACAAGCTGAAAAACAAATGGTGGTACGATA
mGluR3-flip exon   GGCATCTTAGACAAGCTGAAAAACAAATGGTGGTACGATA
mGluR4-flip exon   GGCGTCTTAGACAAGCTGAAAAACAAATGGTGGTACGATA 90       100       110
mGluR1-flop exon   AGGGCGAGTGCGGCAGCGGGGGAGGTGACTCCAAG
mGluR2-flop exon   AAGGAGAGTGCGGCAGCGGGGGAGGTGATTCCAAG
mGluR3-flop exon   AAGGAGAGTGCGGCAGCGGGGGCGGTGACTCCAAG
mGluR4-flop exon   AAGGAGAATGTGGCAGCGGGGGAGGTGACTCCAAG
mGluR1-flip exon   AAGGGGAATGTGGAAGCAAGGACTCCGGAAGTAAG
mGluR2-flip exon   AAGGTGAATGTGGAGCCAAGGACTCGGGAAGTAAG
mGluR3-flip exon   AGGGGGAATGTGGAGCCAAGGACTCCGGGAGTAAG
mGluR4-flip exon   AAGGTGAATGTGGACCCAAGGACTCGGGAAGCAAG
```

FIG. 3

MODULATION OF PRE-MRNA USING SPLICE MODULATING OLIGONUCLEOTIDES AS THERAPEUTIC AGENTS IN THE TREATMENT OF DISEASE

CROSS-REFERENCE TO RELATED APPLICATIONS

This application is a divisional of U.S. patent application Ser. No. 14/188,168, filed Feb. 24, 2014, which is a divisional of U.S. patent application Ser. No. 13/144,409, filed Jul. 13, 2011 (35 USC 371 completion on Aug. 15, 2011), now U.S. Pat. No. 8,680,254, issued Mar. 25, 2014, which is a national stage of International Patent Application No. PCT/US2010/021078, filed Jan. 14, 2010, now expired, which claims the benefit under 35 USC 119(e) of U.S. Provisional Patent Application No. 61/144,543, filed Jan. 14, 2009, now expired, which applications are incorporated by reference herein in their entireties.

STATEMENT REGARDING FEDERALLY SPONSORED RESEARCH OR DEVELOPMENT

This invention was made with government support under Grant No. NIH 1R21NS064223-01A1 awarded by the National Institutes of Health. The U.S. Government has certain rights in the invention.

BACKGROUND OF THE INVENTION

Approximately 90,000 known human proteins are the product of about 20,000 human genes. It is estimated that roughly 75% of human genes are subject to alternative splicing. Alternative splicing is the process responsible for this remarkable diversity of protein expression in general as well as tissue-specific expression of proteins. DNA is initially transcribed "literally" into pre-messenger RNA (pre-mRNA) comprising introns and exons. The average human protein coding gene is 28,000 nucleotides long with 8.8 exons separated by 7.8 introns. Exons are about 120 nucleotides long while introns are anywhere from 100-100,000 nucleotides long. Pre-mRNA is first processed by a spliceosome which recognizes where introns begin and end, removes introns, and joins exons together to form a mature mRNA that is then translated into a protein.

Pre-messenger RNA splicing is an essential process required for the expression of most genes. Improperly spliced mRNA molecules lead to altered proteins that cannot function properly, resulting in disease. Alternative splicing errors are known to contribute to cancer and many neurological diseases, including β-thalassemia, cystic fibrosis, spinal muscular atrophy (SMA), growth deficiencies, ataxia, autism, and muscular dystrophies.

5HT2CR: Prader-Willi Syndrome (PWS)

Prader-Willi syndrome (PWS) is a genetic disorder caused by the deletion of paternal copies of several genes on the 15th chromosome located in the region 15q11-13 leading to deletion of a small nucleolar ribonucleoprotein (snoRNA), HBII-52. Deletion of the same region on the maternal chromosome causes Angelman syndrome. The incidence of PWS is about 1 in 12,000 to 1 in 15,000 live births. Phenotypically, individuals afflicted with PWS typically exhibit significant cognitive impairment, hyperphagia often leading to morbid obesity, an array of compulsive behaviors, and sleep disorders.

After transcription, nascent or pre-mRNA undergoes a series of processing steps in order to generate a mature mRNA molecule. snoRNAs are non-protein coding RNAs that are 60-300 nucleotides (nt) long and that function in guiding methylation and pseudouridylation of ribosomal RNA (rRNA), small nuclear RNAs (snRNAs), and transfer RNAs (tRNAs). Each snoRNA molecule acts as a guide for only one (or two) individual modifications in a target RNA. In order to carry out the modification, each snoRNA associates with at least four protein molecules in an RNA/protein complex referred to as a small nucleolar ribonucleoprotein (snoRNP). The proteins associated with each RNA depend on the type of snoRNA molecule incorporated. The snoRNA molecule contains an antisense element (a stretch of 10-20 nucleotides) which are complementary to the sequence surrounding the nucleotide targeted for modification in the pre-RNA molecule. This enables the snoRNP to recognise and bind to the target RNA. Once the snoRNP has bound to the target site the associated proteins are in the correct physical location to catalyse the chemical modification of the target base.

The two different types of RNA modification (methylation and pseudouridylation) are directed by two different families of snoRNAs. These families of snoRNAs are referred to as antisense C/D box and H/ACA box snoRNAs based on the presence of conserved sequence motifs in the snoRNA. There are exceptions, but as a general rule C/D box members guide methylation and H/ACA members guide pseudouridylation. HBII-52, also known as SNORD115, belongs to the C/D box class of snoRNAs.

In the human genome, HBII-52 is encoded in a tandemly repeated array with another C/D box snoRNA, HBII-85, in the Prader-Willi syndrome (PWS) region of human chromosome 15q11-13. This locus is maternally imprinted, meaning that only the paternal copy of the locus is transcribed.

The snoRNA HBII-52 is exclusively expressed in the brain and is absent in PWS patients. HBII-52 lacks any significant complementarity with ribosomal RNAs, but does have an 18 nucleotide region of conserved complementarity to exon 5 of serotonin 2C receptor (5-HT2CR) pre-mRNA. snoRNA HBII-52 is an example of an RNA that regulates pre-mRNA splicing by binding to a splice suppressor sequence of the 5-HT2CRgene, resulting in enhancement of exon 5b inclusion and the expression of a full-length, functional 5-HT2C receptor.

A recent study showed that these sequences co-varied among species, such that differences in nucleotides in one were always matched by complementary changes in the other; so that 100% complementarity is always present (Kishore and Stamm, 2006, Science 311:230-232). Kishore and Stamm, 2006, Science 311:230-232 also used a minigene construct to demonstrate that interaction of 5-HT2CRand HBII-52 at the consensus sequences is critical for appropriate splicing of the 5b exon so that a functional receptor is generated. When HBII-52 is mutated at sites that prevent its interaction with 5-HT2C, exon 5a is included and exon 5b is excluded. The splice variant containing 5a leads to a nonfunctional, out of frame, truncated transcript (Kishore and Stamm, 2006, Science 311:230-232).

Dysregulation of serotonergic systems appears to play a role in many cognitive disorders, including depression, autism, and obsessive compulsive disorder. Although a direct link between dysfunction of 5-HT2CRand PWS has yet to be demonstrated, 5-HT2CR knockout mice display phenotypic characteristics that are remarkably similar to those observed in PWS, including development of hyperphagia-induced obesity. In patients with PWS, satiety centers seem to be perturbed, leading to excessive overeating and obesity. Similarly, in 5-HT2C receptor knockout mice, obesity develops due to a lack of control of feeding behavior (Nonogaki et al., 1998, Nature Med. 4:1152-1156). 5-HT2CRagonists appear to be effective in inducing satiety (Nilsson, 2006, J. Med. Chem. 49:4023-4034). Another notable characteristic of patients with PWS is compulsive behavior. 5-HT2CR knockout mice also demonstrate compulsive-like behavior (Chou-Green et al., 2003, Physiol. Behav. 78:641-649). Interestingly, 5-HT2CR agonists are effective in animal models of obsessive-compulsive disorder (OCD); suggesting dysfunction of this receptor system could play a role in this disorder (Jenck et al., 1998, Expert. Opin. Invest. Drugs 7:1587-1599; Dunlop et al., 2006, CNS Drug Rev. 12:167-177). The sleep impairment observed in many PWS patients is also found in the 5-HT2CR knockout mouse (Frank et al., 2002, Neuropsychopharmacology 27:869-873). These mice also exhibited reduced hippocampal-dependent learning and deficits in hippocampal synaptic plasticity that appears to be critical in learning and memory (Tecott et al., 1998, Proc. Natl. Acad. Sci. 95:15026-15031). Thus 5-HT2C receptor knockouts may replicate some of the cognitive deficits found in PWS. 5-HT2CR knockout mice therefore share many, but not all (e.g., failure to thrive, which may be mediated by HBII-85 (Ding et al., 2005, Mamm. Genome 16:424-431)), critical phenotypes with PWS patients.

AMPA Receptor: Excitotoxicity, Seizure, and Amyotrophic Lateral Sclerosis (ALS)

The α-amino-3-hydroxy-5-methyl-4-isoxazolepropionic acid receptor (also known as AMPA receptor, AMPAR, or quisqualate receptor) is a non-NMDA-type ionotropic transmembrane receptor for glutamate in the central nervous system (CNS). Postsynaptic ion channels activated by glutamate include NMDA (N-methyl-D-aspartic acid)-type glutamate channels, which are highly $Ca^{2+}$ permeable, and AMPA-type glutamate channels, which mediate the majority of rapid excitatory neurotransmission. AMPA channels are homo- or hetero-oligomeric assemblies composed of various combinations of four possible subunits, GluR1, GluR2, GluR3 and GluR4. The $Ca^{2+}$ conductance of AMPA receptors differs markedly according to whether the GluR2 subunit is present or not and whether it has undergone post-transcriptional RNA editing at the Q/R site. AMPA receptors that contain at least one Q/R edited GluR2 subunit are $Ca^{2+}$ impermeable. These properties of GluR2 are generated by RNA editing at the Q/R site in the putative second transmembrane domain (M2), during which a glutamine (Q) codon is replaced by an arginine (R) codon (Seeburg et al., 2001, Brain Res. 907:233-243). It is thought that arginine in the pore of the channel impedes $Ca^{2+}$ permeation. Analyses of adult rat, mouse, and human brains have demonstrated that almost all GluR2 mRNA in neurons is edited. In contrast, the Q/R site of GluR1, GluR3 and GluR4 subunits are always unedited, and glutamine remains at this crucial position. Therefore, AMPA receptors lacking a Q/R edited GluR2 subunit or lacking GluR2 altogether are highly $Ca^{2+}$ permeable (Kawahara and Kwak, 2005, ALS Other Motor Neuron Disord 6:131-144; Seeburg et al., 2001, Brain Res. 907:233-243).

Alternative splicing of the GluRs plays a critical role in AMPA receptor physiology, influencing sensitivity to glutamate, kinetics of channel desensitization, and intracellular trafficking. Two specific alternatively spliced variants of all GluRs called "flip" and "flop" are normally expressed in the CNS. These consist of 115 base pair exons that constitute the flip/flop cassette (Sommer et al., 1990, Science 249:1580-1585) and encode part of the extracellular segment that precedes the fourth transmembrane domain. This domain appears to modulate receptor desensitization and channel conductance (Mosbacher et al., 1994, Science 266:1059-1062). Generally, the AMPA "flip" variants are resistant to desensitization, whereas the "flop" variants are readily desensitized, although the kinetic difference depends on the subunit and, for heteromeric channels, on subunit compositions (Grosskreutz et al., 2003, Eur. J. Neurosci. 17:1173-1178; Koike et al., 2000, J. Neurosci. 25:199-207; Mosbacher et al., 1994; Sommer et al., 1990, Science 249:1580-1585). The extracellular flip/flop region may also interact with ER luminal proteins to regulate trafficking of AMPA receptors, with flip isoforms inserted into the cell membrane and flop isoforms trapped internally (Coleman et al., 2006, J. Neurosci. 26:11220-11229), although this has yet to be confirmed in neurons. Together these data show that when flip/flop ratio of GluR1, GluR3 and GluR4 is elevated, neurons are more excitable and show greater $Ca^{2+}$ conductance.

In motor neurons (MNs) it has been consistently demonstrated that AMPA receptor desensitization significantly impacts the shape of the glutamatergic synaptic response, as well as robustly regulating network activity (Ballerini et al., 1995, Eur. J. Neurosci. 7:1229-1234; Funk et al., 1995, J. Neurosci. 15:4046-4056). In addition, studies in several different brain regions have found that AMPA receptor desensitization has potent effects on baseline evoked and spontaneous synaptic events (Akopian and Walsh, 2007, J. Physiol. 580:225-240; Atassi and Glavinovic, 1999, Pflugers Arch. 437:471-478; Xia et al., 2005, J. Pharmacol. Exp. Ther. 313:277-285), although this is controversial, especially in hippocampus (Arai and Lynch, 1998, Brain Res. 799:230-234; Hjelmstad et al., 1999, J. Neurophysiol. 81:3096-3099). Further, AMPA receptor desensitization has been shown to be critical in shaping the synaptic response under conditions of higher frequency activity by strongly regulating synaptic integration (Arai and Lynch, 1998, Brain Res. 799:235-234; Chen et al., 2002, Neuron 33:779-788). Prolonging AMPA channel desensitization can also generate excessive network synchronization, leading to paroxysmal bursting that may interfere with normal network function (Funk et al., 1995, J. Neurosci. 15:4046-4056; Pelletier and Hablitz, 1994, J. J. Neurophysiol. 72:1032-1036; Qiu et al., 2008, J. Neurosci. 28:3567-3576). Thus, it is not surprising that reducing AMPA receptor desensitization profoundly increases excitotoxicity induced by glutamate and AMPA.

In spinal MNs, as well as in hippocampus and cerebellar granule cells, treatment with AMPA alone does not induce neurotoxicity. However, AMPA combined with cyclothiazide, which greatly reduces AMPA receptor desensitization, leads to neuronal cell death (Carriedo et al., 2000, J. Neurosci. 20:240-250; May and Robison, 1993, J. Neuroschem. 60:1171-1174; Puia et al., 2000, Prog. Neuropsychopharm. Biol. Psychiatr. 24:1007-1015). AMPA-mediated neurotoxicity is also amplified by cyclothiazide in cerebellar purkinje cells (Brorson et al., 1995, J. Neurosci. 15:4515-4524) and cortical neurons (Jensen et al., 1998, Neurochem. Int. 32:505-513). Further, in HEK293 cells, AMPA induces excitotoxicity when flip but not flop GluR isoforms are expressed (Iizuka et al., 2000, Eur. J. Neurosci. 12:3900-3908). AMPA receptor desensitization can also protect against NMDA receptor mediated excitotoxicity (Jensen et al., 1998, Neurochem. Int. 32:505-513; Zorumski et al., 1990, Neuron 5:61-66). Finally, decreases in AMPA receptor desensitization have been proposed to play a role in excitotoxicity after traumatic brain injury (Goforth et al., 1999, J. Neurosci. 19:7367-7374). Thus, AMPA receptor desensitization plays a critical role in normal neuronal function and excitotoxicity.

Emerging evidence supports the idea that $Ca^{2+}$-permeable AMPA channels, which are highly expressed on MNs, are key contributors to injury of MNs in amyotrophic lateral sclerosis (ALS) (Corona et al., 2007, Expert Opin. Ther. Targets 11:1415-1428; Van Den et al., 2006, Biochem. Biophys. Acta. 1762:1068-1082). Compared to most cell types, MNs have relatively poor capacity to buffer $Ca^{2+}$, due to reduced levels of $Ca^{2+}$ binding proteins including calbindin and parvalbumin (Alexianu et al., 1994, Ann. Neurol. 36:846-858; Ince et al., 1993, Neuropathol. Appl. Neurobiol. 19:291-299; Palecek et al., 1999, J. Physiol. 520 pt 2: 485-502). It appears that spinal MNs of ALS mice have even fewer of these $Ca^{2+}$-binding proteins (Siklos et al., 1998, J. Neuropathol. Exp. Neurol. 57:571-587). Amplifying that point, recent studies have shown that G93A ALS mice interbred with mice overexpressing parvalbumin showed a delayed onset of motor disease (Beers et al., 2001, J. Neurochem. 79:499-509). According to a speculative model of glutamate-mediated excitotoxicity involving AMPA channels in ALS, $Ca^{2+}$ influx through $Ca^{2+}$-permeable AMPA channels is not adequately buffered in MNs and ends up accumulating in mitochondria. High $Ca^{2+}$ is toxic to mitochondria, causing generation of apoptotic mediators such as ROS and cytochrome c, as well as opening of a permeability transition pore through which apoptotic mediators are released. It is thought that these mitochondrial factors are released from MNs and exert deleterious effects on glutamate transporters on adjacent astrocytes. Astrocytic glutamate transporters are responsible for taking up synaptic glutamate, and when they are compromised, glutamate accumulates in the synaptic region. The glutamate transporter with the most functional significance in this context is EAAT2/GLT-1, as it is widely expressed in astrocytes throughout the CNS and as it has the highest affinity for glutamate. In over ~65% of ALS cases, and in ALS mice, EAAT2 activity in the cortex and spinal cord is compromised (Van Den et al., 2006, Biochem. Biophys. Acta. 1762:1068-1082). Thus, in this model, increased glutamate then further stimulates more $Ca^{2+}$ influx though AMPA channels causing a feed-forward cycle that ultimately leads to too much $Ca^{2+}$ in MNs. This sets into motion a cascade that leads by unknown mechanisms to MN cell death.

There is also evidence that decreased desensitization of AMPA channels, due to increased flip/flop expression ratio, may exacerbate glutamate excitotoxicity in ALS. In spinal MNs of ALS subjects, the level of the AMPA receptor flip variants was found to be significantly elevated relative to that of the flop isoforms (Tomiyama et al., 2002, Synapse 45:245-249). Although this work from a highly published neuroanatomy group is the only study thus far to examine flip/flop isoforms in spinal cord of ALS patients, the findings were quite compelling. They observed a 41-66% decrease in the flop isoforms of GluR1-3 only in the ventral horn (layer IX), where MN soma are localized. Further, they provided evidence that their transcript labeling was restricted to MN soma. Unfortunately, flip/flop protein levels were not examined, since specific antibodies for flip and flop isoforms of GluRs do not exist. A remarkably similar change in AMPA receptor flip/flop ratios was independently observed in MNs from G93A SOD1 ALS mice (Spalloni et al., 2004, Neurobiol. Dis. 15:340-350). This study showed increased flip isoforms, especially GluR3 and GluR4, and thus dramatic increases in flip to flop ratios. Interestingly, these changes were specific to mice overexpressing mutant SOD1 but were not found in mice overexpressing normal human SOD1.

Further, electrophysiological studies demonstrated reduced desensitization of AMPA currents in MNs of G93A transgenics compared to control and SOD1 transgenics, as well as robust increases in blockade of desensitization by cyclothiazide. Both of these properties are characteristic of increased flip isoforms (Partin et al., 1994, Mol. Pharm. 46:129-138; Sommer et al., 1990, Science 249:1580-1585). In addition, spontaneous glutamatergic synaptic events are prolonged due to increased decay times in MNs of G93A ALS mice compared to control and SOD1 transgenics, also consistent with an increase in flip isoforms (Pieri et al., 2003, Neurosci. 122:47-58). Together, these studies indicate that aberrant flip-flop ratios are present in MNs of ALS individuals, and that these changes are replicated in a mouse model of the disease. These data strongly implicate a contribution of aberrant flip-flop levels of AMPA channels to MN excitotoxicity in ALS. Specifically, MNs with high levels of $Ca^{2+}$-permable AMPA receptors (Kawahara et al., 2004, Nature 427:801), and especially membrane bound non-desensitizable flip isoforms, permit enhanced postsynaptic $Ca^{2+}$ influx in response to a given glutamate load (FIG. 2).

Increases in the flip to flop ratio in adult hippocampus have also been reported after seizures. This recapitulation of the immature phenotype after seizures is seen for many other neurotransmitter related proteins (Brooks-Kayal et al., 1998). In rat hippocampus, the flip variant of both GluR1 and GluR2 is increased after seizures induced by tetanus toxin (Rosa et al., 1999, Epilepsy Res. 36:243-251) and kindling (Kamphuis et al., 1992, Neurosci. Lett. 148:51-54; Kamphuis et al., 1994, nature 448:39-43). In hippocampal tissue from humans with epilepsy, increases in flip-flop ratios have also been reported. The GluR1 flip variant is increased in hippocampal astrocytes, as assessed both functionally with electrophysiology and at the transcript level with single-cell real time PCR (Seifert et al., 2004, J. Neurosci. 24:1996-2003). In hippocampal neurons, expression of the GluR1 flip variant is increased in CA1 after seizures (Eastwood et al., 1994, Neuroreport 5:1325-1328; de Lanerolle et al., 1998, Eur. J. Neurosci. 10:1687-1703). While the flop variant is found in CA3 and dentate in non-epileptic hippocampus (Eastwood et al., 1994, Neuroreport 5:1325-1328), in tissue from patients with TLE the flop variant of GluR1 is found only in the dentate (de Lanerolle et al., 1998, Eur. J. Neurosci. 10:1687-1703). Thus flop appears to be downregulated in CA3 in epileptic hippocampus. The increase in flip to flop ratios in epileptic hippocampus would increase synaptic gain and could contribute to post-seizure hyperexcitability.

Aph1B: Alzheimer's Disease

Alzheimer's Disease (AD) is a common neurodegenerative disorder and results in a severe decline in cognition, and ultimately dementia, especially in the aged population. Progression of the disease is linked to the characteristic deposition of β-amyloid and tau neurofibrillary tangles (NTs).

Compelling evidence shows that amyloid-beta peptide (Aβ) contributes to the etiology of AD. Aβ is a 38-43 amino acid peptide that is produced in neurons by the sequential proteolytic cleavage of APP by β-secretase and γ-secretase, the latter step yielding isoforms Aβ40 and Aβ42. Aβ42 appears to be the most highly amyloidogenic isoform. In humans, γ-secretase complexes are heterogeneous, comprised of two presenilin genes (PS1 and PS2), along with Aph1A (long or short isoforms) and Aph1B (Shirotani et al., 2004, J. Biol. Chem. 279:41340-41345).

Gamma-secretase is a tri-partite protein complex composed of presenilin, nicastrin, and ApH1. ApH1 is composed of both Aph1A and Aph1B. Transgenic elimination of Aph1B blocked the processing of amyloid precursor protein (APP) to A-beta, but did not effect the processing of other non-amyloidal substrates (Serneels et al., 2009, Science 324:639-642).

A common understanding about AD is that APP processing sequentially by BACE then gamma-secretase, results in the production of Abeta42 among other isoforms. The Abeta42 isoform, which is the direct product of gamma-secretase cleavage is thought to be especially harmful, first as a soluble factor that impairs cognition and later in the production of amyloid plaques that may further enhance disease progression. Therefore, an intense search for compounds that reduce the activity of gamma-secretase is underway.

Unfortunately, in addition to actively cleaving APP, gamma-secretase also cleaves a number of other important non-amyloidal substrates, such as Notch. Thus, there is an urgent need for improved compounds that significantly reduce gamma-secretase production of Aβ-42 in the brain, without affecting its cleavage of other non-APP substrates.

O-GlcNAcase (OGA): Alzheimer's Disease

Levels of N-acetyl-D-glucosamine (O-GlcNAc) modification of proteins are known to be reduced throughout the brains of Alzheimer's Disease (AD) patients due to low glucose availability, and this global alteration is thought to be pathological in AD progression (Fischer, 2008, Nature Chem. Biol. 4:448-449). Dynamic cycling of O-GlcNAc is regulated by addition through N-acetyl-D-glucosamine polypeptidyltransferase (OGT) and removal by O-GlcNAcase (OGA). Removal of O-GlcNAc from proteins by OGA may be involved in controlling multiple cellular pathways. OGA has been shown to mediate transcriptional activation both by directly modifying the transcriptome and by preventing the recycling of transcription factors in the nucleus (Bowe et al., 2006, Mol. Cell Biol. 26:8539-8550). Additionally, OGA has been implicated in chromatin remodeling and transcriptional repression via interactions with OGT/histone deacetylase (MAC) complexes and or C-terminal histone acetyltransferase (HAT) activity (Lazarus et al., 2009, Int. J. Biochem. Cell Biol. 41:2134-2146; Whisenhunt et al., 2006, Glycobiol. 16:551-563). There is also evidence that phosphorylation and O-GlcNAcylation exist in dynamic equilibrium. Serine/threonine residues that otherwise may be phosphorylated by serine/threonine kinases can be instead O-GlcNAc modified, as is the case with tau (Yuzwa et al., 2008, Nat. Chem. Biol. 4:483-490). Further evidence indicates that O-GlcNAcylation of tau can cause trafficking and retention of tau in the nucleus (Guinez et al., 2005, Int. J. Biochem. Cell Biol. 37:765-774) Importantly to AD pathology, low levels of O-GlcNAc on tau may allow for tau hyperphosphorylation, which leads to neurofibrillary tangle (NT) formation. Thus alteration of brain glycosylation will have effects on multiple pathways.

HER3: Cancer

About 25% of breast cancers involve overexpression of the HER2, with highly aggressive metastasis, and poor clinical prognosis. Herceptin shows some success against HER2 overexpressing breast cancer cells (HOBCsa), and tyrosine kinase inhibitors (TKIs) have shown promise in early clinical trials. However, HOBCs show remarkable acquired resistance to current drugs. Recent studies have shown HER3 is overexpressed in HOBCs and exerts a critical role in tumorogenesis, metastasis, and acquisition of resistance to TKIs (Baselga, J. & Swain, S. M. (2009) Novel anticancer targets: revisiting ERBB2 and discovering ERBB3. *Nat Rev Cancer* 9:463-475). For EGFRs, dimerization and transactivation by tyrosine kinase is essential for signaling activity. Although HER3 lacks intrinsic tyrosine kinase activity, the most potent EGFR activated dimers are heterodimers between HER2 and HER3, leading to potent HER3-mediated TKI resistance via activation of the PI3K-Akt pathway (Baselga et al., 2009, Nat Rev Cancer 9:463-475). Since the loss of HER3 function ameliorates the transforming capabilities of HER2, there is a pressing need for new drugs against HER3 for treating breast cancer.

Forkhead Box Protein M1 (FOXM1): Anti-Tumor

Forkhead box protein M1 (FOXM1) is a protein that is encoded by the FOX1 gene and is a member of the FOX family of transcription factors. FOXM1 is known to play a key role in cell cycle progression. There are three FOXM1 isoforms, A, B and C. Isoform FOXM1A has been shown to be a gene transcriptional repressor whereas the remaining isoforms (B and C) are both transcriptional activators. Hence, it is not surprising that FOXM1B and C isoforms have been found to be upregulated in human cancers (Wiestra et al., 2007, Biol. Chem. 388 (12): 1257-74.

The exact mechanism of FOXM1 in cancer formation remains unknown. It is thought that upregulation of FOXM1 promotes oncogenesis through abnormal impact on its multiple roles in cell cycle and chromosomal/genomic maintenance.

FOXM1 overexpression is involved in early events of carcinogenesis

FOXM1 gene is now known as a human proto-oncogene. Abnormal FOXM1 upregulation was subsequently found in the majority of solid human cancers including liver (Teh et al., 2002, Cancer Res. 62: 4773-80) breast (Wonsey et al., 2005, Cancer Res. 65 (12): 5181-9), lung (Kim et al., 2006, Cancer Res. 66 (4): 2153-61), prostate (Kahn et al., 2006, Cancer Res. 66 (3): 1712-20; cervix of uterus (Chan et al., 2008, J. Pathol. 215 (3): 245-52), colon (Douard et al., 2006, Surgery 139 (5): 665-70), pancreas (Wang et al., 2007, Cancer Res. 67 (17): 8293-300), and brain (Liu et al., 2006, Cancer Res. 66 (7): 3593-602).

Cyclophilin D: ALS, Hepatitis B Viral Infection, and Liver Cancer

Cyclophilin D (CypD) is a protein located in the matrix of the mitochondria, and is one of the components of the mitochondrial permeability transition pore (MPTP). Under conditions of oxidative stress, the MPTP becomes extremely permeable to the influx of calcium ions, therein causing mitochondrial swelling eventually leading to cell apoptosis. Targeting the MPTP/CypD complex in hepatitis B virus (HBV) infected hepatocytes using the non-specific CypD inhibitor, Cyclosporin A, inhibits HBV replication (Waldemeier et al., 2003, Current Medicinal Chemistry 10:1485-1506). In addition, when used in patients with neurodegerative diseases, Cyclosporin A exhibits cytoprotective effects by way of blocking the opening of the MPTP. Although shown to be efficacious, Cyclosporin A is an immunosuppressive drug, and can also bind non-specifically to other cyclophilins, therefore causing off-target effects. Inhibition of CypD expression using siRNA has been examined as a potential cardioprotective therapy (Kato et al., 2009, Cardiovasc. Res. 83:335-344). However SMOs have a therapeutic advantage over siRNA in that unlike siRNA, SMOs do not affect transcript degradation through recruitment of RNAase H which can cause immune reactions and other off target effects.

There is presently no known cure for PWS, ALS, AD or any of a number of other diseases that result from aberrant pre-mRNA splicing. There is a need in the art for the development of more selective and efficacious therapeutic agents for the treatments of various diseases and conditions affected or mediated by 5HT2CR, GluRs, OGA, Aph1B, FOXM1, ERBB3, and CypD. In addition, there are a number of diseases where altering pre-mRNA splicing may have a positive therapeutic effect even when that gene is not directly affected by the pathogenesis of the disease. Accordingly, there is an urgent need in the art for compositions and methods related to pre-mRNA splicing as it affects various diseases and disorders. The present invention fills this need.

SUMMARY OF THE INVENTION

In one embodiment, the present invention comprises a method of modulating splicing of a pre-mRNA, the method comprising contacting a cell with an effective amount of a splice modulating oligonucleotide (SMO), where the SMO specifically binds to a complementary sequence on a pre-mRNA in at least one of the group consisting of an intron-exon splice site, an exonic splice enhancer (ESE) site, and an intronic splice enhancer (ISE) site, where when the SMO specifically binds to the complementary sequence, the exon adjacent to the intron-exon boundary is excluded from the resulting mRNA. In one aspect, the resulting mRNA encodes a protein selected from the group consisting of a glutamate activated AMPA receptor subunit (GluR), OGA, Aph1B, FOXM1, HER3, and CypD. In another aspect, the GluR is selected from the group consisting of GluR1, GluR2, GluR3, GluR4 and any combination thereof.

In another embodiment, the present invention comprises a method of modulating splicing of a pre-mRNA, the method comprising contacting a cell with an effective amount of a splice modulating oligonucleotide (SMO), where the SMO specifically binds to a complementary sequence on a pre-mRNA in at least one of the group consisting of an intron-exon splice site, an exonic splice suppressor (ESS) site, and an intronic splice suppressor (ISS) site, where when the SMO specifically binds to the complementary sequence, the exon adjacent to the intron-exon boundary is included in the resulting mRNA. In one aspect, the resulting mRNA encodes a 5-HT2C receptor.

In still another embodiment, the present invention comprises a method of treating a subject afflicted with a 5-HT2CR splicing defect, the method comprising administering a splice modulating oligonucleotide (SMO) to the subject, where an effective amount of the SMO contacts a cell so that the SMO specifically binds to a complementary sequence on a pre-mRNA, where when the SMO specifically binds to the complementary sequence, exon 5b is included in the resulting mRNA encoding a full-length, functional 5-HT2C receptor, and where the SMO increases expression of a full-length, functional 5-HT2C receptor in the subject and treats the subject afflicted with a 5-HT2CR splicing defect. In one aspect, the SMO is an isolated nucleic acid sequence selected from the group consisting of SEQ ID NOs. 1-56.

In another embodiment, the present invention comprises a method of treating a subject afflicted with Prader-Willi Syndrome (PWS), the method comprising administering a splice modulating oligonucleotide (SMO) to the subject, where an effective amount of the SMO contacts a cell so that the SMO specifically binds to a complementary sequence on a pre-mRNA, where when the SMO specifically binds to the complementary sequence, exon 5b is included in the resulting mRNA encoding a full-length, functional 5-HT2C receptor, and where the SMO increases expression of the full-length, functional 5-HT2C receptor in the subject and treats the subject afflicted with PWS. In one aspect, the SMO is an isolated nucleic acid sequence selected from the group consisting of SEQ ID NOs. 1-56.

In yet another embodiment, the present invention comprises, a method of treating a subject afflicted with hyperphagia, the method comprising administering a splice modulating oligonucleotide (SMO) to the subject, where an effective amount of the SMO contacts a cell so that the SMO specifically binds to a complementary sequence on a pre-mRNA, where when the SMO specifically binds to the complementary sequence, exon 5b is included in the resulting mRNA encoding a full-length, functional 5-HT2C receptor, and where the SMO increases expression of the full-length, functional 5-HT2C receptor in the subject and treats the subject afflicted with hyperphagia. In one aspect, the SMO is an isolated nucleic acid sequence selected from the group consisting of SEQ ID NOs. 1-56.

In still another embodiment, the present invention comprises a method of treating a subject afflicted with symptoms of obsessive-compulsive disorder, the method comprising administering a splice modulating oligonucleotide (SMO) to the subject, where an effective amount of the SMO contacts a cell so that the SMO specifically binds to a complementary sequence on a pre-mRNA, where when the SMO specifically binds to the complementary sequence, exon 5b is included in the resulting mRNA encoding a full-length, functional 5-HT2C receptor, and where the SMO increases expression of the full-length, functional 5-HT2C receptor in the subject and treats the subject afflicted with symptoms of obsessive-compulsive disorder. In one aspect, the SMO is an isolated nucleic acid sequence selected from the group consisting of SEQ ID NOs. 1-56.

In another embodiment, the present invention comprises a method of increasing expression of a transmembrane neuronal receptor in a subject, the method comprising contacting a cell with an effective amount of a splice modulating oligonucleotide (SMO), where the SMO specifically binds to a complementary sequence on a pre-mRNA in at least one of an intron-exon splice site, an exonic splice suppressor (ESS) site, and an intronic splice suppressor (ISS) site, where when the SMO specifically binds to the complementary sequence, the exon adjacent to the intron-exon boundary is included in the resulting mRNA encoding a full-length, functional transmembrane neuronal receptor, and where the SMO increases expression of the full-length, functional transmembrane neuronal receptor. In one aspect, the transmembrane neuronal receptor is a 5-HT2C receptor. In another aspect, the subject is afflicted with a disease or disorder selected from the group consisting of PWS, Angelman Syndrome, hyperphagia induced obesity, obsessive/compulsive disorder, depression, psychotic depression, major depressive disorder, bipolar disorder, sleep impairment, autism, schizophrenia, Parkinson's disease, drug addiction, spinal cord injury, traumatic brain injury, neuropathic pain, diabetes, and Alzheimer's disease.

In still another embodiment, the present invention comprises a method of increasing expression of a transmembrane neuronal receptor in a subject, the method comprising contacting a cell with an effective amount of a splice modulating oligonucleotide (SMO), where the SMO specifically binds to a complementary sequence on a pre-mRNA in at least one of the group consisting of an intron-exon splice site, an exonic splice enhancer (ESE) site, and an intronic splice enhancer (ISE) site, where when the SMO specifically binds to the complementary sequence, the exon adjacent to the intron-exon boundary is excluded from the resulting mRNA encoding the transmembrane neuronal receptor, and where the SMO increases expression of the transmembrane neuron receptor. In one aspect, the transmembrane neuron receptor is a glutamate activated AMPA receptor subunit (GluR) selected from the group consisting of GluR1, GluR2, GluR3, GluR4, and any combination thereof.

In another embodiment, the present invention comprises a method of treating a subject afflicted with amyotrophic lateral sclerosis (ALS), the method comprising administering a splice modulating oligonucleotide (SMO) to the subject, where an effective amount of the SMO contacts a cell so that the SMO specifically binds to a complementary sequence on a pre-mRNA in at least one of an intron-exon splice site, an exonic splice enhancer (ESE) site, and an intronic splice enhancer (ISE) site, where when the SMO specifically binds to the complementary sequence, the exon adjacent to the intron-exon boundary is excluded from the resulting mRNA encoding a GluR, where the GluR is selected from the list consisting of GluR1, GluR2, GluR3, GluR4, and any combination thereof, where the SMO decreases expression of the flip isoform of the GluR in the subject and treats the subject afflicted with ALS. In one aspect, the SMO is an isolated nucleic acid sequence selected from the group consisting of SEQ ID NOs. 57-526.

In yet another embodiment, the present invention comprises a method of treating a subject afflicted with epilepsy the method comprising administering a splice modulating oligonucleotide (SMO) to the subject, where an effective amount of the SMO contacts a cell so that the SMO specifically binds to a complementary sequence on a pre-mRNA in at least one of an intron-exon splice site, an exonic splice enhancer (ESE) site, and an intronic splice enhancer (ISE) site, where when the SMO specifically binds to the complementary sequence, the exon adjacent to the intron-exon boundary is excluded from the resulting mRNA encoding a GluR, where the GluR is selected from the list consisting of GluR1, GluR2, GluR3, GluR4, and any combination thereof, where the SMO decreases expression of the flip isoform of the GluR in the subject and treats the subject afflicted with epilepsy. In one aspect, the SMO is an isolated nucleic acid sequence selected from the group consisting of SEQ ID NOs. 57-526.

In another embodiment, the present invention comprises a method of treating a subject afflicted with Alzheimer's Disease (AD), the method comprising administering a splice modulating oligonucleotide (SMO) to the subject, where an effective amount of the SMO contacts a cell so that the SMO specifically binds to a complementary sequence on a pre-mRNA in at least one of an intron-exon splice site, an exonic splice enhancer (ESE) site, and an intronic splice enhancer (ISE) site, where when the SMO specifically binds to the complementary sequence, the exon adjacent to the intron-exon boundary is excluded from the resulting mRNA, where the exon is exon 8 of the mRNA encoding O-GlcNAcase (OGA), where the SMO increases expression of OGAΔ8 in the subject and treats the subject afflicted with AD. In one aspect the SMO is an isolated nucleic acid sequence selected from the group consisting of SEQ ID NOs. 527-611.

In still another embodiment, the present invention comprises a method of treating a subject afflicted with Alzheimer's Disease (AD), the method comprising administering a splice modulating oligonucleotide (SMO) to the subject, where an effective amount of the SMO contacts a cell so that the SMO specifically binds to a complementary sequence on a pre-mRNA in at least one of an intron-exon splice site, an exonic splice suppressor (ESS) site, and an intronic splice suppressor (ISS) site, where when the SMO specifically binds to the complementary sequence, the intron adjacent to the intron-exon boundary is included in the resulting mRNA, where the intron is intron 10 of the mRNA encoding O-GlcNAcase (OGA), and where the SMO increases expression of a truncated OGA protein (OGA10t) in the subject and treats the subject afflicted with AD. In one aspect, the SMO is an isolated nucleic acid sequence selected from the group consisting of SEQ ID NOs. 612-661.

In another embodiment, the present invention comprises a method of treating a subject afflicted with Alzheimer's Disease (AD), the method comprising administering a splice modulating oligonucleotide (SMO) to the subject, where an effective amount of the SMO contacts a cell so that the SMO specifically binds to a complementary sequence on a pre-mRNA in at least one of the group consisting of an intron-exon splice site, an exonic splice enhancer (ESE) site, and an intronic splice enhancer (ISE) site, where when the SMO specifically binds to the complementary sequence, the exon adjacent to the intron-exon boundary is excluded from the resulting mRNA, where the exon is exon 4 of the mRNA encoding Aph1B, where the SMO increases expression of Aph1BΔ4 in the subject and treats the subject afflicted with AD. In one aspect, the SMO is an isolated nucleic acid sequence selected from the group consisting of SEQ ID NOs. 662-728.

In yet another embodiment, the preset invention comprises a method of treating a subject afflicted with a cancer, the method comprising administering a splice modulating oligonucleotide (SMO) to the subject, where an effective amount of the SMO contacts a cell so that the SMO specifically binds to a complementary sequence on a pre-mRNA in at least one of the group consisting of an intron-exon splice site, an exonic splice enhancer (ESE) site, and an intronic splice enhancer (ISE) site, where when the SMO specifically binds to the complementary sequence, the exon adjacent to the intron-exon boundary is excluded from the resulting mRNA, where the exon is exon 3 of the mRNA encoding HER3, and where the SMO increases expression of a HER3Δ3 in the subject and treats the subject afflicted with cancer. In one aspect, the SMO is an isolated nucleic acid sequence selected from the group consisting of SEQ ID NOs. 729-802. In another aspect, the cancer is selected from the group consisting of breast cancer, liver cancer, lung cancer, prostate cancer, cervical cancer, colon cancer, pancreatic cancer, and brain cancer.

In still another embodiment, the present invention comprises a method of treating a subject afflicted with a cancer, the method comprising administering a splice modulating oligonucleotide (SMO) to the subject, where an effective amount of the SMO contacts a cell so that the SMO specifically binds to a complementary sequence on a pre-mRNA in at least one of the group consisting of an intron-exon splice site, an exonic splice suppressor (ESS) site, and an intronic splice suppressor (ISS) site, where when the SMO specifically binds to the complementary sequence, the intron adjacent to the intron-exon boundary is included in the resulting mRNA, where the intron is intron 3 of the mRNA encoding HER3, and where the SMO increases expression of a truncated HER3 protein in the subject and treats the subject afflicted with cancer. In one embodiment of the method, the SMO is an isolated nucleic acid sequence selected from the group consisting of SEQ ID NOs. 729-802. In another aspect, the cancer is selected from the group consisting of breast cancer, liver cancer, lung cancer, prostate cancer, cervical cancer, colon cancer, pancreatic cancer, and brain cancer.

In another embodiment, the present invention comprises a method of treating a subject afflicted with a cancer, the method comprising administering a splice modulating oligonucleotide (SMO) to the subject, where an effective amount of the SMO contacts a cell so that the SMO specifically binds to a complementary sequence on a pre-mRNA in at least one of the group consisting of an intron-exon splice site, an exonic splice enhancer (ESE) site, and an intronic splice enhancer (ISE) site, where when the SMO specifically binds to the complementary sequence, the exon adjacent to the intron-exon boundary is excluded from the resulting mRNA, where the exon is exon 11 of the mRNA encoding HER3, and where the SMO increases expression of a HER3Δ11 in the subject and treats the subject afflicted with cancer. In one aspect, the SMO is an isolated nucleic acid sequence selected from the group consisting of SEQ ID NOs. 803-813. In another aspect, the cancer is selected from the group consisting of a breast cancer, liver cancer, lung cancer, prostate cancer, cervical cancer, colon cancer, pancreatic cancer, and brain cancer.

In yet another embodiment, the present invention comprises a method of treating a subject afflicted with a cancer, the method comprising administering a splice modulating oligonucleotide (SMO) to the subject, where an effective amount of the SMO contacts a cell so that the SMO specifically binds to a complementary sequence on a pre-mRNA in at least one of the group consisting of an intron-exon splice site, an exonic splice enhancer (ESE) site, and an intronic splice enhancer (ISE) site, where when the SMO specifically binds to the complementary sequence, the exon adjacent to the intron-exon boundary is excluded from the resulting mRNA encoding FOXM1, and where the SMO increases expression of a FOXM1Δ3 or FOXM1Δ6 in the subject and treats the subject afflicted with cancer. In one aspect, the SMO is an isolated nucleic acid sequence selected from the group consisting of SEQ ID NOs. 919-1090.

In still another embodiment, the present invention comprises a method of treating a subject afflicted with a hepatitis B virus (HBV) infection, the method comprising administering a splice modulating oligonucleotide (SMO) to the subject, where an effective amount of the SMO contacts a cell so that the SMO specifically binds to a complementary sequence on a pre-mRNA in at least one of the group consisting of an intron-exon splice site, an exonic splice enhancer (ESE) site, and an intronic splice enhancer (ISE) site, where when the SMO specifically binds to the complementary sequence, the exon adjacent to the intron-exon boundary is excluded from the resulting mRNA, where the exon is exon 1 of the mRNA encoding CypD, and where the SMO increases expression of a CypDΔ1 in the subject and treats the subject afflicted with an HBV infection. In one aspect, the SMO is an isolated nucleic acid sequence selected from the group consisting of SEQ ID NOs. 814-857.

In yet another embodiment, the present invention comprises a method of treating a subject afflicted with a hepatitis B virus (HBV) infection, the method comprising administering a splice modulating oligonucleotide (SMO) to the subject, where an effective amount of the SMO contacts a cell so that the SMO specifically binds to a complementary sequence on a pre-mRNA in at least one of the group consisting of an intron-exon splice site, an exonic splice enhancer (ESE) site, and an intronic splice enhancer (ISE) site, where when the SMO specifically binds to the complementary sequence, the exon adjacent to the intron-exon boundary is excluded from the resulting mRNA, where the exon is exon 3 of the mRNA encoding CypD, and where the SMO increases expression of a CypDΔ3 in subject and treats the subject afflicted with an HBV infection. In one aspect, the SMO is an isolated nucleic acid sequence selected from the group consisting of SEQ ID NOs. 858-918.

In another embodiment, the present invention comprises a method of treating a subject afflicted with a cancer, the method comprising administering a splice modulating oligonucleotide (SMO) to the subject, where an effective amount of the SMO contacts a cell so that the SMO specifically binds to a complementary sequence on a pre-mRNA in at least one of the group consisting of an intron-exon splice site, an exonic splice enhancer (ESE) site, and an intronic splice enhancer (ISE) site, where when the SMO specifically binds to the complementary sequence, the exon adjacent to the intron-exon boundary is excluded from the resulting mRNA, where the exon is exon 1 of the mRNA encoding CypD, and where the SMO increases expression of a CypDΔ1 in the subject and treats the subject afflicted with cancer. In one aspect, the the SMO is an isolated nucleic acid sequence selected from the group consisting of SEQ ID NOs. 814-857. In another aspect, the cancer is a liver cancer.

In still another embodiment, the present invention comprises a method of treating a subject afflicted with a cancer, the method comprising administering a splice modulating oligonucleotide (SMO) to the subject, where an effective amount of the SMO contacts a cell so that the SMO specifically binds to a complementary sequence on a pre-mRNA in at least one of the group consisting of an intron-exon splice site, an exonic splice enhancer (ESE) site, and an intronic splice enhancer (ISE) site, where when the SMO specifically binds to the complementary sequence, the exon adjacent to the intron-exon boundary is excluded from the resulting mRNA, where the exon is exon 3 of the mRNA encoding CypD, and where the SMO increases expression of a CypDΔ3 in the subject and treats the subject afflicted with cancer. In one aspect, the SMO is an isolated nucleic acid sequence selected from the group consisting of SEQ ID NOs. 858-918. In another aspect, the cancer is a liver cancer.

In yet another embodiment, the present invention comprises a method of treating a subject afflicted with amyotrophic lateral sclerosis (ALS), the method comprising administering a splice modulating oligonucleotide (SMO) to the subject, where an effective amount of the SMO contacts a cell so that the SMO specifically binds to a complementary sequence on a pre-mRNA in at least one of the group consisting of an intron-exon splice site, an exonic splice enhancer (ESE) site, and an intronic splice enhancer (ISE) site, where when the SMO specifically binds to the complementary sequence, the exon adjacent to the intron-exon boundary is excluded from the resulting mRNA, where the exon is exon 1 of the mRNA encoding CypD, and where the SMO increases expression of a CypDΔ1 in the subject and treats the subject afflicted with ALS. In one aspect, the SMO is an isolated nucleic acid sequence selected from the group consisting of SEQ ID NOs. 814-857.

In another embodiment, the present invention comprises a method of treating a subject afflicted with amyotrophic lateral sclerosis (ALS), the method comprising administering a splice modulating oligonucleotide (SMO) to the subject, where an effective amount of the SMO contacts a cell so that the SMO specifically binds to a complementary sequence on a pre-mRNA in at least one of the group consisting of an intron-exon splice site, an exonic splice enhancer (ESE) site, and an intronic splice enhancer (ISE)

site, where when the SMO specifically binds to the complementary sequence, the exon adjacent to the intron-exon boundary is excluded from the resulting mRNA, where the exon is exon 3 of the mRNA encoding CypD, and where the SMO increases expression of a CypDΔ3 in the subject and treats the subject afflicted with ALS. In one aspect, the SMO is an isolated nucleic acid sequence selected from the group consisting of SEQ ID NOs. 858-918. In another aspect, the isolated nucleic acid selected from the group consisting of SEQ ID NOs. 1-1090.

In one embodiment, the present invention comprises a pharmaceutical composition comprising a splice modulating oligonucleotide (SMO) that targets a pre-mRNA that matures to a 5HT2CR, where the SMO is an isolated nucleic acid sequence selected from the group consisting of SEQ ID NOs. 1-56.

In still another embodiment, the present invention comprises a pharmaceutical composition comprising a splice modulating oligonucleotide (SMO) that targets a pre-mRNA that matures to a GluR, where the SMO is an isolated nucleic acid sequence selected from the group consisting of SEQ ID NOs. 57-526.

In yet another embodiment, the present invention comprises a pharmaceutical composition comprising a splice modulating oligonucleotide (SMO) that targets a pre-mRNA that matures to a OGA, where the SMO is an isolated nucleic acid sequence selected from the group consisting of SEQ ID NOs. 527-661.

In another embodiment, the present invention comprises a pharmaceutical composition comprising a splice modulating oligonucleotide (SMO) that targets a pre-mRNA that matures to a Aph1B, where the SMO is an isolated nucleic acid sequence selected from the group consisting of SEQ ID NOs. 662-728.

In still another embodiment, the present invention a pharmaceutical composition comprising a splice modulating oligonucleotide (SMO) that targets a pre-mRNA that matures to a HER3, where the SMO is an isolated nucleic acid sequence selected from the group consisting of SEQ ID NOs. 729-813.

In yet another embodiment, the present invention also comprises a pharmaceutical composition comprising a splice modulating oligonucleotide (SMO) that targets a pre-mRNA that matures to a CypD, where the SMO is an isolated nucleic acid sequence selected from the group consisting of SEQ ID NOs. 814-918.

In another embodiment, the present invention comprises a pharmaceutical composition comprising a splice modulating oligonucleotide (SMO) that targets a pre-mRNA that matures to a FOXM1, where the SMO is an isolated nucleic acid sequence selected from the group consisting of SEQ ID NOs. 919-1090.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1A through FIG. 1I is a series of images depicting splice modulating oligonucleotide (SMO) mediated induction of full-length survival motor neuron protein (SMN) expression and concomitant phenotypic improvement in spinal muscular atrophy (SMA) mice. FIG. 1A depicts a photomicrograph of brain section in an uninjected control. FIG. 1B depicts SMO fluorescent label broadly distributed throughout brain regions 24 hours following bilateral intracerebroventricular (ICV) injection of the SMO. FIG. 1C is a higher magnification of the area within the box in FIG. 1B. FIG. 1D through FIG. 1I depict results obtained from SMA mice (N=5), injected with 1 µg SMO (per ventricle) on postnatal day 1, 3, 5, 7, 10, and harvested on day 12, and compared with uninjected controls (N=9). FIG. 1D depicts the results of real-time PCR of brain sections taken at the level of hippocampus shows full-length SMN expression was increased in SMA mice following ICV injections of SMO. FIG. 1E and FIG. 1F depict Western analysis of brain sections taken at the level of hippocampus (FIG. 1E) and cervical spinal cord (FIG. 1F) showing SMN expression increases in SMA mice following ICV injections of SMO. FIG. 1G is a graph depicting SMN expression measured by Westerns as significantly increased in brain and spinal cord of SMO-treated SMA mice when measured as a percentage of wild-type controls. FIG. 1H is a graph depicting body weight of SMA mice which was significantly increased relative to un-injected controls at P12 following ICV injections of SMO (P<0.01). FIG. 1I is a graph depicting SMO-treated SMA mice with significant improvement in righting response at P12 compared to untreated controls. In total, all 5 SMO-treated mice could right themselves from at least one side, while only 3 of 9 untreated mice could accomplish this task. However, motor function was not fully restored as most SMO-treated and untreated SMA mice could not right themselves from both sides.

FIG. 3 depicts a ClustalW alignment of flip and flop exons of mouse GluR1-4. Dark shading indicates positions of complete identity, while lighter shading shows divergence. The sequences compared are as follows: mGluR1-flop exon (SEQ ID NO: 1090); mGluR2-flop exon (SEQ ID NO: 1091); mGluR3-flop exon (SEQ ID NO: 1092); mGluR4-flop exon (SEQ ID NO: 1093); mGluR1-flip exon (SEQ ID NO: 1094); mGluR2-flip exon (SEQ ID NO: 1095); mGluR3-flip exon (SEQ ID NO: 1096); and mGluR4-flip exon (SEQ ID NO: 1097).

FIG. 4 also reflects the proposed top 5 antisense oligonucleotides in the bottom two lines of the figure. From left to right and top to bottom, SEQ ID NO: 123, SEQ ID NO: 1102, SEQ ID NO: 1103, SEQ ID NO: 1104, and SEQ ID NO: 1105.

DETAILED DESCRIPTION OF THE INVENTION

Figure 2:
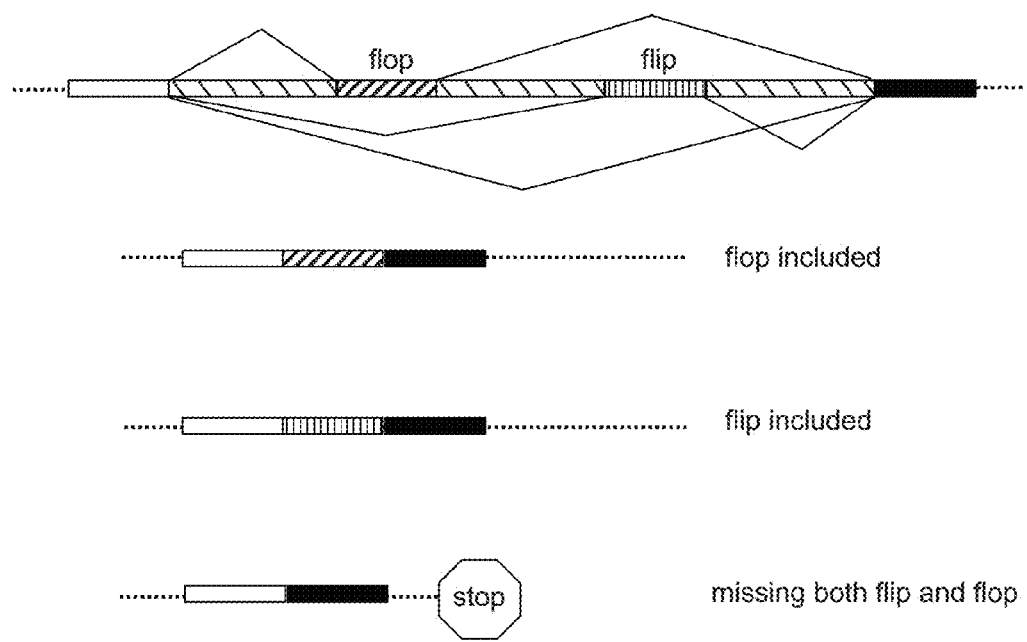
FIG. 2 is a schematic illustration depicting alternative splicing at the flip-flop cassette exons of glutamate receptor (GluR) subunits of AMPA receptors. Alternative splicing of mutually exclusive flip and flop exons of GluR1-4 leads to either flip exon-containing or flop-exon-containing transcripts. Co-skipping of both flip and flop exons results in out-of-frame transcripts that are truncated and unstable.

The present invention relates to splice modulating oligonucleotides (SMOs) affecting splicing of pre-mRNA expressed from various genes. In one embodiment, the instant invention provides compositions and methods for correcting aberrant splicing of pre-mRNA that results in a defective protein and consequently causes a disease or a disorder in a subject, wherein the subject is preferably human.

In another embodiment, the instant invention provides compositions and methods for treating a human disease or disorder by modulating pre-mRNA splicing of a nucleic acid even when that nucleic acid is not aberrantly spliced in the pathogenesis of the disease or disorder being treated.

In one embodiment, the human disease or disorder is neurological. In another embodiment, the human disease is a cancer.

Definitions:

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

By the term "applicator," as the term is used herein, is meant any device including, but not limited to, a hypodermic syringe, a pipette, and the like, for administering the compounds and compositions of the invention.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, preferably at least about 60% and more preferably at least about 80% of corresponding positions in each of the molecules are occupied by nucleotides which normally base pair with each other (e.g., A:T and G:C nucleotide pairs).

A "disease" is a state of health of subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health. In preferred embodiments, the subject is an animal. In more preferred embodiments, the subject is a mammal. In most preferred embodiments, the subject is a human.

A disease or disorder is "alleviated" if the severity of a symptom of the disease or disorder, or the frequency with which such a symptom is experienced by a subject, or both, are reduced.

The terms "effective amount" and "pharmaceutically effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence.

The term "exonic regulatory elements" as used herein refers to sequences present on pre-mRNA that enhance or suppress splicing of an exon. An exonic regulatory element that enhances splicing of an exon is an exonic splicing enhancer (ESE). An exonic regulatory element that suppresses splicing of an exon is an exonic splicing suppressor (ESS). An intronic regulatory element that enhances splicing of an exon is an intronic splicing enhancer (ISE). An intronic regulatory element that suppresses splicing of an exon is called an intronic splicing suppressor (ISS).

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

By "expression cassette" is meant a nucleic acid molecule comprising a coding sequence operably linked to promoter/regulatory sequences necessary for transcription and, optionally, translation of the coding sequence.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a n inducible manner.

An "inducible" promoter is a nucleotide sequence which, when operably linked with a polynucleotide which encodes or specifies a gene product, causes the gene product to be produced substantially only when an inducer which corresponds to the promoter is present.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

A "polynucleotide" means a single strand or parallel and anti-parallel strands of a nucleic acid. Thus, a polynucleotide may be either a single-stranded or a double-stranded nucleic acid. In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

The term "recombinant DNA" as used herein is defined as DNA produced by joining pieces of DNA from different sources.

The term "recombinant polypeptide" as used herein is defined as a polypeptide produced by using recombinant DNA methods.

By the term "specifically binds," as used herein, is meant a molecule, such as an antibody, which recognizes and binds to another molecule or feature, but does not substantially recognize or bind other molecules or features in a sample.

By the term "splice defect of a protein", as used herein, is meant a defective protein resulting from a defect in the splicing of an RNA encoding a protein.

The term "treatment," as used herein, refers to reversing, alleviating, delaying the onset of, inhibiting the progress of, and/or preventing a disease or disorder, or one or more symptoms thereof, to which the term is applied in a subject. In some embodiments, treatment may be applied after one or more symptoms have developed. In other embodiments, treatment may be administered in the absence of symptoms. For example, treatment may be administered prior to symptoms (e.g., in light of a history of symptoms and/or one or more other susceptibility factors), or after symptoms have resolved, for example to prevent or delay their reoccurrence.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual and partial numbers within that range, for example, 1, 2, 3, 4, 5, 5.5 and 6. This applies regardless of the breadth of the range.

Description

The present invention encompasses a class of compounds known as splice modulating oligonucleotides (SMOs) that modulate pre-mRNA splicing, thereby affecting expression and functionality of a specific protein in a cell. A SMO specifically binds to a complementary sequence on a pre-mRNA at an exon or intron splice suppressor or splice enhancer site, or at an intron-exon splice site. When a SMO specifically binds to a splice enhancer site, or an intron-exon splice site, the adjacent exon is excluded from the resulting mRNA. In another embodiment, a SMO specifically binds to a splice suppressor site or an intron-exon site and the adjacent exon is included in the resulting mRNA. In another embodiment, a SMO specifically binds to a splice enhancer site or an intron-exon splice site and shifts the reading frame of the pre-mRNA so that the resulting protein is a truncated. In some cases, the resulting protein is a limited-function, or non-functional protein.

The location of an exonic or intronic splice enhancer or suppressor motif may be found anywhere within the exon and the flanking introns. Similarly, a SMO may either fully or partially overlap a predicted exonic or intronic splice enhancer or suppressor site in proximity to an intron-exon boundary and/or be complementary to the predicted 3' or 5' splice sites.

I. Compositions: Splice Modulating Oligonucleotides

The present invention is directed, in part, to oligonucleotides referred to herein as splice modulating oligonucleotides (SMOs), suitable for use in modulating splicing of a target pre-mRNA both in vitro and in vivo. The present invention also includes a pharmaceutical composition comprising a SMO suitable for modulating splicing of a target pre-mRNA both in vitro and in vivo. In vivo methodologies are useful for both general splice site modulatory purposes, as well as in therapeutic applications in which modulating splicing of a target pre-mRNA is desirable.

A. 5-Hydroxytryptamine (Serotonin) Receptor 2C (5-HT2CR)

The present invention provides SMOs based on the consensus sequence of the 5-HT2CR (HTR2C; MIM: 312861 GeneID: 3358), including upstream and downstream nucleotides (Table 1). These SMOs are used according to the methods of the invention to modulate splicing of 5-HT2CR pre-mRNA. In one embodiment, these SMOs are used according to the methods of the invention to modulate splicing of 5-HT2CR pre-mRNA caused by a deletion of the 15q11-13 region of the $15^{th}$ chromosome that results in a deletion of the snoRNA HBII-52. In another embodiment, a SMO of the invention functions to mimic the function of HBII-52. In another embodiment, a SMO of the invention functions to increase expression of a functional 5-HT2CR transcript containing exon 5b.

In some embodiments, the invention includes a pharmaceutical composition that comprises a SMO that functions to modulate splicing of 5-HT2CR pre-mRNA. In other embodiments, the invention includes a pharmaceutical composition that comprises a SMO that functions to modulate splicing of 5-HT2CR pre-mRNA caused by a deletion of the 15q11-13 region of the $15^{th}$ chromosome that results in a deletion of the snoRNA HBII-52. In another embodiment, the invention includes a pharmaceutical composition that comprises a SMO that functions to mimic the function of HBII-52. In still another embodiment, the invention includes a pharmaceutical composition that comprises a SMO that functions to increase expression of a functional 5-HT2CR transcript containing exon 5b.

Table 1 depicts exemplary SMOs useful for modulating splicing of 5-HT2CR pre-mRNA in order to mimic the effect of HBII-52 snoRNA or increase the expression or function of 5HT2CR containing exon 5b.

TABLE 1

| 3' to 5' SMOs targeting the 5-HT2C pre-mRNA | SEQ ID NO. |
|---|---|
| 5-HT2C sequence: 3'-CGA<u>UACGAGUUAUCCUAAUGC</u>AUA-5' | 1 |
| 15 nucleotide (nt) SMO | |
| GGAUAACUCGUAUCG | 2 |
| AGGAUAACUCGUAUC | 3 |
| UAGGAUAACUCGUAU | 4 |
| UUAGGAUAACUCGUA | 5 |
| AUUAGGAUAACUCGU | 6 |
| CAUUAGGAUAACUCG | 7 |
| GCAUUAGGAUAACUC | 8 |
| UGCAUUAGGAUAACU | 9 |
| AUGCAUUAGGAUAAC | 10 |
| UAUGCAUUAGGAUAA | 11 |
| 16 nt SMO | |
| AGGAUAACUCGUAUCG | 12 |
| UAGGAUAACUCGUAUC | 13 |
| UUAGGAUAACUCGUAU | 14 |
| AUUAGGAUAACUCGUA | 15 |
| CAUUAGGAUAACUCGU | 16 |
| GCAUUAGGAUAACUCG | 17 |
| UGCAUUAGGAUAACUC | 18 |
| AUGCAUUAGGAUAACU | 19 |
| UAUGCAUUAGGAUAAC | 20 |
| 17 nt SMO | |
| UAGGAUAACUCGUAUCG | 21 |
| UUAGGAUAACUCGUAUC | 22 |
| AUUAGGAUAACUCGUAU | 23 |
| CAUUAGGAUAACUCGUA | 24 |
| GCAUUAGGAUAACUCGU | 25 |
| UGCAUUAGGAUAACUCG | 26 |

TABLE 1-continued

| 3' to 5' SMOs targeting the 5-HT2C pre-mRNA | SEQ ID NO. |
|---|---|
| AUGCAUUAGGAUAACUC | 27 |
| UAUGCAUUAGGAUAACU | 28 |
| 18 nt SMO | |
| GCAUUAGGAUAACUCGUA | 29 |
| UUAGGAUAACUCGUAUCG | 30 |
| AUUAGGAUAACUCGUAUC | 31 |
| CAUUAGGAUAACUCGUAU | 32 |
| UGCAUUAGGAUAACUCGU | 33 |
| AUGCAUUAGGAUAACUCG | 34 |
| UAUGCAUUAGGAUAACUC | 35 |
| 19 nt SMO | |
| AUUAGGAUAACUCGUAUCG | 36 |
| CAUUAGGAUAACUCGUAUC | 37 |
| GCAUUAGGAUAACUCGUAU | 38 |
| UGCAUUAGGAUAACUCGUA | 39 |
| AUGCAUUAGGAUAACUCGU | 40 |
| UAUGCAUUAGGAUAACUCG | 41 |
| 20 nt SMO | |
| CAUUAGGAUAACUCGUAUCG | 42 |
| GCAUUAGGAUAACUCGUAUC | 43 |
| UGCAUUAGGAUAACUCGUAU | 44 |
| AUGCAUUAGGAUAACUCGUA | 45 |
| UAUGCAUUAGGAUAACUCGU | 46 |
| 21 nt SMO | |
| GCAUUAGGAUAACUCGUAUCG | 47 |
| UGCAUUAGGAUAACUCGUAUC | 48 |
| AUGCAUUAGGAUAACUCGUAU | 49 |
| UAUGCAUUAGGAUAACUCGUA | 50 |
| 22 nt SMO | |
| UGCAUUAGGAUAACUCGUAUCG | 51 |
| AUGCAUUAGGAUAACUCGUAUC | 52 |
| UAUGCAUUAGGAUAACUCGUAU | 53 |
| 23 nt SMO | |
| AUGCAUUAGGAUAACUCGUAUCG | 54 |
| UAUGCAUUAGGAUAACUCGUAUC | 55 |
| 24 nt SMO | |
| UAUGCAUUAGGAUAACUCGUAUCG | 56 |

B. Glutamate Receptors

The present invention further provides SMOs based on the sequences of the flip and flop isoforms of GluR1 (GRIA1; MIM: 138248 GeneID: 2890), GluR2 (GRIA2; MIM: 138247 GeneID: 2891), GluR3 (GRIA3; MIM: 305915 GeneID: 2892), and GluR4 (GRIA4; MIM: 138246 GeneID: 2893). These SMOs are used according to the methods of the invention to modulate splicing of GluR pre-mRNA. In one embodiment, a SMO of the invention functions to decrease GluR flip isoform expression. In another embodiment, a SMO of the invention functions to decrease the GluR flip/flop isoform ratio. In yet another embodiment, a SMO of the invention functions to increase the GluR flop isoform. In still another embodiment, a SMO of the invention functions to increase the GluR flop isoforms. In various embodiments, a SMO of the invention functions to decrease both the GluR flip and GluR flop isoform expression.

In various embodiments, the invention includes a pharmaceutical composition comprising a SMO of the invention, where the pharmaceutical composition of the invention comprises a SMO that functions to decrease the GluR flip isoform expression. In other embodiments, the invention includes a pharmaceutical composition comprising a SMO that decrease the GluR flip/flop isoform ratio of expression. In another embodiment, the invention includes a pharmaceutical composition comprising a SMO that functions to increase the GluR flop isoform expression. In yet another embodiment, the invention includes a pharmaceutical composition comprising a SMO of the invention that functions to decrease both the GluR flip and GluR flop isoform expression.

Table 2 depicts exemplary SMOs useful for modulating splicing of GluR3 pre-mRNA in order to decrease GluR3-flip expression or increase GluR3-flop expression in a cell.

TABLE 2

| 3' to 5' Splice modulating oligonucleotides directed to GluR3-flip pre-mRNA | SEQ ID NO. |
|---|---|
| aaagggugcacuucUUGCGGACAU | 57 |
| aagggugcacuucUUGCGGACAUU | 58 |
| agggugcacuucUUGCGGACAUUU | 59 |
| gggugcacuucUUGCGGACAUUUG | 60 |
| ggugcacuucUUGCGGACAUUUGG | 61 |
| gugcacuucUUGCGGACAUUUGGA | 62 |
| ugcacuucUUGCGGACAUUUGGAA | 63 |
| gcacuucUUGCGGACAUUUGGAAC | 64 |
| cacuucUUGCGGACAUUUGGAACG | 65 |
| acuucUUGCGGACAUUUGGAACGU | 66 |
| cuucUUGCGGACAUUUGGAACGUC | 67 |
| uucUUGCGGACAUUUGGAACGUCA | 68 |
| ucUUGCGGACAUUUGGAACGUCAU | 69 |
| cUUGCGGACAUUUGGAACGUCAUA | 70 |
| UUGCGGACAUUUGGAACGUCAUAA | 71 |
| UGCGGACAUUUGGAACGUCAUAAC | 72 |

TABLE 2-continued

| 3' to 5' Splice modulating oligonucleotides directed to GluR3-flip pre-mRNA | SEQ ID NO. |
|---|---|
| GCGGACAUUUGGAACGUCAUAACU | 73 |
| aaagggugcacuucUUGCGGACA | 74 |
| aagggugcacuucUUGCGGACAU | 75 |
| agggugcacuucUUGCGGACAUU | 76 |
| gggugcacuucUUGCGGACAUUU | 77 |
| ggugcacuucUUGCGGACAUUUG | 78 |
| gugcacuucUUGCGGACAUUUGG | 79 |
| ugcacuucUUGCGGACAUUUGGA | 80 |
| gcacuucUUGCGGACAUUUGGAA | 81 |
| cacuucUUGCGGACAUUUGGAAC | 82 |
| acuucUUGCGGACAUUUGGAACG | 83 |
| cuucUUGCGGACAUUUGGAACGU | 84 |
| uucUUGCGGACAUUUGGAACGUC | 85 |
| ucUUGCGGACAUUUGGAACGUCA | 86 |
| cUUGCGGACAUUUGGAACGUCAU | 87 |
| UUGCGGACAUUUGGAACGUCAUA | 88 |
| UGCGGACAUUUGGAACGUCAUAA | 89 |
| GCGGACAUUUGGAACGUCAUAAC | 90 |
| CGGACAUUUGGAACGUCAUAACU | 91 |
| aaagggugcacuucUUGCGGAC | 92 |
| aagggugcacuucUUGCGGACA | 93 |
| agggugcacuucUUGCGGACAU | 94 |
| gggugcacuucUUGCGGACAUU | 95 |
| ggugcacuucUUGCGGACAUUU | 96 |
| gugcacuucUUGCGGACAUUUG | 97 |
| ugcacuucUUGCGGACAUUUGG | 98 |
| gcacuucUUGCGGACAUUUGGA | 99 |
| cacuucUUGCGGACAUUUGGAA | 100 |
| acuucUUGCGGACAUUUGGAAC | 101 |
| cuucUUGCGGACAUUUGGAACG | 102 |
| uucUUGCGGACAUUUGGAACGU | 103 |
| ucUUGCGGACAUUUGGAACGUC | 104 |
| cUUGCGGACAUUUGGAACGUCA | 105 |
| UUGCGGACAUUUGGAACGUCAU | 106 |
| UGCGGACAUUUGGAACGUCAUA | 107 |
| GCGGACAUUUGGAACGUCAUAA | 108 |
| CGGACAUUUGGAACGUCAUAAC | 109 |
| GGACAUUUGGAACGUCAUAACU | 110 |

TABLE 2-continued

| 3' to 5' Splice modulating oligonucleotides directed to GluR3-flip pre-mRNA | SEQ ID NO. |
|---|---|
| aaagggugcacuucUUGCGGA | 111 |
| aagggugcacuucUUGCGGAC | 112 |
| agggugcacuucUUGCGGACA | 113 |
| gggugcacuucUUGCGGACAU | 114 |
| ggugcacuucUUGCGGACAUU | 115 |
| gugcacuucUUGCGGACAUUU | 116 |
| ugcacuucUUGCGGACAUUUG | 117 |
| gcacuucUUGCGGACAUUUGG | 118 |
| cacuucUUGCGGACAUUUGGA | 119 |
| acuucUUGCGGACAUUUGGAA | 120 |
| cuucUUGCGGACAUUUGGAAC | 121 |
| uucUUGCGGACAUUUGGAACG | 122 |
| ucUUGCGGACAUUUGGAACGU | 123 |
| cUUGCGGACAUUUGGAACGUC | 124 |
| UUGCGGACAUUUGGAACGUCA | 125 |
| UGCGGACAUUUGGAACGUCAU | 126 |
| GCGGACAUUUGGAACGUCAUA | 127 |
| CGGACAUUUGGAACGUCAUAA | 128 |
| GGACAUUUGGAACGUCAUAAC | 129 |
| GACAUUUGGAACGUCAUAACU | 130 |
| aaagggugcacuucUUGCGG | 131 |
| aagggugcacuucUUGCGGA | 132 |
| agggugcacuucUUGCGGAC | 133 |
| gggugcacuucUUGCGGACA | 134 |
| ggugcacuucUUGCGGACAU | 135 |
| gugcacuucUUGCGGACAUU | 136 |
| ugcacuucUUGCGGACAUUU | 137 |
| gcacuucUUGCGGACAUUUG | 138 |
| cacuucUUGCGGACAUUUGG | 139 |
| acuucUUGCGGACAUUUGGA | 140 |
| cuucUUGCGGACAUUUGGAA | 141 |
| uucUUGCGGACAUUUGGAAC | 142 |
| ucUUGCGGACAUUUGGAACG | 143 |
| cUUGCGGACAUUUGGAACGU | 144 |
| UUGCGGACAUUUGGAACGUC | 145 |
| UGCGGACAUUUGGAACGUCA | 146 |
| GCGGACAUUUGGAACGUCAU | 147 |
| CGGACAUUUGGAACGUCAUA | 148 |

TABLE 2-continued

| 3' to 5' Splice modulating oligonucleotides directed to GluR3-flip pre-mRNA | SEQ ID NO. |
|---|---|
| GGACAUUUGGAACGUCAUAA | 149 |
| aaagggugcacuucUUGCG | 150 |
| aagggugcacuucUUGCGG | 151 |
| agggugcacuucUUGCGGA | 152 |
| gggugcacuucUUGCGGAC | 153 |
| ggugcacuucUUGCGGACA | 154 |
| gugcacuucUUGCGGACAU | 155 |
| ugcacuucUUGCGGACAUU | 156 |
| gcacuucUUGCGGACAUUU | 157 |
| cacuucUUGCGGACAUUUG | 158 |
| acuucUUGCGGACAUUUGG | 159 |
| cuucUUGCGGACAUUUGGA | 160 |
| uucUUGCGGACAUUUGGAA | 161 |
| ucUUGCGGACAUUUGGAAC | 162 |
| cUUGCGGACAUUUGGAACG | 163 |
| UUGCGGACAUUUGGAACGU | 164 |
| UGCGGACAUUUGGAACGUC | 165 |
| GCGGACAUUUGGAACGUCA | 166 |
| CGGACAUUUGGAACGUCAU | 167 |
| GGACAUUUGGAACGUCAUA | 168 |
| aaagggugcacuucUUGC | 169 |
| aagggugcacuucUUGCG | 170 |
| agggugcacuucUUGCGG | 171 |
| gggugcacuucUUGCGGA | 172 |
| ggugcacuucUUGCGGAC | 173 |
| gugcacuucUUGCGGACA | 174 |
| ugcacuucUUGCGGACAU | 175 |
| gcacuucUUGCGGACAUU | 176 |
| cacuucUUGCGGACAUUU | 177 |
| acuucUUGCGGACAUUUG | 178 |
| cuucUUGCGGACAUUUGG | 179 |
| uucUUGCGGACAUUUGGA | 180 |
| ucUUGCGGACAUUUGGAA | 181 |
| cUUGCGGACAUUUGGAAC | 182 |
| UUGCGGACAUUUGGAACG | 183 |
| UGCGGACAUUUGGAACGU | 184 |
| GCGGACAUUUGGAACGUC | 185 |
| CGGACAUUUGGAACGUCA | 186 |
| GGACAUUUGGAACGUCAU | 187 |

Table 3 depicts exemplary SMOs for modulating splicing of GluR1 pre-mRNA in order to decrease GluR1-flip expression or increase GluR1-flop expression in a cell.

TABLE 3

| 3' to 5' Splice modulating oligonucleotides directed to GluR1-flip pre-mRNA | SEQ ID NO. |
|---|---|
| caacuucUCCAGGGCAUUUGGAUC | 188 |
| aacuucUCCAGGGCAUUUGGAUCG | 189 |
| acuucUCCAGGGCAUUUGGAUCGC | 190 |
| cuucUCCAGGGCAUUUGGAUCGCC | 191 |
| uucUCCAGGGCAUUUGGAUCGCCA | 192 |
| ucUCCAGGGCAUUUGGAUCGCCAA | 193 |
| cUCCAGGGCAUUUGGAUCGCCAAA | 194 |
| UCCAGGGCAUUUGGAUCGCCAAAA | 195 |
| caacuucUCCAGGGCAUUUGGAU | 196 |
| aacuucUCCAGGGCAUUUGGAUC | 197 |
| acuucUCCAGGGCAUUUGGAUCG | 198 |
| cuucUCCAGGGCAUUUGGAUCGC | 199 |
| uucUCCAGGGCAUUUGGAUCGCC | 200 |
| ucUCCAGGGCAUUUGGAUCGCCA | 201 |
| cUCCAGGGCAUUUGGAUCGCCAA | 202 |
| UCCAGGGCAUUUGGAUCGCCAAA | 203 |
| CCAGGGCAUUUGGAUCGCCAAAA | 204 |
| caacuucUCCAGGGCAUUUGGA | 205 |
| aacuucUCCAGGGCAUUUGGAU | 206 |
| acuucUCCAGGGCAUUUGGAUC | 207 |
| cuucUCCAGGGCAUUUGGAUCG | 208 |
| uucUCCAGGGCAUUUGGAUCGC | 209 |
| ucUCCAGGGCAUUUGGAUCGCC | 210 |
| cUCCAGGGCAUUUGGAUCGCCA | 211 |
| UCCAGGGCAUUUGGAUCGCCAA | 212 |
| CCAGGGCAUUUGGAUCGCCAAA | 213 |
| caacuucUCCAGGGCAUUUGG | 214 |
| aacuucUCCAGGGCAUUUGGA | 215 |
| acuucUCCAGGGCAUUUGGAU | 216 |
| cuucUCCAGGGCAUUUGGAUC | 217 |
| uucUCCAGGGCAUUUGGAUCG | 218 |
| ucUCCAGGGCAUUUGGAUCGC | 219 |

TABLE 3-continued

| 3' to 5' Splice modulating oligonucleotides directed to GluR1-flip pre-mRNA | SEQ ID NO. |
|---|---|
| cUCCAGGGCAUUUGGAUCGCC | 220 |
| UCCAGGGCAUUUGGAUCGCCA | 221 |
| CCAGGGCAUUUGGAUCGCCAA | 222 |
| caacuucUCCAGGGCAUUUG | 223 |
| aacuucUCCAGGGCAUUUGG | 224 |
| acuucUCCAGGGCAUUUGGA | 225 |
| cuucUCCAGGGCAUUUGGAU | 226 |
| uucUCCAGGGCAUUUGGAUC | 227 |
| ucUCCAGGGCAUUUGGAUCG | 228 |
| cUCCAGGGCAUUUGGAUCGC | 229 |
| UCCAGGGCAUUUGGAUCGCC | 230 |
| CCAGGGCAUUUGGAUCGCCA | 231 |
| caacuucUCCAGGGCAUUU | 232 |
| aacuucUCCAGGGCAUUUG | 233 |
| acuucUCCAGGGCAUUUGG | 234 |
| cuucUCCAGGGCAUUUGGA | 235 |
| uucUCCAGGGCAUUUGGAU | 236 |
| ucUCCAGGGCAUUUGGAUC | 237 |
| cUCCAGGGCAUUUGGAUCG | 238 |
| UCCAGGGCAUUUGGAUCGC | 239 |
| CCAGGGCAUUUGGAUCGCC | 240 |
| caacuucUCCAGGGCAUU | 241 |
| aacuucUCCAGGGCAUUU | 242 |
| acuucUCCAGGGCAUUUG | 243 |
| cuucUCCAGGGCAUUUGG | 244 |
| uucUCCAGGGCAUUUGGA | 245 |
| ucUCCAGGGCAUUUGGAU | 246 |
| cUCCAGGGCAUUUGGAUC | 247 |
| UCCAGGGCAUUUGGAUCG | 248 |
| CCAGGGCAUUUGGAUCGC | 249 |
| ACCUUCGUUCCUGAGGCCUUCAUU | 250 |
| CCUUCGUUCCUGAGGCCUUCAUUC | 251 |
| CUUCGUUCCUGAGGCCUUCAUUCc | 252 |
| UUCGUUCCUGAGGCCUUCAUUCca | 253 |
| UCGUUCCUGAGGCCUUCAUUCcag | 254 |
| CGUUCCUGAGGCCUUCAUUCcagu | 255 |
| GUUCCUGAGGCCUUCAUUCcaguc | 256 |
| UUCCUGAGGCCUUCAUUCcaguca | 257 |
| CCUUCGUUCCUGAGGCCUUCAUU | 258 |
| CUUCGUUCCUGAGGCCUUCAUUC | 259 |
| UUCGUUCCUGAGGCCUUCAUUCc | 260 |
| UCGUUCCUGAGGCCUUCAUUCca | 261 |
| CGUUCCUGAGGCCUUCAUUCcag | 262 |
| GUUCCUGAGGCCUUCAUUCcagu | 263 |
| UUCCUGAGGCCUUCAUUCcaguc | 264 |
| UCCUGAGGCCUUCAUUCcaguca | 265 |
| CUUCGUUCCUGAGGCCUUCAUU | 266 |
| UUCGUUCCUGAGGCCUUCAUUC | 267 |
| UCGUUCCUGAGGCCUUCAUUCc | 268 |
| CGUUCCUGAGGCCUUCAUUCca | 269 |
| GUUCCUGAGGCCUUCAUUCcag | 270 |
| UUCCUGAGGCCUUCAUUCcagu | 271 |
| UCCUGAGGCCUUCAUUCcaguc | 272 |
| CCUGAGGCCUUCAUUCcaguca | 273 |
| UUCGUUCCUGAGGCCUUCAUU | 274 |
| UCGUUCCUGAGGCCUUCAUUC | 275 |
| CGUUCCUGAGGCCUUCAUUCc | 276 |
| GUUCCUGAGGCCUUCAUUCca | 277 |
| UUCCUGAGGCCUUCAUUCcag | 278 |
| UCCUGAGGCCUUCAUUCcagu | 279 |
| CCUGAGGCCUUCAUUCcaguc | 280 |
| CUGAGGCCUUCAUUCcaguca | 281 |
| UCGUUCCUGAGGCCUUCAUU | 282 |
| CGUUCCUGAGGCCUUCAUUC | 283 |
| GUUCCUGAGGCCUUCAUUCc | 284 |
| UUCCUGAGGCCUUCAUUCca | 285 |
| UCCUGAGGCCUUCAUUCcag | 286 |
| CCUGAGGCCUUCAUUCcagu | 287 |
| CUGAGGCCUUCAUUCcaguc | 288 |
| UGAGGCCUUCAUUCcaguca | 289 |
| CGUUCCUGAGGCCUUCAUU | 290 |
| GUUCCUGAGGCCUUCAUUC | 291 |
| UUCCUGAGGCCUUCAUUCc | 292 |
| UCCUGAGGCCUUCAUUCca | 293 |
| CCUGAGGCCUUCAUUCcag | 294 |
| CUGAGGCCUUCAUUCcagu | 295 |

TABLE 3-continued

| 3' to 5' Splice modulating oligonucleotides directed to GluR1-flip pre-mRNA | SEQ ID NO. |
|---|---|
| UGAGGCCUUCAUUCcaguc | 296 |
| GAGGCCUUCAUUCcaguca | 297 |
| GUUCCUGAGGCCUUCAUU | 298 |
| UUCCUGAGGCCUUCAUUC | 299 |
| UCCUGAGGCCUUCAUUCc | 300 |
| CCUGAGGCCUUCAUUCca | 301 |
| CUGAGGCCUUCAUUCcag | 302 |
| UGAGGCCUUCAUUCcagu | 303 |
| GAGGCCUUCAUUCcaguc | 304 |
| AGGCCUUCAUUCcaguca | 305 |

Table 4 depicts exemplary SMOs for modulating splicing of all GluR subtypes, including GluR1, GluR2, GluR3, and GluR4 pre-mRNA in order to decrease GluR1-4-flip expression or increase GluR1-4-flop expression in a cell.

TABLE 4

| 3' to 5' SMOs targeting GluR1, GluR2, GluR3, and GluR4 | SEQ ID NO. |
|---|---|
| UUCCGCAGAUUCUGUUCGACUUUU | 306 |
| UUCCGCAGAUUCUGUUCGACUUU | 307 |
| UCCGCAGAUUCUGUUCGACUUUU | 308 |
| UUCCGCAGAUUCUGUUCGACUU | 309 |
| UCCGCAGAUUCUGUUCGACUUU | 310 |
| CCGCAGAUUCUGUUCGACUUUU | 311 |
| UUCCGCAGAUUCUGUUCGACU | 312 |
| UCCGCAGAUUCUGUUCGACUU | 313 |
| CCGCAGAUUCUGUUCGACUUU | 314 |
| CGCAGAUUCUGUUCGACUUUU | 315 |
| UUCCGCAGAUUCUGUUCGAC | 316 |
| UCCGCAGAUUCUGUUCGACU | 317 |
| CCGCAGAUUCUGUUCGACUU | 318 |
| CGCAGAUUCUGUUCGACUUU | 319 |
| GCAGAUUCUGUUCGACUUUU | 320 |
| UUCCGCAGAUUCUGUUCGA | 321 |
| UCCGCAGAUUCUGUUCGAC | 322 |
| CCGCAGAUUCUGUUCGACU | 323 |
| CGCAGAUUCUGUUCGACUU | 324 |
| GCAGAUUCUGUUCGACUUU | 325 |
| CAGAUUCUGUUCGACUUUU | 326 |
| UUCCGCAGAUUCUGUUCG | 327 |

TABLE 4-continued

| 3' to 5' SMOs targeting GluR1, GluR2, GluR3, and GluR4 | SEQ ID NO. |
|---|---|
| UCCGCAGAUUCUGUUCGA | 328 |
| CCGCAGAUUCUGUUCGAC | 329 |
| CGCAGAUUCUGUUCGACU | 330 |
| GCAGAUUCUGUUCGACUU | 331 |
| CAGAUUCUGUUCGACUUU | 332 |
| AGAUUCUGUUCGACUUUU | 333 |
| UUGUUCCGUAGAAUCUGUUCGACU | 334 |
| UGUUCCGUAGAAUCUGUUCGACUU | 335 |
| GUUCCGUAGAAUCUGUUCGACUUU | 336 |
| UUCCGUAGAAUCUGUUCGACUUUU | 337 |
| UUGUUCCGUAGAAUCUGUUCGAC | 338 |
| UGUUCCGUAGAAUCUGUUCGACU | 339 |
| GUUCCGUAGAAUCUGUUCGACUU | 340 |
| UUCCGUAGAAUCUGUUCGACUUU | 341 |
| UCCGUAGAAUCUGUUCGACUUUU | 342 |
| UUGUUCCGUAGAAUCUGUUCGA | 343 |
| UGUUCCGUAGAAUCUGUUCGAC | 344 |
| GUUCCGUAGAAUCUGUUCGACU | 345 |
| UUCCGUAGAAUCUGUUCGACUU | 346 |
| UCCGUAGAAUCUGUUCGACUUU | 347 |
| CCGUAGAAUCUGUUCGACUUUU | 348 |
| UUGUUCCGUAGAAUCUGUUCG | 349 |
| UGUUCCGUAGAAUCUGUUCGA | 350 |
| GUUCCGUAGAAUCUGUUCGAC | 351 |
| UUCCGUAGAAUCUGUUCGACU | 352 |
| UCCGUAGAAUCUGUUCGACUU | 353 |
| CCGUAGAAUCUGUUCGACUUU | 354 |
| CGUAGAAUCUGUUCGACUUUU | 355 |
| UUGUUCCGUAGAAUCUGUUC | 356 |
| UGUUCCGUAGAAUCUGUUCG | 357 |
| GUUCCGUAGAAUCUGUUCGA | 358 |
| UUCCGUAGAAUCUGUUCGAC | 359 |
| UCCGUAGAAUCUGUUCGACU | 360 |
| CCGUAGAAUCUGUUCGACUU | 361 |
| UUCCGUAGAAUCUGUUCGA | 362 |
| UCCGUAGAAUCUGUUCGAC | 363 |
| CCGUAGAAUCUGUUCGACU | 364 |
| CGUAGAAUCUGUUCGACUU | 365 |

TABLE 4-continued

| 3' to 5' SMOs targeting GluR1, GluR2, GluR3, and GluR4 | SEQ ID NO. |
|---|---|
| UUCCGUAGAAUCUGUUCG | 366 |
| UCCGUAGAAUCUGUUCGA | 367 |
| CCGUAGAAUCUGUUCGAC | 368 |
| CGUAGAAUCUGUUCGACU | 369 |
| ACUUUUCGUUUACCACCAUGCU | 370 |
| ACUUUUCGUUUACCACCAUGC | 371 |
| CUUUUCGUUUACCACCAUGCU | 372 |
| CUUUUCGUUUACCACCAUGC | 373 |
| CUUUUCGUUUACCACCAUGC | 374 |
| UUUUCGUUUACCACCAUGCU | 375 |
| UUUGAGUCACUUGUUCCGUAGAAU | 376 |
| UUUGAGUCACUUGUUCCGUAGAA | 377 |
| UUGAGUCACUUGUUCCGUAGAAU | 378 |
| UUUGAGUCACUUGUUCCGUAGA | 379 |
| UUGAGUCACUUGUUCCGUAGAA | 380 |
| UGAGUCACUUGUUCCGUAGAAU | 381 |
| UUUGAGUCACUUGUUCCGUAG | 382 |
| UUGAGUCACUUGUUCCGUAGA | 383 |
| UGAGUCACUUGUUCCGUAGAA | 384 |
| GAGUCACUUGUUCCGUAGAAU | 385 |
| UUUGAGUCACUUGUUCCGUA | 386 |
| UUGAGUCACUUGUUCCGUAG | 387 |
| UGAGUCACUUGUUCCGUAGA | 388 |
| GAGUCACUUGUUCCGUAGAA | 389 |
| AGUCACUUGUUCCGUAGAAU | 390 |
| UUUGAGUCACUUGUUCCGU | 391 |
| UUGAGUCACUUGUUCCGUA | 392 |
| UGAGUCACUUGUUCCGUAG | 393 |
| GAGUCACUUGUUCCGUAGA | 394 |
| AGUCACUUGUUCCGUAGAA | 395 |
| GUCACUUGUUCCGUAGAAU | 396 |
| UUGAGUCACUUGUUCCGU | 397 |
| UGAGUCACUUGUUCCGUA | 398 |
| GAGUCACUUGUUCCGUAG | 399 |
| AGUCACUUGUUCCGUAGA | 400 |

Table 5 depicts exemplary SMOs for modulating splicing of GluR2 pre-mRNA in order to decrease GluR2-flip expression or increase GluR2-flop expression in a cell.

TABLE 5

| 3' to 5' Splice modulating oligonucleotides directed to flip GluR2 | SEQ ID NO. |
|---|---|
| gcacuucUUGGGGUCAUUUAGAAC | 401 |
| cacuucUUGGGGUCAUUUAGAACG | 402 |
| acuucUUGGGGUCAUUUAGAACGU | 403 |
| cuucUUGGGGUCAUUUAGAACGUC | 404 |
| uucUUGGGGUCAUUUAGAACGUCA | 405 |
| ucUUGGGGUCAUUUAGAACGUCAU | 406 |
| cUUGGGGUCAUUUAGAACGUCAUA | 407 |
| UUGGGGUCAUUUAGAACGUCAUAA | 408 |
| UGGGGUCAUUUAGAACGUCAUAAC | 409 |
| gcacuucUUGGGGUCAUUUAGAA | 410 |
| cacuucUUGGGGUCAUUUAGAAC | 411 |
| acuucUUGGGGUCAUUUAGAACG | 412 |
| cuucUUGGGGUCAUUUAGAACGU | 413 |
| uucUUGGGGUCAUUUAGAACGUC | 414 |
| ucUUGGGGUCAUUUAGAACGUCA | 415 |
| cUUGGGGUCAUUUAGAACGUCAU | 416 |
| UUGGGGUCAUUUAGAACGUCAUA | 417 |
| UGGGGUCAUUUAGAACGUCAUAA | 418 |
| gcacuucUUGGGGUCAUUUAGA | 419 |
| cacuucUUGGGGUCAUUUAGAA | 420 |
| acuucUUGGGGUCAUUUAGAAC | 421 |
| cuucUUGGGGUCAUUUAGAACG | 422 |
| uucUUGGGGUCAUUUAGAACGU | 423 |
| ucUUGGGGUCAUUUAGAACGUC | 424 |
| cUUGGGGUCAUUUAGAACGUCA | 425 |
| UUGGGGUCAUUUAGAACGUCAU | 426 |
| UGGGGUCAUUUAGAACGUCAUA | 427 |
| gcacuucUUGGGGUCAUUUAG | 428 |
| cacuucUUGGGGUCAUUUAGA | 429 |
| acuucUUGGGGUCAUUUAGAA | 430 |
| cuucUUGGGGUCAUUUAGAAC | 431 |
| uucUUGGGGUCAUUUAGAACG | 432 |
| ucUUGGGGUCAUUUAGAACGU | 433 |
| cUUGGGGUCAUUUAGAACGUC | 434 |
| UUGGGGUCAUUUAGAACGUCA | 435 |
| UGGGGUCAUUUAGAACGUCAU | 436 |

TABLE 5-continued

| 3' to 5' Splice modulating oligonucleotides directed to flip GluR2 | SEQ ID NO. |
|---|---|
| gcacuucUUGGGGUCAUUUA | 437 |
| cacuucUUGGGGUCAUUUAG | 438 |
| acuucUUGGGGUCAUUUAGA | 439 |
| cuucUUGGGGUCAUUUAGAA | 440 |
| uucUUGGGGUCAUUUAGAAC | 441 |
| ucUUGGGGUCAUUUAGAACG | 442 |
| cUUGGGGUCAUUUAGAACGU | 443 |
| UUGGGGUCAUUUAGAACGUC | 444 |
| UGGGGUCAUUUAGAACGUCA | 445 |
| gcacuucUUGGGGUCAUUU | 446 |
| cacuucUUGGGGUCAUUUA | 447 |
| acuucUUGGGGUCAUUUAG | 448 |
| cuucUUGGGGUCAUUUAGA | 449 |
| uucUUGGGGUCAUUUAGAA | 450 |
| ucUUGGGGUCAUUUAGAAC | 451 |
| cUUGGGGUCAUUUAGAACG | 452 |
| UUGGGGUCAUUUAGAACGU | 453 |
| UGGGGUCAUUUAGAACGUC | 454 |
| gcacuucUUGGGGUCAUU | 455 |
| cacuucUUGGGGUCAUUU | 456 |
| acuucUUGGGGUCAUUUA | 457 |
| cuucUUGGGGUCAUUUAG | 458 |
| uucUUGGGGUCAUUUAGA | 459 |
| ucUUGGGGUCAUUUAGAA | 460 |
| cUUGGGGUCAUUUAGAAC | 461 |
| UUGGGGUCAUUUAGAACG | 462 |
| UGGGGUCAUUUAGAACGU | 463 |

Table 6 depicts exemplary SMOs for modulating splicing of GluR4 pre-mRNA in order to decrease GluR4-flip expression or increase GluR4-flop expression in a cell.

TABLE 6

| 3' to 5' Splice modulating oligonucleotides directed to all flip GluR4 | SEQ ID NO. |
|---|---|
| gcacuucUUGAGGACAUUUGGAAC | 464 |
| cacuucUUGAGGUCAUUUGGAACG | 465 |
| acuucUUGAGGUCAUUUGGAACGG | 466 |
| cuucUUGAGGUCAUUUGGAACGGC | 467 |
| uucUUGAGGUCAUUUGGAACGGCA | 468 |
| ucUUGAGGUCAUUUGGAACGGCAA | 469 |

TABLE 6-continued

| 3' to 5' Splice modulating oligonucleotides directed to all flip GluR4 | SEQ ID NO. |
|---|---|
| cUUGAGGUCAUUUGGAACGGCAAA | 470 |
| UUGAGGUCAUUUGGAACGGCAAAA | 471 |
| UGAGGUCAUUUGGAACGGCAAAAC | 472 |
| gcacuucUUGAGGACAUUUGGAA | 473 |
| cacuucUUGAGGUCAUUUGGAAC | 474 |
| acuucUUGAGGUCAUUUGGAACG | 475 |
| cuucUUGAGGUCAUUUGGAACGG | 476 |
| uucUUGAGGUCAUUUGGAACGGC | 477 |
| ucUUGAGGUCAUUUGGAACGGCA | 478 |
| cUUGAGGUCAUUUGGAACGGCAA | 479 |
| UUGAGGUCAUUUGGAACGGCAAA | 480 |
| UGAGGUCAUUUGGAACGGCAAAA | 481 |
| gcacuucUUGAGGACAUUUGGA | 482 |
| cacuucUUGAGGUCAUUUGGAA | 483 |
| acuucUUGAGGUCAUUUGGAAC | 484 |
| cuucUUGAGGUCAUUUGGAACG | 485 |
| uucUUGAGGUCAUUUGGAACGG | 486 |
| ucUUGAGGUCAUUUGGAACGGC | 487 |
| cUUGAGGUCAUUUGGAACGGCA | 488 |
| UUGAGGUCAUUUGGAACGGCAA | 489 |
| UGAGGUCAUUUGGAACGGCAAA | 490 |
| gcacuucUUGAGGACAUUUGG | 491 |
| cacuucUUGAGGUCAUUUGGA | 492 |
| acuucUUGAGGUCAUUUGGAA | 493 |
| cuucUUGAGGUCAUUUGGAAC | 494 |
| uucUUGAGGUCAUUUGGAACG | 495 |
| ucUUGAGGUCAUUUGGAACGG | 496 |
| cUUGAGGUCAUUUGGAACGGC | 497 |
| UUGAGGUCAUUUGGAACGGCA | 498 |
| UGAGGUCAUUUGGAACGGCAA | 499 |
| gcacuucUUGAGGACAUUUG | 500 |
| cacuucUUGAGGUCAUUUGG | 501 |
| acuucUUGAGGUCAUUUGGA | 502 |
| cuucUUGAGGUCAUUUGGAA | 503 |
| uucUUGAGGUCAUUUGGAAC | 504 |
| ucUUGAGGUCAUUUGGAACG | 505 |
| cUUGAGGUCAUUUGGAACGG | 506 |
| UUGAGGUCAUUUGGAACGGC | 507 |

TABLE 6-continued

| 3' to 5' Splice modulating oligonucleotides directed to all flip GluR4 | SEQ ID NO. |
|---|---|
| UGAGGUCAUUUGGAACGGCA | 508 |
| gcacuucUUGAGGACAUUU | 509 |
| cacuucUUGAGGUCAUUUG | 510 |
| acuucUUGAGGUCAUUUGG | 511 |
| cuucUUGAGGUCAUUUGGA | 512 |
| uucUUGAGGUCAUUUGGAA | 513 |
| ucUUGAGGUCAUUUGGAAC | 514 |
| cUUGAGGUCAUUUGGAACG | 515 |
| UUGAGGUCAUUUGGAACGG | 516 |
| UGAGGUCAUUUGGAACGGC | 517 |
| gcacuucUUGAGGACAUU | 518 |
| cacuucUUGAGGUCAUUU | 519 |
| acuucUUGAGGUCAUUUG | 520 |
| cuucUUGAGGUCAUUUGG | 521 |
| uucUUGAGGUCAUUUGGA | 522 |
| ucUUGAGGUCAUUUGGAA | 523 |
| cUUGAGGUCAUUUGGAAC | 524 |
| UUGAGGUCAUUUGGAACG | 525 |
| UGAGGUCAUUUGGAACGG | 526 |

C. O-GlcNAcase (OGA)

The present invention further provides SMOs based on the sequences of OGA (MGEA5; MIM: 604039; GeneID: 10724). These SMOs are used according to the methods of the invention to modulate splicing of OGA pre-mRNA. In one embodiment, a SMO of the invention functions to decrease OGA expression or function. In another embodiment, the invention includes a pharmaceutical composition comprising a SMO of the invention, where the pharmaceutical composition of the invention comprises a SMO that functions to decrease the OGA expression or function. In one aspect, an alternative splice variant of OGA with reduced catalytic activity comprises OGA10t, a read-through variant which results in 15 amino acids being added from intron 10. In another aspect, an alternative splice variant of OGA with reduced catalytic activity comprises OGAΔ8 wherein exon 8 of the OGA gene is excluded.

Table 7 depicts exemplary SMOs for modulating splicing of exon 8 of OGA pre-mRNA in order to produce an OGA protein with lower enzymatic activity in a cell.

TABLE 7

| 3' to 5' Splice modulating oligonucleotides targeting Exon 8 of OGA | SEQ ID NO. |
|---|---|
| gucGACUGUCACUUCUGUCAUGAC | 527 |
| ucGACUGUCACUUCUGUCAUGACA | 528 |
| cGACUGUCACUUCUGUCAUGACAU | 529 |
| UCUUUUACUUCCGUCACUGCUUCU | 530 |
| CACUGCUUCUGUAACUUUGACUAC | 531 |
| ACUGCUUCUGUAACUUUGACUACA | 532 |
| gucGACUGUCACUUCUGUCAUGA | 533 |
| ucGACUGUCACUUCUGUCAUGAC | 534 |
| cGACUGUCACUUCUGUCAUGACA | 535 |
| UCUUUUACUUCCGUCACUGCUUC | 536 |
| CUUUUACUUCCGUCACUGCUUCU | 537 |
| CACUGCUUCUGUAACUUUGACUA | 538 |
| ACUGCUUCUGUAACUUUGACUAC | 539 |
| CUGCUUCUGUAACUUUGACUACA | 540 |
| GGAGUAGUUAUGUCGUcacucaa | 541 |
| gucGACUGUCACUUCUGUCAUG | 542 |
| ucGACUGUCACUUCUGUCAUGA | 543 |
| cGACUGUCACUUCUGUCAUGAC | 544 |
| UCUUUUACUUCCGUCACUGCUU | 545 |
| CUUUUACUUCCGUCACUGCUUC | 546 |
| UUUUACUUCCGUCACUGCUUCU | 547 |
| CACUGCUUCUGUAACUUUGACU | 548 |
| ACUGCUUCUGUAACUUUGACUA | 549 |
| CUGCUUCUGUAACUUUGACUAC | 550 |
| UGCUUCUGUAACUUUGACUACA | 551 |
| GGAGUAGUUAUGUCGUcacuca | 552 |
| GAGUAGUUAUGUCGUcacucaa | 553 |
| gucGACUGUCACUUCUGUCAU | 554 |
| ucGACUGUCACUUCUGUCAUG | 555 |
| cGACUGUCACUUCUGUCAUGA | 556 |
| UCUUUUACUUCCGUCACUGCU | 557 |
| CUUUUACUUCCGUCACUGCUU | 558 |
| UUUUACUUCCGUCACUGCUUC | 559 |
| UUUACUUCCGUCACUGCUUCU | 560 |
| CACUGCUUCUGUAACUUUGAC | 561 |
| ACUGCUUCUGUAACUUUGACU | 562 |
| CUGCUUCUGUAACUUUGACUA | 563 |
| UGCUUCUGUAACUUUGACUAC | 564 |
| GCUUCUGUAACUUUGACUACA | 565 |
| GGAGUAGUUAUGUCGUcacuc | 566 |
| GAGUAGUUAUGUCGUcacuca | 567 |

TABLE 7-continued

| 3' to 5' Splice modulating oligonucleotides targeting Exon 8 of OGA | SEQ ID NO. |
|---|---|
| AGUAGUUAUGUCGUcacucaa | 568 |
| gucGACUGUCACUUCUGUCA | 569 |
| ucGACUGUCACUUCUGUCAU | 570 |
| cGACUGUCACUUCUGUCAUG | 571 |
| UCUUUUACUUCCGUCACUGC | 572 |
| CUUUUACUUCCGUCACUGCU | 573 |
| UUUUACUUCCGUCACUGCUU | 574 |
| UUUACUUCCGUCACUGCUUC | 575 |
| UUACUUCCGUCACUGCUUCU | 576 |
| CACUGCUUCUGUAACUUUGA | 577 |
| ACUGCUUCUGUAACUUUGAC | 578 |
| CUGCUUCUGUAACUUUGACU | 579 |
| UGCUUCUGUAACUUUGACUA | 580 |
| GCUUCUGUAACUUUGACUAC | 581 |
| CUUCUGUAACUUUGACUACA | 582 |
| GGAGUAGUUAUGUCGUcacu | 583 |
| GAGUAGUUAUGUCGUcacuc | 584 |
| AGUAGUUAUGUCGUcacuca | 585 |
| GUAGUUAUGUCGUcacucaa | 586 |
| gucGACUGUCACUUCUGUC | 587 |
| ucGACUGUCACUUCUGUCA | 588 |
| cGACUGUCACUUCUGUCAU | 589 |
| UCUUUUACUUCCGUCACUG | 590 |
| CUUUUACUUCCGUCACUGC | 591 |
| UUUUACUUCCGUCACUGCU | 592 |
| UUUACUUCCGUCACUGCUU | 593 |
| UUACUUCCGUCACUGCUUC | 594 |
| UACUUCCGUCACUGCUUCU | 595 |
| GGAGUAGUUAUGUCGUcac | 596 |
| GAGUAGUUAUGUCGUcacu | 597 |
| AGUAGUUAUGUCGUcacuc | 598 |
| GUAGUUAUGUCGUcacuca | 599 |
| UAGUUAUGUCGUcacucaa | 600 |
| agugucGACUGUCACUUC | 601 |
| gucGACUGUCACUUCUGU | 602 |
| ucGACUGUCACUUCUGUC | 603 |
| cGACUGUCACUUCUGUCA | 604 |
| ACUUCCGUCACUGCUUCU | 605 |
| GGAGUAGUUAUGUCGUca | 606 |
| GAGUAGUUAUGUCGUcac | 607 |
| AGUAGUUAUGUCGUcacu | 608 |
| GUAGUUAUGUCGUcacuc | 609 |
| UAGUUAUGUCGUcacuca | 610 |
| AGUUAUGUCGUcacucaa | 611 |

Table 8 depicts exemplary SMOs for modulating splicing of exon 10 of OGA pre-mRNA in order to produce an OGA protein with lower enzymatic activity in a cell.

TABLE 8

| 3' to 5' Splice modulating oligonucleotides directed exon 10 of OGA | SEQ ID NO. |
|---|---|
| UUUAGAAAACAUGUCACCAAUCca | 612 |
| UUAGAAAACAUGUCACCAAUCcau | 613 |
| UAGAAAACAUGUCACCAAUCcauc | 614 |
| AGAAAACAUGUCACCAAUCcaucc | 615 |
| GAAAACAUGUCACCAAUCcaucca | 616 |
| UUAGAAAACAUGUCACCAAUCca | 617 |
| UAGAAAACAUGUCACCAAUCcau | 618 |
| AGAAAACAUGUCACCAAUCcauc | 619 |
| GAAAACAUGUCACCAAUCcaucc | 620 |
| AAAACAUGUCACCAAUCcaucca | 621 |
| UAGAAAACAUGUCACCAAUCca | 622 |
| AGAAAACAUGUCACCAAUCcau | 623 |
| GAAAACAUGUCACCAAUCcauc | 624 |
| AAAACAUGUCACCAAUCcaucc | 625 |
| AAACAUGUCACCAAUCcaucca | 626 |
| GAUACCACUUUAGAAAACAUGU | 627 |
| AGAAAACAUGUCACCAAUCca | 628 |
| GAAAACAUGUCACCAAUCcau | 629 |
| AAAACAUGUCACCAAUCcauc | 630 |
| AAACAUGUCACCAAUCcaucc | 631 |
| AACAUGUCACCAAUCcaucca | 632 |
| GAUACCACUUUAGAAAACAUG | 633 |
| AUACCACUUUAGAAAACAUGU | 634 |
| GAAAACAUGUCACCAAUCca | 635 |
| AAAACAUGUCACCAAUCcau | 636 |
| AAACAUGUCACCAAUCcauc | 637 |
| AACAUGUCACCAAUCcaucc | 638 |

TABLE 8-continued

| 3' to 5' Splice modulating oligonucleotides directed exon 10 of OGA | SEQ ID NO. |
|---|---|
| ACAUGUCACCAAUCcaucca | 639 |
| GAUACCACUUUAGAAAACAU | 640 |
| AUACCACUUUAGAAAACAUG | 641 |
| UACCACUUUAGAAAACAUGU | 642 |
| AAAACAUGUCACCAAUCca | 643 |
| AAACAUGUCACCAAUCcau | 644 |
| AACAUGUCACCAAUCcauc | 645 |
| ACAUGUCACCAAUCcaucc | 646 |
| CAUGUCACCAAUCcaucca | 647 |
| GAUACCACUUUAGAAAACA | 648 |
| AUACCACUUUAGAAAACAU | 649 |
| UACCACUUUAGAAAACAUG | 650 |
| ACCACUUUAGAAAACAUGU | 651 |
| AAACAUGUCACCAAUCca | 652 |
| AACAUGUCACCAAUCcau | 653 |
| ACAUGUCACCAAUCcauc | 654 |
| CAUGUCACCAAUCcaucc | 655 |
| AUGUCACCAAUCcaucca | 656 |
| GAUACCACUUUAGAAAAC | 657 |
| AUACCACUUUAGAAAACA | 658 |
| UACCACUUUAGAAAACAU | 659 |
| ACCACUUUAGAAAACAUG | 660 |
| CCACUUUAGAAAACAUGU | 661 |

D. Aph1B

The present invention further provides SMOs based on the sequences of Aph1B (APH1B; MIM: 607630; GeneID: 83464). These SMOs are used according to the methods of the invention to modulate splicing of Aph1B pre-mRNA. In one embodiment, a SMO of the invention functions to decrease Aph1B expression or function. In another embodiment, the invention includes a pharmaceutical composition comprising a SMO of the invention, where the pharmaceutical composition of the invention comprises a SMO that functions to decrease the Aph1B expression or function. In one aspect, the SMO contacts an Aph1B pre-mRNA and modulates the splicing of the Aph1B pre-mRNA such that "in-frame" exon 4 is skipped, resulting in Aph1BΔ4, a non-functional protein.

Table 9 depicts exemplary SMOs for modulating splicing of Alph1B pre-mRNA in order to produce a non-functional protein with lower enzymatic activity in a cell.

TABLE 9

| 3' to 5' Splice modulating oligonucleotides directed to exon 4 of Aph1B | SEQ ID NO. |
|---|---|
| aaaagaaggacaaaucAAAGAC | 662 |
| aaagaaggacaaaucAAAGACC | 663 |
| aagaaggacaaaucAAAGACC | 664 |
| aagaaggacaaaucAAAGAC | 665 |
| agaaggacaaaucAAAGACC | 666 |
| agaaggacaaaucAAAGAC | 667 |
| gaaggacaaaucAAAGACC | 668 |
| aaggacaaaucAAAGACC | 669 |
| GAAACCUUAGUACUCACCUCA | 670 |
| AAACCUUAGUACUCACCUCA | 671 |
| AACCUUAGUACUCACCUCA | 672 |
| AACCUUAGUACUCACCUC | 673 |
| GAAACCUUAGUACUCACCUC | 674 |
| AACCUUAGUACUCACCUCAU | 675 |
| ACCUUAGUACUCACCUCAUA | 676 |
| CCUUAGUACUCACCUCAUAA | 677 |
| GAAACCUUAGUACUCACCU | 678 |
| AAACCUUAGUACUCACCUC | 679 |
| ACCUUAGUACUCACCUCAU | 680 |
| CCUUAGUACUCACCUCAUA | 681 |
| ACCUUAGUACUCACCUCA | 682 |
| CCUUAGUACUCACCUCAU | 683 |
| GGUCCGUGUCACCCGUAAGU | 684 |
| GUCCGUGUCACCCGUAAGUA | 685 |
| UCCGUGUCACCCGUAAGUAC | 686 |
| CCGUGUCACCCGUAAGUACC | 687 |
| GGUCCGUGUCACCCGUAAG | 688 |
| GUCCGUGUCACCCGUAAGU | 689 |
| UCCGUGUCACCCGUAAGUA | 690 |
| CCGUGUCACCCGUAAGUAC | 691 |
| CGUGUCACCCGUAAGUACC | 692 |
| GGUCCGUGUCACCCGUAA | 693 |
| GUCCGUGUCACCCGUAAG | 694 |
| UCCGUGUCACCCGUAAGU | 695 |
| CCGUGUCACCCGUAAGUA | 696 |
| CGUGUCACCCGUAAGUAC | 697 |
| GUGUCACCCGUAAGUACC | 698 |
| AUAAGUCcauacacagaguauc | 699 |
| UAAGUCcauacacagaguaucg | 700 |

TABLE 9-continued

| 3' to 5' Splice modulating oligonucleotides directed to exon 4 of Aph1B | SEQ ID NO. |
|---|---|
| AAGUCcauacacagaguaucga | 701 |
| AGUCcauacacagaguaucgac | 702 |
| GUCcauacacagaguaucgaca | 703 |
| UCcauacacagaguaucgacag | 704 |
| Ccauacacagaguaucgacagu | 705 |
| AUAAGUCcauacacagaguau | 706 |
| UAAGUCcauacacagaguauc | 707 |
| AAGUCcauacacagaguaucg | 708 |
| AGUCcauacacagaguaucga | 709 |
| GUCcauacacagaguaucgac | 710 |
| UCcauacacagaguaucgaca | 711 |
| AUAAGUCcauacacagagua | 712 |
| UAAGUCcauacacagaguau | 713 |
| AAGUCcauacacagaguauc | 714 |
| AGUCcauacacagaguaucg | 715 |
| GUCcauacacagaguaucga | 716 |
| UCcauacacagaguaucgac | 717 |
| Ccauacacagaguaucgaca | 718 |
| AUAAGUCcauacacagagu | 719 |
| AAGUCcauacacagaguau | 720 |
| AGUCcauacacagaguauc | 721 |
| GUCcauacacagaguaucg | 722 |
| UCcauacacagaguaucga | 723 |
| Ccauacacagaguaucgac | 724 |
| GUCcauacacagaguauc | 725 |
| UCcauacacagaguaucg | 726 |
| Ccauacacagaguaucga | 727 |
| UAAGUCcauacac | 728 |

E. HER3

The present invention further provides SMOs based on the sequences of HER3 (ERBB3; MIM 190151; 2065). These SMOs are used according to the methods of the invention to modulate splicing of HER3 pre-mRNA. In one embodiment, a SMO of the invention functions to decrease HER3 expression or function. In another embodiment, the invention includes a pharmaceutical composition comprising a SMO of the invention, where the pharmaceutical composition of the invention comprises a SMO that functions to decrease HER3 expression or function. In one aspect, the SMO contacts a HER3 pre-mRNA and modulates the splicing of the HER3 pre-mRNA to favor expression of HER3Δ3, a variant in which exon 3 of HER3 is deleted and is, thus, non-functional. In another aspect, the SMO contacts a HER3 pre-mRNA and modulates the splicing of the HER3 pre-mRNA to favor expression of HER3Δ11, a variant in which exon 11 of HER3 is deleted and the mature protein is non-functional. In still another aspect, the SMO contacts a HER pre-mRNA and modulates splicing of the HER3 pre-mRNA to favor inclusion of intron 3 of HER3, thus enhancing expression of a truncated, non-functional protein.

Table 10 depicts exemplary SMOs for modulating splicing of HER3 pre-mRNA in order to either block a 3' splice site of exon 3 or include intron 3, thereby increasing expression of a truncated protein in a cell.

TABLE 10

| 3' to 5' Splice modulating oligonucleotides targeting exon 3 of HER3 | SEQ ID NO. |
|---|---|
| CGGUCGAGGCGAACUGAGUCGAGU | 729 |
| UGAGUCGAGUGGCcagucaaggg | 730 |
| GGCGAACUGAGUCGAGUGGCca | 731 |
| GCGAACUGAGUCGAGUGGCcag | 732 |
| CGAACUGAGUCGAGUGGCcagu | 733 |
| GAACUGAGUCGAGUGGCcaguc | 734 |
| AACUGAGUCGAGUGGCcaguca | 735 |
| ACUGAGUCGAGUGGCcagucaa | 736 |
| CUGAGUCGAGUGGCcagucaag | 737 |
| UGAGUCGAGUGGCcagucaagg | 738 |
| GAGUCGAGUGGCcagucaaggg | 739 |
| GCGAACUGAGUCGAGUGGCca | 740 |
| CGAACUGAGUCGAGUGGCcag | 741 |
| GAACUGAGUCGAGUGGCcagu | 742 |
| AACUGAGUCGAGUGGCcaguc | 743 |
| ACUGAGUCGAGUGGCcaguca | 744 |
| CUGAGUCGAGUGGCcagucaa | 745 |
| UGAGUCGAGUGGCcagucaag | 746 |
| GAGUCGAGUGGCcagucaagg | 747 |
| AGUCGAGUGGCcagucaaggg | 748 |
| CGAACUGAGUCGAGUGGCca | 749 |
| GAACUGAGUCGAGUGGCcag | 750 |
| AACUGAGUCGAGUGGCcagu | 751 |
| ACUGAGUCGAGUGGCcaguc | 752 |
| CUGAGUCGAGUGGCcaguca | 753 |
| UGAGUCGAGUGGCcagucaa | 754 |
| GAGUCGAGUGGCcagucaag | 755 |
| AGUCGAGUGGCcagucaagg | 756 |
| GUCGAGUGGCcagucaaggg | 757 |
| GAACUGAGUCGAGUGGCca | 758 |
| AACUGAGUCGAGUGGCcag | 759 |
| ACUGAGUCGAGUGGCcagu | 760 |

TABLE 10-continued

| 3' to 5' Splice modulating oligonucleotides targeting exon 3 of HER3 | SEQ ID NO. |
|---|---|
| CUGAGUCGAGUGGCcaguc | 761 |
| UGAGUCGAGUGGCcaguca | 762 |
| GAGUCGAGUGGCcagucaa | 763 |
| AGUCGAGUGGCcagucaag | 764 |
| GUCGAGUGGCcagucaagg | 765 |
| UCGAGUGGCcagucaaggg | 766 |
| AACUGAGUCGAGUGGCca | 767 |
| ACUGAGUCGAGUGGCcag | 768 |
| CUGAGUCGAGUGGCcagu | 769 |
| UGAGUCGAGUGGCcaguc | 770 |
| GAGUCGAGUGGCcaguca | 771 |
| AGUCGAGUGGCcagucaa | 772 |
| GUCGAGUGGCcagucaag | 773 |
| UCGAGUGGCcagucaagg | 774 |
| CGAGUGGCcagucaaggg | 775 |
| ACUGAGUCGAGUGGCca | 776 |
| CUGAGUCGAGUGGCcag | 777 |
| UGAGUCGAGUGGCcagu | 778 |
| GAGUCGAGUGGCcaguc | 779 |
| AGUCGAGUGGCcaguca | 780 |
| GUCGAGUGGCcagucaa | 781 |
| UCGAGUGGCcagucaag | 782 |
| CGAGUGGCcagucaagg | 783 |
| GAGUGGCcagucaaggg | 784 |
| CUGAGUCGAGUGGCca | 785 |
| UGAGUCGAGUGGCcag | 786 |
| GAGUCGAGUGGCcagu | 787 |
| AGUCGAGUGGCcaguc | 788 |
| GUCGAGUGGCcaguca | 789 |
| UCGAGUGGCcagucaa | 790 |
| CGAGUGGCcagucaag | 791 |
| GAGUGGCcagucaagg | 792 |
| AGUGGCcagucaaggg | 793 |
| UGAGUCGAGUGGCca | 794 |
| GAGUCGAGUGGCcag | 795 |
| AGUCGAGUGGCcagu | 796 |
| GUCGAGUGGCcaguc | 797 |
| UCGAGUGGCcaguca | 798 |
| CGAGUGGCcagucaa | 799 |
| GAGUGGCcagucaag | 800 |
| AGUGGCcagucaagg | 801 |
| GUGGCcagucaaggg | 802 |

Table 11 depicts exemplary SMOs for modulating splicing of HER3 pre-mRNA in order to exclude exon 11 thereby increasing expression of a non-functional protein in a cell.

TABLE 11

3' to 5' Splice modulating oligonucleotides directed to exon 11 of HER3

| [[Should refer to them ONLY as SMOs or oligonucleotides throughout]] | SEQ ID NO. |
|---|---|
| cggagagagguuggggagucCAAU | 803 |
| ggggagucCAAUGGACUUGUAGGU | 804 |
| gggagucCAAUGGACUUGUAGGUC | 805 |
| cggagagagguuggggagucCAA | 806 |
| ggagucCAAUGGACUUGUAGGUC | 807 |
| cggagagagguuggggagucCA | 808 |
| gagucCAAUGGACUUGUAGGUC | 809 |
| agucCAAUGGACUUGUAGGUC | 810 |
| gucCAAUGGACUUGUAGGUC | 811 |
| ucCAAUGGACUUGUAGGUC | 812 |
| ucCAAUGGACUUGUAGGU | 813 |

F. Cyclophilin D

The present invention further provides SMOs based on the sequences of CypD (PPID; MIM: 601753 GeneID: 5481). These SMOs are used according to the methods of the invention to modulate splicing of CypD pre-mRNA. In one embodiment, a SMO of the invention functions to decrease CypD expression or function. In another embodiment, the invention includes a pharmaceutical composition comprising a SMO of the invention, where the pharmaceutical composition of the invention comprises a SMO that functions to decrease the CypD expression or function. In one aspect, the SMO contacts a CypD pre-mRNA and modulates the splicing of the CypD pre-mRNA to favor expression of CypDΔ1, a variant in which exon 1 of CypD is deleted and is, thus, non-functional. In another aspect, the SMO contacts an CypD pre-mRNA and modulates the splicing of the CypD pre-mRNA to favor expression of CypDΔ3, a variant in which exon 3 of CypD is deleted and is, thus, non-functional.

Table 12 depicts exemplary SMOs for modulating splicing of CypD pre-mRNA in order to exclude exon 1 thereby decreasing expression of a functional CypD protein in a cell.

TABLE 12

| 3' to 5' Splice modulating oligonucleotides directed to targeting exon 1 of CypD | SEQ ID NO. |
|---|---|
| UGCAGACGUUCAGUUCUACAGCGU | 814 |
| UGCAGACGUUCAGUUCUACAGCG | 815 |
| UGCAGACGUUCAGUUCUACAGC | 816 |
| UGCAGACGUUCAGUUCUACAG | 817 |
| UGCAGACGUUCAGUUCUACA | 818 |
| UGCAGACGUUCAGUUCUAC | 819 |
| AGACGUUCAGUUCUACAGCGUGGG | 820 |
| AGACGUUCAGUUCUACAGCGUGG | 821 |
| AGACGUUCAGUUCUACAGCGUG | 822 |
| AGACGUUCAGUUCUACAGCGU | 823 |
| AGACGUUCAGUUCUACAGCG | 824 |
| UGUAGCCUCCCCUCGCUCcacucg | 825 |
| GUAGCCUCCCCUCGCUCcacucg | 826 |
| UAGCCUCCCCUCGCUCcacucg | 827 |
| AGCCUCCCCUCGCUCcacucg | 828 |
| GCCUCCCCUCGCUCcacucg | 829 |
| CCUCCCCUCGCUCcacucg | 830 |
| CUGUAGCCUCCCCUCGCUCcacuc | 831 |
| UGUAGCCUCCCCUCGCUCcacuc | 832 |
| GUAGCCUCCCCUCGCUCcacuc | 833 |
| UAGCCUCCCCUCGCUCcacuc | 834 |
| AGCCUCCCCUCGCUCcacuc | 835 |
| GCCUCCCCUCGCUCcacuc | 836 |
| CCUGUACCUCCCCUCGCUCcacu | 837 |
| CUGUACCUCCCCUCGCUCcacu | 838 |
| UGUACCUCCCCUCGCUCcacu | 839 |
| GUACCUCCCCUCGCUCcacu | 840 |
| UACCUCCCCUCGCUCcacu | 841 |
| ACCUCCCCUCGCUCcacu | 842 |
| ACCUGUAGCCUCCCCUCGCUCcac | 843 |
| CCUGUAGCCUCCCCUCGCUCcac | 844 |
| CUGUAGCCUCCCCUCGCUCcac | 845 |
| UGUAGCCUCCCCUCGCUCcac | 846 |
| GUAGCCUCCCCUCGCUCcac | 847 |
| CACCUGUACCUCCCCUCGCUCca | 848 |
| ACCUGUACCUCCCCUCGCUCca | 849 |
| CCUGUACCUCCCCUCGCUCca | 850 |
| CUGUACCUCCCCUCGCUCca | 851 |
| UGUACCUCCCCUCGCUCca | 852 |
| GCACCUGUAGCCUCCCCUCGCUCc | 853 |
| CACCUGUAGCCUCCCCUCGCUCc | 854 |
| ACCUGUAGCCUCCCCUCGCUCc | 855 |
| CCUGUAGCCUCCCCUCGCUCc | 856 |
| CUGUAGCCUCCCCUCGCUCc | 857 |

Table 13 depicts exemplary SMOs for modulating splicing of CypD pre-mRNA in order to exclude exon 3 thereby decreasing expression of a functional CypD protein in a cell.

TABLE 13

| 3' to 5' Splice modulating oligonucleotides directed to targeting exon 3 of CypD | SEQ ID NO. |
|---|---|
| acaucAAUAAUUCUUUAAAUACUA | 858 |
| acaucAAUAAUUCUUUAAAUACU | 859 |
| acaucAAUAAUUCUUUAAAUAC | 860 |
| acaucAAUAAUUCUUUAAAUA | 861 |
| acaucAAUAAUUCUUUAAAU | 862 |
| acaucAAUAAUUCUUUAA | 863 |
| caucAAUAAUUCUUUAAAUACUAA | 864 |
| caucAAUAAUUCUUUAAAUACUA | 865 |
| caucAAUAAUUCUUUAAAUACU | 866 |
| caucAAUAAUUCUUUAAAUAC | 867 |
| caucAAUAAUUCUUUAAAUA | 868 |
| caucAAUAAUUCUUUAAAU | 869 |
| aucAAUAAUUCUUUAAAUACUAAG | 870 |
| aucAAUAAUUCUUUAAAUACUAA | 871 |
| aucAAUAAUUCUUUAAAUACUA | 872 |
| aucAAUAAUUCUUUAAAUACU | 873 |
| aucAAUAAUUCUUUAAAUAC | 874 |
| aucAAUAAUUCUUUAAAUA | 875 |
| ucAAUAAUUCUUUAAAUACAAAGU | 876 |
| ucAAUAAUUCUUUAAAUACAAAG | 877 |
| ucAAUAAUUCUUUAAAUACAAA | 878 |
| ucAAUAAUUCUUUAAAUACAA | 879 |
| ucAAUAAUUCUUUAAAUACA | 880 |
| ucAAUAAUUCUUUAAAUAC | 881 |
| cAAUAAUUCUUUAAAUACUAAGUC | 882 |
| cAAUAAUUCUUUAAAUACUAAGU | 883 |
| cAAUAAUUCUUUAAAUACUAAG | 884 |
| cAAUAAUUCUUUAAAUACUAA | 885 |

TABLE 13-continued

| 3' to 5' Splice modulating oligonucleotides directed to targeting exon 3 of CypD | SEQ ID NO. |
|---|---|
| cAAUAAUUCUUUAAAUACUA | 886 |
| cAAUAAUUCUUUAAAUAC | 887 |
| UUUAGUCUUACCCUGUCCACCUCU | 888 |
| UUAGUCUUACCCUGUCCACCUCU | 889 |
| UAGUCUUACCCUGUCCACCUCU | 890 |
| AGUCUUACCCUGUCCACCUCU | 891 |
| AGUCUUACCCUGUCCACCUC | 892 |
| AGUCUUACCCUGUCCACCU | 893 |
| GUCUUACCCUGUCCACCUCUUUCA | 894 |
| UCUUACCCUGUCCACCUCUUUCA | 895 |
| CUUACCCUGUCCACCUCUUUCA | 896 |
| UUACCCUGUCCACCUCUUUCA | 897 |
| UACCCUGUCCACCUCUUUCA | 898 |
| ACCCUGUCCACCUCUUUCA | 899 |
| ACUUUUUAAACUUCUACUUU | 900 |
| UUCUACUUUUAAAGGUAAUGUUCc | 901 |
| UCUACUUUUAAAGGUAAUGUUCc | 902 |
| CUACUUUUAAAGGUAAUGUUCc | 903 |
| UACUUUUAAAGGUAAUGUUCc | 904 |
| ACUUUUAAAGGUAAUGUUCc | 905 |
| CUUUUAAAGGUAAUGUUCc | 906 |
| CUACUUUUAAAGGUAAUGUUCca | 907 |
| UACUUUUAAAGGUAAUGUUCca | 908 |
| ACUUUUAAAGGUAAUGUUCca | 909 |
| CUUUUAAAGGUAAUGUUCca | 910 |
| UUUUAAAGGUAAUGUUCca | 911 |
| UUUAAAGGUAAUGUUCca | 912 |
| CUACUUUUAAAGGUAAUGUUCcau | 913 |
| UACUUUUAAAGGUAAUGUUCcau | 914 |
| ACUUUUAAAGGUAAUGUUCcau | 915 |
| CUUUUAAAGGUAAUGUUCcau | 916 |
| UUUUAAAGGUAAUGUUCcau | 917 |
| UUUAAAGGUAAUGUUCcau | 918 |

G. FOXM1

The present invention further provides SMOs based on the sequences of FOXM1 (FOXM1; MIM: 602341; GeneID: 2305). These SMOs are used according to the methods of the invention to modulate splicing of FOXM1 pre-mRNA. In one embodiment, a SMO of the invention functions to decrease FOXM1 expression. In another embodiment, the invention includes a pharmaceutical composition comprising a SMO of the invention, where the pharmaceutical composition of the invention comprises a SMO that functions to decrease the FOXM1 expression. In one aspect, the SMO contacts a FOXM1 pre-mRNA and modulates the splicing of the FOXM1 pre-mRNA to favor expression of FOXM1Δ3, a variant in which exon 3 of FOXM1 D is excluded. In another aspect, the SMO contacts an FOXM1 pre-mRNA and modulates the splicing of the FOXM1 pre-mRNA to favor expression of FOXM1Δ6, a variant in which exon 6 of FOXM1 is excluded.

Table 14 depicts exemplary SMOs for modulating splicing of FOXM1 pre-mRNA in order to exclude exon 3 thereby decreasing expression of a functional FOXM1 protein in a cell.

TABLE 14

| 3' to 5' Splice modulating oligonucleotides directed to targeting Exon 3 of FOXM1 | SEQ ID NO. |
|---|---|
| GUAGGUCACCGAAGCUUUCUAC | 919 |
| GUAGGUCACCGAAGCUUUCUA | 920 |
| GUAGGUCACCGAAGCUUUCU | 921 |
| CCUCUUAACAGUGGACCUCGUC | 922 |
| CCUCUUAACAGUGGACCUCGU | 923 |
| CUCUUAACAGUGGACCUCGU | 924 |
| CUCUUAACAGUGGACCUCG | 925 |
| CUCUUAACAGUGGACCUC | 926 |
| ACCUCGUCGCUGUCCAAUUCca | 927 |
| CCUCGUCGCUGUCCAAUUCcau | 928 |
| CUCGUCGCUGUCCAAUUCcacu | 929 |
| UCGUCGCUGUCCAAUUCcacuu | 930 |
| CCUCGUCGCUGUCCAAUUCca | 931 |
| CUCGUCGCUGUCCAAUUCcac | 932 |
| UCGUCGCUGUCCAAUUCcacu | 933 |
| CGUCGCUGUCCAAUUCcacuu | 934 |
| GUCGCUGUCCAAUUCcacuua | 935 |
| UCGCUGUCCAAUUCcacuuaa | 936 |
| CUCGUCGCUGUCCAAUUCca | 937 |
| UCGUCGCUGUCCAAUUCcac | 938 |
| CGUCGCUGUCCAAUUCcacu | 939 |
| GUCGCUGUCCAAUUCcacuu | 940 |
| UCGCUGUCCAAUUCcacuua | 941 |
| CGCUGUCCAAUUCcacuuaa | 942 |
| UCGUCGCUGUCCAAUUCca | 943 |
| CGUCGCUGUCCAAUUCcac | 944 |
| GUCGCUGUCCAAUUCcacu | 945 |
| UCGCUGUCCAAUUCcacuu | 946 |
| CGCUGUCCAAUUCcacuua | 947 |

TABLE 14-continued

| 3' to 5' Splice modulating oligonucleotides directed to targeting Exon 3 of FOXM1 | SEQ ID NO. |
|---|---|
| GCUGUCCAAUUCcacuuaa | 948 |
| CGUCGCUGUCCAAUUCca | 949 |
| GUCGCUGUCCAAUUCcac | 950 |
| UCGCUGUCCAAUUCcacu | 951 |
| CGCUGUCCAAUUCcacuu | 952 |
| GCUGUCCAAUUCcacuua | 953 |

Table 15 depicts exemplary SMOs for modulating splicing of FOXM1 pre-mRNA in order to exclude exon 6 decreasing expression of a functional FOXM1 protein in a cell.

TABLE 15

| 3' to 5' Splice modulating oligonucleotides directed to targeting Exon 6 of FOXM1 | SEQ ID NO. |
|---|---|
| GGCGGUGGUCGGCGGUGGUCGG | 954 |
| GGCGGUGGUCGGCGGUGGUCGGU | 955 |
| GGCGGUGGUCGGCGGUGGUCGG | 956 |
| GGCGGUGGUCGGCGGUGGUCG | 957 |
| GGCGGUGGUCGGCGGUGGUC | 958 |
| GGCGGUGGUCGGCGGUGGU | 959 |
| cGGCGGUGGUCGGUGACCUGGGUC | 960 |
| cGGCGGUGGUCGGUGACCUGGGU | 961 |
| cGGCGGUGGUCGGUGACCUGGG | 962 |
| cGGCGGUGGUCGGUGACCUGG | 963 |
| cGGCGGUGGUCGGUGACCUG | 964 |
| cGGCGGUGGUCGGUGACCU | 965 |
| ccGGCGGUGGUCGGCGGUGGUCGG | 966 |
| ccGGCGGUGGUCGGCGGUGGUCG | 967 |
| ccGGCGGUGGUCGGCGGUGGUC | 968 |
| ccGGCGGUGGUCGGCGGUGGU | 969 |
| ccGGCGGUGGUCGGCGGUGG | 970 |
| ccGGCGGUGGUCGGCGGUG | 971 |
| accGGCGGUGGUCGGCGGUGGUCG | 972 |
| accGGCGGUGGUCGGCGGUGGUC | 973 |
| accGGCGGUGGUCGGCGGUGGU | 974 |
| accGGCGGUGGUCGGCGGUGG | 975 |
| accGGCGGUGGUCGGCGGUG | 976 |
| accGGCGGUGGUCGGCGGU | 977 |
| gaccGGCGGUGGUCGGCGGUGGUC | 978 |
| gaccGGCGGUGGUCGGCGGUGGU | 979 |

TABLE 15-continued

| 3' to 5' Splice modulating oligonucleotides directed to targeting Exon 6 of FOXM1 | SEQ ID NO. |
|---|---|
| gaccGGCGGUGGUCGGCGGUGG | 980 |
| gaccGGCGGUGGUCGGCGGUG | 981 |
| gaccGGCGGUGGUCGGCGGU | 982 |
| gaccGGCGGUGGUCGGCGG | 983 |
| ggaccGGCGGUGGUCGGCGGUGGU | 984 |
| ggaccGGCGGUGGUCGGCGGUGG | 985 |
| ggaccGGCGGUGGUCGGCGGUG | 986 |
| ggaccGGCGGUGGUCGGCGGU | 987 |
| ggaccGGCGGUGGUCGGCGG | 988 |
| ggaccGGCGGUGGUCGGCG | 989 |
| cggaccGGCGGUGGUCGGCGGUGG | 990 |
| cggaccGGCGGUGGUCGGCGGUG | 991 |
| cggaccGGCGGUGGUCGGCGGU | 992 |
| cggaccGGCGGUGGUCGGCGG | 993 |
| cggaccGGCGGUGGUCGGCG | 994 |
| cggaccGGCGGUGGUCGGC | 995 |
| CGGUGGUCGGUGACCUGGGUCCCA | 996 |
| CGGUGGUCGGUGACCUGGGUCCC | 997 |
| CGGUGGUCGGUGACCUGGGUCC | 998 |
| CGGUGGUCGGUGACCUGGGUC | 999 |
| CGGUGGUCGGUGACCUGGGU | 1000 |
| GGUGGUCGGUGACCUGGGUCCCAG | 1001 |
| GGUGGUCGGUGACCUGGGUCCCA | 1002 |
| GGUGGUCGGUGACCUGGGUCCC | 1003 |
| GGUGGUCGGUGACCUGGGUCC | 1004 |
| GGUGGUCGGUGACCUGGGUC | 1005 |
| GUGGUCGGUGACCUGGGUCCCAGA | 1006 |
| GUGGUCGGUGACCUGGGUCCCAG | 1007 |
| GUGGUCGGUGACCUGGGUCCCA | 1008 |
| GUGGUCGGUGACCUGGGUCCC | 1009 |
| GUGGUCGGUGACCUGGGUCC | 1010 |
| UGGGUCCCAGAGGUGUUAACGGGC | 1011 |
| UGGGUCCCAGAGGUGUUAACGGG | 1012 |
| UGGGUCCCAGAGGUGUUAACGG | 1013 |
| UGGGUCCCAGAGGUGUUAACG | 1014 |
| UGGGUCCCAGAGGUGUUAAC | 1015 |
| GGGUCCCAGAGGUGUUAACGGGCU | 1016 |
| GGGUCCCAGAGGUGUUAACGGGC | 1017 |

TABLE 15-continued

| 3' to 5' Splice modulating oligonucleotides directed to targeting Exon 6 of FOXM1 | SEQ ID NO. |
|---|---|
| GGGUCCCAGAGGUGUUAACGGG | 1018 |
| GGGUCCCAGAGGUGUUAACGG | 1019 |
| GGGUCCCAGAGGUGUUAACG | 1020 |
| CCCAGAGGUGUUAACGGGCUCGUG | 1021 |
| CCCAGAGGUGUUAACGGGCUCGU | 1022 |
| CCCAGAGGUGUUAACGGGCUCG | 1023 |
| CCCAGAGGUGUUAACGGGCUC | 1024 |
| CCCAGAGGUGUUAACGGGCU | 1025 |
| AGAGGUGUUAACGGGCUCGUGAAC | 1026 |
| AGAGGUGUUAACGGGCUCGUGAA | 1027 |
| AGAGGUGUUAACGGGCUCGUGA | 1028 |
| AGAGGUGUUAACGGGCUCGUG | 1029 |
| AGAGGUGUUAACGGGCUCGU | 1030 |
| GAGGUGUUAACGGGCUCGUGAACC | 1031 |
| GAGGUGUUAACGGGCUCGUGAAC | 1032 |
| GAGGUGUUAACGGGCUCGUGAA | 1033 |
| GAGGUGUUAACGGGCUCGUGA | 1034 |
| GAGGUGUUAACGGGCUCGUG | 1035 |
| GUUAACGGGCUCGUGAACCUUAGU | 1036 |
| GUUAACGGGCUCGUGAACCUUAG | 1037 |
| GUUAACGGGCUCGUGAACCUUA | 1038 |
| GUUAACGGGCUCGUGAACCUU | 1039 |
| GUUAACGGGCUCGUGAACCU | 1040 |
| GUUAACGGGCUCGUGAACC | 1041 |
| UUAACGGGCUCGUGAACCUUAGUc | 1042 |
| UAACGGGCUCGUGAACCUUAGUc | 1043 |
| AACGGGCUCGUGAACCUUAGUc | 1044 |
| ACGGGCUCGUGAACCUUAGUc | 1045 |
| CGGGCUCGUGAACCUUAGUc | 1046 |
| GGGCUCGUGAACCUUAGUc | 1047 |
| UAACGGGCUCGUGAACCUUAGUca | 1048 |
| AACGGGCUCGUGAACCUUAGUca | 1049 |
| ACGGGCUCGUGAACCUUAGUca | 1050 |
| CGGGCUCGUGAACCUUAGUca | 1051 |
| GGGCUCGUGAACCUUAGUca | 1052 |
| GGCUCGUGAACCUUAGUca | 1053 |
| AACGGGCUCGUGAACCUUAGUcau | 1054 |
| ACGGGCUCGUGAACCUUAGUcau | 1055 |
| CGGGCUCGUGAACCUUAGUcau | 1056 |
| GGGCUCGUGAACCUUAGUcau | 1057 |
| GGCUCGUGAACCUUAGUcau | 1058 |
| GCUCGUGAACCUUAGUcau | 1059 |
| ACGGGCUCGUGAACCUUAGUcauu | 1060 |
| CGGGCUCGUGAACCUUAGUcauu | 1061 |
| GGGCUCGUGAACCUUAGUcauu | 1062 |
| GGCUCGUGAACCUUAGUcauu | 1063 |
| GCUCGUGAACCUUAGUcauu | 1064 |
| CUCGUGAACCUUAGUcauu | 1065 |
| CGGGCUCGUGAACCUUAGUcauuc | 1066 |
| GGGCUCGUGAACCUUAGUcauuc | 1067 |
| GGCUCGUGAACCUUAGUcauuc | 1068 |
| GCUCGUGAACCUUAGUcauuc | 1069 |
| CUCGUGAACCUUAGUcauuc | 1070 |
| UCGUGAACCUUAGUcauuc | 1071 |
| GGGCUCGUGAACCUUAGUcauucc | 1072 |
| GGCUCGUGAACCUUAGUcauucc | 1073 |
| GCUCGUGAACCUUAGUcauucc | 1074 |
| CUCGUGAACCUUAGUcauucc | 1075 |
| UCGUGAACCUUAGUcauucc | 1076 |
| CGUGAACCUUAGUcauucc | 1077 |
| GGCUCGUGAACCUUAGUcauucca | 1078 |
| GCUCGUGAACCUUAGUcauucca | 1079 |
| CUCGUGAACCUUAGUcauucca | 1080 |
| UCGUGAACCUUAGUcauucca | 1081 |
| CGUGAACCUUAGUcauucca | 1082 |
| GUGAACCUUAGUcauucca | 1083 |
| GCUCGUGAACCUUAGUcauuccaa | 1084 |
| CUCGUGAACCUUAGUcauuccaa | 1085 |
| UCGUGAACCUUAGUcauuccaa | 1086 |
| CGUGAACCUUAGUcauuccaa | 1087 |
| GUGAACCUUAGUcauuccaa | 1088 |
| UGAACCUUAGUcauuccaa | 1089 |

It will be appreciated by the skilled artisan that a SMO useful in practicing the methods of the invention should not be considered to be limited to those SMO sequences explicitly recited herein, but rather should be considered to include any SMO sufficiently complementary to a target pre-mRNA in such a way as to modulate its splicing. The invention also encompasses all derivatives, variants, and modifications of the SMOs of the invention, as described elsewhere herein.

Oligonucleotides of the invention are of any size and/or chemical composition sufficient to specifically bind to a target RNA (e.g., pre-mRNA). In exemplary embodiments, the oligonucleotides of the invention are oligonucleotides of between about 5-300 nucleotides (or modified nucleotides), preferably between about 10-100 nucleotides (or modified nucleotides; e.g., ribonucleotides or modified ribonucleotides), for example, between about 15-35, e.g., about 15-20, 20-25, 25-30, 30-35 (31, 32, 33, 34, 35), or 35-40 nucleotides (or modified nucleotides; e.g., ribonucleotides or modified ribonucleotides).

Synthesis of SMOs

An oligonucleotide of the invention, i.e. the SMO, can be synthesized using any procedure known in the art, including chemical synthesis, enzymatic ligation, organic synthesis, and biological synthesis.

In one embodiment, an RNA molecule, e.g., SMO, is prepared chemically. Methods of synthesizing RNA and DNA molecules are known in the art, in particular, the chemical synthesis methods as described in Verma and Eckstein (1998) Annul Rev. Biochem. 67:99-134. RNA can be purified from a mixture by extraction with a solvent or resin, precipitation, electrophoresis, chromatography, or a combination thereof. Alternatively, the RNA may be used with no or a minimum of purification to avoid losses due to sample processing.

Modifications of SMOs

In a preferred aspect, the oligonucleotides of the present invention (i.e. SMOs) are modified to improve stability in serum or growth medium for cell cultures, or otherwise to enhance stability during delivery to subjects and/or cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine can be tolerated without affecting the efficiency of oligonucleotide reagent-induced modulation of splice site selection. For example, the absence of a 2' hydroxyl may significantly enhance the nuclease resistance of the oligonucleotides in tissue culture medium.

In an embodiment of the present invention the oligonucleotides, e.g., SMOs, may contain at least one modified nucleotide analogue. The nucleotide analogues may be located at positions where the target-specific activity, e.g., the splice site selection modulating activity is not substantially effected, e.g., in a region at the 5'-end and/or the 3'-end of the oligonucleotide molecule. Particularly, the ends may be stabilized by incorporating modified nucleotide analogues.

Preferred nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from $CH_3$, H, OR, R, halo, SH, SR, $NH_2$, NHR, $NR_2$ or ON, wherein R is $C_1$-$C_6$ alkyl, alkenyl or alkynyl and halo is F, Cl, Br or I. In a preferred embodiment, the 2' OH-group is replaced by $CH_3$.

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to phosphorothioate derivatives and acridine substituted nucleotides, 2'O-methyl substitutions, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine. It should be noted that the above modifications may be combined. Oligonucleotides of the invention also may be modified with chemical moieties (e.g., cholesterol) that improve the in vivo pharmacological properties of the oligonucleotides.

Within the oligonucleotides (e.g., oligoribonucleotides) of the invention, as few as one and as many as all nucleotides of the oligonucleotide can be modified. For example, a 20-mer oligonucleotide (e.g., oligoribonucleotide) of the invention may contain 1, 2, 3, 4, 5, 6, 7, 8, 9, 10, 11, 12, 13, 14, 15, 16, 17, 18, 19 or 20 modified nucleotides. In preferred embodiments, the modified oligonucleotides (e.g., oligoribonucleotides) of the invention will contain as few modified nucleotides as are necessary to achieve a desired level of in vivo stability and/or bioaccessibility while maintaining cost effectiveness. An SMOs of the invention include oligonucleotides synthesized to include any combination of modified bases disclosed herein in order to optimize function. In one embodiment, a SMO of the invention comprises at least two different modified bases. In another embodiment, a SMO of the invention may comprise alternating 2'O-methyl substitutions and LNA bases.

An oligonucleotide of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, Nucleic Acids Res. 15:6625-6641). The oligonucleotide can also comprise a 2'-o-methylribonucleotide (Inoue et al., 1987, Nucleic Acids Res. 15:6131-6148) or a chimeric RNA-DNA analogue (Inoue et al., 1987, FEBS Lett. 215:327-330).

In various embodiments, the oligonucleotides of the invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, Bioorganic & Medicinal Chemistry 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) Proc. Natl. Acad. Sci. USA 93:14670-675.

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) Nucleic Acids Res. 24(17):3357-63. For example, a DNA chain can be synthesized on a solid support using standard phosphoramiditea coupling chemistry and modified nucleoside analogs. Compounds such as 5'-(4-methoxytritypamino-5'-deoxy-thymidine phosphoramidite can be used as a link between the PNA and the 5' end of DNA (Mag et al., 1989, Nucleic Acids Res. 17:5973-88). PNA monomers are then coupled in a step-wise manner to produce a chimeric molecule with a 5' PNA segment and a 3' DNA segment (Finn et al., 1996, Nucleic Acids Res. 24(17): 3357-63). Alternatively, chimeric molecules can be synthesized with a 5' DNA segment and a 3' PNA segment (Peterser et al., 1975, Bioorganic Med. Chem. Lett. 5: 1119-11124).

The oligonucleotides of the invention can also be formulated as morpholino oligonucleotides. In such embodiments, the riboside moiety of each subunit of an oligonucleotide of the oligonucleotide is converted to a morpholine moiety (morpholine=$C_4H_9NO$; refer to Heasman, J. 2002 Developmental Biology 243, 209-214, the entire contents of which are incorporated herein by reference).

A further preferred oligonucleotide modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne ($-CH_2-$)$_n$ group bridging the 2' oxygen atom and the 4' carbon atom wherein n is 1 or 2. LNAs and preparation thereof are described in WO 98/39352 and WO 99/14226, the entire contents of which are incorporated by reference herein.

In other embodiments, the oligonucleotide can include other appended groups such as peptides (e.g., for targeting host cell receptors in vivo), or agents facilitating transport across the cell membrane (see, e.g., Letsinger et al., 1989, Proc. Natl. Acad. Sci. USA 86:6553-6556; Lemaitre et al., 1987, Proc. Natl. Acad. Sci. USA 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, Bio/Techniques 6:958-976) or intercalating agents (see, e.g., Zon, 1988, Pharm. Res. 5:539-549). To this end, the oligonucleotide can be conjugated to another molecule, e.g., a peptide, hybridization triggered cross-linking agent, transport agent, hybridization-triggered cleavage agent, etc.

The invention also includes molecular beacon nucleic acid molecules having at least one region which is complementary to a nucleic acid molecule of the invention, such that the molecular beacon is useful for quantitating the presence of the nucleic acid molecule of the invention in a sample. A "molecular beacon" nucleic acid is a nucleic acid molecule comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid molecules are not annealed with one another, fluorescence of the fluorophore is quenched to a lesser degree. Molecular beacon nucleic acid molecules are described, for example, in U.S. Pat. No. 5,876,930.

The target RNA (e.g., pre-mRNA) splice-modifying reaction guided by oligonucleotides of the invention is highly sequence specific. In general, oligonucleotides containing nucleotide sequences perfectly complementary to a portion of the target RNA are preferred for blocking of the target RNA. However, 100% sequence complementarity between the oligonucleotide and the target RNA is not required to practice the present invention. Thus, the invention may tolerate sequence variations that might be expected due to genetic mutation, strain polymorphism, or evolutionary divergence. For example, oligonucleotide sequences with insertions, deletions, and single point mutations relative to the target sequence may also be effective for inhibition. Alternatively, oligonucleotide sequences with nucleotide analog substitutions or insertions can be effective for blocking.

Greater than 70% sequence identity (or complementarity), e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, and any and all whole or partial increments there between the oligonucleotide and the target RNA, e.g., target pre-mRNA, is preferred.

Sequence identity, including determination of sequence complementarity for nucleic acid sequences, may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Alternatively, the oligonucleotide may be defined functionally as a nucleotide sequence (or oligonucleotide sequence) a portion of which is capable of hybridizing with the target RNA (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, $Tm(°C.)=2(\text{number of A+T bases})+4(\text{number of G+C bases})$. For hybrids between 18 and 49 base pairs in length, $Tm(°C.)=81.5+16.6(\log_{10}[Na^+])+0.41(\% G+C)-(600/N)$, where N is the number of bases in the hybrid, and $[Na^+]$ is the concentration of sodium ions in the hybridization buffer ($[Na^+]$ for 1×SSC=0.165 M). Additional examples of stringency conditions for polynucleotide hybridization are provided in Sambrook, et al., 2001, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference. The length of the identical nucleotide sequences may be at least about 10, 12, 15, 17, 20, 22, 25, 27, 30, 32, 35, 37, 40, 42, 45, 47 or 50 bases.

II. Methods

The present invention provides compositions and methods for modulating pre-mRNA splicing using a SMO of the invention to abrogate disease-causing mutations in a protein. An SMO of the invention may modulate pre-mRNA splicing by blocking cryptic splice sites, removing an exon, including an exon, or shifting the reading frame of the pre-mRNA in order to alter protein isoform expression.

Accordingly, the present invention provides compositions and methods of treating a subject at risk of, susceptible to, or having a disease, disorder, or condition associated with aberrant or unwanted target pre-mRNA expression or function. In one embodiment, a target pre-mRNA of the invention is any aberrantly spliced or unwanted pre-mRNA encoding a protein that results in, causes, produces, or predisposes a subject to a disease or disorder. In another embodiment, aberrant splicing of a target pre-mRNA if the invention is not a cause of a disease or disorder, but modulation of the target pre-mRNA reduces at least one symptom of the disease or disorder.

In another embodiment, the invention provides a method of preventing in a subject, a disease, disorder, or condition associated with aberrant or unwanted pre-mRNA splicing of a protein and altered protein expression or function, the method comprising administering to the subject a pharmaceutical composition comprising a SMO, or vector, or transgene encoding same.

A target pre-mRNA of the invention is any pre-mRNA that is abnormally spliced or a pre-mRNA whose altered activity is likely to have a beneficial effect on a subject. In one embodiment, a target pre-mRNA of the invention comprises a 5-HT2C receptor. In yet another embodiment, a target pre-mRNA of the invention is an aberrantly spliced 5-HT2CR pre-mRNA in a subject that results in a truncated, non-functional 5-HT2C receptor.

In yet another embodiment, a target pre-mRNA of the invention is an AMPA glutamate receptor (GluR) subunit comprising GluR1, GluR2, Glur3, GluR4, or any combination thereof. In a further embodiment, a target pre-mRNA of the invention is an AMPA glutamate receptor (GluR) subunit comprising GluR1, GluR2, Glur3, GluR4, or any combination thereof where it is desirable to alter the ratio of flip and flop isoforms of any one of, or any combination of these GluRs. In yet another embodiment, a target pre-mRNA of the invention is an aberrantly spliced GluR pre-mRNA in a subject that results in a truncated, non-functional glutamate receptor.

In still another embodiment, a target pre-mRNA of the invention is OGA.

In yet another embodiment of the invention, a target pre-mRNA of the invention is Aph1B. In another embodiment, a target pre-mRNA of the invention is HER3. In still another embodiment, a target pre-mRNA of the invention is FOXM1. In yet another embodiment, a target pre-mRNA of the invention is CypD.

Subjects at risk for a disease which is caused or contributed to by aberrant or unwanted target pre-mRNA expression or activity can be identified by, for example, any or a combination of diagnostic or prognostic assays known in the art. Administration of a prophylactic agent comprising a SMO can occur prior to the manifestation of symptoms characteristic of the target pre-mRNA aberrancy, such that a disease or disorder is prevented or, alternatively, delayed in its progression.

The invention encompasses methods of modulating target pre-mRNA splicing and thus expression or activity of the specified protein for therapeutic purposes. In an exemplary embodiment, the modulatory method of the invention involves contacting a cell capable of expressing a target pre-mRNA with a pharmaceutical composition comprising a SMO or vector or transgene encoding same, that is specific for the target pre-mRNA (e.g., is specific for the pre-mRNA) such that expression or one or more of the activities of target pre-mRNA is modulated. These modulatory methods can be performed in vitro (e.g., by culturing the cell with the agent) or, alternatively, in vivo (e.g., by administering the agent to a subject). As such, the present invention provides methods of treating a subject afflicted with a disease or disorder characterized by aberrant splicing of a target pre-mRNA molecule resulting in deleterious protein expression or activity.

A. Method of Modulating 5-HT2C Receptor Pre-mRNA Splicing

In one embodiment, the present invention provides a method of modulating 5-HT2C receptor pre-mRNA splicing using a SMO to mimic the function of the snoRNA, HBII-52, in a subject. The method comprises administering a SMO of the invention, or a composition comprising a SMO of the invention, to a subject, wherein the SMO contacts 5-HT2CR pre-mRNA and modulates the splicing of the 5-HT2CR pre-mRNA to include exon 5b in the mature mRNA.

Diseases and disorders where increasing 5-HT2CR expression is believed to provide a therapeutic benefit to the subject afflicted with the disease include, but are not limited to, PWS and Angelman Syndrome (Kishore et al., 2006, Cold Spring Harbor Symp. Quant. Biol. 71: 329-334; Kishore et al., 2006, Science, 311: 230-232; Sridhar et al., 2008, J. Biomed. Sci., 15: 697-705); hyperphagia induced obesity (Dunlop et al., 2006, CNS Drug Rev., 12: 167-177; Nilsson, 2006, J. Med. Chem., 49: 4023-4034); obsessive/compulsive disorder (Flaisher-Grinberg et al., 2008, Int. J. Neuropsychopharmacology, 11: 811-825); depression, including psychotic depression, major depressive disorder, bipolar disorder (Rosenzweig-Lipson et al., 2007, Psychopharmacology (Berl), 192: 159-170; Dunlop et al., 2006, CNS Drug Rev., 12: 167-177; Rosenzweig-Lipson et al., 2007, Drug News Perspect., 20: 565-571); sleep impairment (Monti et al., 2008, Prog. Brain Res., 172: 625-646); autism (Tandon et al., 2008, Mol. Med., 105: 79-84); epilepsy (Bagdy et al., 2007, J Neurochem., 100: 857-873; Tupal et al., 2006, Epilepsia, 47: 21-26); schizophrenia (Rosenzweig-Lipson et al., 2007, Drug News Perspect., 20: 565-571); Parkinson's disease (Di et al., 2006, Curr. Med. Chem., 13: 3069-3081); drug addiction (Bubar et al., 2008, Prog. Brain Res., 172: 319-346); spinal cord injury or traumatic brain injury (Kao et al., 2006, Brain Res., 1112: 159-168); neuopathic pain (Nakae et al., 2008, Eur. J. Neurosci. 27: 2373-2379; Nakae et al., 2008, Neurosci. Res., 60: 228-231); diabetes (Wade et al., 2008, Endocrinology, 149: 955-961); Alzheimer's disease (Pritchard et al., 2008, Neurobiol. Aging, 29: 341-347; Arjona et al., 2002, Brain Res., 951: 135-140), and chronic pain.

In another embodiment, the present invention provides a method of treating a subject afflicted with PWS. The method comprises administering a SMO of the invention, or a composition comprising a SMO of the invention, to a subject afflicted with PWS, wherein the SMO contacts 5-HT2CR pre-mRNA and modulates the splicing of the 5-HT2CR pre-mRNA to include exon 5b from the mRNA, thereby resulting in expression of a full-length, functional 5-HT2CR protein in the subject.

In yet another embodiment, the present invention provides a method of treating a subject afflicted with a 5-HT2CR splicing defect, where the defect results in a non-functional truncated 5-HT2C receptor that includes exon 5a, but not exon 5b. The method comprises administering a SMO of the invention, or a composition comprising a SMO of the invention to a subject afflicted with a 5-HT2CR splicing defect, wherein the SMO contacts 5-HT2CR pre-mRNA and modulates the splicing of the 5-HT2CR pre-mRNA, thereby resulting in expression of a full-length, functional 5-HT2CR protein in the subject.

In still another embodiment, the present invention provides a method of treating a subject afflicted with hyperphagia. In one aspect, the hyperphagia is caused by a 5-HT2CR splicing defect. In another aspect, the hyperphagia is not caused by a 5-HT2CR splicing defect, but the subject afflicted with hyperphagia experiences a therapeutic benefit from increasing expression of the 5-HT2CR. The method comprises administering a SMO of the invention, or a composition comprising a SMO of the invention, to a subject afflicted with hyperphagia, wherein the SMO contacts 5-HT2CR pre-mRNA and modulates the splicing of the 5-HT2CR pre-mRNA, thereby resulting in increased expression of a full-length, functional 5-HT2CR protein and reducing hyperphagia in the subject.

In yet another embodiment, the present invention provides a method of treating a subject afflicted with obsessive-compulsive disorder (OCD), or a subject afflicted with the symptoms of OCD, In one aspect, the OCD is caused by a 5-HT2CR splicing defect. In another aspect, the OCD is not caused by a 5-HT2CR splicing defect, but the subject afflicted with OCD experiences a therapeutic benefit from increasing expression of the 5-HT2CR. The method comprises administering a SMO of the invention, or a composition comprising a SMO of the invention, to a subject afflicted with OCD, wherein the SMO contacts 5-HT2CR pre-mRNA and modulates the splicing of the 5-HT2CR pre-mRNA, thereby resulting in expression of a full-length, functional 5-HT2CR protein and a reductions of the symptoms of OCD in the subject.

B. Method of Modulating GluR Receptor Pre-mRNA Splicing

In one embodiment, the present invention provides a method of treating a subject afflicted with a GluR splicing defect, where the defect results in a non-functional GluR. The method comprises administering a SMO of the invention, or a composition comprising a SMO of the invention to a subject afflicted with a GluR splicing defect, wherein the SMO contacts GluR pre-mRNA and modulates the splicing of the GluR pre-mRNA, thereby resulting in expression of a full-length, functional GluR protein in the subject. A skilled artisan will appreciate that the method may be used to modulate splicing of a GluR1, GluR2, GluR3, or Glur4 subunit, as well as any combination thereof.

In another embodiment, the present invention provides a method of modulating splicing of a GluR receptor pre-mRNA using a SMO to decrease the GluR flip isoform expression in a subject. The method comprises administering a SMO of the invention, or a composition comprising a SMO of the invention, to a subject, wherein the SMO contacts a GluR pre-mRNA and modulates the splicing of the GluR to decrease the GluR flip isoform expression and in the subject. A skilled artisan will appreciate that the method may be used to modulate splicing of a GluR1, GluR2, GluR3, or Glur4 subunit, as well as any combination thereof.

In yet another embodiment, the present invention provides a method of treating a subject afflicted with a GluR splicing defect, where the deficit results in a decreased flip:flop isoform ratio for a GluR subunit. The method comprises administering a SMO of the invention, or a composition comprising a SMO of the invention, to a subject afflicted with an abnormal flip:flop ratio, wherein the SMO contacts GluR pre-mRNA and modulates the splicing of the GluR pre-mRNA, thereby resulting in decreased flip:flop isoform ratio for a GluR subunit. A skilled artisan will appreciate that the method may be used to modulate splicing of a GluR1, GluR2, GluR3, or Glur4 subunit, as well as any combination thereof.

In still another embodiment, the present invention provides a method of treating a subject afflicted with amyotrophic lateral sclerosis (ALS; Sandyk, R., 2006, Int. J. Neurosci. 116: 775-826; Ionov, I. D., 2007, Amyotroph. Lateral Scler. 8:260-265). The method comprises administering a SMO of the invention, or a composition comprising a SMO of the invention, to a subject, wherein the SMO contacts a GluR pre-mRNA and modulates the splicing of the GluR pre-mRNA to decrease the GluR flip isoform expression and/or decrease the GluR flip/flop isoform ratio in the subject.

In another embodiment, the present invention provides a method of treating a subject afflicted with epilepsy. The method comprises administering a SMO of the invention, or a composition comprising a SMO of the invention, to a subject, wherein the SMO contacts a GluR pre-mRNA and modulates the splicing of the GluR pre-mRNA to decrease the GluR flip isoform expression and/or decrease the GluR flip/flop isoform ratio.

In yet another embodiment, the present invention provides a method of decreasing neuronal excitability in a subject. The method comprises administering a SMO of the invention, or a composition comprising a SMO of the invention to a subject afflicted with neuronal excitotoxicity, wherein the SMO contacts GluR pre-mRNA and modulates the splicing of the GluR pre-mRNA, thereby resulting in decreased flip:flop isoform ratio for a GluR subunit. A skilled artisan will appreciate that the method may be used to modulate splicing of a GluR1, GluR2, GluR3, or Glur4 subunit, as well as any combination thereof.

In yet another embodiment, the present invention provides a method of decreasing a $Ca^{2+}$-conductance through a GluR in a subject. The method comprises administering a SMO of the invention, or a composition comprising a SMO of the invention to a subject, wherein the SMO contacts GluR pre-mRNA and modulates the splicing of the GluR pre-mRNA, thereby resulting in a decreased $Ca^{2+}$-conductance through an AMPA channel in a subject. A skilled artisan will appreciate that the method may be used to modulate splicing of a GluR1, GluR2, GluR3, or Glur4 subunit, as well as any combination thereof.

In yet another embodiment, the present invention provides a method of increasing GluR desensitization in a subject. The method comprises administering a SMO of the invention, or a composition comprising a SMO of the invention to a subject, wherein the SMO contacts GluR pre-mRNA and modulates the splicing of the GluR pre-mRNA to decrease the GluR flip isoform expression and/or decrease the GluR flip/flop isoform ratio, thereby resulting in a increased AMPA channel desensitization in a subject. A skilled artisan will appreciate that the method may be used to modulate splicing of a GluR1, GluR2, GluR3, or Glur4 subunit, as well as any combination thereof.

C. Method of Modulating OGA Receptor Pre-mRNA Splicing

In another embodiment, the present invention provides a method of modulating splicing of OGA pre-mRNA using a SMO to decrease expression or functionality of OGA in a subject. The method comprises administering a SMO of the invention, or a composition comprising a SMO of the invention, to a subject, wherein the SMO contacts an OGA pre-mRNA and modulates the splicing of the OGA pre-mRNA to favor expression of naturally occurring splice variants which have reduced catalytic activity. In one aspect, an alternative splice variant of OGA with reduced catalytic activity comprises OGA10t, a read through variant which results in 15 amino acids being added from intron 10. In another aspect, the method comprises administering a SMO of the invention, or a pharmaceutical composition comprising a SMO of the invention, to a subject, wherein the SMO contacts an OGA pre-mRNA and modulates the splicing of the OGA pre-mRNA to favor expression of a non-natural alternative splice variant of OGA with reduced catalytic activity. In one aspect, an alternative splice variant of OGA with reduced catalytic activity comprises OGA□10 wherein exon 10 of the gene is excluded. In another aspect, an alternative splice variant of OGA with reduced catalytic activity comprises OGAΔ8 wherein exon 8 of the OGA gene is excluded. Diseases and disorders where decreasing OGA expression is believed to provide a therapeutic benefit to the subject afflicted with the disease include, but are not limited to, Alzheimer's Disease.

In another embodiment, the present invention provides a method of treating a subject afflicted with Alzheimer's Disease. The method comprises administering a SMO of the invention, or a composition comprising a SMO of the invention, to a subject, wherein the SMO contacts an OGA pre-mRNA and modulates the splicing of the OGA pre-mRNA to favor expression of naturally occurring splice variants which have reduced catalytic activity, as described elsewhere herein.

D. Method of Modulating Aph1B Receptor Pre-mRNA Splicing

In one embodiment, the present invention provides a method of modulating splicing of Aph1B pre-mRNA using a SMO to decrease expression or functionality of Aph1B in a subject. The method comprises administering a SMO of the invention, or a pharmaceutical composition comprising a SMO of the invention, to a subject, wherein the SMO contacts an Aph1B pre-mRNA and modulates the splicing of the Aph1B pre-mRNA to favor expression of Aph1BΔ4, a variant in which exon 4 of Aph1B is deleted and is, thus, non-functional. Diseases and disorders where increasing Aph1B expression is believed to provide a therapeutic benefit to the subject afflicted with the disease include, but are not limited to, Alzheimer's Disease.

In another embodiment, the present invention provides a method of treating a subject afflicted with Alzheimer's Disease. The method comprises administering a SMO of the invention, or a composition comprising a SMO of the invention, to a subject, wherein the SMO contacts an Aph1B pre-mRNA and modulates the splicing of the Aph1B pre-mRNA to favor expression of Aph1BΔ4, as described elsewhere herein.

E. Method of Modulating FOXM1 Receptor Pre-mRNA Splicing

In another embodiment, the present invention provides a method of modulating splicing of FOXM1 pre-mRNA using a SMO to decrease expression or functionality of FOXM1 in a subject. The method comprises administering a SMO of the invention, or a composition comprising a SMO of the invention, to a subject, wherein the SMO contacts a FOXM1 pre-mRNA and modulates the splicing of the Aph1B pre-mRNA to favor expression of FOXM1Δ3 or FOXM1Δ6. Diseases and disorders where increasing FOXM1 expression is believed to provide a therapeutic benefit to the subject afflicted with the disease include, but are not limited to, aberrant cell growth, cell differentiation, aberrant cell migration, tumorigenesis, or cancer including a liver cancer (The et al., 2002, Cancer Res. 62: 4773-80), abreast cancer (Wonsey et al., 2005, Cancer Res. 65(12): 5181-9), a lung cancer (Kim et al., 2006, Cancer Res. 66(4): 2153-61), a prostate cancer (Kalin et al., 2006, Cancer Res. 66(3): 1712-20; a cervical cancer of the uterus (Chan et al., 2008, J. Pathol. 215 (3): 245-52), a colon cancer (Douard et al., 2006, Surgery 139 (5): 665-70), a pancreatic cancer (Wang et al., 2007, Cancer Res. 67 (17): 8293-300), and a brain cancer (Liu et al., 2006, Cancer Res. 66 (7): 3593-602).

In another embodiment, the present invention provides a method of treating a subject afflicted with aberrant cell growth, cell differentiation, aberrant cell migration, tumerigenesis, or cancer. The method comprises administering a SMO of the invention, or a composition comprising a SMO of the invention, to a subject, wherein the SMO contacts a FOXM1 pre-mRNA and modulates the splicing of the FOXM1 pre-mRNA to inhibit expression of FOXML as described elsewhere herein.

F. Method of Modulating HER3 Receptor Pre-mRNA Splicing

In one embodiment, the present invention provides a method of modulating splicing of HER3 pre-mRNA using a SMO to decrease expression or functionality of HER3 in a subject. The method comprises administering a SMO of the invention, or a composition comprising a SMO of the invention, to a subject, wherein the SMO contacts a HER3 pre-mRNA and modulates the splicing of the HER3 pre-mRNA. In one aspect, the SMO specifically binds to the complementary sequence and enhances inclusion of intron 3 favoring expression of a truncated, non-functional HER3 protein. In another aspect, the SMO specifically binds to the complementary sequence and enhances exclusion of exon 3 to favor expression of HER3Δ3 to produce a non-functional protein. In still another aspect, the SMO contacts a HER3 pre-mRNA and enhances the exclusion of exon 11 to favor expression of HER3Δ11 to produce a non-functional protein. Diseases and disorders where decreasing HER3 expression is believed to provide a therapeutic benefit to the subject afflicted with the disease include, but are not limited to, aberrant cell growth, cell differentiation, aberrant cell migration, tumerigenesis, cancer, and a metastatic cancer.

In another embodiment, the present invention provides a method of treating a subject afflicted with aberrant cell growth, cell differentiation, aberrant cell migration, tumerigenesis, or a cancer (Baselga et al., 2009, Nat Rev Cancer 9:463-475) including liver (The et al., 2002, Cancer Res. 62: 4773-80) breast, or a metastatic cancer derived from breast (Wonsey et al., 2005, Cancer Res. 65 (12): 5181-9), lung (Kim et al., 2006, Cancer Res. 66 (4): 2153-61), prostate (Kalin et al., 2006, Cancer Res. 66 (3): 1712-20; cervix of uterus (Chan et al., 2008, J. Pathol. 215 (3): 245-52), colon (Douard et al., 2006, Surgery 139 (5): 665-70), pancreas (Wang et al., 2007, Cancer Res. 67 (17): 8293-300), and brain (Liu et al., 2006, Cancer Res. 66 (7): 3593-602). The method comprises administering a SMO of the invention, or a composition comprising a SMO of the invention, to a subject, wherein the SMO contacts a HER3 pre-mRNA and modulates the splicing of the Her3 pre-mRNA to inhibit expression or function of HER3, as described elsewhere herein.

G. Method of Modulating CypD Receptor Pre-mRNA Splicing

In one embodiment, the present invention provides a method of modulating splicing of CypD pre-mRNA using a SMO to inhibit expression or functionality of CypD in a subject. The method comprises administering a SMO of the invention, or a composition comprising a SMO of the invention, to a subject, wherein the SMO contacts a CypD pre-mRNA and modulates the splicing of the CypD pre-mRNA to favor expression of CypDΔ1 or CypDΔ3 which exclude exons 1 and 3 respectively. Diseases and disorders where decreasing CypD expression is believed to provide a therapeutic benefit to the subject afflicted with the disease include, but are not limited to, ALS, aberrant cell growth, cell differentiation, aberrant cell migration, tumerigenesis, Hepatitis B infection, and liver cancer.

In another embodiment, the present invention provides a method of treating a subject afflicted with amyotrophic lateral sclerosis (ALS; Sandyk, R., 2006, Int. J. Neurosci. 116: 775-826; Ionov, I. D., 2007, Amyotroph. Lateral Scler. 8:260-265). The method comprises administering a SMO of the invention, or a composition comprising a SMO of the invention, to a subject, wherein the SMO contacts a cyclophilin-D pre-mRNA and modulates the splicing of the CypD pre-mRNA in the subject.

In another embodiment, the present invention provides a method of treating a subject afflicted with aberrant cell growth, cell differentiation, aberrant cell migration, tumerigenesis, hepatitis B infection, and liver cancer. The method comprises administering a SMO of the invention, or a composition comprising a SMO of the invention, to a subject, wherein the SMO contacts a CypD pre-mRNA and modulates the splicing of the CypD pre-mRNA to inhibit expression of CypD, as described elsewhere herein.

Methods of Administration

Examples of methods for introducing oligonucleotides into cells encompass in vivo and ex vivo methods. The oligonucleotides of the invention, i.e. SMOs, are typically administered to a subject or generated in situ such that they hybridize with or bind to pre-mRNA of a specific protein. In one embodiment, the pre-mRNA encodes a 5-HT2CR. In another embodiment, the SMO enhances inclusion of exon 5b during splicing of a 5-HT2CR pre-mRNA. In still another embodiment, the pre-mRNA encodes a glutamate receptor selected from the group consisting of GluR1-4. In yet another embodiment, the SMO modulates the ratio of flip and flop isoforms of any one of, or any combination of, the GluRs. In another embodiment, the pre-mRNA encodes OGA. In yet another embodiment, the pre-mRNA encodes Aph1B. In still another embodiment, the pre-mRNA encodes FOXM1. In still another embodiment, the pre-mRNA encodes HER3. In another embodiment, the pre-mRNA encodes CypD.

The hybridization can be by conventional Watson-Crick base pairing by nucleotide complementarity and/or wobble pairing of U-G or U-A nucleic acids to form a stable duplex. Hybridization can also occur, for example, in the case of an oligonucleotide which binds to DNA duplexes, through specific interactions in the major groove of the double helix.

Conjugation of a SMO to a peptide, liposomes, colloidal polymeric particles as well as other means known in the art may be used to deliver the oligonucleotides to a cell. The method of delivery selected will depend at least on the cells to be treated and the location of the cells and will be known to those skilled in the art. Localization can be achieved by liposomes, having specific markers on the surface for directing the liposome, by having injection directly into the tissue containing the target cells, by having depot associated in spatial proximity with the target cells, specific receptor mediated uptake, or the like.

As described elsewhere herein and in the art, oligonucleotides may be delivered using, e.g., methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (refer to Dokka and Rojanasakul, Advanced Drug Delivery Reviews 44, 35-49, incorporated in its entirety herein by reference). Methods of delivery may also include:

Cationic Lipids: Naked DNA can be introduced into cells in vivo by complexing the DNA with cationic lipids or encapsulating the DNA in cationic liposomes. Examples of suitable cationic lipid formulations include N-[-1-(2,3-dioleoyloxy)propyl]N,N,N-triethylammonium chloride (DOTMA) and a 1:1 molar ratio of 1,2-dimyristyloxypropyl-3-dimethylhydroxyethylammonium bromide (DMRIE) and dioleoyl phosphatidylethanolamine (DOPE) (see e.g., Logan, J. J. et al. (1995) Gene Therapy 2:38-49; San, H. et al. (1993) Human Gene Therapy 4:781-788).

Receptor-Mediated DNA Uptake: Naked DNA can also be introduced into cells in vivo by complexing the DNA to a cation, such as polylysine, which is coupled to a ligand for a cell-surface receptor (see for example Wu, G. and Wu, C. H. (1988) J. Biol. Chem. 263:14621; Wilson et al. (1992) J. Biol. Chem. 267:963-967; and U.S. Pat. No. 5,166,320). Binding of the DNA-ligand complex to the receptor facilitates uptake of the DNA by receptor-mediated endocytosis. A DNA-ligand complex linked to adenovirus capsids which naturally disrupt endosomes, thereby releasing material into the cytoplasm can be used to avoid degradation of the complex by intracellular lysosomes (see for example Curiel et al. (1991) Proc. Natl. Acad. Sci. USA 88:8850; Cristiano et al. (1993) Proc. Natl. Acad. Sci. USA 90:2122-2126). Carrier mediated gene transfer may also involve the use of lipid-based compounds which are not liposomes. For example, lipofectins and cytofectins are lipid-based positive ions that bind to negatively charged DNA and form a complex that can ferry the DNA across a cell membrane. Another method of carrier mediated gene transfer involves receptor-based endocytosis. In this method, a ligand (specific to a cell surface receptor) is made to form a complex with a gene of interest and then injected into the bloodstream. Target cells that have the cell surface receptor will specifically bind the ligand and transport the ligand-DNA complex into the cell.

Oligonucleotides may be directly introduced into the cell (i.e., intracellularly); or introduced extracellularly into a cavity, interstitial space, into the circulation of an organism, introduced orally, or may be introduced by bathing a cell or organism in a solution containing the RNA using methods known in the art for introducing nucleic acid (e.g., DNA) into cells in vivo. Vascular or extravascular circulation, the blood or lymph system, and the cerebrospinal fluid are sites where the RNA may be introduced.

The oligonucleotides of the invention can be delivered to a subject by any art-recognized method. For example, peripheral blood injection of the oligonucleotides of the invention can be used to deliver the reagents via diffusive and/or active means. Alternatively, the oligonucleotides of the invention can be modified to promote crossing of the blood-brain-barrier (BBB) to achieve delivery of said reagents to neuronal cells of the central nervous system (CNS). Specific recent advancements in oligonucleotide technology and delivery strategies have broadened the scope of oligonucleotide usage for neuronal disorders (Forte, A., et al. 2005. Curr. Drug Targets 6:21-29; Jaeger, L. B., and W. A. Banks. 2005. Methods Mol. Med. 106:237-251; Vinogradov, S. V., et al. 2004. Bioconjug. Chem. 5:50-60; the preceding are incorporated herein in their entirety by reference).

In certain embodiments, the oligonucleotides of the invention can be delivered by transdermal methods (e.g., via incorporation of the oligonucleotide reagent(s) of the invention into, e.g., emulsions, with such oligonucleotides optionally packaged into liposomes). Such transdermal and emulsion/liposome-mediated methods of delivery are described for delivery of antisense oligonucleotides in the art, e.g., in U.S. Pat. No. 6,965,025, the contents of which are incorporated in their entirety by reference herein.

The oligonucleotides of the invention may also be delivered via an implantable device (e.g., an infusion pump or other such implantable device). Design of such a device is an art-recognized process.

In one embodiment, a SMO is delivered directly into the cerebral spinal fluid (CSF) of a subject. Delivery of a SMO into the CSF of a subject may be accomplished by any means known in the art, including, but not limited to, epidural injection or intrathecal injection via an infusion pump.

In one embodiment, SMOs are conjugated to a peptide to facilitate delivery of the SMO across the blood brain barrier (BBB) following parenteral administration to a subject. The SMO may be either directly conjugated to the peptide or indirectly conjugated to the peptide via a linker molecule such as a poly amino acid linker, or by electrostatic interaction. Peptides useful in delivering SMOs across the BBB include, but are not limited to, peptides derived from the rabies virus glycoprotein (RVG) that specifically bind to the nicotinic acetylcholine receptor (AchR) present on neurons and the vascular endothelium of the BBB thereby allowing transvascular delivery, probably by receptor-mediated transcytosis (Kumar et al., 2007, Nature 448:39-43, encompassed by reference in its entirety); Kunitz domain-derived peptides called angiopeps (Demeule et al., 2008, J. Neurochem. 106:1534-1544; Demeule et al., 2008, J. Pharmacol. Exp. Ther. 324:1064-1072).

Recombinant methods known in the art can also be used to achieve oligonucleotide reagent-induced modulation of splicing in a target nucleic acid. For example, vectors containing oligonucleotides can be employed to express, e.g., an antisense oligonucleotide to modulate splicing of an exon of a targeted pre-mRNA.

For oligonucleotide reagent-mediated modulation of an RNA in a cell line or whole organism, gene expression may be assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentarnycin, hygromycin, kanamycin, lincomycin, methotrexate, phosphinothricin, puromycin, and tetracyclin. Depending on the assay, quantitation of the amount of gene expression allows one to determine a degree of modulation which is greater than 10%, 33%, 50%, 90%, 95% or 99% as compared to a cell not treated according to the present invention. Lower doses of injected material and longer times after administration of oligonucleotides may result in modulation in a smaller fraction of cells (e.g., at least 10%, 20%, 50%, 75%, 90%, or 95% of targeted cells). Quantitation of gene expression in a cell may show similar amounts of modulation at the level of accumulation of target mRNA or translation of target protein. As an example, the efficiency of modulation may be determined by assessing the amount of gene product in the cell; pre-mRNA or mRNA may be detected with a hybridization probe having a nucleotide sequence outside the region used for the oligonucleotide reagent, or translated polypeptide may be detected with an antibody raised against the polypeptide sequence of that region.

H. Method of Identifying SMOs for Skipping Exons

In general, SMOs function by sterically blocking or weakening interactions between elements of the spliceosomal complex and the pre-mRNA. Factors that influence whether an exon is spliced from its pre-mRNA and included in the mRNA include the strength of the intron-exon splice sites at either end of the exon, and on exonic and intronic regulatory motifs. In general, to facilitate exclusion (skipping) of exons from being included in mRNA of a targeted gene, the SMOs of the invention are designed to be complimentary to sequences encompassing the 5' and/or 3' splice sites and/or ESEs and ISEs and are not-complimentary to (avoid) ESSs and ISSs. Another major determinant of the functionality of SMOs are its thermodynamic properties. The skipping of exons from mRNA transcripts of targeted genes is enhanced by SMOs of the invention using the following set of methods.

(a) Ranking of 5' Splice Site Strength

The relative strength of exonic 5' splice sites is determined by the combination of splice regulatory elements such as ESEs, ESSs, ISEs, and ISSs, as well as how complementary the site is to the binding of the U1 splicing factor. U1 splice site binding is ranked by two criterion: (i) complementarity (Roca, X. et al., 2005, RNA, 11: 683-698) and (ii) thermodynamics of U1 binding to the splice site (Garland, J. A. et al., 2004, Phys Rev E Stat Nonlin Soft Matter Phys, 69: 041903).

(b) Identification ESE/ESS/ISE Motifs

ESE motifs are defined using three prediction tools: ESE Finder (Cartegni, L. et al., 2003, Nucleic Acids Res, 31: 3568-3571), RESCUE-ESE (Fairbrother, W. G. et al., 2002, Science, 297: 1007-1013), and PESX (Zhang, X. H. et al., 2004, Genes Dev, 18: 1241-1250). ESSs are defined using three prediction tools PESX, and a two hexamer data set analysis by FAS-ESS (Wang, Z. et al., 2004, Cell, 119: 831-845). Finally, ISEs are predicted using the ACESCAN2 application (Yeo, G. W. et al., 2005, Proc Natl Acad Sci USA, 102: 2850-2855; Yeo, G. W. et al., 2007, PLoS Genet, 3: e85).

(c) RNA Structure and Oligo Walk

The Oligo Walk function of the publicly available "RNA Structure" program (Mathews, D. H. et al., 2004, Proc Natl Acad Sci USA, 101: 7287-7292) is used to evaluate the predicted open secondary structure of pre-mRNA sequences and the thermodynamic properties of the pre-mRNA. "RNA Structure" also provides analysis of thermodynamic parameters that determine SMO binding strength and efficiency at a given site on the target pre-mRNA.

(1) Duplex $\Delta G°_{37}$: Estimates the Gibbs free energy of the SMO to pre-mRNA binding. More negative values for duplex $\Delta G°_{37}$ will improve SMO binding to its target.

(2) Oligo-self $\Delta G°_{37}$: Estimates the free energy of intramolecular SMO structures. More negative values indicate increasing stability of intermolecular structures which may interfere with target binding.

(3) Oligo-oligo $\Delta G°_{37}$: Provides the free energy of intermolecular SMO structures. Negative values indicate more stable SMO-SMO duplexes, thus values of oligo-oligo $\Delta G°_{37}$ closer to zero will improve SMO functionality.

(4) $T_m$: Estimates the melting temperature of SMO-target sequence duplex formation. Higher $T_m$ values will improve SMO binding and specificity.

(5) Break-Target: Provides the energy penalty for breaking of intramolecular RNA target base pairs when oligo is bound. Thus Optimal Break-point $\Delta G°_{37}$: ≥0 kcal/mol (d) BLAST Analysis of Potential Off-Target Hybridization SMOs are screened using BLASTN analysis for potential hybridization to off-target sites in the human genome. Generally, SMOs with greater than 85% off-target hybridization to any other known pre-mRNA are eliminated from consideration.

(e) Prioritization of SMOs Based on Combined Properties

SMOs are ranked for each of the five thermodynamic criterion with approximate thresholds for criteria 1-3 as in (Matveeva, O. V. et al., 2003, Nucleic Acids Res, 31: 4989-4994) and criterion 4. Criterion 5 is ranked but is not exclusionary. The thermodynamic criterion are combined with the information on splice site strength and splice enhancer motifs to establish candidate SMOs for empirical evaluation of splicing specificity and efficiency.

It is apparent to someone skilled in the art that in most cases SMOs do not meet all criterion and there are necessary compromises made in selecting SMOs for empirical testing. For example a SMO and its target pre-mRNA sequence may be exceptionally favorable from a thermodynamic standpoint, and splice site strength and ESE elements may be strong. However, there may be predicted ESSs that would potentially lower SMO efficiency. The prioritization or weighting of the various factors in are taken into account on a case-by-case basis, when selecting SMOs at a given gene target.

Certain SMOs of the invention are designed to skip 'out of frame' (OOF) exons (coding exon not divisible by 3) that are not alternatively spliced. When constitutive OOF exons are skipped, the codon reading frame is shifted, resulting in an mRNA that encodes inappropriate amino acids followed soon after by a pre-mature stop codon. The protein produced by such OOF exon skipping is non-functional and is degraded. This functions to block protein expression in a cell. Examples exon skipping of OOF exons for the purpose of preventing protein expression in a cell are demonstrated elsewhere herein in the cases of FoxM1, HER3, and CypD.

IV. Pharmaceutical Compositions and Therapies

An SMO of the invention may be administered to a subject in a pharmaceutical composition. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described below.

Depending on the particular target RNA and the dose of oligonucleotide material delivered, this process may modulate function of the target gene. In one embodiment of the instant invention, exon 5b-containing 5-HT2CR protein production is enhanced in a treated cell, cell extract, organism or patient, with an enhancement of exon 5b-containing 5-HT2CR protein levels of at least about 1.1-, 1.2-, 1.5-, 2-, 3-, 4-, 5-, 7-, 10-, 20-, 100-fold and higher values being exemplary. In another embodiment of the invention, flop exon containing GluR protein production is reduced in a treated cell, cell extract, organism, or patient, with a decrease of flip exon GluR protein levels of at least 1.1-, 1.2-, 1.5-, 2-, 3-, 4-, 5-, 7-, 10-, 20-, 100-fold and higher values being exemplary. Enhancement of gene expression refers to the presence (or observable increase) in the level of protein and/or mRNA product from a target RNA. Specificity refers to the ability to act on the target RNA without manifest effects on other genes of the cell. The consequences of modulation of the target RNA can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

The oligonucleotide, i.e. the SMO, may be introduced in an amount which allows delivery of at least one copy per cell. Higher doses (e.g., at least 5, 10, 100, 500 or 1000 copies per cell) of material may yield more effective modulation; lower doses may also be useful for specific applications.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, parenteral, intranasal, buccal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrastemal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

The therapeutic and prophylactic methods of the invention thus encompass the use of pharmaceutical compositions comprising a splice modifying oligonucleotide of the invention to practice the methods of the invention. The precise dosage administered will vary depending upon any number of factors, including but not limited to, the type of animal and type of disease state being treated, the age of the animal and the route of administration.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

III. Kits

Kits for practicing the methods of the invention are further provided. By "kit" is intended any manufacture (e.g., a package or a container) comprising at least one reagent, e.g., at least one SMO for specifically enhancing inclusion of exon 5b in the 5-HT2C receptor for the treatment of Prader-Willi Syndrome, a 5-HT2CR splicing deficit, hyperphagia resulting from a 5-HT2CR splicing deficit, and/or symptoms of obsessive-compulsive disorder resulting from a 5-HT2CR splicing deficit. In one embodiment, the kit includes at least one SMO directed to a GluR for the treatment of epilepsy, a seizure disorder, or ALS. In still another embodiment, the kit includes at least one SMO directed to Aph1B for the treatment of Alzheimer's Disease. In yet another embodiment, the kit of the invention includes at least one SMO directed to OGA for the treatment of Alzheimer's Disease. In a still further embodiment, the kit includes at least one SMO directed to FOXM1 for the treatment of a carcinoma. In still another embodiment, the kit includes at least one SMO directed to HER3 for the treatment of breast cancer. In yet another embodiment, the kit includes at least one SMO directed to CypD for the treatment of ALS or liver cancer. The kit may be promoted, distributed, or sold as a unit for performing the methods of the present invention. Additionally, the kits may contain a package insert describing the kit and including instructional material for its use.

Positive, negative, and/or comparator controls may be included in the kits to validate the activity and correct usage of reagents employed in accordance with the invention. Controls may include samples, such as tissue sections, cells fixed on glass slides, etc., known to be either positive or negative for the presence of the biomarker of interest. The design and use of controls is standard and well within the routine capabilities of those of ordinary skill in the art.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The materials and methods employed in the experiments and the results of the experiments presented in these Examples are now described.

Experimental Example 1

Design and Validation of Antisense Oligonucleotides to Increase Inclusion of Exon 5b in the 5-HT2C Receptor The snoRNA HBII-52 promotes inclusion of exon Vb in the 5-HT2C receptor by blocking a splice silencing element in the consensus region of 5-HT2C. Thus an oligonucleotide identical to the consensus sequence of MBII-52 (the mouse homolog) was designed to block the silencing site on 5-HT2C. The first oligonucleotide was designed using a phosporothioate linkages between nucleotides and O-methyl substitutions on the 2' ribose and is identical to the MBII-52 complementary box as follows:

(SEQ ID NO. 29)
AUGCUCAAUAGGAUUACG.

Smaller SMOs may permit more specific targeting of inhibitory elements in 5-HT2C. Therefore, a series of SMOs of varying lengths were designed using an "antisense walk strategy" that has been recently used to successfully target inhibitory regions in the SMN gene to correct splicing (Hua et al., 2007, Public Library of Science Biol. 5:e73). The SMO was "walked" base by base beginning with the 5'-most nucleotide (nt) aligned at the +3 nt position relative to the consensus sequence on 5-HT2CR pre-mRNA and ending with the 3'-most nt of the oligomer at the −3 nt position of the consensus sequence. This strategy resulted in SMOs that incrementally span the consensus region (Table 1 through Table 15). To ensure proper hybridization efficiency, these smaller SMOs may be composed of an appropriate number of locked nucleic acid (LNA) residues substituted for 2'-O-methyl nucleotides.

To validate these SMOs, the SMOs are transfected into undifferentiated NG108-15 cells that have previously been demonstrated to express both 5-HT2CR splice isoforms (5a and 5b), the ratio of which can be detectably altered by differentiation (Tohda et al., 2002, Jpn. J. Pharmacol. 90:138-144; Sukma et al., 2003, J. Pharmacol. Sci. 92:433-436; Tohda et al., 2004, J. Pharmacol. Sci. 96:164-169). Cells are harvested 48 hours post-transfection. Real-time PCR is used to quantify amounts of 5-HT2CR containing exon 5a and 5b. An SMO that mimics the effect of MBII-52 increases the ratio of 5b to 5a transcripts. Western blotting is also performed using a rabbit polyclonal antibody (Abcam) to quantify upregulation of full-length 5-HT2CR protein.

Experimental Example 2

Phenotypic Improvement in Spinal Muscular Atrophy (SMA) Mice by SMO-Mediated Induction of SMN Expression Spinal Muscular Atrophy (SMA) is caused by mutations in the SMN1 gene, which encodes a protein called 'survival of motor neuron" or SMN, a ubiquitous protein involved in RNA processing (Gubitz et al., 2004, Exp. Cell Res. 296:51-56; Monani, 2005, Neuron 48:885-896). The potential of the SMO developed by the Singh group (Singh et al., 2006, Mol. Cell Biol. 26:1333-1346) to induce SMN expression and improve functional performance in vivo in the SMN$\Delta 7^{+/+}$; SMN2$^{+/+}$; Smn$^{-/-}$ mice with severe type 1 SMA phenotype was recently examined (Le et al., 2005, Hum. Mol. Genet. 14:845-857). First, to assess SMO distribution throughout the CNS, FAM-SMO was delivered intracerebroventricular (ICV) and fluorescent label was imaged in cryosections of brains and spinal cords (FIGS. 1A-1C). SMO was found to be broadly but not uniformly distributed throughout the brain and spinal cord regions. These data were in accordance with previous studies showing very effective CNS biodistribution of SMOs of similar chemistry after both intrathecal and ICV delivery (Smith et al., 2006, J. Clin. Invest. 116:2290-2296).

When SMA mice were given periodic intracerebroventricular injections of SMO they showed greatly enhanced SMN expression at post-natal day 12 in both brain and spinal cord, reaching 35-50% of the levels in wild-type littermates (FIGS. 1D-1E). On average, SMN expression in the hippocampus region of SMA mice injected with SMO was 34.4±1.8%, which was significantly greater than the 13.8±1.0% in un-injected SMA controls (2.5-fold increase; P<0.001). Importantly, the high level of SMN expression in brain and spinal cord of SMA mice after ICV injection of SMO alone was accompanied by a significant improvement in body weight during post-natal development compared with un-treated SMA mice (FIG. 1E). These data represent the highest level of SMN expression reported to date in CNS of SMA mice. These data document that SMOs are broadly distributed and biologically active in CNS after ICV delivery.

Experimental Example 3

Determination of the Ability of Optimal SMO to Increase Inclusion of 5-HT2CR Vb In Vivo SMOs are injected ICV into brains of normal mice (C57bl/6J) for 1 week via a cannula. Optimal dose and dosing regimens are around 2 µg/day for 1 week, but can be optimized by the skilled artisan. Mouse brains are harvested one day after final injection, sub-regions are dissected out (hippocampus, cortex, hypothalamus) and trizol-extracted. Real time (RT) PCR is performed using primers previously shown to be able to distinguish Va and Vb splice variants (Kishore and Stamm, 2006, Science 311:230-232). Since both splice variants are present and detectable in normal mouse brain (Canton et al., 1996, Mol. Pharm. 50:799-807), injection of SMOs will lead to a detectable increase in the ratio of exon 5b to exon 5a-containing isoforms. Western blotting using a rabbit polyclonal antibody (Abcam) is used to determine whether expression of full-length 5-HT2CR protein has been up-regulated.

Experimental Example 4

Examination of Functional Consequence of Modulating 5-HT2CR Splicing Using Electrophysiological Techniques in Hippocampal Slices By increasing inclusion of exon 5b in 5-HT2CR, the expression of functional receptor is also increased. Both 5a and 5b-containing transcripts are abundantly present in hippocampus (Canton et al., 1996, Mol. Pharmacol. 50:799-807), and it has been demonstrated elsewhere herein that SMO injected ICV can notably increase SMN levels in this brain region. Therefore initial electrophysiological assessment is in hippocampal slices. Activation of 5-HT2CR leads to an increase in intrinsic neuronal excitability and glutamate-mediated excitatory postsynaptic current (EPSC) amplitudes in hippocampal CA1 pyramidal neurons (Beck, 1992, Synapse 10:334-340). These studies are done using the selective 5-HT2CR agonist Ro 60-175 (100 nM). The hippocampal slice preparation and whole-cell patch clamping techniques are used to record from CA1 pyramidal neurons. Intrinsic excitability is measured using current-clamp protocols to measure firing properties of neurons in response to voltage steps. EPSC measurements are done using voltage-clamp, and measuring synaptic responses to stimulation of Schaffer collateral input. These techniques are described in (Tallent and Siggins, 1999, J. Neurophysiol. 81:1626-1635; Tallent et al., 2001, J. Neurosci. 21:6940-6948), incorporated herein by reference, in their entirety. An enhancement in the ability of Ro 60-175 to increase excitability and EPSC amplitude after ICV injection of an optimal SMO is due to increases in the expression of functional receptor in CA1 neurons.

Experimental Example 5

GluR Subunit Selection and SMO Design

The pre-mRNA splicing pattern of GluR subunits of the AMPA receptor is shown in FIG. 2. GluRs typically contain either of two mutually-exclusive alternative exons, flip or flop. Thus, the flip/flop exons constitute classical cassette exons, as opposed to constitutive exons which are always retained in mRNA transcripts.

2' OMe SMO that target exonic splice enhancers (ESEs) and splice site of the flip exons of GluRs are developed that facilitate specific skipping of flip exons of GluR pre-mRNAs by masking exon recognition by the spliceosome proteins. When an exon does not get spliced, it is removed (skipped) along with the introns on either side of it. The specific GluR flip subunits to be targeted as potential therapeutic agents for treating ALS include GluR 3, GluR3+GluR4, GluR1, GluR1+GluR3, and GluR1+GluR2+GluR3+GluR4. Because of the nature of conservation/divergence in ESEs and splice junctions of the flip exons of GluRs, it is possible to selectively target any individual GluR for flip exon skipping, but it is not possible to target all possible combinations. For example it may be difficult to target ESEs of both GluR1 and GluR3 in tandem without also impacting an ESE of GluR2. It would likely be even more difficult to target only the GluRs that provide $Ca^{2+}$ permeability to the AMPA receptor (GluR1, GluR3, and GluR4), without also impacting GluR2. Given these constraints, GluR pre-mRNA targets for treating ALS would be as follows:

(a) Ranking of 5' Splice Site Strength

The relative strength of exonic 5' splice sites is determined by the combination of splice regulatory elements such as ESEs, ESSs, ISEs, and ISSs, as well as how complementary the site is to the binding of the U1 splicing factor. U1 splice site binding is ranked by two criterion: (i) complementarity (Roca, X. et al., 2005, RNA, 11: 683-698) and (ii) thermodynamics of U1 binding to the splice site (Garland, J. A. et al., 2004, Phys Rev E Stat Nonlin Soft Matter Phys, 69: 041903).

(b) Identification ESE/ESS/ISE Motifs

ESE motifs are defined using three prediction tools: ESE Finder (Cartegni, L. et al., 2003, Nucleic Acids Res, 31: 3568-3571), RESCUE-ESE (Fairbrother, W. G. et al., 2002, Science, 297: 1007-1013), and PESX (Zhang, X. H. et al., 2004, Genes Dev, 18: 1241-1250). ESSs are defined using three prediction tools PESX, and a two hexamer data set analysis by FAS-ESS (Wang, Z. et al., 2004, Cell, 119: 831-845). Finally, ISEs are predicted using the ACESCAN2 application (Yeo, G. W. et al., 2005, Proc Natl Acad Sci USA, 102: 2850-2855; Yeo, G. W. et al., 2007, PLoS Genet, 3: e85).

(c) RNA Structure and Oligo Walk

The Oligo Walk function of the publicly available "RNA Structure" program (Mathews, D. H. et al., 2004, Proc Natl Acad Sci US A, 101: 7287-7292) is used to evaluate the predicted open secondary structure of pre-mRNA sequences and the thermodynamic properties of the pre-mRNA. "RNA Structure" also provides analysis of thermodynamic parameters that determine SMO binding strength and efficiency at a given site on the target pre-mRNA.

(1) Duplex $\Delta G°_{37}$: Estimates the Gibbs free energy of the SMO to pre-mRNA binding. More negative values for duplex $\Delta G°_{37}$ will improve SMO binding to its target.

(2) Oligo-self $\Delta G°_{37}$: Estimates the free energy of intramolecular SMO structures. More negative values indicate increasing stability of intermolecular structures which may interfere with target binding.

(3) Oligo-oligo $\Delta G°_{37}$: Provides the free energy of intermolecular SMO structures. Negative values indicate more stable SMO-SMO duplexes, thus values of oligo-oligo $\Delta G°_{37}$ closer to zero will improve SMO functionality.

(4) $T_m$: Estimates the melting temperature of SMO-target sequence duplex formation. Higher $T_m$ values will improve SMO binding and specificity.

(5) Break-Target: Provides the energy penalty for breaking of intramolecular RNA target base pairs when oligo is bound. Thus Optimal Break-point $\Delta G°_{37}$: $\geq 0$ kcal/mol (d) BLAST Analysis of Potential Off-Target Hybridization SMOs are screened using BLASTN analysis for potential hybridization to off-target sites in the human genome. Generally, SMOs with greater than 85% off-target hybridization to any other known pre-mRNA are eliminated from consideration.

(e) Prioritization of SMOs Based on Combined Properties

SMOs are ranked for each of the five thermodynamic criterion with approximate thresholds for criteria 1-3 as in (Matveeva, 0. V. et al., 2003, Nucleic Acids Res, 31: 4989-4994) and criterion 4. Criterion 5 is ranked but is not exclusionary. The thermodynamic criterion are combined with the information on splice site strength and splice enhancer motifs to establish candidate SMOs for empirical evaluation of splicing specificity and efficiency.

Experimental Example 6

Measure Relative Efficacy of SMOs Using Mouse Line Endogenously Expressing all Four GluRs For analysis of SMO effectiveness, SMOs designed against the targets listed in Table 2 through Table 7 are transfected into NSC-34 cells which are mouse neuroblastoma-spinal neuron hybrids that endogenously express all four mouse GluRs (Eggett et al., 2000, J. Neurochem. 74:1895-1902; Rembach et al., 2004, J. Neurosci. Res. 77:573-582). The NSC-34 cell line is used widely as a culture model system for the study of motor neurons (Cashman et al., 1992, Dev. Dyn. 194:209-221; Eggett et al., 2000, J. Neurochem. 74:1895-1902). NSC-34 cells were found to express low levels of GluR2 compared to GluR1, 3, and 4. This is consistent with published reports that motor neurons are deficient in GluR2, thus rendering these cells vulnerable to calcium-mediated damage and excitotoxicity (Bar-Peled et al., 1999, Neuroreport 10:855-859; Heath et al., 2002, Neuroreport 13:1753-1757; Van et al., 2002, J. Neurophysiol. 88:1279-1287; Williams et al., 1997, Ann. Neurol. 42:200-207). NSC-34 cells have also been shown to efficiently uptake SMOs in culture (Rembach et al., 2004, J. Neurosci. Res. 77:573-582). Briefly, SMOs are complexed with lipofectamine and applied to NSC-34 cells (100 µM SMO) in reduced serum medium for 4-6 hours (Cashman et al., 1992, Dev. Dyn. 194:209-221; Eggett et al., 2000, J. Neurochem. 74:1895-1902). Medium is replaced and cells are grown for an additional 24-48 hours in serum-containing medium and harvested. Cells are lysed, total RNA extracted (Trizol), and cDNA generated a reverse transcriptase (MultiScribe) using dNTPs and random hexamers. The level of both flip- and flop-containing mRNA transcripts is determined for each of the GluRs using real-time PCR (TaqMan PCR system).

Next, SMOs that show the greatest decrease in the targeted flip isoforms are evaluated more extensively. The dose-response of lead SMOs are analyzed by treating cells with concentrations ranging from 0-100 µM. Westerns blots are used to quantify GluR protein levels with antibodies to GluR1 (1:100, AB5849; Chemicon), GluR2 (1:100, AB1768; Chemicon), GluR3 (1:1,500; (Gahring et al., 1998, Autoimmunity 28:243-248)), and GluR4 (1:100, AB1508; Chemicon). Toxicity is quantified by documenting morphology of nuclei (DAPI), a known hallmark of cell damage.

An iterative process of SMO evaluation and optimization is used where the efficacy of the 2 top-ranked SMOs is performed, and these data used to make the next SMO choices in a strategic manner. For example if a SMO shows a significant but incomplete reduction in flip isoform expression, bases are added or subtracted from either end to further improve efficacy.

Experimental Example 7

Determine Changes in Electrophysiological Properties of AMPA Currents after Treatment with Lead SMOs The SMOs that produce the most efficacious skipping of flip exons are transfected into NSC-34 cells and AMPA-receptor mediated currents are studied using whole cell patch clamp. Changes in flip/flop ratios of GluRs change properties of AMPA receptor-mediated currents. Increases in the flop to flip ratio result in the following changes in AMPA receptor currents: (i) An increase in desensitization kinetics (Sommer et al., 1990, Science 249:1580-1585). (ii) A decrease in the sensitivity to cyclothiazide (Johansen et al., 1995, Mol. Pharm. 48:946-955; Partin et al., 1994, Neuron 14:833-843) and an increase in the sensitivity to PEPA (Sekiguchi et al., 1998, Br. J. Pharmacol. 123:1294-1303). (iii) A decrease in sensitivity for glutamate (Partin et al., 1995, Neuron 14:833-843; Sommer et al., 1990, Science 249:1580-1585).

NSC-34 cells have also been shown to efficiently uptake SMOs in culture (Rembach et al., 2004, J. Neurosci. Res. 77:573-582). Briefly, SMOs are complexed with lipofectamine and applied to NSC-34 cells (100 $\mu$M SMO) in reduced serum medium for 4-6 hours (to induce differentiation (Eggett et al., 2000, J. Neurochem. 74:1895-1902; Rembach et al., 2004, J. Neurosci. Res. 77:573-582). Medium is replaced and cells grown for an additional 24-48 hours in serum-containing medium and harvested. Cells are lysed, total RNA extracted (Trizol), and cDNA generated with a reverse transcriptase (MultiScribe) using dNTPs and random hexamers. The level of both flip- and flop-containing mRNA transcripts is determined using real-time PCR using the TaqMan PCR system.

The whole-cell patch clamp method is used to record from treated and untreated cells using a perfusion chamber. Cells are voltage-clamped at −70 mV and 1 mM or 10 mM glutamate or AMPA is applied using a rapid superfusion system. AP5 is used to block NMDA receptors. To evaluate desensitization kinetics, 100 millisecond (ms) pulses of glutamate (Gardner et al., 2001, J. Neurosci. 21:7428-7437) are used. Desensitization kinetics are measured by fitting the decay of the AMPA current with single and double exponentials using Clampfit software (Molecular Devices).

To determine cyclothiazide sensitivity, this drug (1-100 $\mu$M) is co-applied with 10 mM glutamate for 3 sec. For PEPA experiments, 10 mM glutamate and 1-1000 $\mu$M PEPA are co-applied for 1 sec. Dose-response curves are generated and desensitization kinetics determined as described above. Difference in sensitivity to PEPA is greatest for GluR3 flip vs. flop, so this drug may be especially useful in determining an increase in GluR3 flop (Sekiguchi et al., 1998, Br. J. Pharmacol. 123:1294-1303).

Glutamate sensitivity is determined by applying different concentrations of glutamate (50 to 5000 $\mu$M) and generating dose-response curves of maximal current response. Since flip isoforms have a higher relative sensitivity to glutamate vs. kainate, the responsiveness of individual cells to 300 $\mu$M glutamate vs. 300 µM kainite is also assessed (Partin et al., 1995, Neuron 14:833-843; Sommer et al., 1990, Science 249:1580-1585).

Experimental Example 8

In Vivo Application of SMOs

A cannula is implanted into the third ventricle (coordinates: midline, 0.25 mm posterior to the bregma and 3 mm below the pial surface). Injection into the third ventricle (ICV) gives good access to the hippocampus (Chauhan et al., 2001, J. Neurosci. Res. 66:231-235). Forty eight hours following surgery, delivery of SMO ICV is begun daily for 1 week. SMOs are dissolved in sterile saline at 1 µg/µL. Optimal dose and dosing regimens can be determined by the skilled artisan, but based on previous experience, is around 2 µg/day for 1 week. Mouse brains are harvested one day after final injection, hippocampus dissected out and trizol-extracted. Real time (RT) PCR is performed using primers previously shown to specifically amplify flip and flop splice variants (Seifert et al., 2003, Mol. Cell. Neurosci. 22:248-258; Gomes et al., 2007, Mol. Cell. Neurosci. 37(2): 323-334). Significant changes in splicing are confirmed using Western blotting to determine if there are detectable changes in GluR1 protein levels.

ICV injection of the SMOs (N=5) that target GluR3-flip and GluR1-flip were made in neonatal FVB mice on postnatal days 1, 3, and 5. Control injections of saline were also made (N=4). ICV injection of the SMOs that target GluR3-flip and GluR1-flip produce potent and specific reduction in targeted transcript expression in brain tissue harvested 24 hours after the final administration of SMO (FIG. 3). Flip and flop transcript levels of all GluRs were measured using real-time PCR. Both the GluR3 and the GluR1 SMOs produced nearly complete reduction in targeted transcription expression with no significant effect on other GluR isoforms. Decreasing flip in principle neurons and glia is protective against seizures (Seifert et al., 2004, J. Neurosci. 24:1996-2003; Ge et al., 2006, Science 312:1533-1537).

Figure 4:
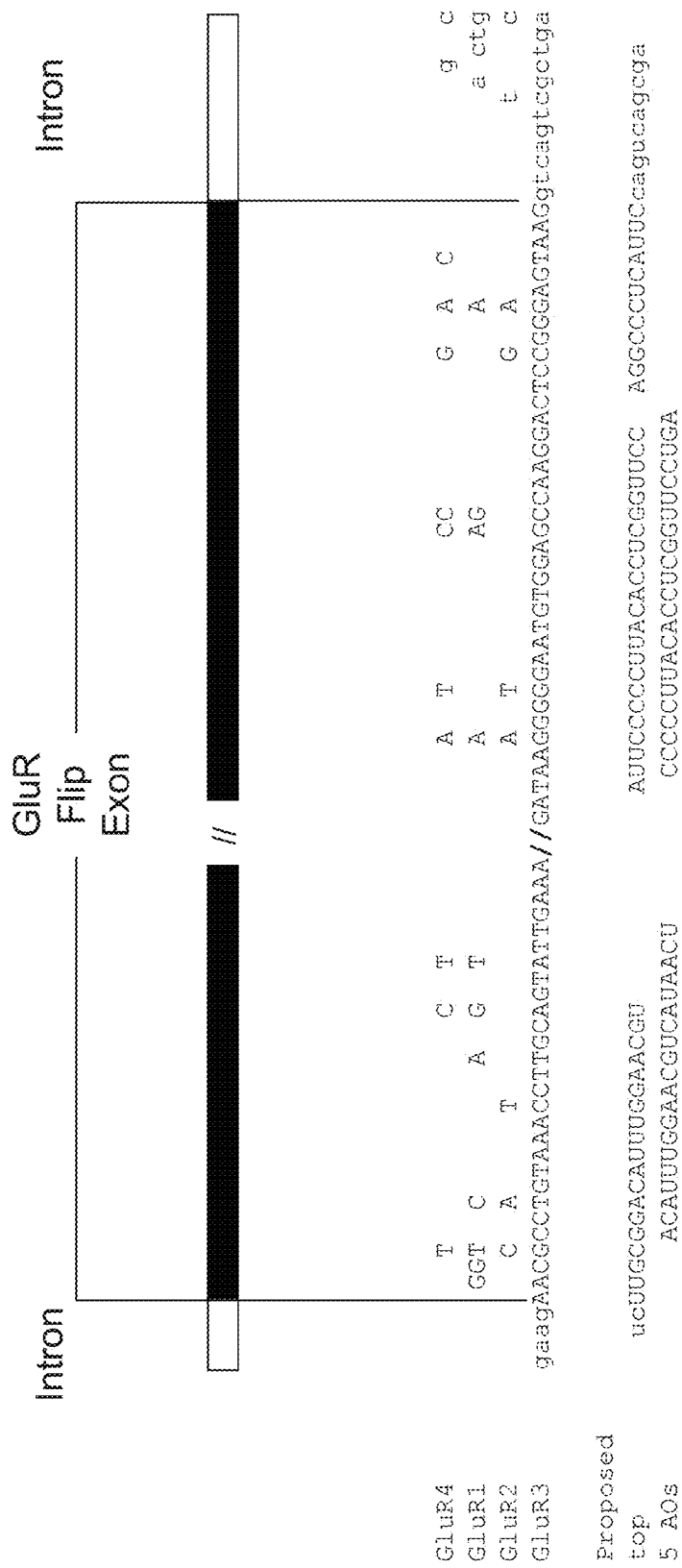
FIG. 4 is a schematic illustration of candidate SMOs evaluated for skipping GluR3 flip exon. All SMO-target pairs have favorable thermodynamic properties and are complementary to splice sites and/or ESEs. The GluR3 flip exon, and adjoining intron nucleotides, is reflected in the fourth line of FIG. 4 (SEQ ID NO: 1101). The GluR4 flip exon, and adjoining intron nucleotides, is reflected in the first line of FIG. 4 (SEQ ID NO: 1098), showing only nucleotides differing from SEQ ID NO: 1101. The GluR1 flip exon, and adjoining intron nucleotides, is reflected in the second line of FIG. 4 (SEQ ID NO: 1099), showing only nucleotides differing from SEQ ID NO: 1101. The GluR2 flip exon, and adjoining intron nucleotides, is reflected in the third line of FIG. 4 (SEQ ID NO: 1100), showing only nucleotides differing from SEQ ID NO: 1101.

ICV injections of the SMOs that target all four GluR flip isoforms neonatal FVB mice on postnatal days 1, 3, and 5 produce potent reduction in GluR1, GluR2, and GluR3 flip transcript expression in brain tissue harvested 24 hours after the final administration of SMO (FIG. 4). A concomitant increase in flop transcripts was also observed.

Experimental Example 9

Efficacy of SMO in Modulating Seizure Activity in Mice

Figure 5:
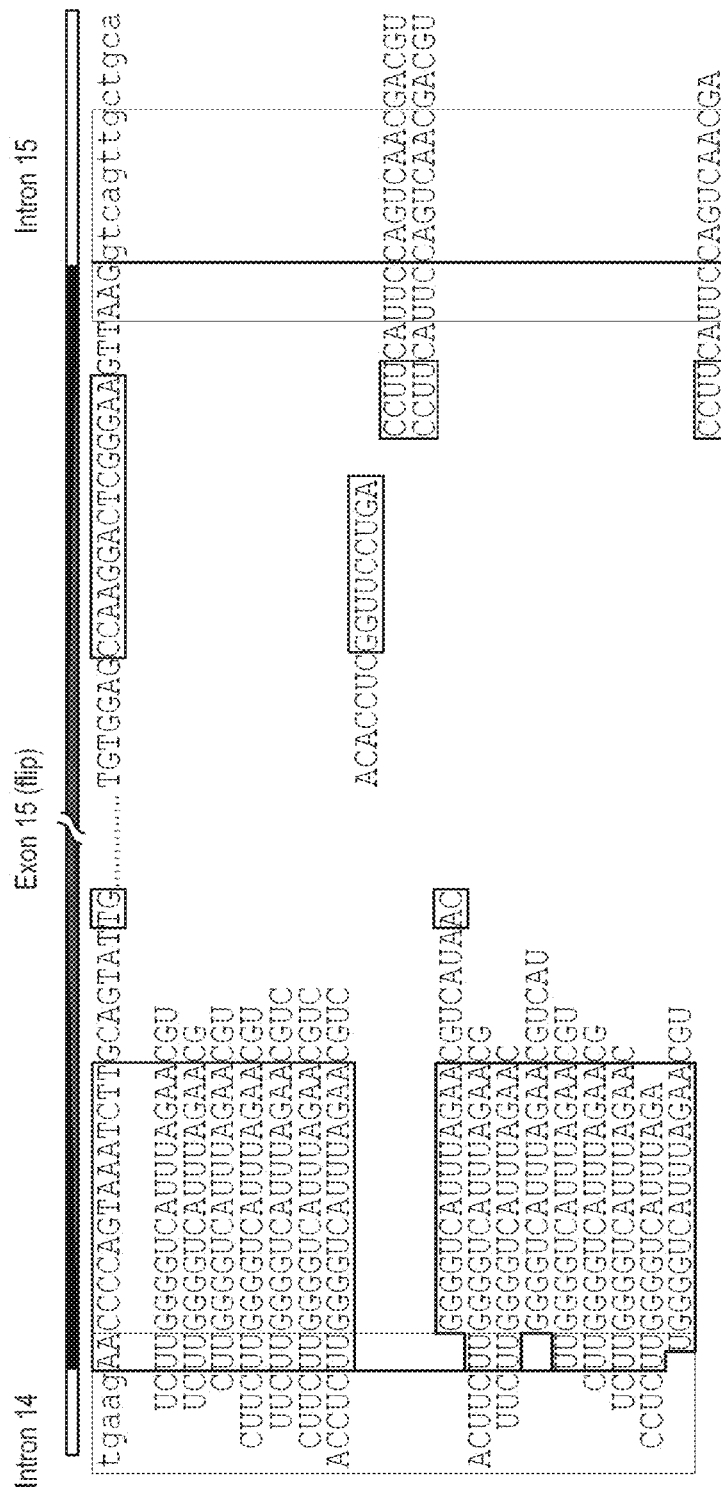
FIG. 5 is a schematic illustration of candidate SMOs evaluated for skipping GluR2 exon 15 (flip). All SMO-target pairs have favorable thermodynamic properties and are complementary to splice sites and/or ESEs. The GluR2 exon 15 (flip), and adjoining intron nucleotides, is reflected in the first line of FIG. 5 (SEQ ID NO: 1106). The candidate SMOs follow below in the following order: SEQ ID NO: 433, SEQ ID NO: 442, SEQ ID NO: 443, SEQ ID NO: 413, SEQ ID NO: 414, SEQ ID NO: 404, SEQ ID NO: 1107, SEQ ID NO: 1108 (aligned center), SEQ ID NO: 1109 (aligned right), SEQ ID NO: 1110 (aligned right), SEQ ID NO: 1111, SEQ ID NO: 412, SEQ ID NO: 441, SEQ ID NO: 1112, SEQ ID NO: 453, SEQ ID NO: 452, SEQ ID NO: 451, SEQ ID NO: 449, SEQ ID NO: 463, and SEQ ID NO: 1113 (aligned right).
Figure 6:
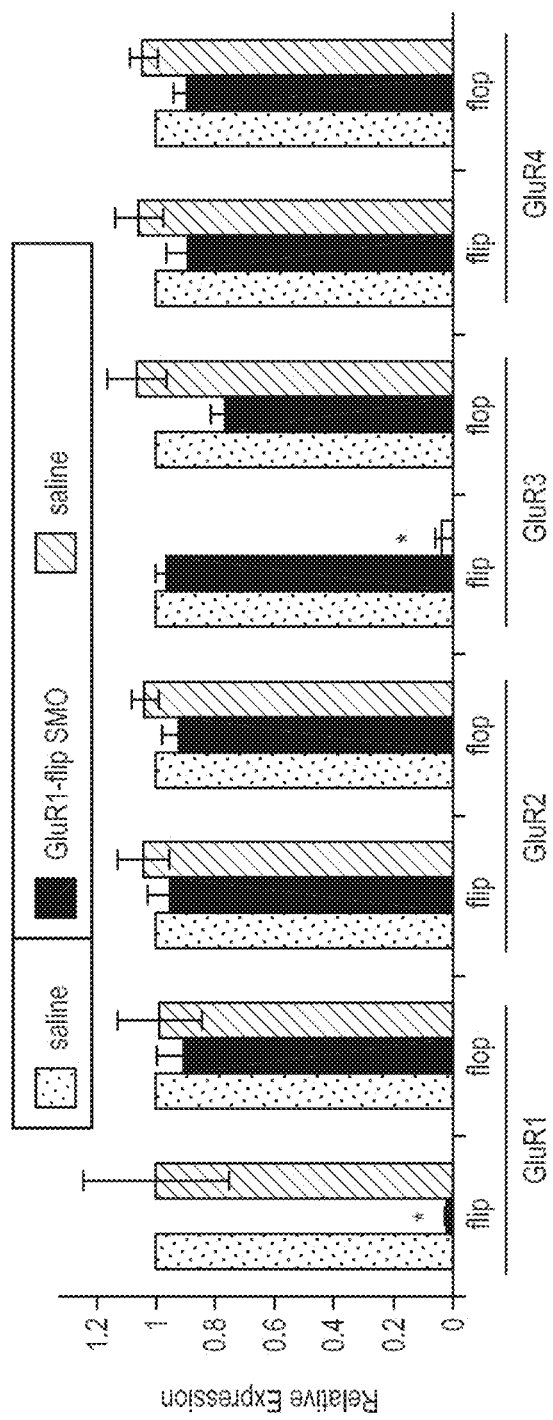
FIG. 6 is a graph depicting the relative expression of GluR1, GluR2, Glur3 and GluR4 flip and flop isoforms following ICV injections of SMOs targeting GluR1-flip and GluR3-flip isoforms.
Figure 7:
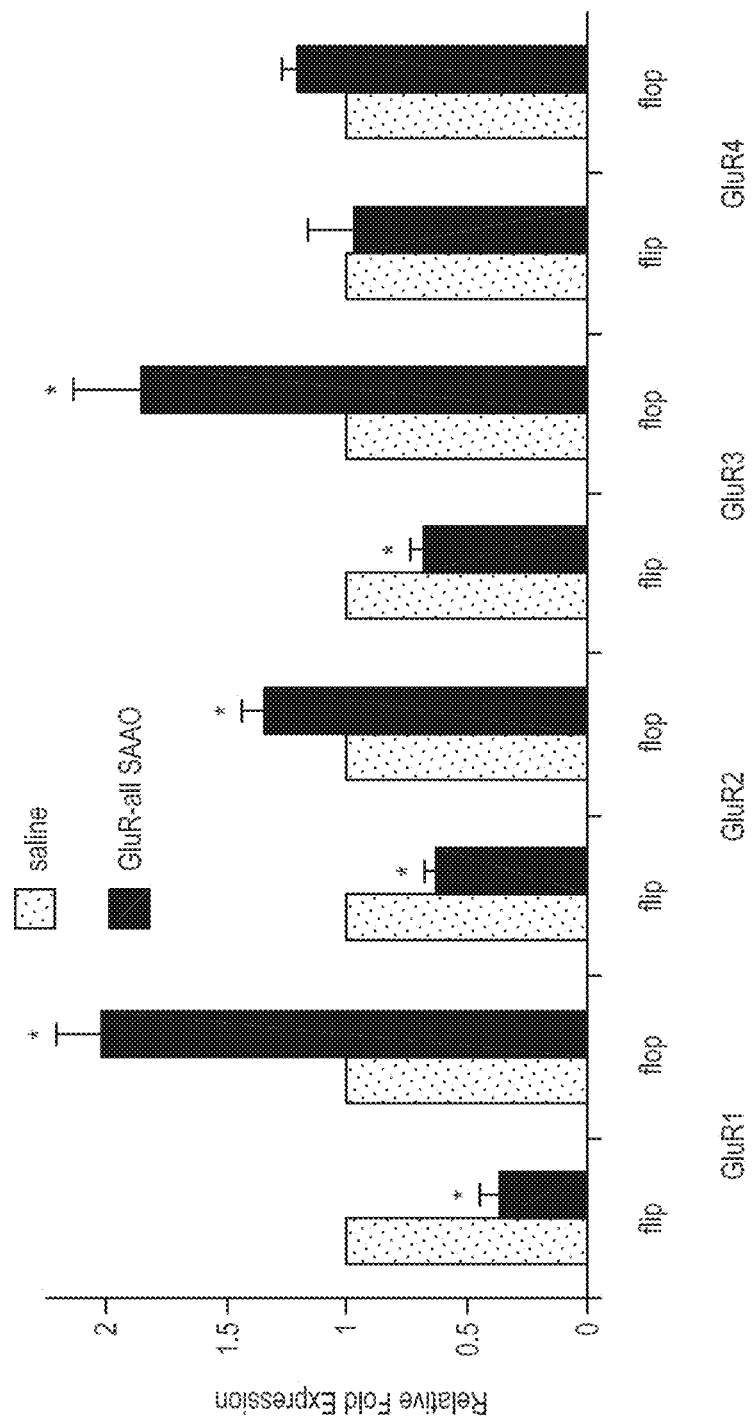
FIG. 7 is a graph depicting the relative change in expression of GluR1, GluR2, Glur3 and GluR4 flip and flop isoforms following ICV injections of SMOs targeting all four GluR flip isoforms.
Figure 8:
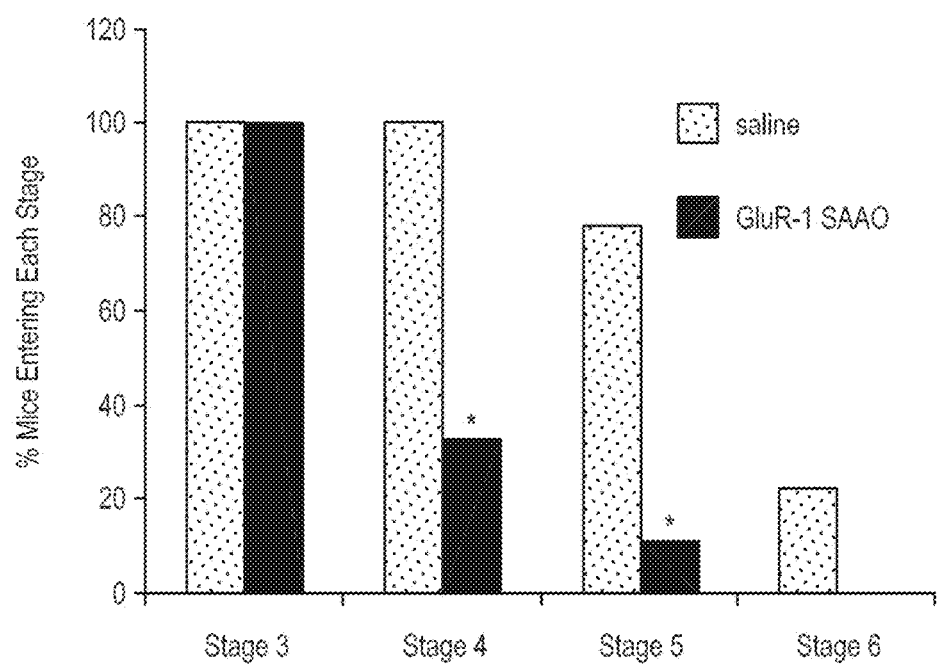
FIG. 8 is a graph depicting the effect of ICV administration of a SMO targeting GluR-1 on seizure activity in mice.

Neonatal mice were administered ICV injections of GluR1 SMO on postnatal day 1, 3, and 5 and tested for seizure activity on postnatal day 10. Control ICV injections of saline were also done. Seizures were induced via an intraperitoneal injection of kainic acid and the stage of seizure was evaluate from the least severe (stage 3) to status epilepticus (stage 6). GluR1 SMO administration significantly reduces the percent of mice entering stage 4, stage 5, and stage 6 seizures (FIG. 5).

Experimental Example 10

Using SMOs to Target HER3 and Treat Breast Cancer

SMOs as described elsewhere herein are developed which potently and specifically reduce HER3 expression in a cell, reduce tumorigenesis of HER2 overexpressing breast cancer cells (HOBCs) in vitro, and block metastasis in vivo. The SMOs specifically modulate HER3 pre-mRNA splicing, resulting in downregulation of functional full-length HER3. All SMOs are synthesized using of 2'MOE chemistry and designed to target identified naturally occurring non-functional alternative splice variants of HER3, as well as novel isoforms. HER3-specific SMOs are evaluated for efficacy by transfecting HOBC lines (including SKBR3, BT474, and MDA-MB-453 cell lines). Changes in HER3 expression in cells transfected with SMOs are evaluated using real-time PCR and Western blot analysis to determine the level of HER3 expression at the nucleic acid and protein level. The effects of SMOs on activation of Akt pathway in breast cancer cells using phosphospecific antibodies is also done. Cell lines are also transfected with scrambled SMOs as a negative controls.

SMOs are evaluated in HBOCs (primarily SKBR3 cells) by measuring several indices of oncogenic activity including effects on: (i) growth in soft agar, (ii) survival from matrix detachment, and (iii) invasion using transwell invasion assays.

Liver is a primary site of metastasis of HOBCs. SMOs localize most specifically to liver after IV and IP delivery (Yu et al., 2009, Biochem. Pharmacol. 77:910-919). The efficacy of SMOs directed against HER3 in blocking breast cancer cell metastasis in liver is evaluated as follows. SKBR3 cells ($1 \times 10^6$), stably transformed to express luciferase reporter, are administered through the tail vein of scid mice (N=10), immediately followed by IV injection of an HER3 targeted SMO. SMOs are injected weekly (IV) for about 6 weeks. The determination of the optimal interval for administering a SMO is well without routine experimental optimization in the art. Metastasis in liver and other organs is visualized with the quantitative IVIS Lumina Imaging System. Livers are then removed and analyzed for indices of macro and micrometastasis. HER3 expression is measured using immunohistochemistry. Mice (N=10) injected with SKBR3 cells and scrambled SMOs are controls.

Experimental Example 11

Using SMOs to Target OGA to Reduce Tau Hyperphosphorylation in Treat Alzheimer's Disease SMOs which target splicing of both human and mouse OGA pre-mRNA to generate splice isoforms with dominant negative properties and reduced catalytic efficiency have been developed according to the methods described elsewhere herein. Exemplary SMOs targeted to produce the OGA10t and OGAΔ8 isoforms are depicted in Table 7 and Table 8.

SMOs are evaluated for their effect on O-GlcNAc levels by western blot of total protein in a cell using anti-O-GlcNAc antibody CTD110.6 (Dorfmueller et al., 2009, Biochem. J. 420:221-227). OGA splice isoforms with lowered catalytic activity result in increases of O-GlcNAcylation of proteins, since OGA will continue to attach O-GlcNAc residues on nuclear and cytoplasmic targets more rapidly than they can be removed (Yuzwa et al., 2008, Nat. Chem. Biol. 4:483-490).

SMOs are specifically delivered to the CNS by ICV injection to avoid off target peripheral effects. SMOs are delivered using short term continuous infusion of a pharmaceutical composition comprising an SMO by a stereotaxically implanted cannulae in the lateral brain ventricle and connected to a sub-cutaneously implanted osmotic pump (Alzet). Normal mice are administered either saline or a dose of SMO ranging from 1-10 µg of SMO daily for 3 weeks (Smith et al., 2006, J. Clin. Invest. 116:2290-2296). During the 3 weeks of SMO infusion, mice are evaluated weekly for declarative and spatial memory, and motor deficits by Morris water maze, novel object recognition, and rotarod testing.

Following the period of SMO administration, mice are euthanized and brain tissue (including cortex and hippocampus) extracted for testing. Real-time PCR performed on brain sections to determine transcript levels of the desired OGA10t or OGAΔ8 alternative splice isoforms. Brain tissue from saline and SMO dosed mice is also be evaluated by western blot for global increases in O-GlcNAc levels.

Triple Transgenic Alzheimer's (3×Tg) mice are administered SMOs at a dose which provides optimal effects on increasing O-GlcNAc levels. The 3×Tg mice are transgenic for $PS1_{M146V}$, $APP_{Swe}$, and $tau_{p301L}$ mutations and demonstrate earlier onset of cognitive and synaptic dysfunction as compared to other AD mouse models. Onset of obvious pathology in 3x-Tg mice occurs at 6 months of age with the presence of synaptic and cognitive deficits and at 12 months the presence of tau immunoreactivity can be detected (Oddo et al., 2003, Neuron 39:409-421; Pietropaolo et al., 2008, Behav. Neurosci. 122:733-747). Thus, SMO treatment from 11-12 months of age when tau should be in a hyperphosphorylated state in addition to the presence of synaptic and cognitive deficits due to Aβ deposition, allows for short term evaluation of the effects of increased O-GlcNAc levels on overall cognitive symptoms as well as tau phosphorylation state.

Eleven month old 3×Tg mice are treated with saline or an SMO using the ICV infusion method described elsewhere for 3 weeks. During infusion period, mice are evaluated weekly for cognitive, memory, and motor deficits by Morris water maze, novel object recognition, and rotarod testing. These mice are also tested for effect on total brain O-GlcNAc levels. The mice are euthanized after 3 weeks of infusion (at ~12 months of age). Brain tissue samples from SMO treated 3×Tg mice is evaluated at the end of the dosing period for total O-GlcNAcylation levels by western blot as compared to saline controls.

The effect of SMO that target OGA pre-mRNA on tau phosphorylation is evaluated using the same protocol described above. Samples are taken from the cortex and hippocampus and evaluated for total tau phosphorylation using tau epitope 5 antibody, modification-state specific antibodies (pSer422, pSer262, pSer396, and pThr231), and tau epitope 1 antibody directed against non-phosphorylated residues at Ser198, Ser199 and Ser202. By using this panel of antibodies, changes in phosphorylation state of all the relevant phosphorylation sites is evaluated by Western blot (Yuzwa et al., 2008, Nat. Chem. Biol. 4:483-490). Prevention of tau phosphorylation at these residues by altering splicing of OGA pre-mRNA will block progression of tau pathology in AD.

Experimental Example 12

Using SMOs to Target Aph1B to Treat Alzheimer's Disease

A "triple-transgenic" mouse model, 3×-tg AD mice, expresses mutant APP, PSN1 (presenilin), and tau transgenes. These mice have cognitive and synaptic dysfunction similar to those in other AD mice, but with earlier onset (Oddo et al., 2003, Neuron 39:409-421). Specifically, the 3×-tg Ad mice show significant memory deficits when tested using the Morris Water Maze paradigm as early as 120 days of age.

SMOs that target Aph1B, as exemplified by oligonucleotides listed in Table 9, are used to modulate splicing Aph1B pre-mRNA. An SMO that targets Aph1B pre-mRNA is infused ICV for about a 3 week period beginning at 100 days of age. This provides adequate time for the SMO to exert its effect on Aph1B pre-mRNA splicing. In addition, mice are ~4 months of age at the end of the infusion period when they are evaluated for changes in cognitive performance.

For continuous delivery of SMO to the CSF, mice are cannulated stereotaxically into the lateral ventricle, with the cannula tubing already connected to a sub-cutaneously implanted Alzet mini pump pre-loaded with a pharmaceutical composition comprising a SMO. The pharmaceutical composition comprising the SMO is equilibrated for 2 days in sterile saline at 37° C. In this system, the cannulae, tubing, and pump is surgically implanted beneath the skin. The model pump used in these experiments delivers its contents at a constant rate of 4 µL per day and holds enough volume (100 µL) to last about 25 days. We use dosing rates of 1 to 10 µg SMO per day in mice.

Examples of SMOs that specifically skip exon 4 of the Aph1B pre-mRNA are provided in Table 9. These SMOs were developed according to the following rational: Aph1B naturally expresses a non-functional alternative splice variant missing exon 4 (Saito et al., 2005, Biochem. Biophys. Res. Comm. 330:1068-1072). Alternatively spliced exons are known to be more readily modulated by oligomers than constitutive exons. Second, exon 4 of Aph1B contains a conserved GXXXG motif, critical for the assembly and activity of the γ-secretase complex (Lee et al., J. Biol. Chem. 279:4144-4152). Thus, Aph1B protein missing exon 4 is non-functional and unstable (Saito et al., 2005, Biochem. Biophys. Res. Comm. 330:1068-1072).

An SMO is transfected into neuroblastoma SY5Y cells that express γ-secretase. SMOs are complexed with lipofectamine and applied to SY5Y cells at a concentration of 100 µM SMO for 4 hours. The bathing medium is replaced and cells are maintained in culture for an additional 24 hours before they are and harvested. RNA is extracted using standard techniques known in the art, and cDNA generated with superscript RT using oligo-dT and random hexamers. The level of Aph1B mRNA transcripts with and without exon 4 is determined using Real-time PCR. The dose-response of lead SMOs will is analyzed using Westerns blots to quantify Aph1B protein expression in transfected cells. Toxicity is also quantified by documenting morphology of nuclei and using DAPI staining, a known hallmark of cell damage (Martin et al., 2005, Cytometry Part A 67A:45-52).

At the end of the infusion period, mice are evaluated for changes in cognitive performance using the Morris Water Maze test with training beginning at the end of the 3 week drug infusion period. The Morris Water Maze comprises a 25 gallon tub 71 cm in diameter and 33 cm high containing water maintained at 23° C. A platform 6 cm in diameter is placed in the center of one quadrant. The mice have 2 blocks of 4 visible platform trials where they are given 60 seconds to reach the platform, with a 5 min inter-trial interval (Varvel et al., 2005, Psychopharmacol. (Berl) 179:863-872). Location of the platform is changed semi-randomly between trials. Mice are videotaped and latency to reach the platform is recorded. The following day the mice begin hidden platform training where the platform is submerged in opaque water. 2 blocks of 4 trials each (5 minute inter-trial interval) are run each day for 4 days, with 1 hour between blocks. A trial consists of semi-randomly placing the mouse in one of three quadrants without the platform and giving the mouse 60 seconds to locate the platform. The platform remains in the same location for the 4 days of hidden platform training.

Probe tests are run 24 and 72 hours after the final day of training. The platform is removed from the tub and the mice are semirandomly placed in one of the four quadrants and allowed to swim for 30 seconds. After the 24 hour probe the platform is placed back in the same location and the mouse allowed to find it, to minimize extinction. The percent time spent in each quadrant is recorded. A one way ANOVA is run (Statistica) to determine significance in probe trials. A repeated measures ANOVA is used to determine differences in latencies to reach the platform during training, with a post-hoc Tukey's test to determine where the significant differences occur.

Following the final behavioral test, mice are euthanized and brains rapidly removed. The left and right hippocampus and cortex are quickly excised. To alleviate biases due to potential differences between the left and right hemisphere tissues, each assay is performed on an equal number of left and right hemisphere tissues. RNA is immediately extracted from half of the hippocampus and cortex tissues, and cDNA prepared according to standard techniques known in the art. The remaining tissue is immediately processed for protein extraction and the preparation of a soluble fraction and a membrane fraction. Both soluble and membrane fraction preparations will be treated as described below.

Transcript and protein levels of Aph1B in the hippocampus and cortex are measured for all groups. Transcript levels of Aph1B will be measured by Real-time PCR, using custom primer-probe sets using GAPDH as the internal control. Aph1B protein content is measured by Western blot analysis of the soluble and membrane fractions with a polyclonal antibody (Santa Cruz; sc-49358).

Aβ40 and Aβ42 levels in hippocampus and cortex are measured in both the soluble and membrane fractions using sandwich ELISA with antibodies against human Aβ40 (2G3 antibody) and human Aβ42 (21F12 antibody), both detected with biotin-3D6 antibody (Kanekivo et al., 2009, J. Biol. Chem. 284:33352-33359)

In addition, extracts from the various brain sections are also be probed for changes in activated Notch intracellular domain (MCD), the well documented released product of Notch cleavage by γ-secretase. Another known non-amyloidal substrate of γ-secretase is N-cadherin. Western blot analysis will be used to measure levels of MCD (Cell Signaling) and N-cadherin (Santa Cruz; sc-7939).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A composition comprising a splice modulating oligonucleotide (SMO) that specifically binds a complementary sequence of a pre-mRNA that undergoes exon 3 or exon 11 splicing to form a mRNA encoding HER3, wherein said SMO is selected from at least one of SEQ ID NOs: 729 through 813, or a sequence having at least 90% identity over the full sequence of any of SEQ ID NOs: 729 through 813, wherein at least one nucleotide in said SMO contains a non-naturally occurring modification.

2. The composition according to claim 1, wherein the SMO binds the pre-mRNA that undergoes exon 3 splicing and is selected from SEQ ID NO: 729 to SEQ ID NO: 802.

3. The composition according to claim 1, wherein the SMO binds the pre-mRNA that undergoes exon 11 splicing and is selected from SEQ ID NO: 803 to SEQ ID NO: 813.

4. The composition of claim 1, wherein said modification comprises one or more modifications selected from phosphorothioate 2'-O-methyl nucleotides, 2'-O-methoxyethyl (2'-MOE) nucleotides, locked nucleic acids (LNAs), peptide nucleic acids (PNAs), phosphorodiamidate morpholinos (PMOs), and cholesterol conjugates.

5. The composition of claim 1, wherein at least one nucleotide in the SMO is a phosphorothioate 2'-O-methyl modified nucleotide.

6. The composition according to claim 1, further comprising a pharmaceutically acceptable carrier.

7. The composition according to claim 1, wherein said SMO is a sequence having at least 95% identity over the full sequence of any of SEQ ID NO: 729 through SEQ ID NO: 813.

8. The composition according to claim 1, wherein said SMO is conjugated or complexes to a peptide, liposome, a cationic lipid, a cation coupled to a ligand for a cell-surface receptor, or a colloidal polymeric particle.

* * * * *

SEQUENCE LISTING

<160> NUMBER OF SEQ ID NOS: 1113

<210> SEQ ID NO 1
<211> LENGTH: 24

-continued

```
<212> TYPE: RNA
<213> ORGANISM: Artificial Sequence
<220> FEATURE:
<223> OTHER INFORMATION: Synthetic

<400> SEQUENCE: 1
auacguaauc cuauugagca uagc                                            24

<210> SEQ ID NO 2
<211> LENGTH: 15
<212> TYPE: RNA
<213> ORGANISM: Artificial Sequence
<220> FEATURE:
<223> OTHER INFORMATION: Synthetic

<400> SEQUENCE: 2
gcuaugcuca auagg                                                      15

<210> SEQ ID NO 3
<211> LENGTH: 15
<212> TYPE: RNA
<213> ORGANISM: Artificial Sequence
<220> FEATURE:
<223> OTHER INFORMATION: Synthetic

<400> SEQUENCE: 3
cuaugcucaa uagga                                                      15

<210> SEQ ID NO 4
<211> LENGTH: 15
<212> TYPE: RNA
<213> ORGANISM: Artificial Sequence
<220> FEATURE:
<223> OTHER INFORMATION: Synthetic

<400> SEQUENCE: 4
uaugcucaau aggau                                                      15

<210> SEQ ID NO 5
<211> LENGTH: 15
<212> TYPE: RNA
<213> ORGANISM: Artificial Sequence
<220> FEATURE:
<223> OTHER INFORMATION: Synthetic

<400> SEQUENCE: 5
augcucaaua ggauu                                                      15

<210> SEQ ID NO 6
<211> LENGTH: 15
<212> TYPE: RNA
<213> ORGANISM: Artificial Sequence
<220> FEATURE:
<223> OTHER INFORMATION: Synthetic

<400> SEQUENCE: 6
ugcucaauag gauua                                                      15

<210> SEQ ID NO 7
<211> LENGTH: 15
<212> TYPE: RNA
<213> ORGANISM: Artificial Sequence
<220> FEATURE:
<223> OTHER INFORMATION: Synthetic

<400> SEQUENCE: 7
```

```
gcucaauagg auuac                                                        15

<210> SEQ ID NO 8
<211> LENGTH: 15
<212> TYPE: RNA
<213> ORGANISM: Artificial Sequence
<220> FEATURE:
<223> OTHER INFORMATION: Synthetic

<400> SEQUENCE: 8
cucaauagga uuacg                                                        15

<210> SEQ ID NO 9
<211> LENGTH: 15
<212> TYPE: RNA
<213> ORGANISM: Artificial Sequence
<220> FEATURE:
<223> OTHER INFORMATION: Synthetic

<400> SEQUENCE: 9
ucaauaggau uacgu                                                        15

<210> SEQ ID NO 10
<211> LENGTH: 15
<212> TYPE: RNA
<213> ORGANISM: Artificial Sequence
<220> FEATURE:
<223> OTHER INFORMATION: Synthetic

<400> SEQUENCE: 10
caauaggauu acgua                                                        15

<210> SEQ ID NO 11
<211> LENGTH: 15
<212> TYPE: RNA
<213> ORGANISM: Artificial Sequence
<220> FEATURE:
<223> OTHER INFORMATION: Synthetic

<400> SEQUENCE: 11
aauaggauua cguau                                                        15

<210> SEQ ID NO 12
<211> LENGTH: 16
<212> TYPE: RNA
<213> ORGANISM: Artificial Sequence
<220> FEATURE:
<223> OTHER INFORMATION: Synthetic

<400> SEQUENCE: 12
gcuaugcuca auagga                                                       16

<210> SEQ ID NO 13
<211> LENGTH: 16
<212> TYPE: RNA
<213> ORGANISM: Artificial Sequence
<220> FEATURE:
<223> OTHER INFORMATION: Synthetic

<400> SEQUENCE: 13
cuaugcucaa uaggau                                                       16

<210> SEQ ID NO 14
<211> LENGTH: 16
<212> TYPE: RNA
<213> ORGANISM: Artificial Sequence
```

```
<220> FEATURE:
<223> OTHER INFORMATION: Synthetic

<400> SEQUENCE: 14
uaugcucaau aggauu                                                    16

<210> SEQ ID NO 15
<211> LENGTH: 16
<212> TYPE: RNA
<213> ORGANISM: Artificial Sequence
<220> FEATURE:
<223> OTHER INFORMATION: Synthetic

<400> SEQUENCE: 15
augcucaaua ggauua                                                    16

<210> SEQ ID NO 16
<211> LENGTH: 16
<212> TYPE: RNA
<213> ORGANISM: Artificial Sequence
<220> FEATURE:
<223> OTHER INFORMATION: Synthetic

<400> SEQUENCE: 16
ugcucaauag gauuac                                                    16

<210> SEQ ID NO 17
<211> LENGTH: 16
<212> TYPE: RNA
<213> ORGANISM: Artificial Sequence
<220> FEATURE:
<223> OTHER INFORMATION: Synthetic

<400> SEQUENCE: 17
gcucaauagg auuacg                                                    16

<210> SEQ ID NO 18
<211> LENGTH: 16
<212> TYPE: RNA
<213> ORGANISM: Artificial Sequence
<220> FEATURE:
<223> OTHER INFORMATION: Synthetic

<400> SEQUENCE: 18
cucaauagga uuacgu                                                    16

<210> SEQ ID NO 19
<211> LENGTH: 16
<212> TYPE: RNA
<213> ORGANISM: Artificial Sequence
<220> FEATURE:
<223> OTHER INFORMATION: Synthetic

<400> SEQUENCE: 19
ucaauaggau uacgua                                                    16

<210> SEQ ID NO 20
<211> LENGTH: 16
<212> TYPE: RNA
<213> ORGANISM: Artificial Sequence
<220> FEATURE:
<223> OTHER INFORMATION: Synthetic

<400> SEQUENCE: 20
caauaggauu acguau                                                    16
```

<210> SEQ ID NO 21
<211> LENGTH: 17
<212> TYPE: RNA
<213> ORGANISM: Artificial Sequence
<220> FEATURE:
<223> OTHER INFORMATION: Synthetic

<400> SEQUENCE: 21
gcuaugcuca auaggau                                                        17

<210> SEQ ID NO 22
<211> LENGTH: 17
<212> TYPE: RNA
<213> ORGANISM: Artificial Sequence
<220> FEATURE:
<223> OTHER INFORMATION: Synthetic

<400> SEQUENCE: 22
cuaugcucaa uaggauu                                                        17

<210> SEQ ID NO 23
<211> LENGTH: 17
<212> TYPE: RNA
<213> ORGANISM: Artificial Sequence
<220> FEATURE:
<223> OTHER INFORMATION: Synthetic

<400> SEQUENCE: 23
uaugcucaau aggauua                                                        17

<210> SEQ ID NO 24
<211> LENGTH: 17
<212> TYPE: RNA
<213> ORGANISM: Artificial Sequence
<220> FEATURE:
<223> OTHER INFORMATION: Synthetic

<400> SEQUENCE: 24
augcucaaua ggauuac                                                        17

<210> SEQ ID NO 25
<211> LENGTH: 17
<212> TYPE: RNA
<213> ORGANISM: Artificial Sequence
<220> FEATURE:
<223> OTHER INFORMATION: Synthetic

<400> SEQUENCE: 25
ugcucaauag gauuacg                                                        17

<210> SEQ ID NO 26
<211> LENGTH: 17
<212> TYPE: RNA
<213> ORGANISM: Artificial Sequence
<220> FEATURE:
<223> OTHER INFORMATION: Synthetic

<400> SEQUENCE: 26
gcucaauagg auuacgu                                                        17

<210> SEQ ID NO 27
<211> LENGTH: 17
<212> TYPE: RNA
<213> ORGANISM: Artificial Sequence
<220> FEATURE:
<223> OTHER INFORMATION: Synthetic

<400> SEQUENCE: 27
cucaauagga uuacgua                                                    17

<210> SEQ ID NO 28
<211> LENGTH: 17
<212> TYPE: RNA
<213> ORGANISM: Artificial Sequence
<220> FEATURE:
<223> OTHER INFORMATION: Synthetic

<400> SEQUENCE: 28
ucaauaggau uacguau                                                    17

<210> SEQ ID NO 29
<211> LENGTH: 18
<212> TYPE: RNA
<213> ORGANISM: Artificial Sequence
<220> FEATURE:
<223> OTHER INFORMATION: Synthetic

<400> SEQUENCE: 29
augcucaaua ggauuacg                                                   18

<210> SEQ ID NO 30
<211> LENGTH: 18
<212> TYPE: RNA
<213> ORGANISM: Artificial Sequence
<220> FEATURE:
<223> OTHER INFORMATION: Synthetic

<400> SEQUENCE: 30
gcuaugcuca auaggauu                                                   18

<210> SEQ ID NO 31
<211> LENGTH: 18
<212> TYPE: RNA
<213> ORGANISM: Artificial Sequence
<220> FEATURE:
<223> OTHER INFORMATION: Synthetic

<400> SEQUENCE: 31
cuaugcucaa uaggauua                                                   18

<210> SEQ ID NO 32
<211> LENGTH: 18
<212> TYPE: RNA
<213> ORGANISM: Artificial Sequence
<220> FEATURE:
<223> OTHER INFORMATION: Synthetic

<400> SEQUENCE: 32
uaugcucaau aggauuac                                                   18

<210> SEQ ID NO 33
<211> LENGTH: 18
<212> TYPE: RNA
<213> ORGANISM: Artificial Sequence
<220> FEATURE:
<223> OTHER INFORMATION: Synthetic

<400> SEQUENCE: 33
ugcucaauag gauuacgu                                                   18

<210> SEQ ID NO 34

```
<211> LENGTH: 18
<212> TYPE: RNA
<213> ORGANISM: Artificial Sequence
<220> FEATURE:
<223> OTHER INFORMATION: Synthetic

<400> SEQUENCE: 34
gcucaauagg auuacgua                                                 18

<210> SEQ ID NO 35
<211> LENGTH: 18
<212> TYPE: RNA
<213> ORGANISM: Artificial Sequence
<220> FEATURE:
<223> OTHER INFORMATION: Synthetic

<400> SEQUENCE: 35
cucaauagga uuacguau                                                 18

<210> SEQ ID NO 36
<211> LENGTH: 19
<212> TYPE: RNA
<213> ORGANISM: Artificial Sequence
<220> FEATURE:
<223> OTHER INFORMATION: Synthetic

<400> SEQUENCE: 36
gcuaugcuca auaggauua                                                19

<210> SEQ ID NO 37
<211> LENGTH: 19
<212> TYPE: RNA
<213> ORGANISM: Artificial Sequence
<220> FEATURE:
<223> OTHER INFORMATION: Synthetic

<400> SEQUENCE: 37
cuaugcucaa uaggauuac                                                19

<210> SEQ ID NO 38
<211> LENGTH: 19
<212> TYPE: RNA
<213> ORGANISM: Artificial Sequence
<220> FEATURE:
<223> OTHER INFORMATION: Synthetic

<400> SEQUENCE: 38
uaugcucaau aggauuacg                                                19

<210> SEQ ID NO 39
<211> LENGTH: 19
<212> TYPE: RNA
<213> ORGANISM: Artificial Sequence
<220> FEATURE:
<223> OTHER INFORMATION: Synthetic

<400> SEQUENCE: 39
augcucaaua ggauuacgu                                                19

<210> SEQ ID NO 40
<211> LENGTH: 19
<212> TYPE: RNA
<213> ORGANISM: Artificial Sequence
<220> FEATURE:
<223> OTHER INFORMATION: Synthetic

<400> SEQUENCE: 40
```
ugcucaauag gauuacgua                                                19

<210> SEQ ID NO 41
<211> LENGTH: 19
<212> TYPE: RNA
<213> ORGANISM: Artificial Sequence
<220> FEATURE:
<223> OTHER INFORMATION: Synthetic

<400> SEQUENCE: 41
gcucaauagg auuacguau                                                19

<210> SEQ ID NO 42
<211> LENGTH: 20
<212> TYPE: RNA
<213> ORGANISM: Artificial Sequence
<220> FEATURE:
<223> OTHER INFORMATION: Synthetic

<400> SEQUENCE: 42
gcuaugcuca auaggauuac                                               20

<210> SEQ ID NO 43
<211> LENGTH: 20
<212> TYPE: RNA
<213> ORGANISM: Artificial Sequence
<220> FEATURE:
<223> OTHER INFORMATION: Synthetic

<400> SEQUENCE: 43
cuaugcucaa uaggauuacg                                               20

<210> SEQ ID NO 44
<211> LENGTH: 20
<212> TYPE: RNA
<213> ORGANISM: Artificial Sequence
<220> FEATURE:
<223> OTHER INFORMATION: Synthetic

<400> SEQUENCE: 44
uaugcucaau aggauuacgu                                               20

<210> SEQ ID NO 45
<211> LENGTH: 20
<212> TYPE: RNA
<213> ORGANISM: Artificial Sequence
<220> FEATURE:
<223> OTHER INFORMATION: Synthetic

<400> SEQUENCE: 45
augcucaaua ggauuacgua                                               20

<210> SEQ ID NO 46
<211> LENGTH: 20
<212> TYPE: RNA
<213> ORGANISM: Artificial Sequence
<220> FEATURE:
<223> OTHER INFORMATION: Synthetic

<400> SEQUENCE: 46
ugcucaauag gauuacguau                                               20

<210> SEQ ID NO 47
<211> LENGTH: 21
<212> TYPE: RNA

```
<213> ORGANISM: Artificial Sequence
<220> FEATURE:
<223> OTHER INFORMATION: Synthetic

<400> SEQUENCE: 47
gcuaugcuca auaggauuac g                                              21

<210> SEQ ID NO 48
<211> LENGTH: 21
<212> TYPE: RNA
<213> ORGANISM: Artificial Sequence
<220> FEATURE:
<223> OTHER INFORMATION: Synthetic

<400> SEQUENCE: 48
cuaugcucaa uaggauuacg u                                              21

<210> SEQ ID NO 49
<211> LENGTH: 21
<212> TYPE: RNA
<213> ORGANISM: Artificial Sequence
<220> FEATURE:
<223> OTHER INFORMATION: Synthetic

<400> SEQUENCE: 49
uaugcucaau aggauuacgu a                                              21

<210> SEQ ID NO 50
<211> LENGTH: 21
<212> TYPE: RNA
<213> ORGANISM: Artificial Sequence
<220> FEATURE:
<223> OTHER INFORMATION: Synthetic

<400> SEQUENCE: 50
augcucaaua ggauuacgua u                                              21

<210> SEQ ID NO 51
<211> LENGTH: 22
<212> TYPE: RNA
<213> ORGANISM: Artificial Sequence
<220> FEATURE:
<223> OTHER INFORMATION: Synthetic

<400> SEQUENCE: 51
gcuaugcuca auaggauuac gu                                             22

<210> SEQ ID NO 52
<211> LENGTH: 22
<212> TYPE: RNA
<213> ORGANISM: Artificial Sequence
<220> FEATURE:
<223> OTHER INFORMATION: Synthetic

<400> SEQUENCE: 52
cuaugcucaa uaggauuacg ua                                             22

<210> SEQ ID NO 53
<211> LENGTH: 22
<212> TYPE: RNA
<213> ORGANISM: Artificial Sequence
<220> FEATURE:
<223> OTHER INFORMATION: Synthetic

<400> SEQUENCE: 53
uaugcucaau aggauuacgu au                                             22
```

-continued

<210> SEQ ID NO 54
<211> LENGTH: 23
<212> TYPE: RNA
<213> ORGANISM: Artificial Sequence
<220> FEATURE:
<223> OTHER INFORMATION: Synthetic

<400> SEQUENCE: 54
gcuaugcuca auaggauuac gua                                              23

<210> SEQ ID NO 55
<211> LENGTH: 23
<212> TYPE: RNA
<213> ORGANISM: Artificial Sequence
<220> FEATURE:
<223> OTHER INFORMATION: Synthetic

<400> SEQUENCE: 55
cuaugcucaa uaggauuacg uau                                              23

<210> SEQ ID NO 56
<211> LENGTH: 24
<212> TYPE: RNA
<213> ORGANISM: Artificial Sequence
<220> FEATURE:
<223> OTHER INFORMATION: Synthetic

<400> SEQUENCE: 56
gcuaugcuca auaggauuac guau                                             24

<210> SEQ ID NO 57
<211> LENGTH: 24
<212> TYPE: RNA
<213> ORGANISM: Artificial Sequence
<220> FEATURE:
<223> OTHER INFORMATION: Synthetic

<400> SEQUENCE: 57
uacaggcguu cuucacgugg gaaa                                             24

<210> SEQ ID NO 58
<211> LENGTH: 24
<212> TYPE: RNA
<213> ORGANISM: Artificial Sequence
<220> FEATURE:
<223> OTHER INFORMATION: Synthetic

<400> SEQUENCE: 58
uuacaggcgu ucuucacgug ggaa                                             24

<210> SEQ ID NO 59
<211> LENGTH: 24
<212> TYPE: RNA
<213> ORGANISM: Artificial Sequence
<220> FEATURE:
<223> OTHER INFORMATION: Synthetic

<400> SEQUENCE: 59
uuuacaggcg uucuucacgu ggga                                             24

<210> SEQ ID NO 60
<211> LENGTH: 24
<212> TYPE: RNA
<213> ORGANISM: Artificial Sequence
<220> FEATURE:

<223> OTHER INFORMATION: Synthetic

<400> SEQUENCE: 60
guuuacaggc guucuucacg uggg                                            24

<210> SEQ ID NO 61
<211> LENGTH: 24
<212> TYPE: RNA
<213> ORGANISM: Artificial Sequence
<220> FEATURE:
<223> OTHER INFORMATION: Synthetic

<400> SEQUENCE: 61
gguuuacagg cguucuucac gugg                                            24

<210> SEQ ID NO 62
<211> LENGTH: 24
<212> TYPE: RNA
<213> ORGANISM: Artificial Sequence
<220> FEATURE:
<223> OTHER INFORMATION: Synthetic

<400> SEQUENCE: 62
agguuuacag gcguucuuca cgug                                            24

<210> SEQ ID NO 63
<211> LENGTH: 24
<212> TYPE: RNA
<213> ORGANISM: Artificial Sequence
<220> FEATURE:
<223> OTHER INFORMATION: Synthetic

<400> SEQUENCE: 63
aagguuuaca ggcguucuuc acgu                                            24

<210> SEQ ID NO 64
<211> LENGTH: 24
<212> TYPE: RNA
<213> ORGANISM: Artificial Sequence
<220> FEATURE:
<223> OTHER INFORMATION: Synthetic

<400> SEQUENCE: 64
caagguuuac aggcguucuu cacg                                            24

<210> SEQ ID NO 65
<211> LENGTH: 24
<212> TYPE: RNA
<213> ORGANISM: Artificial Sequence
<220> FEATURE:
<223> OTHER INFORMATION: Synthetic

<400> SEQUENCE: 65
gcaagguuua caggcguucu ucac                                            24

<210> SEQ ID NO 66
<211> LENGTH: 24
<212> TYPE: RNA
<213> ORGANISM: Artificial Sequence
<220> FEATURE:
<223> OTHER INFORMATION: Synthetic

<400> SEQUENCE: 66
ugcaagguuu acaggcguuc uuca                                            24

```
<210> SEQ ID NO 67
<211> LENGTH: 24
<212> TYPE: RNA
<213> ORGANISM: Artificial Sequence
<220> FEATURE:
<223> OTHER INFORMATION: Synthetic

<400> SEQUENCE: 67
cugcaagguu uacaggcguu cuuc                                              24

<210> SEQ ID NO 68
<211> LENGTH: 24
<212> TYPE: RNA
<213> ORGANISM: Artificial Sequence
<220> FEATURE:
<223> OTHER INFORMATION: Synthetic

<400> SEQUENCE: 68
acugcaaggu uuacaggcgu ucuu                                              24

<210> SEQ ID NO 69
<211> LENGTH: 24
<212> TYPE: RNA
<213> ORGANISM: Artificial Sequence
<220> FEATURE:
<223> OTHER INFORMATION: Synthetic

<400> SEQUENCE: 69
uacugcaagg uuuacaggcg uucu                                              24

<210> SEQ ID NO 70
<211> LENGTH: 24
<212> TYPE: RNA
<213> ORGANISM: Artificial Sequence
<220> FEATURE:
<223> OTHER INFORMATION: Synthetic

<400> SEQUENCE: 70
auacugcaag guuuacaggc guuc                                              24

<210> SEQ ID NO 71
<211> LENGTH: 24
<212> TYPE: RNA
<213> ORGANISM: Artificial Sequence
<220> FEATURE:
<223> OTHER INFORMATION: Synthetic

<400> SEQUENCE: 71
aauacugcaa gguuuacagg cguu                                              24

<210> SEQ ID NO 72
<211> LENGTH: 24
<212> TYPE: RNA
<213> ORGANISM: Artificial Sequence
<220> FEATURE:
<223> OTHER INFORMATION: Synthetic

<400> SEQUENCE: 72
caauacugca agguuuacag gcgu                                              24

<210> SEQ ID NO 73
<211> LENGTH: 24
<212> TYPE: RNA
<213> ORGANISM: Artificial Sequence
<220> FEATURE:
<223> OTHER INFORMATION: Synthetic
```

```
<400> SEQUENCE: 73
ucaauacugc aagguuuaca ggcg                                          24

<210> SEQ ID NO 74
<211> LENGTH: 23
<212> TYPE: RNA
<213> ORGANISM: Artificial Sequence
<220> FEATURE:
<223> OTHER INFORMATION: Synthetic

<400> SEQUENCE: 74
acaggcguuc uucacguggg aaa                                           23

<210> SEQ ID NO 75
<211> LENGTH: 23
<212> TYPE: RNA
<213> ORGANISM: Artificial Sequence
<220> FEATURE:
<223> OTHER INFORMATION: Synthetic

<400> SEQUENCE: 75
uacaggcguu cuucacgugg gaa                                           23

<210> SEQ ID NO 76
<211> LENGTH: 23
<212> TYPE: RNA
<213> ORGANISM: Artificial Sequence
<220> FEATURE:
<223> OTHER INFORMATION: Synthetic

<400> SEQUENCE: 76
uuacaggcgu ucuucacgug gga                                           23

<210> SEQ ID NO 77
<211> LENGTH: 23
<212> TYPE: RNA
<213> ORGANISM: Artificial Sequence
<220> FEATURE:
<223> OTHER INFORMATION: Synthetic

<400> SEQUENCE: 77
uuuacaggcg uucuucacgu ggg                                           23

<210> SEQ ID NO 78
<211> LENGTH: 23
<212> TYPE: RNA
<213> ORGANISM: Artificial Sequence
<220> FEATURE:
<223> OTHER INFORMATION: Synthetic

<400> SEQUENCE: 78
guuuacaggc guucuucacg ugg                                           23

<210> SEQ ID NO 79
<211> LENGTH: 23
<212> TYPE: RNA
<213> ORGANISM: Artificial Sequence
<220> FEATURE:
<223> OTHER INFORMATION: Synthetic

<400> SEQUENCE: 79
gguuuacagg cguucuucac gug                                           23

<210> SEQ ID NO 80
<211> LENGTH: 23
```

```
<212> TYPE: RNA
<213> ORGANISM: Artificial Sequence
<220> FEATURE:
<223> OTHER INFORMATION: Synthetic

<400> SEQUENCE: 80
agguuuacag gcguucuuca cgu                                              23

<210> SEQ ID NO 81
<211> LENGTH: 23
<212> TYPE: RNA
<213> ORGANISM: Artificial Sequence
<220> FEATURE:
<223> OTHER INFORMATION: Synthetic

<400> SEQUENCE: 81
aagguuuaca ggcguucuuc acg                                              23

<210> SEQ ID NO 82
<211> LENGTH: 23
<212> TYPE: RNA
<213> ORGANISM: Artificial Sequence
<220> FEATURE:
<223> OTHER INFORMATION: Synthetic

<400> SEQUENCE: 82
caagguuuac aggcguucuu cac                                              23

<210> SEQ ID NO 83
<211> LENGTH: 23
<212> TYPE: RNA
<213> ORGANISM: Artificial Sequence
<220> FEATURE:
<223> OTHER INFORMATION: Synthetic

<400> SEQUENCE: 83
gcaagguuua caggcguucu uca                                              23

<210> SEQ ID NO 84
<211> LENGTH: 23
<212> TYPE: RNA
<213> ORGANISM: Artificial Sequence
<220> FEATURE:
<223> OTHER INFORMATION: Synthetic

<400> SEQUENCE: 84
ugcaagguuu acaggcguuc uuc                                              23

<210> SEQ ID NO 85
<211> LENGTH: 23
<212> TYPE: RNA
<213> ORGANISM: Artificial Sequence
<220> FEATURE:
<223> OTHER INFORMATION: Synthetic

<400> SEQUENCE: 85
cugcaagguu uacaggcguu cuu                                              23

<210> SEQ ID NO 86
<211> LENGTH: 23
<212> TYPE: RNA
<213> ORGANISM: Artificial Sequence
<220> FEATURE:
<223> OTHER INFORMATION: Synthetic

<400> SEQUENCE: 86
```

```
acugcaaggu uuacaggcgu ucu                                            23

<210> SEQ ID NO 87
<211> LENGTH: 23
<212> TYPE: RNA
<213> ORGANISM: Artificial Sequence
<220> FEATURE:
<223> OTHER INFORMATION: Synthetic

<400> SEQUENCE: 87
uacugcaagg uuuacaggcg uuc                                            23

<210> SEQ ID NO 88
<211> LENGTH: 23
<212> TYPE: RNA
<213> ORGANISM: Artificial Sequence
<220> FEATURE:
<223> OTHER INFORMATION: Synthetic

<400> SEQUENCE: 88
auacugcaag guuuacaggc guu                                            23

<210> SEQ ID NO 89
<211> LENGTH: 23
<212> TYPE: RNA
<213> ORGANISM: Artificial Sequence
<220> FEATURE:
<223> OTHER INFORMATION: Synthetic

<400> SEQUENCE: 89
aauacugcaa gguuuacagg cgu                                            23

<210> SEQ ID NO 90
<211> LENGTH: 23
<212> TYPE: RNA
<213> ORGANISM: Artificial Sequence
<220> FEATURE:
<223> OTHER INFORMATION: Synthetic

<400> SEQUENCE: 90
caauacugca agguuuacag gcg                                            23

<210> SEQ ID NO 91
<211> LENGTH: 23
<212> TYPE: RNA
<213> ORGANISM: Artificial Sequence
<220> FEATURE:
<223> OTHER INFORMATION: Synthetic

<400> SEQUENCE: 91
ucaauacugc aagguuuaca ggc                                            23

<210> SEQ ID NO 92
<211> LENGTH: 22
<212> TYPE: RNA
<213> ORGANISM: Artificial Sequence
<220> FEATURE:
<223> OTHER INFORMATION: Synthetic

<400> SEQUENCE: 92
caggcguucu ucacguggga aa                                             22

<210> SEQ ID NO 93
<211> LENGTH: 22
<212> TYPE: RNA
<213> ORGANISM: Artificial Sequence
```

```
<220> FEATURE:
<223> OTHER INFORMATION: Synthetic

<400> SEQUENCE: 93
acaggcguuc uucacguggg aa                                              22

<210> SEQ ID NO 94
<211> LENGTH: 22
<212> TYPE: RNA
<213> ORGANISM: Artificial Sequence
<220> FEATURE:
<223> OTHER INFORMATION: Synthetic

<400> SEQUENCE: 94
uacaggcguu cuucacgugg ga                                              22

<210> SEQ ID NO 95
<211> LENGTH: 22
<212> TYPE: RNA
<213> ORGANISM: Artificial Sequence
<220> FEATURE:
<223> OTHER INFORMATION: Synthetic

<400> SEQUENCE: 95
uuacaggcgu ucuucacgug gg                                              22

<210> SEQ ID NO 96
<211> LENGTH: 22
<212> TYPE: RNA
<213> ORGANISM: Artificial Sequence
<220> FEATURE:
<223> OTHER INFORMATION: Synthetic

<400> SEQUENCE: 96
uuuacaggcg uucuucacgu gg                                              22

<210> SEQ ID NO 97
<211> LENGTH: 22
<212> TYPE: RNA
<213> ORGANISM: Artificial Sequence
<220> FEATURE:
<223> OTHER INFORMATION: Synthetic

<400> SEQUENCE: 97
guuuacaggc guucuucacg ug                                              22

<210> SEQ ID NO 98
<211> LENGTH: 22
<212> TYPE: RNA
<213> ORGANISM: Artificial Sequence
<220> FEATURE:
<223> OTHER INFORMATION: Synthetic

<400> SEQUENCE: 98
gguuuacagg cguucuucac gu                                              22

<210> SEQ ID NO 99
<211> LENGTH: 22
<212> TYPE: RNA
<213> ORGANISM: Artificial Sequence
<220> FEATURE:
<223> OTHER INFORMATION: Synthetic

<400> SEQUENCE: 99
agguuuacag gcguucuuca cg                                              22
```

```
<210> SEQ ID NO 100
<211> LENGTH: 22
<212> TYPE: RNA
<213> ORGANISM: Artificial Sequence
<220> FEATURE:
<223> OTHER INFORMATION: Synthetic

<400> SEQUENCE: 100
aagguuuaca ggcguucuuc ac                                              22

<210> SEQ ID NO 101
<211> LENGTH: 22
<212> TYPE: RNA
<213> ORGANISM: Artificial Sequence
<220> FEATURE:
<223> OTHER INFORMATION: Synthetic

<400> SEQUENCE: 101
caagguuuac aggcguucuu ca                                              22

<210> SEQ ID NO 102
<211> LENGTH: 22
<212> TYPE: RNA
<213> ORGANISM: Artificial Sequence
<220> FEATURE:
<223> OTHER INFORMATION: Synthetic

<400> SEQUENCE: 102
gcaagguuua caggcguucu uc                                              22

<210> SEQ ID NO 103
<211> LENGTH: 22
<212> TYPE: RNA
<213> ORGANISM: Artificial Sequence
<220> FEATURE:
<223> OTHER INFORMATION: Synthetic

<400> SEQUENCE: 103
ugcaagguuu acaggcguuc uu                                              22

<210> SEQ ID NO 104
<211> LENGTH: 22
<212> TYPE: RNA
<213> ORGANISM: Artificial Sequence
<220> FEATURE:
<223> OTHER INFORMATION: Synthetic

<400> SEQUENCE: 104
cugcaagguu uacaggcguu cu                                              22

<210> SEQ ID NO 105
<211> LENGTH: 22
<212> TYPE: RNA
<213> ORGANISM: Artificial Sequence
<220> FEATURE:
<223> OTHER INFORMATION: Synthetic

<400> SEQUENCE: 105
acugcaaggu uuacaggcgu uc                                              22

<210> SEQ ID NO 106
<211> LENGTH: 22
<212> TYPE: RNA
<213> ORGANISM: Artificial Sequence
<220> FEATURE:
<223> OTHER INFORMATION: Synthetic
```

<400> SEQUENCE: 106
uacugcaagg uuuacaggcg uu                22

<210> SEQ ID NO 107
<211> LENGTH: 22
<212> TYPE: RNA
<213> ORGANISM: Artificial Sequence
<220> FEATURE:
<223> OTHER INFORMATION: Synthetic

<400> SEQUENCE: 107
auacugcaag guuuacaggc gu                22

<210> SEQ ID NO 108
<211> LENGTH: 22
<212> TYPE: RNA
<213> ORGANISM: Artificial Sequence
<220> FEATURE:
<223> OTHER INFORMATION: Synthetic

<400> SEQUENCE: 108
aauacugcaa gguuuacagg cg                22

<210> SEQ ID NO 109
<211> LENGTH: 22
<212> TYPE: RNA
<213> ORGANISM: Artificial Sequence
<220> FEATURE:
<223> OTHER INFORMATION: Synthetic

<400> SEQUENCE: 109
caauacugca agguuuacag gc                22

<210> SEQ ID NO 110
<211> LENGTH: 22
<212> TYPE: RNA
<213> ORGANISM: Artificial Sequence
<220> FEATURE:
<223> OTHER INFORMATION: Synthetic

<400> SEQUENCE: 110
ucaauacugc aagguuuaca gg                22

<210> SEQ ID NO 111
<211> LENGTH: 21
<212> TYPE: RNA
<213> ORGANISM: Artificial Sequence
<220> FEATURE:
<223> OTHER INFORMATION: Synthetic

<400> SEQUENCE: 111
aggcguucuu cacgugggaa a                 21

<210> SEQ ID NO 112
<211> LENGTH: 21
<212> TYPE: RNA
<213> ORGANISM: Artificial Sequence
<220> FEATURE:
<223> OTHER INFORMATION: Synthetic

<400> SEQUENCE: 112
caggcguucu ucacguggga a                 21

<210> SEQ ID NO 113

```
<211> LENGTH: 21
<212> TYPE: RNA
<213> ORGANISM: Artificial Sequence
<220> FEATURE:
<223> OTHER INFORMATION: Synthetic

<400> SEQUENCE: 113
acaggcguuc uucacguggg a                                              21

<210> SEQ ID NO 114
<211> LENGTH: 21
<212> TYPE: RNA
<213> ORGANISM: Artificial Sequence
<220> FEATURE:
<223> OTHER INFORMATION: Synthetic

<400> SEQUENCE: 114
uacaggcguu cuucacgugg g                                              21

<210> SEQ ID NO 115
<211> LENGTH: 21
<212> TYPE: RNA
<213> ORGANISM: Artificial Sequence
<220> FEATURE:
<223> OTHER INFORMATION: Synthetic

<400> SEQUENCE: 115
uuacaggcgu ucuucacgug g                                              21

<210> SEQ ID NO 116
<211> LENGTH: 21
<212> TYPE: RNA
<213> ORGANISM: Artificial Sequence
<220> FEATURE:
<223> OTHER INFORMATION: Synthetic

<400> SEQUENCE: 116
uuuacaggcg uucuucacgu g                                              21

<210> SEQ ID NO 117
<211> LENGTH: 21
<212> TYPE: RNA
<213> ORGANISM: Artificial Sequence
<220> FEATURE:
<223> OTHER INFORMATION: Synthetic

<400> SEQUENCE: 117
guuuacaggc guucuucacg u                                              21

<210> SEQ ID NO 118
<211> LENGTH: 21
<212> TYPE: RNA
<213> ORGANISM: Artificial Sequence
<220> FEATURE:
<223> OTHER INFORMATION: Synthetic

<400> SEQUENCE: 118
gguuuacagg cguucuucac g                                              21

<210> SEQ ID NO 119
<211> LENGTH: 21
<212> TYPE: RNA
<213> ORGANISM: Artificial Sequence
<220> FEATURE:
<223> OTHER INFORMATION: Synthetic

<400> SEQUENCE: 119
```
agguuuacag gcguucuuca c        21

<210> SEQ ID NO 120
<211> LENGTH: 21
<212> TYPE: RNA
<213> ORGANISM: Artificial Sequence
<220> FEATURE:
<223> OTHER INFORMATION: Synthetic

<400> SEQUENCE: 120
aagguuuaca ggcguucuuc a        21

<210> SEQ ID NO 121
<211> LENGTH: 21
<212> TYPE: RNA
<213> ORGANISM: Artificial Sequence
<220> FEATURE:
<223> OTHER INFORMATION: Synthetic

<400> SEQUENCE: 121
caagguuuac aggcguucuu c        21

<210> SEQ ID NO 122
<211> LENGTH: 21
<212> TYPE: RNA
<213> ORGANISM: Artificial Sequence
<220> FEATURE:
<223> OTHER INFORMATION: Synthetic

<400> SEQUENCE: 122
gcaagguuua caggcguucu u        21

<210> SEQ ID NO 123
<211> LENGTH: 21
<212> TYPE: RNA
<213> ORGANISM: Artificial Sequence
<220> FEATURE:
<223> OTHER INFORMATION: Synthetic

<400> SEQUENCE: 123
ugcaagguuu acaggcguuc u        21

<210> SEQ ID NO 124
<211> LENGTH: 21
<212> TYPE: RNA
<213> ORGANISM: Artificial Sequence
<220> FEATURE:
<223> OTHER INFORMATION: Synthetic

<400> SEQUENCE: 124
cugcaagguu uacaggcguu c        21

<210> SEQ ID NO 125
<211> LENGTH: 21
<212> TYPE: RNA
<213> ORGANISM: Artificial Sequence
<220> FEATURE:
<223> OTHER INFORMATION: Synthetic

<400> SEQUENCE: 125
acugcaaggu uuacaggcgu u        21

<210> SEQ ID NO 126
<211> LENGTH: 21
<212> TYPE: RNA

```
<213> ORGANISM: Artificial Sequence
<220> FEATURE:
<223> OTHER INFORMATION: Synthetic

<400> SEQUENCE: 126
uacugcaagg uuuacaggcg u                                              21

<210> SEQ ID NO 127
<211> LENGTH: 21
<212> TYPE: RNA
<213> ORGANISM: Artificial Sequence
<220> FEATURE:
<223> OTHER INFORMATION: Synthetic

<400> SEQUENCE: 127
auacugcaag guuuacaggc g                                              21

<210> SEQ ID NO 128
<211> LENGTH: 21
<212> TYPE: RNA
<213> ORGANISM: Artificial Sequence
<220> FEATURE:
<223> OTHER INFORMATION: Synthetic

<400> SEQUENCE: 128
aauacugcaa gguuuacagg c                                              21

<210> SEQ ID NO 129
<211> LENGTH: 21
<212> TYPE: RNA
<213> ORGANISM: Artificial Sequence
<220> FEATURE:
<223> OTHER INFORMATION: Synthetic

<400> SEQUENCE: 129
caauacugca agguuuacag g                                              21

<210> SEQ ID NO 130
<211> LENGTH: 21
<212> TYPE: RNA
<213> ORGANISM: Artificial Sequence
<220> FEATURE:
<223> OTHER INFORMATION: Synthetic

<400> SEQUENCE: 130
ucaauacugc aagguuuaca g                                              21

<210> SEQ ID NO 131
<211> LENGTH: 20
<212> TYPE: RNA
<213> ORGANISM: Artificial Sequence
<220> FEATURE:
<223> OTHER INFORMATION: Synthetic

<400> SEQUENCE: 131
ggcguucuuc acgugggaaa                                                20

<210> SEQ ID NO 132
<211> LENGTH: 20
<212> TYPE: RNA
<213> ORGANISM: Artificial Sequence
<220> FEATURE:
<223> OTHER INFORMATION: Synthetic

<400> SEQUENCE: 132
aggcguucuu cacgugggaa                                                20
```

<210> SEQ ID NO 133
<211> LENGTH: 20
<212> TYPE: RNA
<213> ORGANISM: Artificial Sequence
<220> FEATURE:
<223> OTHER INFORMATION: Synthetic

<400> SEQUENCE: 133
caggcguucu ucacguggga                                                    20

<210> SEQ ID NO 134
<211> LENGTH: 20
<212> TYPE: RNA
<213> ORGANISM: Artificial Sequence
<220> FEATURE:
<223> OTHER INFORMATION: Synthetic

<400> SEQUENCE: 134
acaggcguuc uucacguggg                                                    20

<210> SEQ ID NO 135
<211> LENGTH: 20
<212> TYPE: RNA
<213> ORGANISM: Artificial Sequence
<220> FEATURE:
<223> OTHER INFORMATION: Synthetic

<400> SEQUENCE: 135
uacaggcguu cuucacgugg                                                    20

<210> SEQ ID NO 136
<211> LENGTH: 20
<212> TYPE: RNA
<213> ORGANISM: Artificial Sequence
<220> FEATURE:
<223> OTHER INFORMATION: Synthetic

<400> SEQUENCE: 136
uuacaggcgu ucuucacgug                                                    20

<210> SEQ ID NO 137
<211> LENGTH: 20
<212> TYPE: RNA
<213> ORGANISM: Artificial Sequence
<220> FEATURE:
<223> OTHER INFORMATION: Synthetic

<400> SEQUENCE: 137
uuuacaggcg uucuucacgu                                                    20

<210> SEQ ID NO 138
<211> LENGTH: 20
<212> TYPE: RNA
<213> ORGANISM: Artificial Sequence
<220> FEATURE:
<223> OTHER INFORMATION: Synthetic

<400> SEQUENCE: 138
guuuacaggc guucuucacg                                                    20

<210> SEQ ID NO 139
<211> LENGTH: 20
<212> TYPE: RNA
<213> ORGANISM: Artificial Sequence
<220> FEATURE:

<223> OTHER INFORMATION: Synthetic

<400> SEQUENCE: 139
gguuuacagg cguucuucac                                                    20

<210> SEQ ID NO 140
<211> LENGTH: 20
<212> TYPE: RNA
<213> ORGANISM: Artificial Sequence
<220> FEATURE:
<223> OTHER INFORMATION: Synthetic

<400> SEQUENCE: 140
agguuuacag gcguucuuca                                                    20

<210> SEQ ID NO 141
<211> LENGTH: 20
<212> TYPE: RNA
<213> ORGANISM: Artificial Sequence
<220> FEATURE:
<223> OTHER INFORMATION: Synthetic

<400> SEQUENCE: 141
aagguuuaca ggcguucuuc                                                    20

<210> SEQ ID NO 142
<211> LENGTH: 20
<212> TYPE: RNA
<213> ORGANISM: Artificial Sequence
<220> FEATURE:
<223> OTHER INFORMATION: Synthetic

<400> SEQUENCE: 142
caagguuuac aggcguucuu                                                    20

<210> SEQ ID NO 143
<211> LENGTH: 20
<212> TYPE: RNA
<213> ORGANISM: Artificial Sequence
<220> FEATURE:
<223> OTHER INFORMATION: Synthetic

<400> SEQUENCE: 143
gcaagguuua caggcguucu                                                    20

<210> SEQ ID NO 144
<211> LENGTH: 20
<212> TYPE: RNA
<213> ORGANISM: Artificial Sequence
<220> FEATURE:
<223> OTHER INFORMATION: Synthetic

<400> SEQUENCE: 144
ugcaagguuu acaggcguuc                                                    20

<210> SEQ ID NO 145
<211> LENGTH: 20
<212> TYPE: RNA
<213> ORGANISM: Artificial Sequence
<220> FEATURE:
<223> OTHER INFORMATION: Synthetic

<400> SEQUENCE: 145
cugcaagguu uacaggcguu                                                    20

```
<210> SEQ ID NO 146
<211> LENGTH: 20
<212> TYPE: RNA
<213> ORGANISM: Artificial Sequence
<220> FEATURE:
<223> OTHER INFORMATION: Synthetic

<400> SEQUENCE: 146
acugcaaggu uuacaggcgu                                                 20

<210> SEQ ID NO 147
<211> LENGTH: 20
<212> TYPE: RNA
<213> ORGANISM: Artificial Sequence
<220> FEATURE:
<223> OTHER INFORMATION: Synthetic

<400> SEQUENCE: 147
uacugcaagg uuuacaggcg                                                 20

<210> SEQ ID NO 148
<211> LENGTH: 20
<212> TYPE: RNA
<213> ORGANISM: Artificial Sequence
<220> FEATURE:
<223> OTHER INFORMATION: Synthetic

<400> SEQUENCE: 148
auacugcaag guuuacaggc                                                 20

<210> SEQ ID NO 149
<211> LENGTH: 20
<212> TYPE: RNA
<213> ORGANISM: Artificial Sequence
<220> FEATURE:
<223> OTHER INFORMATION: Synthetic

<400> SEQUENCE: 149
aauacugcaa gguuuacagg                                                 20

<210> SEQ ID NO 150
<211> LENGTH: 19
<212> TYPE: RNA
<213> ORGANISM: Artificial Sequence
<220> FEATURE:
<223> OTHER INFORMATION: Synthetic

<400> SEQUENCE: 150
gcguucuuca cgugggaaa                                                  19

<210> SEQ ID NO 151
<211> LENGTH: 19
<212> TYPE: RNA
<213> ORGANISM: Artificial Sequence
<220> FEATURE:
<223> OTHER INFORMATION: Synthetic

<400> SEQUENCE: 151
ggcguucuuc acgugggaa                                                  19

<210> SEQ ID NO 152
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 152
aggcguucuu cacguggga                                              19

<210> SEQ ID NO 153
<211> LENGTH: 19
<212> TYPE: RNA
<213> ORGANISM: Artificial Sequence
<220> FEATURE:
<223> OTHER INFORMATION: Synthetic

<400> SEQUENCE: 153
caggcguucu ucacguggg                                              19

<210> SEQ ID NO 154
<211> LENGTH: 19
<212> TYPE: RNA
<213> ORGANISM: Artificial Sequence
<220> FEATURE:
<223> OTHER INFORMATION: Synthetic

<400> SEQUENCE: 154
acaggcguuc uucacgugg                                              19

<210> SEQ ID NO 155
<211> LENGTH: 19
<212> TYPE: RNA
<213> ORGANISM: Artificial Sequence
<220> FEATURE:
<223> OTHER INFORMATION: Synthetic

<400> SEQUENCE: 155
uacaggcguu cuucacgug                                              19

<210> SEQ ID NO 156
<211> LENGTH: 19
<212> TYPE: RNA
<213> ORGANISM: Artificial Sequence
<220> FEATURE:
<223> OTHER INFORMATION: Synthetic

<400> SEQUENCE: 156
uuacaggcgu ucuucacgu                                              19

<210> SEQ ID NO 157
<211> LENGTH: 19
<212> TYPE: RNA
<213> ORGANISM: Artificial Sequence
<220> FEATURE:
<223> OTHER INFORMATION: Synthetic

<400> SEQUENCE: 157
uuuacaggcg uucuucacg                                              19

<210> SEQ ID NO 158
<211> LENGTH: 19
<212> TYPE: RNA
<213> ORGANISM: Artificial Sequence
<220> FEATURE:
<223> OTHER INFORMATION: Synthetic

<400> SEQUENCE: 158
guuuacaggc guucuucac                                              19

<210> SEQ ID NO 159
<211> LENGTH: 19
```

```
<212> TYPE: RNA
<213> ORGANISM: Artificial Sequence
<220> FEATURE:
<223> OTHER INFORMATION: Synthetic

<400> SEQUENCE: 159
gguuuacagg cguucuuca                                                    19

<210> SEQ ID NO 160
<211> LENGTH: 19
<212> TYPE: RNA
<213> ORGANISM: Artificial Sequence
<220> FEATURE:
<223> OTHER INFORMATION: Synthetic

<400> SEQUENCE: 160
agguuuacag gcguucuuc                                                    19

<210> SEQ ID NO 161
<211> LENGTH: 19
<212> TYPE: RNA
<213> ORGANISM: Artificial Sequence
<220> FEATURE:
<223> OTHER INFORMATION: Synthetic

<400> SEQUENCE: 161
aagguuuaca ggcguucuu                                                    19

<210> SEQ ID NO 162
<211> LENGTH: 19
<212> TYPE: RNA
<213> ORGANISM: Artificial Sequence
<220> FEATURE:
<223> OTHER INFORMATION: Synthetic

<400> SEQUENCE: 162
caagguuuac aggcguucu                                                    19

<210> SEQ ID NO 163
<211> LENGTH: 19
<212> TYPE: RNA
<213> ORGANISM: Artificial Sequence
<220> FEATURE:
<223> OTHER INFORMATION: Synthetic

<400> SEQUENCE: 163
gcaagguuua caggcguuc                                                    19

<210> SEQ ID NO 164
<211> LENGTH: 19
<212> TYPE: RNA
<213> ORGANISM: Artificial Sequence
<220> FEATURE:
<223> OTHER INFORMATION: Synthetic

<400> SEQUENCE: 164
ugcaagguuu acaggcguu                                                    19

<210> SEQ ID NO 165
<211> LENGTH: 19
<212> TYPE: RNA
<213> ORGANISM: Artificial Sequence
<220> FEATURE:
<223> OTHER INFORMATION: Synthetic

<400> SEQUENCE: 165
```

| | |
|---|---|
| cugcaagguu uacaggcgu | 19 |

<210> SEQ ID NO 166
<211> LENGTH: 19
<212> TYPE: RNA
<213> ORGANISM: Artificial Sequence
<220> FEATURE:
<223> OTHER INFORMATION: Synthetic

<400> SEQUENCE: 166

| | |
|---|---|
| acugcaaggu uuacaggcg | 19 |

<210> SEQ ID NO 167
<211> LENGTH: 19
<212> TYPE: RNA
<213> ORGANISM: Artificial Sequence
<220> FEATURE:
<223> OTHER INFORMATION: Synthetic

<400> SEQUENCE: 167

| | |
|---|---|
| uacugcaagg uuuacaggc | 19 |

<210> SEQ ID NO 168
<211> LENGTH: 19
<212> TYPE: RNA
<213> ORGANISM: Artificial Sequence
<220> FEATURE:
<223> OTHER INFORMATION: Synthetic

<400> SEQUENCE: 168

| | |
|---|---|
| auacugcaag guuuacagg | 19 |

<210> SEQ ID NO 169
<211> LENGTH: 18
<212> TYPE: RNA
<213> ORGANISM: Artificial Sequence
<220> FEATURE:
<223> OTHER INFORMATION: Synthetic

<400> SEQUENCE: 169

| | |
|---|---|
| cguucuucac gugggaaa | 18 |

<210> SEQ ID NO 170
<211> LENGTH: 18
<212> TYPE: RNA
<213> ORGANISM: Artificial Sequence
<220> FEATURE:
<223> OTHER INFORMATION: Synthetic

<400> SEQUENCE: 170

| | |
|---|---|
| gcguucuuca cgugggaa | 18 |

<210> SEQ ID NO 171
<211> LENGTH: 18
<212> TYPE: RNA
<213> ORGANISM: Artificial Sequence
<220> FEATURE:
<223> OTHER INFORMATION: Synthetic

<400> SEQUENCE: 171

| | |
|---|---|
| ggcguucuuc acguggga | 18 |

<210> SEQ ID NO 172
<211> LENGTH: 18
<212> TYPE: RNA
<213> ORGANISM: Artificial Sequence

```
<220> FEATURE:
<223> OTHER INFORMATION: Synthetic

<400> SEQUENCE: 172
aggcguucuu cacguggg                                                    18

<210> SEQ ID NO 173
<211> LENGTH: 18
<212> TYPE: RNA
<213> ORGANISM: Artificial Sequence
<220> FEATURE:
<223> OTHER INFORMATION: Synthetic

<400> SEQUENCE: 173
caggcguucu ucacgugg                                                    18

<210> SEQ ID NO 174
<211> LENGTH: 18
<212> TYPE: RNA
<213> ORGANISM: Artificial Sequence
<220> FEATURE:
<223> OTHER INFORMATION: Synthetic

<400> SEQUENCE: 174
acaggcguuc uucacgug                                                    18

<210> SEQ ID NO 175
<211> LENGTH: 18
<212> TYPE: RNA
<213> ORGANISM: Artificial Sequence
<220> FEATURE:
<223> OTHER INFORMATION: Synthetic

<400> SEQUENCE: 175
uacaggcguu cuucacgu                                                    18

<210> SEQ ID NO 176
<211> LENGTH: 18
<212> TYPE: RNA
<213> ORGANISM: Artificial Sequence
<220> FEATURE:
<223> OTHER INFORMATION: Synthetic

<400> SEQUENCE: 176
uuacaggcgu ucuucacg                                                    18

<210> SEQ ID NO 177
<211> LENGTH: 18
<212> TYPE: RNA
<213> ORGANISM: Artificial Sequence
<220> FEATURE:
<223> OTHER INFORMATION: Synthetic

<400> SEQUENCE: 177
uuuacaggcg uucuucac                                                    18

<210> SEQ ID NO 178
<211> LENGTH: 18
<212> TYPE: RNA
<213> ORGANISM: Artificial Sequence
<220> FEATURE:
<223> OTHER INFORMATION: Synthetic

<400> SEQUENCE: 178
guuuacaggc guucuuca                                                    18
```

<210> SEQ ID NO 179
<211> LENGTH: 18
<212> TYPE: RNA
<213> ORGANISM: Artificial Sequence
<220> FEATURE:
<223> OTHER INFORMATION: Synthetic

<400> SEQUENCE: 179
gguuuacagg cguucuuc                                                 18

<210> SEQ ID NO 180
<211> LENGTH: 18
<212> TYPE: RNA
<213> ORGANISM: Artificial Sequence
<220> FEATURE:
<223> OTHER INFORMATION: Synthetic

<400> SEQUENCE: 180
agguuuacag gcguucuu                                                 18

<210> SEQ ID NO 181
<211> LENGTH: 18
<212> TYPE: RNA
<213> ORGANISM: Artificial Sequence
<220> FEATURE:
<223> OTHER INFORMATION: Synthetic

<400> SEQUENCE: 181
aagguuuaca ggcguucu                                                 18

<210> SEQ ID NO 182
<211> LENGTH: 18
<212> TYPE: RNA
<213> ORGANISM: Artificial Sequence
<220> FEATURE:
<223> OTHER INFORMATION: Synthetic

<400> SEQUENCE: 182
caagguuuac aggcguuc                                                 18

<210> SEQ ID NO 183
<211> LENGTH: 18
<212> TYPE: RNA
<213> ORGANISM: Artificial Sequence
<220> FEATURE:
<223> OTHER INFORMATION: Synthetic

<400> SEQUENCE: 183
gcaagguuua caggcguu                                                 18

<210> SEQ ID NO 184
<211> LENGTH: 18
<212> TYPE: RNA
<213> ORGANISM: Artificial Sequence
<220> FEATURE:
<223> OTHER INFORMATION: Synthetic

<400> SEQUENCE: 184
ugcaagguuu acaggcgu                                                 18

<210> SEQ ID NO 185
<211> LENGTH: 18
<212> TYPE: RNA
<213> ORGANISM: Artificial Sequence
<220> FEATURE:
<223> OTHER INFORMATION: Synthetic

```
<400> SEQUENCE: 185
cugcaagguu uacaggcg                                                 18

<210> SEQ ID NO 186
<211> LENGTH: 18
<212> TYPE: RNA
<213> ORGANISM: Artificial Sequence
<220> FEATURE:
<223> OTHER INFORMATION: Synthetic

<400> SEQUENCE: 186
acugcaaggu uuacaggc                                                 18

<210> SEQ ID NO 187
<211> LENGTH: 18
<212> TYPE: RNA
<213> ORGANISM: Artificial Sequence
<220> FEATURE:
<223> OTHER INFORMATION: Synthetic

<400> SEQUENCE: 187
uacugcaagg uuuacagg                                                 18

<210> SEQ ID NO 188
<211> LENGTH: 24
<212> TYPE: RNA
<213> ORGANISM: Artificial Sequence
<220> FEATURE:
<223> OTHER INFORMATION: Synthetic

<400> SEQUENCE: 188
cuagguuuac gggaccucuu caac                                          24

<210> SEQ ID NO 189
<211> LENGTH: 24
<212> TYPE: RNA
<213> ORGANISM: Artificial Sequence
<220> FEATURE:
<223> OTHER INFORMATION: Synthetic

<400> SEQUENCE: 189
gcuagguuua cgggaccucu ucaa                                          24

<210> SEQ ID NO 190
<211> LENGTH: 24
<212> TYPE: RNA
<213> ORGANISM: Artificial Sequence
<220> FEATURE:
<223> OTHER INFORMATION: Synthetic

<400> SEQUENCE: 190
cgcuagguuu acgggaccuc uuca                                          24

<210> SEQ ID NO 191
<211> LENGTH: 24
<212> TYPE: RNA
<213> ORGANISM: Artificial Sequence
<220> FEATURE:
<223> OTHER INFORMATION: Synthetic

<400> SEQUENCE: 191
ccgcuagguu uacgggaccu cuuc                                          24

<210> SEQ ID NO 192
```

```
<211> LENGTH: 24
<212> TYPE: RNA
<213> ORGANISM: Artificial Sequence
<220> FEATURE:
<223> OTHER INFORMATION: Synthetic

<400> SEQUENCE: 192
accgcuaggu uuacgggacc ucuu                                              24

<210> SEQ ID NO 193
<211> LENGTH: 24
<212> TYPE: RNA
<213> ORGANISM: Artificial Sequence
<220> FEATURE:
<223> OTHER INFORMATION: Synthetic

<400> SEQUENCE: 193
aaccgcuagg uuuacgggac cucu                                              24

<210> SEQ ID NO 194
<211> LENGTH: 24
<212> TYPE: RNA
<213> ORGANISM: Artificial Sequence
<220> FEATURE:
<223> OTHER INFORMATION: Synthetic

<400> SEQUENCE: 194
aaaccgcuag guuuacggga ccuc                                              24

<210> SEQ ID NO 195
<211> LENGTH: 24
<212> TYPE: RNA
<213> ORGANISM: Artificial Sequence
<220> FEATURE:
<223> OTHER INFORMATION: Synthetic

<400> SEQUENCE: 195
aaaaccgcua gguuuacggg accu                                              24

<210> SEQ ID NO 196
<211> LENGTH: 23
<212> TYPE: RNA
<213> ORGANISM: Artificial Sequence
<220> FEATURE:
<223> OTHER INFORMATION: Synthetic

<400> SEQUENCE: 196
uagguuuacg ggaccucuuc aac                                               23

<210> SEQ ID NO 197
<211> LENGTH: 23
<212> TYPE: RNA
<213> ORGANISM: Artificial Sequence
<220> FEATURE:
<223> OTHER INFORMATION: Synthetic

<400> SEQUENCE: 197
cuagguuuac gggaccucuu caa                                               23

<210> SEQ ID NO 198
<211> LENGTH: 23
<212> TYPE: RNA
<213> ORGANISM: Artificial Sequence
<220> FEATURE:
<223> OTHER INFORMATION: Synthetic

<400> SEQUENCE: 198
```

```
gcuagguuua cgggaccucu uca                                              23

<210> SEQ ID NO 199
<211> LENGTH: 23
<212> TYPE: RNA
<213> ORGANISM: Artificial Sequence
<220> FEATURE:
<223> OTHER INFORMATION: Synthetic

<400> SEQUENCE: 199
cgcuagguuu acgggaccuc uuc                                              23

<210> SEQ ID NO 200
<211> LENGTH: 23
<212> TYPE: RNA
<213> ORGANISM: Artificial Sequence
<220> FEATURE:
<223> OTHER INFORMATION: Synthetic

<400> SEQUENCE: 200
ccgcuagguu uacgggaccu cuu                                              23

<210> SEQ ID NO 201
<211> LENGTH: 23
<212> TYPE: RNA
<213> ORGANISM: Artificial Sequence
<220> FEATURE:
<223> OTHER INFORMATION: Synthetic

<400> SEQUENCE: 201
accgcuaggu uuacgggacc ucu                                              23

<210> SEQ ID NO 202
<211> LENGTH: 23
<212> TYPE: RNA
<213> ORGANISM: Artificial Sequence
<220> FEATURE:
<223> OTHER INFORMATION: Synthetic

<400> SEQUENCE: 202
aaccgcuagg uuuacgggac cuc                                              23

<210> SEQ ID NO 203
<211> LENGTH: 23
<212> TYPE: RNA
<213> ORGANISM: Artificial Sequence
<220> FEATURE:
<223> OTHER INFORMATION: Synthetic

<400> SEQUENCE: 203
aaaccgcuag guuuacggga ccu                                              23

<210> SEQ ID NO 204
<211> LENGTH: 23
<212> TYPE: RNA
<213> ORGANISM: Artificial Sequence
<220> FEATURE:
<223> OTHER INFORMATION: Synthetic

<400> SEQUENCE: 204
aaaaccgcua gguuuacggg acc                                              23

<210> SEQ ID NO 205
<211> LENGTH: 22
<212> TYPE: RNA
```

```
<213> ORGANISM: Artificial Sequence
<220> FEATURE:
<223> OTHER INFORMATION: Synthetic

<400> SEQUENCE: 205
agguuuacgg gaccucuuca ac                                              22

<210> SEQ ID NO 206
<211> LENGTH: 22
<212> TYPE: RNA
<213> ORGANISM: Artificial Sequence
<220> FEATURE:
<223> OTHER INFORMATION: Synthetic

<400> SEQUENCE: 206
uagguuuacg ggaccucuuc aa                                              22

<210> SEQ ID NO 207
<211> LENGTH: 22
<212> TYPE: RNA
<213> ORGANISM: Artificial Sequence
<220> FEATURE:
<223> OTHER INFORMATION: Synthetic

<400> SEQUENCE: 207
cuagguuuac gggaccucuu ca                                              22

<210> SEQ ID NO 208
<211> LENGTH: 22
<212> TYPE: RNA
<213> ORGANISM: Artificial Sequence
<220> FEATURE:
<223> OTHER INFORMATION: Synthetic

<400> SEQUENCE: 208
gcuagguuua cgggaccucu uc                                              22

<210> SEQ ID NO 209
<211> LENGTH: 22
<212> TYPE: RNA
<213> ORGANISM: Artificial Sequence
<220> FEATURE:
<223> OTHER INFORMATION: Synthetic

<400> SEQUENCE: 209
cgcuagguuu acgggaccuc uu                                              22

<210> SEQ ID NO 210
<211> LENGTH: 22
<212> TYPE: RNA
<213> ORGANISM: Artificial Sequence
<220> FEATURE:
<223> OTHER INFORMATION: Synthetic

<400> SEQUENCE: 210
ccgcuagguu uacgggaccu cu                                              22

<210> SEQ ID NO 211
<211> LENGTH: 22
<212> TYPE: RNA
<213> ORGANISM: Artificial Sequence
<220> FEATURE:
<223> OTHER INFORMATION: Synthetic

<400> SEQUENCE: 211
accgcuaggu uuacgggacc uc                                              22
```

<210> SEQ ID NO 212
<211> LENGTH: 22
<212> TYPE: RNA
<213> ORGANISM: Artificial Sequence
<220> FEATURE:
<223> OTHER INFORMATION: Synthetic

<400> SEQUENCE: 212
aaccgcuagg uuuacgggac cu                                              22

<210> SEQ ID NO 213
<211> LENGTH: 22
<212> TYPE: RNA
<213> ORGANISM: Artificial Sequence
<220> FEATURE:
<223> OTHER INFORMATION: Synthetic

<400> SEQUENCE: 213
aaaccgcuag guuuacggga cc                                              22

<210> SEQ ID NO 214
<211> LENGTH: 21
<212> TYPE: RNA
<213> ORGANISM: Artificial Sequence
<220> FEATURE:
<223> OTHER INFORMATION: Synthetic

<400> SEQUENCE: 214
gguuuacggg accucuucaa c                                               21

<210> SEQ ID NO 215
<211> LENGTH: 21
<212> TYPE: RNA
<213> ORGANISM: Artificial Sequence
<220> FEATURE:
<223> OTHER INFORMATION: Synthetic

<400> SEQUENCE: 215
agguuuacgg gaccucuuca a                                               21

<210> SEQ ID NO 216
<211> LENGTH: 21
<212> TYPE: RNA
<213> ORGANISM: Artificial Sequence
<220> FEATURE:
<223> OTHER INFORMATION: Synthetic

<400> SEQUENCE: 216
uagguuuacg ggaccucuuc a                                               21

<210> SEQ ID NO 217
<211> LENGTH: 21
<212> TYPE: RNA
<213> ORGANISM: Artificial Sequence
<220> FEATURE:
<223> OTHER INFORMATION: Synthetic

<400> SEQUENCE: 217
cuagguuuac gggaccucuu c                                               21

<210> SEQ ID NO 218
<211> LENGTH: 21
<212> TYPE: RNA
<213> ORGANISM: Artificial Sequence
<220> FEATURE:

```
<223> OTHER INFORMATION: Synthetic

<400> SEQUENCE: 218
gcuagguuua cgggaccucu u                                          21

<210> SEQ ID NO 219
<211> LENGTH: 21
<212> TYPE: RNA
<213> ORGANISM: Artificial Sequence
<220> FEATURE:
<223> OTHER INFORMATION: Synthetic

<400> SEQUENCE: 219
cgcuagguuu acgggaccuc u                                          21

<210> SEQ ID NO 220
<211> LENGTH: 21
<212> TYPE: RNA
<213> ORGANISM: Artificial Sequence
<220> FEATURE:
<223> OTHER INFORMATION: Synthetic

<400> SEQUENCE: 220
ccgcuagguu uacgggaccu c                                          21

<210> SEQ ID NO 221
<211> LENGTH: 21
<212> TYPE: RNA
<213> ORGANISM: Artificial Sequence
<220> FEATURE:
<223> OTHER INFORMATION: Synthetic

<400> SEQUENCE: 221
accgcuaggu uuacgggacc u                                          21

<210> SEQ ID NO 222
<211> LENGTH: 21
<212> TYPE: RNA
<213> ORGANISM: Artificial Sequence
<220> FEATURE:
<223> OTHER INFORMATION: Synthetic

<400> SEQUENCE: 222
aaccgcuagg uuuacgggac c                                          21

<210> SEQ ID NO 223
<211> LENGTH: 20
<212> TYPE: RNA
<213> ORGANISM: Artificial Sequence
<220> FEATURE:
<223> OTHER INFORMATION: Synthetic

<400> SEQUENCE: 223
guuuacggga ccucuucaac                                            20

<210> SEQ ID NO 224
<211> LENGTH: 20
<212> TYPE: RNA
<213> ORGANISM: Artificial Sequence
<220> FEATURE:
<223> OTHER INFORMATION: Synthetic

<400> SEQUENCE: 224
gguuuacggg accucuucaa                                            20
```

```
<210> SEQ ID NO 225
<211> LENGTH: 20
<212> TYPE: RNA
<213> ORGANISM: Artificial Sequence
<220> FEATURE:
<223> OTHER INFORMATION: Synthetic

<400> SEQUENCE: 225
agguuuacgg gaccucuuca                                              20

<210> SEQ ID NO 226
<211> LENGTH: 20
<212> TYPE: RNA
<213> ORGANISM: Artificial Sequence
<220> FEATURE:
<223> OTHER INFORMATION: Synthetic

<400> SEQUENCE: 226
uagguuuacg ggaccucuuc                                              20

<210> SEQ ID NO 227
<211> LENGTH: 20
<212> TYPE: RNA
<213> ORGANISM: Artificial Sequence
<220> FEATURE:
<223> OTHER INFORMATION: Synthetic

<400> SEQUENCE: 227
cuagguuuac gggaccucuu                                              20

<210> SEQ ID NO 228
<211> LENGTH: 20
<212> TYPE: RNA
<213> ORGANISM: Artificial Sequence
<220> FEATURE:
<223> OTHER INFORMATION: Synthetic

<400> SEQUENCE: 228
gcuagguuua cgggaccucu                                              20

<210> SEQ ID NO 229
<211> LENGTH: 20
<212> TYPE: RNA
<213> ORGANISM: Artificial Sequence
<220> FEATURE:
<223> OTHER INFORMATION: Synthetic

<400> SEQUENCE: 229
cgcuagguuu acgggaccuc                                              20

<210> SEQ ID NO 230
<211> LENGTH: 20
<212> TYPE: RNA
<213> ORGANISM: Artificial Sequence
<220> FEATURE:
<223> OTHER INFORMATION: Synthetic

<400> SEQUENCE: 230
ccgcuagguu uacgggaccu                                              20

<210> SEQ ID NO 231
<211> LENGTH: 20
<212> TYPE: RNA
<213> ORGANISM: Artificial Sequence
<220> FEATURE:
<223> OTHER INFORMATION: Synthetic
```

<400> SEQUENCE: 231
accgcuaggu uuacgggacc                                              20

<210> SEQ ID NO 232
<211> LENGTH: 19
<212> TYPE: RNA
<213> ORGANISM: Artificial Sequence
<220> FEATURE:
<223> OTHER INFORMATION: Synthetic

<400> SEQUENCE: 232
uuuacgggac cucuucaac                                               19

<210> SEQ ID NO 233
<211> LENGTH: 19
<212> TYPE: RNA
<213> ORGANISM: Artificial Sequence
<220> FEATURE:
<223> OTHER INFORMATION: Synthetic

<400> SEQUENCE: 233
guuuacggga ccucuucaa                                               19

<210> SEQ ID NO 234
<211> LENGTH: 19
<212> TYPE: RNA
<213> ORGANISM: Artificial Sequence
<220> FEATURE:
<223> OTHER INFORMATION: Synthetic

<400> SEQUENCE: 234
gguuuacggg accucuuca                                               19

<210> SEQ ID NO 235
<211> LENGTH: 19
<212> TYPE: RNA
<213> ORGANISM: Artificial Sequence
<220> FEATURE:
<223> OTHER INFORMATION: Synthetic

<400> SEQUENCE: 235
agguuuacgg gaccucuuc                                               19

<210> SEQ ID NO 236
<211> LENGTH: 19
<212> TYPE: RNA
<213> ORGANISM: Artificial Sequence
<220> FEATURE:
<223> OTHER INFORMATION: Synthetic

<400> SEQUENCE: 236
uagguuuacg ggaccucuu                                               19

<210> SEQ ID NO 237
<211> LENGTH: 19
<212> TYPE: RNA
<213> ORGANISM: Artificial Sequence
<220> FEATURE:
<223> OTHER INFORMATION: Synthetic

<400> SEQUENCE: 237
cuagguuuac gggaccucu                                               19

<210> SEQ ID NO 238
<211> LENGTH: 19

```
<212> TYPE: RNA
<213> ORGANISM: Artificial Sequence
<220> FEATURE:
<223> OTHER INFORMATION: Synthetic

<400> SEQUENCE: 238
gcuagguuua cgggaccuc                                             19

<210> SEQ ID NO 239
<211> LENGTH: 19
<212> TYPE: RNA
<213> ORGANISM: Artificial Sequence
<220> FEATURE:
<223> OTHER INFORMATION: Synthetic

<400> SEQUENCE: 239
cgcuagguuu acgggaccu                                             19

<210> SEQ ID NO 240
<211> LENGTH: 19
<212> TYPE: RNA
<213> ORGANISM: Artificial Sequence
<220> FEATURE:
<223> OTHER INFORMATION: Synthetic

<400> SEQUENCE: 240
ccgcuagguu uacgggacc                                             19

<210> SEQ ID NO 241
<211> LENGTH: 18
<212> TYPE: RNA
<213> ORGANISM: Artificial Sequence
<220> FEATURE:
<223> OTHER INFORMATION: Synthetic

<400> SEQUENCE: 241
uuacgggacc ucuucaac                                              18

<210> SEQ ID NO 242
<211> LENGTH: 18
<212> TYPE: RNA
<213> ORGANISM: Artificial Sequence
<220> FEATURE:
<223> OTHER INFORMATION: Synthetic

<400> SEQUENCE: 242
uuuacgggac cucuucaa                                              18

<210> SEQ ID NO 243
<211> LENGTH: 18
<212> TYPE: RNA
<213> ORGANISM: Artificial Sequence
<220> FEATURE:
<223> OTHER INFORMATION: Synthetic

<400> SEQUENCE: 243
guuuacggga ccucuuca                                              18

<210> SEQ ID NO 244
<211> LENGTH: 18
<212> TYPE: RNA
<213> ORGANISM: Artificial Sequence
<220> FEATURE:
<223> OTHER INFORMATION: Synthetic

<400> SEQUENCE: 244
```
gguuuacggg accucuuc                           18

<210> SEQ ID NO 245
<211> LENGTH: 18
<212> TYPE: RNA
<213> ORGANISM: Artificial Sequence
<220> FEATURE:
<223> OTHER INFORMATION: Synthetic

<400> SEQUENCE: 245
agguuuacgg gaccucuu                           18

<210> SEQ ID NO 246
<211> LENGTH: 18
<212> TYPE: RNA
<213> ORGANISM: Artificial Sequence
<220> FEATURE:
<223> OTHER INFORMATION: Synthetic

<400> SEQUENCE: 246
uagguuuacg ggaccucu                           18

<210> SEQ ID NO 247
<211> LENGTH: 18
<212> TYPE: RNA
<213> ORGANISM: Artificial Sequence
<220> FEATURE:
<223> OTHER INFORMATION: Synthetic

<400> SEQUENCE: 247
cuagguuuac gggaccuc                           18

<210> SEQ ID NO 248
<211> LENGTH: 18
<212> TYPE: RNA
<213> ORGANISM: Artificial Sequence
<220> FEATURE:
<223> OTHER INFORMATION: Synthetic

<400> SEQUENCE: 248
gcuagguuua cgggaccu                           18

<210> SEQ ID NO 249
<211> LENGTH: 18
<212> TYPE: RNA
<213> ORGANISM: Artificial Sequence
<220> FEATURE:
<223> OTHER INFORMATION: Synthetic

<400> SEQUENCE: 249
cgcuagguuu acgggacc                           18

<210> SEQ ID NO 250
<211> LENGTH: 24
<212> TYPE: RNA
<213> ORGANISM: Artificial Sequence
<220> FEATURE:
<223> OTHER INFORMATION: Synthetic

<400> SEQUENCE: 250
uuacuuccgg aguccuugcu ucca                    24

<210> SEQ ID NO 251
<211> LENGTH: 24
<212> TYPE: RNA
<213> ORGANISM: Artificial Sequence

```
<220> FEATURE:
<223> OTHER INFORMATION: Synthetic

<400> SEQUENCE: 251
cuuacuuccg gaguccuugc uucc                                                24

<210> SEQ ID NO 252
<211> LENGTH: 24
<212> TYPE: RNA
<213> ORGANISM: Artificial Sequence
<220> FEATURE:
<223> OTHER INFORMATION: Synthetic

<400> SEQUENCE: 252
ccuuacuucc ggaguccuug cuuc                                                24

<210> SEQ ID NO 253
<211> LENGTH: 24
<212> TYPE: RNA
<213> ORGANISM: Artificial Sequence
<220> FEATURE:
<223> OTHER INFORMATION: Synthetic

<400> SEQUENCE: 253
accuuacuuc cggaguccuu gcuu                                                24

<210> SEQ ID NO 254
<211> LENGTH: 24
<212> TYPE: RNA
<213> ORGANISM: Artificial Sequence
<220> FEATURE:
<223> OTHER INFORMATION: Synthetic

<400> SEQUENCE: 254
gaccuuacuu ccggaguccu ugcu                                                24

<210> SEQ ID NO 255
<211> LENGTH: 24
<212> TYPE: RNA
<213> ORGANISM: Artificial Sequence
<220> FEATURE:
<223> OTHER INFORMATION: Synthetic

<400> SEQUENCE: 255
ugaccuuacu uccggagucc uugc                                                24

<210> SEQ ID NO 256
<211> LENGTH: 24
<212> TYPE: RNA
<213> ORGANISM: Artificial Sequence
<220> FEATURE:
<223> OTHER INFORMATION: Synthetic

<400> SEQUENCE: 256
cugaccuuac uuccggaguc cuug                                                24

<210> SEQ ID NO 257
<211> LENGTH: 24
<212> TYPE: RNA
<213> ORGANISM: Artificial Sequence
<220> FEATURE:
<223> OTHER INFORMATION: Synthetic

<400> SEQUENCE: 257
acugaccuua cuuccggagu ccuu                                                24
```

```
<210> SEQ ID NO 258
<211> LENGTH: 23
<212> TYPE: RNA
<213> ORGANISM: Artificial Sequence
<220> FEATURE:
<223> OTHER INFORMATION: Synthetic

<400> SEQUENCE: 258
uuacuuccgg aguccuugcu ucc                                              23

<210> SEQ ID NO 259
<211> LENGTH: 23
<212> TYPE: RNA
<213> ORGANISM: Artificial Sequence
<220> FEATURE:
<223> OTHER INFORMATION: Synthetic

<400> SEQUENCE: 259
cuuacuuccg gaguccuugc uuc                                              23

<210> SEQ ID NO 260
<211> LENGTH: 23
<212> TYPE: RNA
<213> ORGANISM: Artificial Sequence
<220> FEATURE:
<223> OTHER INFORMATION: Synthetic

<400> SEQUENCE: 260
ccuuacuucc ggaguccuug cuu                                              23

<210> SEQ ID NO 261
<211> LENGTH: 23
<212> TYPE: RNA
<213> ORGANISM: Artificial Sequence
<220> FEATURE:
<223> OTHER INFORMATION: Synthetic

<400> SEQUENCE: 261
accuuacuuc cggaguccuu gcu                                              23

<210> SEQ ID NO 262
<211> LENGTH: 23
<212> TYPE: RNA
<213> ORGANISM: Artificial Sequence
<220> FEATURE:
<223> OTHER INFORMATION: Synthetic

<400> SEQUENCE: 262
gaccuuacuu ccggaguccu ugc                                              23

<210> SEQ ID NO 263
<211> LENGTH: 23
<212> TYPE: RNA
<213> ORGANISM: Artificial Sequence
<220> FEATURE:
<223> OTHER INFORMATION: Synthetic

<400> SEQUENCE: 263
ugaccuuacu uccggagucc uug                                              23

<210> SEQ ID NO 264
<211> LENGTH: 23
<212> TYPE: RNA
<213> ORGANISM: Artificial Sequence
<220> FEATURE:
<223> OTHER INFORMATION: Synthetic
```

```
<400> SEQUENCE: 264
cugaccuuac uuccggaguc cuu                                           23

<210> SEQ ID NO 265
<211> LENGTH: 23
<212> TYPE: RNA
<213> ORGANISM: Artificial Sequence
<220> FEATURE:
<223> OTHER INFORMATION: Synthetic

<400> SEQUENCE: 265
acugaccuua cuuccggagu ccu                                           23

<210> SEQ ID NO 266
<211> LENGTH: 22
<212> TYPE: RNA
<213> ORGANISM: Artificial Sequence
<220> FEATURE:
<223> OTHER INFORMATION: Synthetic

<400> SEQUENCE: 266
uuacuuccgg aguccuugcu uc                                            22

<210> SEQ ID NO 267
<211> LENGTH: 22
<212> TYPE: RNA
<213> ORGANISM: Artificial Sequence
<220> FEATURE:
<223> OTHER INFORMATION: Synthetic

<400> SEQUENCE: 267
cuuacuuccg gaguccuugc uu                                            22

<210> SEQ ID NO 268
<211> LENGTH: 22
<212> TYPE: RNA
<213> ORGANISM: Artificial Sequence
<220> FEATURE:
<223> OTHER INFORMATION: Synthetic

<400> SEQUENCE: 268
ccuuacuucc ggaguccuug cu                                            22

<210> SEQ ID NO 269
<211> LENGTH: 22
<212> TYPE: RNA
<213> ORGANISM: Artificial Sequence
<220> FEATURE:
<223> OTHER INFORMATION: Synthetic

<400> SEQUENCE: 269
accuuacuuc cggaguccuu gc                                            22

<210> SEQ ID NO 270
<211> LENGTH: 22
<212> TYPE: RNA
<213> ORGANISM: Artificial Sequence
<220> FEATURE:
<223> OTHER INFORMATION: Synthetic

<400> SEQUENCE: 270
gaccuuacuu ccggaguccu ug                                            22

<210> SEQ ID NO 271
```

```
<211> LENGTH: 22
<212> TYPE: RNA
<213> ORGANISM: Artificial Sequence
<220> FEATURE:
<223> OTHER INFORMATION: Synthetic

<400> SEQUENCE: 271
ugaccuuacu uccggagucc uu                                                    22

<210> SEQ ID NO 272
<211> LENGTH: 22
<212> TYPE: RNA
<213> ORGANISM: Artificial Sequence
<220> FEATURE:
<223> OTHER INFORMATION: Synthetic

<400> SEQUENCE: 272
cugaccuuac uuccggaguc cu                                                    22

<210> SEQ ID NO 273
<211> LENGTH: 22
<212> TYPE: RNA
<213> ORGANISM: Artificial Sequence
<220> FEATURE:
<223> OTHER INFORMATION: Synthetic

<400> SEQUENCE: 273
acugaccuua cuuccggagu cc                                                    22

<210> SEQ ID NO 274
<211> LENGTH: 21
<212> TYPE: RNA
<213> ORGANISM: Artificial Sequence
<220> FEATURE:
<223> OTHER INFORMATION: Synthetic

<400> SEQUENCE: 274
uuacuuccgg aguccuugcu u                                                     21

<210> SEQ ID NO 275
<211> LENGTH: 21
<212> TYPE: RNA
<213> ORGANISM: Artificial Sequence
<220> FEATURE:
<223> OTHER INFORMATION: Synthetic

<400> SEQUENCE: 275
cuuacuuccg gaguccuugc u                                                     21

<210> SEQ ID NO 276
<211> LENGTH: 21
<212> TYPE: RNA
<213> ORGANISM: Artificial Sequence
<220> FEATURE:
<223> OTHER INFORMATION: Synthetic

<400> SEQUENCE: 276
ccuuacuucc ggaguccuug c                                                     21

<210> SEQ ID NO 277
<211> LENGTH: 21
<212> TYPE: RNA
<213> ORGANISM: Artificial Sequence
<220> FEATURE:
<223> OTHER INFORMATION: Synthetic

<400> SEQUENCE: 277
```
accuuacuuc cggaguccuu g                                              21

<210> SEQ ID NO 278
<211> LENGTH: 21
<212> TYPE: RNA
<213> ORGANISM: Artificial Sequence
<220> FEATURE:
<223> OTHER INFORMATION: Synthetic

<400> SEQUENCE: 278
gaccuuacuu ccggaguccu u                                              21

<210> SEQ ID NO 279
<211> LENGTH: 21
<212> TYPE: RNA
<213> ORGANISM: Artificial Sequence
<220> FEATURE:
<223> OTHER INFORMATION: Synthetic

<400> SEQUENCE: 279
ugaccuuacu uccggagucc u                                              21

<210> SEQ ID NO 280
<211> LENGTH: 21
<212> TYPE: RNA
<213> ORGANISM: Artificial Sequence
<220> FEATURE:
<223> OTHER INFORMATION: Synthetic

<400> SEQUENCE: 280
cugaccuuac uuccggaguc c                                              21

<210> SEQ ID NO 281
<211> LENGTH: 21
<212> TYPE: RNA
<213> ORGANISM: Artificial Sequence
<220> FEATURE:
<223> OTHER INFORMATION: Synthetic

<400> SEQUENCE: 281
acugaccuua cuuccggagu c                                              21

<210> SEQ ID NO 282
<211> LENGTH: 20
<212> TYPE: RNA
<213> ORGANISM: Artificial Sequence
<220> FEATURE:
<223> OTHER INFORMATION: Synthetic

<400> SEQUENCE: 282
uuacuuccgg aguccuugcu                                                20

<210> SEQ ID NO 283
<211> LENGTH: 20
<212> TYPE: RNA
<213> ORGANISM: Artificial Sequence
<220> FEATURE:
<223> OTHER INFORMATION: Synthetic

<400> SEQUENCE: 283
cuuacuuccg gaguccuugc                                                20

<210> SEQ ID NO 284
<211> LENGTH: 20
<212> TYPE: RNA

```
<213> ORGANISM: Artificial Sequence
<220> FEATURE:
<223> OTHER INFORMATION: Synthetic

<400> SEQUENCE: 284
ccuuacuucc ggaguccuug                                                    20

<210> SEQ ID NO 285
<211> LENGTH: 20
<212> TYPE: RNA
<213> ORGANISM: Artificial Sequence
<220> FEATURE:
<223> OTHER INFORMATION: Synthetic

<400> SEQUENCE: 285
accuuacuuc cggaguccuu                                                    20

<210> SEQ ID NO 286
<211> LENGTH: 20
<212> TYPE: RNA
<213> ORGANISM: Artificial Sequence
<220> FEATURE:
<223> OTHER INFORMATION: Synthetic

<400> SEQUENCE: 286
gaccuuacuu ccggagsuccu                                                   20

<210> SEQ ID NO 287
<211> LENGTH: 20
<212> TYPE: RNA
<213> ORGANISM: Artificial Sequence
<220> FEATURE:
<223> OTHER INFORMATION: Synthetic

<400> SEQUENCE: 287
ugaccuuacu uccggagucc                                                    20

<210> SEQ ID NO 288
<211> LENGTH: 20
<212> TYPE: RNA
<213> ORGANISM: Artificial Sequence
<220> FEATURE:
<223> OTHER INFORMATION: Synthetic

<400> SEQUENCE: 288
cugaccuuac uuccggaguc                                                    20

<210> SEQ ID NO 289
<211> LENGTH: 20
<212> TYPE: RNA
<213> ORGANISM: Artificial Sequence
<220> FEATURE:
<223> OTHER INFORMATION: Synthetic

<400> SEQUENCE: 289
acugaccuua cuuccggagu                                                    20

<210> SEQ ID NO 290
<211> LENGTH: 19
<212> TYPE: RNA
<213> ORGANISM: Artificial Sequence
<220> FEATURE:
<223> OTHER INFORMATION: Synthetic

<400> SEQUENCE: 290
uuacuuccgg aguccuugc                                                     19
```

<210> SEQ ID NO 291
<211> LENGTH: 19
<212> TYPE: RNA
<213> ORGANISM: Artificial Sequence
<220> FEATURE:
<223> OTHER INFORMATION: Synthetic

<400> SEQUENCE: 291
cuuacuuccg gaguccuug                                                    19

<210> SEQ ID NO 292
<211> LENGTH: 19
<212> TYPE: RNA
<213> ORGANISM: Artificial Sequence
<220> FEATURE:
<223> OTHER INFORMATION: Synthetic

<400> SEQUENCE: 292
ccuuacuucc ggaguccuu                                                    19

<210> SEQ ID NO 293
<211> LENGTH: 19
<212> TYPE: RNA
<213> ORGANISM: Artificial Sequence
<220> FEATURE:
<223> OTHER INFORMATION: Synthetic

<400> SEQUENCE: 293
accuuacuuc cggaguccu                                                    19

<210> SEQ ID NO 294
<211> LENGTH: 19
<212> TYPE: RNA
<213> ORGANISM: Artificial Sequence
<220> FEATURE:
<223> OTHER INFORMATION: Synthetic

<400> SEQUENCE: 294
gaccuuacuu ccggagucc                                                    19

<210> SEQ ID NO 295
<211> LENGTH: 19
<212> TYPE: RNA
<213> ORGANISM: Artificial Sequence
<220> FEATURE:
<223> OTHER INFORMATION: Synthetic

<400> SEQUENCE: 295
ugaccuuacu uccggaguc                                                    19

<210> SEQ ID NO 296
<211> LENGTH: 19
<212> TYPE: RNA
<213> ORGANISM: Artificial Sequence
<220> FEATURE:
<223> OTHER INFORMATION: Synthetic

<400> SEQUENCE: 296
cugaccuuac uuccggagu                                                    19

<210> SEQ ID NO 297
<211> LENGTH: 19
<212> TYPE: RNA
<213> ORGANISM: Artificial Sequence
<220> FEATURE:

<223> OTHER INFORMATION: Synthetic

<400> SEQUENCE: 297
acugaccuua cuuccggag                                                        19

<210> SEQ ID NO 298
<211> LENGTH: 18
<212> TYPE: RNA
<213> ORGANISM: Artificial Sequence
<220> FEATURE:
<223> OTHER INFORMATION: Synthetic

<400> SEQUENCE: 298
uuacuuccgg aguccuug                                                         18

<210> SEQ ID NO 299
<211> LENGTH: 18
<212> TYPE: RNA
<213> ORGANISM: Artificial Sequence
<220> FEATURE:
<223> OTHER INFORMATION: Synthetic

<400> SEQUENCE: 299
cuuacuuccg gaguccuu                                                         18

<210> SEQ ID NO 300
<211> LENGTH: 18
<212> TYPE: RNA
<213> ORGANISM: Artificial Sequence
<220> FEATURE:
<223> OTHER INFORMATION: Synthetic

<400> SEQUENCE: 300
ccuuacuucc ggaguccu                                                         18

<210> SEQ ID NO 301
<211> LENGTH: 18
<212> TYPE: RNA
<213> ORGANISM: Artificial Sequence
<220> FEATURE:
<223> OTHER INFORMATION: Synthetic

<400> SEQUENCE: 301
accuuacuuc cggagucc                                                         18

<210> SEQ ID NO 302
<211> LENGTH: 18
<212> TYPE: RNA
<213> ORGANISM: Artificial Sequence
<220> FEATURE:
<223> OTHER INFORMATION: Synthetic

<400> SEQUENCE: 302
gaccuuacuu ccggaguc                                                         18

<210> SEQ ID NO 303
<211> LENGTH: 18
<212> TYPE: RNA
<213> ORGANISM: Artificial Sequence
<220> FEATURE:
<223> OTHER INFORMATION: Synthetic

<400> SEQUENCE: 303
ugaccuuacu uccggagu                                                         18

```
<210> SEQ ID NO 304
<211> LENGTH: 18
<212> TYPE: RNA
<213> ORGANISM: Artificial Sequence
<220> FEATURE:
<223> OTHER INFORMATION: Synthetic

<400> SEQUENCE: 304
cugaccuuac uuccggag                                                 18

<210> SEQ ID NO 305
<211> LENGTH: 18
<212> TYPE: RNA
<213> ORGANISM: Artificial Sequence
<220> FEATURE:
<223> OTHER INFORMATION: Synthetic

<400> SEQUENCE: 305
acugaccuua cuuccgga                                                 18

<210> SEQ ID NO 306
<211> LENGTH: 24
<212> TYPE: RNA
<213> ORGANISM: Artificial Sequence
<220> FEATURE:
<223> OTHER INFORMATION: Synthetic

<400> SEQUENCE: 306
uuuucagcuu gucuuagacg ccuu                                          24

<210> SEQ ID NO 307
<211> LENGTH: 23
<212> TYPE: RNA
<213> ORGANISM: Artificial Sequence
<220> FEATURE:
<223> OTHER INFORMATION: Synthetic

<400> SEQUENCE: 307
uuucagcuug ucuuagacgc cuu                                           23

<210> SEQ ID NO 308
<211> LENGTH: 23
<212> TYPE: RNA
<213> ORGANISM: Artificial Sequence
<220> FEATURE:
<223> OTHER INFORMATION: Synthetic

<400> SEQUENCE: 308
uuuucagcuu gucuuagacg ccu                                           23

<210> SEQ ID NO 309
<211> LENGTH: 22
<212> TYPE: RNA
<213> ORGANISM: Artificial Sequence
<220> FEATURE:
<223> OTHER INFORMATION: Synthetic

<400> SEQUENCE: 309
uucagcuugu cuuagacgcc uu                                            22

<210> SEQ ID NO 310
<211> LENGTH: 22
<212> TYPE: RNA
<213> ORGANISM: Artificial Sequence
<220> FEATURE:
<223> OTHER INFORMATION: Synthetic
```

```
<400> SEQUENCE: 310
uuucagcuug ucuuagacgc cu                                          22

<210> SEQ ID NO 311
<211> LENGTH: 22
<212> TYPE: RNA
<213> ORGANISM: Artificial Sequence
<220> FEATURE:
<223> OTHER INFORMATION: Synthetic

<400> SEQUENCE: 311
uuuucagcuu gucuuagacg cc                                          22

<210> SEQ ID NO 312
<211> LENGTH: 21
<212> TYPE: RNA
<213> ORGANISM: Artificial Sequence
<220> FEATURE:
<223> OTHER INFORMATION: Synthetic

<400> SEQUENCE: 312
ucagcuuguc uuagacgccu u                                           21

<210> SEQ ID NO 313
<211> LENGTH: 21
<212> TYPE: RNA
<213> ORGANISM: Artificial Sequence
<220> FEATURE:
<223> OTHER INFORMATION: Synthetic

<400> SEQUENCE: 313
uucagcuugu cuuagacgcc u                                           21

<210> SEQ ID NO 314
<211> LENGTH: 21
<212> TYPE: RNA
<213> ORGANISM: Artificial Sequence
<220> FEATURE:
<223> OTHER INFORMATION: Synthetic

<400> SEQUENCE: 314
uuucagcuug ucuuagacgc c                                           21

<210> SEQ ID NO 315
<211> LENGTH: 21
<212> TYPE: RNA
<213> ORGANISM: Artificial Sequence
<220> FEATURE:
<223> OTHER INFORMATION: Synthetic

<400> SEQUENCE: 315
uuuucagcuu gucuuagacg c                                           21

<210> SEQ ID NO 316
<211> LENGTH: 20
<212> TYPE: RNA
<213> ORGANISM: Artificial Sequence
<220> FEATURE:
<223> OTHER INFORMATION: Synthetic

<400> SEQUENCE: 316
cagcuugucu uagacgccuu                                             20

<210> SEQ ID NO 317
<211> LENGTH: 20
```

```
<212> TYPE: RNA
<213> ORGANISM: Artificial Sequence
<220> FEATURE:
<223> OTHER INFORMATION: Synthetic

<400> SEQUENCE: 317
ucagcuuguc uuagacgccu                                              20

<210> SEQ ID NO 318
<211> LENGTH: 20
<212> TYPE: RNA
<213> ORGANISM: Artificial Sequence
<220> FEATURE:
<223> OTHER INFORMATION: Synthetic

<400> SEQUENCE: 318
uucagcuugu cuuagacgcc                                              20

<210> SEQ ID NO 319
<211> LENGTH: 20
<212> TYPE: RNA
<213> ORGANISM: Artificial Sequence
<220> FEATURE:
<223> OTHER INFORMATION: Synthetic

<400> SEQUENCE: 319
uuucagcuug ucuuagacgc                                              20

<210> SEQ ID NO 320
<211> LENGTH: 20
<212> TYPE: RNA
<213> ORGANISM: Artificial Sequence
<220> FEATURE:
<223> OTHER INFORMATION: Synthetic

<400> SEQUENCE: 320
uuuucagcuu gucuuagacg                                              20

<210> SEQ ID NO 321
<211> LENGTH: 19
<212> TYPE: RNA
<213> ORGANISM: Artificial Sequence
<220> FEATURE:
<223> OTHER INFORMATION: Synthetic

<400> SEQUENCE: 321
agcuugucuu agacgccuu                                               19

<210> SEQ ID NO 322
<211> LENGTH: 19
<212> TYPE: RNA
<213> ORGANISM: Artificial Sequence
<220> FEATURE:
<223> OTHER INFORMATION: Synthetic

<400> SEQUENCE: 322
cagcuugucu uagacgccu                                               19

<210> SEQ ID NO 323
<211> LENGTH: 19
<212> TYPE: RNA
<213> ORGANISM: Artificial Sequence
<220> FEATURE:
<223> OTHER INFORMATION: Synthetic

<400> SEQUENCE: 323
```

-continued ucagcuuguc uuagacgcc 19

<210> SEQ ID NO 324
<211> LENGTH: 19
<212> TYPE: RNA
<213> ORGANISM: Artificial Sequence
<220> FEATURE:
<223> OTHER INFORMATION: Synthetic

<400> SEQUENCE: 324
uucagcuugu cuuagacgc 19

<210> SEQ ID NO 325
<211> LENGTH: 19
<212> TYPE: RNA
<213> ORGANISM: Artificial Sequence
<220> FEATURE:
<223> OTHER INFORMATION: Synthetic

<400> SEQUENCE: 325
uuucagcuug ucuuagacg 19

<210> SEQ ID NO 326
<211> LENGTH: 19
<212> TYPE: RNA
<213> ORGANISM: Artificial Sequence
<220> FEATURE:
<223> OTHER INFORMATION: Synthetic

<400> SEQUENCE: 326
uuuucagcuu gucuuagac 19

<210> SEQ ID NO 327
<211> LENGTH: 18
<212> TYPE: RNA
<213> ORGANISM: Artificial Sequence
<220> FEATURE:
<223> OTHER INFORMATION: Synthetic

<400> SEQUENCE: 327
gcuugucuua gacgccuu 18

<210> SEQ ID NO 328
<211> LENGTH: 18
<212> TYPE: RNA
<213> ORGANISM: Artificial Sequence
<220> FEATURE:
<223> OTHER INFORMATION: Synthetic

<400> SEQUENCE: 328
agcuugucuu agacgccu 18

<210> SEQ ID NO 329
<211> LENGTH: 18
<212> TYPE: RNA
<213> ORGANISM: Artificial Sequence
<220> FEATURE:
<223> OTHER INFORMATION: Synthetic

<400> SEQUENCE: 329
cagcuugucu uagacgcc 18

<210> SEQ ID NO 330
<211> LENGTH: 18
<212> TYPE: RNA
<213> ORGANISM: Artificial Sequence

```
<220> FEATURE:
<223> OTHER INFORMATION: Synthetic

<400> SEQUENCE: 330
ucagcuuguc uuagacgc                                              18

<210> SEQ ID NO 331
<211> LENGTH: 18
<212> TYPE: RNA
<213> ORGANISM: Artificial Sequence
<220> FEATURE:
<223> OTHER INFORMATION: Synthetic

<400> SEQUENCE: 331
uucagcuugu cuuagacg                                              18

<210> SEQ ID NO 332
<211> LENGTH: 18
<212> TYPE: RNA
<213> ORGANISM: Artificial Sequence
<220> FEATURE:
<223> OTHER INFORMATION: Synthetic

<400> SEQUENCE: 332
uuucagcuug ucuuagac                                              18

<210> SEQ ID NO 333
<211> LENGTH: 18
<212> TYPE: RNA
<213> ORGANISM: Artificial Sequence
<220> FEATURE:
<223> OTHER INFORMATION: Synthetic

<400> SEQUENCE: 333
uuuucagcuu gucuuaga                                              18

<210> SEQ ID NO 334
<211> LENGTH: 24
<212> TYPE: RNA
<213> ORGANISM: Artificial Sequence
<220> FEATURE:
<223> OTHER INFORMATION: Synthetic

<400> SEQUENCE: 334
ucagcuuguc uaagaugccu uguu                                       24

<210> SEQ ID NO 335
<211> LENGTH: 24
<212> TYPE: RNA
<213> ORGANISM: Artificial Sequence
<220> FEATURE:
<223> OTHER INFORMATION: Synthetic

<400> SEQUENCE: 335
uucagcuugu cuaagaugcc uugu                                       24

<210> SEQ ID NO 336
<211> LENGTH: 24
<212> TYPE: RNA
<213> ORGANISM: Artificial Sequence
<220> FEATURE:
<223> OTHER INFORMATION: Synthetic

<400> SEQUENCE: 336
uuucagcuug ucuaagaugc cuug                                       24
```

```
<210> SEQ ID NO 337
<211> LENGTH: 24
<212> TYPE: RNA
<213> ORGANISM: Artificial Sequence
<220> FEATURE:
<223> OTHER INFORMATION: Synthetic

<400> SEQUENCE: 337
uuuucagcuu gucuaagaug ccuu                                          24

<210> SEQ ID NO 338
<211> LENGTH: 23
<212> TYPE: RNA
<213> ORGANISM: Artificial Sequence
<220> FEATURE:
<223> OTHER INFORMATION: Synthetic

<400> SEQUENCE: 338
cagcuugucu aagaugccuu guu                                           23

<210> SEQ ID NO 339
<211> LENGTH: 23
<212> TYPE: RNA
<213> ORGANISM: Artificial Sequence
<220> FEATURE:
<223> OTHER INFORMATION: Synthetic

<400> SEQUENCE: 339
ucagcuuguc uaagaugccu ugu                                           23

<210> SEQ ID NO 340
<211> LENGTH: 23
<212> TYPE: RNA
<213> ORGANISM: Artificial Sequence
<220> FEATURE:
<223> OTHER INFORMATION: Synthetic

<400> SEQUENCE: 340
uucagcuugu cuaagaugcc uug                                           23

<210> SEQ ID NO 341
<211> LENGTH: 23
<212> TYPE: RNA
<213> ORGANISM: Artificial Sequence
<220> FEATURE:
<223> OTHER INFORMATION: Synthetic

<400> SEQUENCE: 341
uuucagcuug ucuaagaugc cuu                                           23

<210> SEQ ID NO 342
<211> LENGTH: 23
<212> TYPE: RNA
<213> ORGANISM: Artificial Sequence
<220> FEATURE:
<223> OTHER INFORMATION: Synthetic

<400> SEQUENCE: 342
uuuucagcuu gucuaagaug ccu                                           23

<210> SEQ ID NO 343
<211> LENGTH: 22
<212> TYPE: RNA
<213> ORGANISM: Artificial Sequence
<220> FEATURE:
<223> OTHER INFORMATION: Synthetic
```

```
<400> SEQUENCE: 343
agcuugucua agaugccuug uu                                              22

<210> SEQ ID NO 344
<211> LENGTH: 22
<212> TYPE: RNA
<213> ORGANISM: Artificial Sequence
<220> FEATURE:
<223> OTHER INFORMATION: Synthetic

<400> SEQUENCE: 344
cagcuugucu aagaugccuu gu                                              22

<210> SEQ ID NO 345
<211> LENGTH: 22
<212> TYPE: RNA
<213> ORGANISM: Artificial Sequence
<220> FEATURE:
<223> OTHER INFORMATION: Synthetic

<400> SEQUENCE: 345
ucagcuuguc uaagaugccu ug                                              22

<210> SEQ ID NO 346
<211> LENGTH: 22
<212> TYPE: RNA
<213> ORGANISM: Artificial Sequence
<220> FEATURE:
<223> OTHER INFORMATION: Synthetic

<400> SEQUENCE: 346
uucagcuugu cuaagaugcc uu                                              22

<210> SEQ ID NO 347
<211> LENGTH: 22
<212> TYPE: RNA
<213> ORGANISM: Artificial Sequence
<220> FEATURE:
<223> OTHER INFORMATION: Synthetic

<400> SEQUENCE: 347
uuucagcuug ucuaagaugc cu                                              22

<210> SEQ ID NO 348
<211> LENGTH: 22
<212> TYPE: RNA
<213> ORGANISM: Artificial Sequence
<220> FEATURE:
<223> OTHER INFORMATION: Synthetic

<400> SEQUENCE: 348
uuuucagcuu gucuaagaug cc                                              22

<210> SEQ ID NO 349
<211> LENGTH: 21
<212> TYPE: RNA
<213> ORGANISM: Artificial Sequence
<220> FEATURE:
<223> OTHER INFORMATION: Synthetic

<400> SEQUENCE: 349
gcuugucuaa gaugccuugu u                                               21

<210> SEQ ID NO 350
```

```
<211> LENGTH: 21
<212> TYPE: RNA
<213> ORGANISM: Artificial Sequence
<220> FEATURE:
<223> OTHER INFORMATION: Synthetic

<400> SEQUENCE: 350
agcuugucua agaugccuug u                                              21

<210> SEQ ID NO 351
<211> LENGTH: 21
<212> TYPE: RNA
<213> ORGANISM: Artificial Sequence
<220> FEATURE:
<223> OTHER INFORMATION: Synthetic

<400> SEQUENCE: 351
cagcuugucu aagaugccuu g                                              21

<210> SEQ ID NO 352
<211> LENGTH: 21
<212> TYPE: RNA
<213> ORGANISM: Artificial Sequence
<220> FEATURE:
<223> OTHER INFORMATION: Synthetic

<400> SEQUENCE: 352
ucagcuuguc uaagaugccu u                                              21

<210> SEQ ID NO 353
<211> LENGTH: 21
<212> TYPE: RNA
<213> ORGANISM: Artificial Sequence
<220> FEATURE:
<223> OTHER INFORMATION: Synthetic

<400> SEQUENCE: 353
uucagcuugu cuaagaugcc u                                              21

<210> SEQ ID NO 354
<211> LENGTH: 21
<212> TYPE: RNA
<213> ORGANISM: Artificial Sequence
<220> FEATURE:
<223> OTHER INFORMATION: Synthetic

<400> SEQUENCE: 354
uuucagcuug ucuaagaugc c                                              21

<210> SEQ ID NO 355
<211> LENGTH: 21
<212> TYPE: RNA
<213> ORGANISM: Artificial Sequence
<220> FEATURE:
<223> OTHER INFORMATION: Synthetic

<400> SEQUENCE: 355
uuuucagcuu gucuaagaug c                                              21

<210> SEQ ID NO 356
<211> LENGTH: 20
<212> TYPE: RNA
<213> ORGANISM: Artificial Sequence
<220> FEATURE:
<223> OTHER INFORMATION: Synthetic

<400> SEQUENCE: 356
```
cuugucuaag augccuuguu                                               20

<210> SEQ ID NO 357
<211> LENGTH: 20
<212> TYPE: RNA
<213> ORGANISM: Artificial Sequence
<220> FEATURE:
<223> OTHER INFORMATION: Synthetic

<400> SEQUENCE: 357
gcuugucuaa gaugccuugu                                               20

<210> SEQ ID NO 358
<211> LENGTH: 20
<212> TYPE: RNA
<213> ORGANISM: Artificial Sequence
<220> FEATURE:
<223> OTHER INFORMATION: Synthetic

<400> SEQUENCE: 358
agcuugucua agaugccuug                                               20

<210> SEQ ID NO 359
<211> LENGTH: 20
<212> TYPE: RNA
<213> ORGANISM: Artificial Sequence
<220> FEATURE:
<223> OTHER INFORMATION: Synthetic

<400> SEQUENCE: 359
cagcuugucu aagaugccuu                                               20

<210> SEQ ID NO 360
<211> LENGTH: 20
<212> TYPE: RNA
<213> ORGANISM: Artificial Sequence
<220> FEATURE:
<223> OTHER INFORMATION: Synthetic

<400> SEQUENCE: 360
ucagcuuguc uaagaugccu                                               20

<210> SEQ ID NO 361
<211> LENGTH: 20
<212> TYPE: RNA
<213> ORGANISM: Artificial Sequence
<220> FEATURE:
<223> OTHER INFORMATION: Synthetic

<400> SEQUENCE: 361
uucagcuugu cuaagaugcc                                               20

<210> SEQ ID NO 362
<211> LENGTH: 19
<212> TYPE: RNA
<213> ORGANISM: Artificial Sequence
<220> FEATURE:
<223> OTHER INFORMATION: Synthetic

<400> SEQUENCE: 362
agcuugucua agaugccuu                                                19

<210> SEQ ID NO 363
<211> LENGTH: 19
<212> TYPE: RNA

```
<213> ORGANISM: Artificial Sequence
<220> FEATURE:
<223> OTHER INFORMATION: Synthetic

<400> SEQUENCE: 363
cagcuugucu aagaugccu                                          19

<210> SEQ ID NO 364
<211> LENGTH: 19
<212> TYPE: RNA
<213> ORGANISM: Artificial Sequence
<220> FEATURE:
<223> OTHER INFORMATION: Synthetic

<400> SEQUENCE: 364
ucagcuuguc uaagaugcc                                          19

<210> SEQ ID NO 365
<211> LENGTH: 19
<212> TYPE: RNA
<213> ORGANISM: Artificial Sequence
<220> FEATURE:
<223> OTHER INFORMATION: Synthetic

<400> SEQUENCE: 365
uucagcuugu cuaagaugc                                          19

<210> SEQ ID NO 366
<211> LENGTH: 18
<212> TYPE: RNA
<213> ORGANISM: Artificial Sequence
<220> FEATURE:
<223> OTHER INFORMATION: Synthetic

<400> SEQUENCE: 366
gcuugucuaa gaugccuu                                           18

<210> SEQ ID NO 367
<211> LENGTH: 18
<212> TYPE: RNA
<213> ORGANISM: Artificial Sequence
<220> FEATURE:
<223> OTHER INFORMATION: Synthetic

<400> SEQUENCE: 367
agcuugucua agaugccu                                           18

<210> SEQ ID NO 368
<211> LENGTH: 18
<212> TYPE: RNA
<213> ORGANISM: Artificial Sequence
<220> FEATURE:
<223> OTHER INFORMATION: Synthetic

<400> SEQUENCE: 368
cagcuugucu aagaugcc                                           18

<210> SEQ ID NO 369
<211> LENGTH: 18
<212> TYPE: RNA
<213> ORGANISM: Artificial Sequence
<220> FEATURE:
<223> OTHER INFORMATION: Synthetic

<400> SEQUENCE: 369
ucagcuuguc uaagaugc                                           18
```

<210> SEQ ID NO 370
<211> LENGTH: 22
<212> TYPE: RNA
<213> ORGANISM: Artificial Sequence
<220> FEATURE:
<223> OTHER INFORMATION: Synthetic

<400> SEQUENCE: 370
ucguaccacc auuugcuuuu ca                                              22

<210> SEQ ID NO 371
<211> LENGTH: 21
<212> TYPE: RNA
<213> ORGANISM: Artificial Sequence
<220> FEATURE:
<223> OTHER INFORMATION: Synthetic

<400> SEQUENCE: 371
cguaccacca uuugcuuuuc a                                               21

<210> SEQ ID NO 372
<211> LENGTH: 21
<212> TYPE: RNA
<213> ORGANISM: Artificial Sequence
<220> FEATURE:
<223> OTHER INFORMATION: Synthetic

<400> SEQUENCE: 372
ucguaccacc auuugcuuuu c                                               21

<210> SEQ ID NO 373
<211> LENGTH: 20
<212> TYPE: RNA
<213> ORGANISM: Artificial Sequence
<220> FEATURE:
<223> OTHER INFORMATION: Synthetic

<400> SEQUENCE: 373
cguaccacca uuugcuuuuc                                                 20

<210> SEQ ID NO 374
<211> LENGTH: 20
<212> TYPE: RNA
<213> ORGANISM: Artificial Sequence
<220> FEATURE:
<223> OTHER INFORMATION: Synthetic

<400> SEQUENCE: 374
cguaccacca uuugcuuuuc                                                 20

<210> SEQ ID NO 375
<211> LENGTH: 20
<212> TYPE: RNA
<213> ORGANISM: Artificial Sequence
<220> FEATURE:
<223> OTHER INFORMATION: Synthetic

<400> SEQUENCE: 375
ucguaccacc auuugcuuuu                                                 20

<210> SEQ ID NO 376
<211> LENGTH: 24
<212> TYPE: RNA
<213> ORGANISM: Artificial Sequence
<220> FEATURE:

<223> OTHER INFORMATION: Synthetic

<400> SEQUENCE: 376
uaagaugccu uguucacuga guuu                                           24

<210> SEQ ID NO 377
<211> LENGTH: 23
<212> TYPE: RNA
<213> ORGANISM: Artificial Sequence
<220> FEATURE:
<223> OTHER INFORMATION: Synthetic

<400> SEQUENCE: 377
aagaugccuu guucacugag uuu                                            23

<210> SEQ ID NO 378
<211> LENGTH: 23
<212> TYPE: RNA
<213> ORGANISM: Artificial Sequence
<220> FEATURE:
<223> OTHER INFORMATION: Synthetic

<400> SEQUENCE: 378
uaagaugccu uguucacuga guu                                            23

<210> SEQ ID NO 379
<211> LENGTH: 22
<212> TYPE: RNA
<213> ORGANISM: Artificial Sequence
<220> FEATURE:
<223> OTHER INFORMATION: Synthetic

<400> SEQUENCE: 379
agaugccuug uucacugagu uu                                             22

<210> SEQ ID NO 380
<211> LENGTH: 22
<212> TYPE: RNA
<213> ORGANISM: Artificial Sequence
<220> FEATURE:
<223> OTHER INFORMATION: Synthetic

<400> SEQUENCE: 380
aagaugccuu guucacugag uu                                             22

<210> SEQ ID NO 381
<211> LENGTH: 22
<212> TYPE: RNA
<213> ORGANISM: Artificial Sequence
<220> FEATURE:
<223> OTHER INFORMATION: Synthetic

<400> SEQUENCE: 381
uaagaugccu uguucacuga gu                                             22

<210> SEQ ID NO 382
<211> LENGTH: 21
<212> TYPE: RNA
<213> ORGANISM: Artificial Sequence
<220> FEATURE:
<223> OTHER INFORMATION: Synthetic

<400> SEQUENCE: 382
gaugccuugu ucacugaguu u                                              21

```
<210> SEQ ID NO 383
<211> LENGTH: 21
<212> TYPE: RNA
<213> ORGANISM: Artificial Sequence
<220> FEATURE:
<223> OTHER INFORMATION: Synthetic

<400> SEQUENCE: 383
agaugccuug uucacugagu u                                              21

<210> SEQ ID NO 384
<211> LENGTH: 21
<212> TYPE: RNA
<213> ORGANISM: Artificial Sequence
<220> FEATURE:
<223> OTHER INFORMATION: Synthetic

<400> SEQUENCE: 384
aagaugccuu guucacugag u                                              21

<210> SEQ ID NO 385
<211> LENGTH: 21
<212> TYPE: RNA
<213> ORGANISM: Artificial Sequence
<220> FEATURE:
<223> OTHER INFORMATION: Synthetic

<400> SEQUENCE: 385
uaagaugccu uguucacuga g                                              21

<210> SEQ ID NO 386
<211> LENGTH: 20
<212> TYPE: RNA
<213> ORGANISM: Artificial Sequence
<220> FEATURE:
<223> OTHER INFORMATION: Synthetic

<400> SEQUENCE: 386
augccuuguu cacugaguuu                                                20

<210> SEQ ID NO 387
<211> LENGTH: 20
<212> TYPE: RNA
<213> ORGANISM: Artificial Sequence
<220> FEATURE:
<223> OTHER INFORMATION: Synthetic

<400> SEQUENCE: 387
gaugccuugu ucacugaguu                                                20

<210> SEQ ID NO 388
<211> LENGTH: 20
<212> TYPE: RNA
<213> ORGANISM: Artificial Sequence
<220> FEATURE:
<223> OTHER INFORMATION: Synthetic

<400> SEQUENCE: 388
agaugccuug uucacugagu                                                20

<210> SEQ ID NO 389
<211> LENGTH: 20
<212> TYPE: RNA
<213> ORGANISM: Artificial Sequence
<220> FEATURE:
<223> OTHER INFORMATION: Synthetic
```

```
<400> SEQUENCE: 389
aagaugccuu guucacugag                                           20

<210> SEQ ID NO 390
<211> LENGTH: 20
<212> TYPE: RNA
<213> ORGANISM: Artificial Sequence
<220> FEATURE:
<223> OTHER INFORMATION: Synthetic

<400> SEQUENCE: 390
uaagaugccu uguucacuga                                           20

<210> SEQ ID NO 391
<211> LENGTH: 19
<212> TYPE: RNA
<213> ORGANISM: Artificial Sequence
<220> FEATURE:
<223> OTHER INFORMATION: Synthetic

<400> SEQUENCE: 391
ugccuuguuc acugaguuu                                            19

<210> SEQ ID NO 392
<211> LENGTH: 19
<212> TYPE: RNA
<213> ORGANISM: Artificial Sequence
<220> FEATURE:
<223> OTHER INFORMATION: Synthetic

<400> SEQUENCE: 392
augccuuguu cacugaguu                                            19

<210> SEQ ID NO 393
<211> LENGTH: 19
<212> TYPE: RNA
<213> ORGANISM: Artificial Sequence
<220> FEATURE:
<223> OTHER INFORMATION: Synthetic

<400> SEQUENCE: 393
gaugccuugu ucacugagu                                            19

<210> SEQ ID NO 394
<211> LENGTH: 19
<212> TYPE: RNA
<213> ORGANISM: Artificial Sequence
<220> FEATURE:
<223> OTHER INFORMATION: Synthetic

<400> SEQUENCE: 394
agaugccuug uucacugag                                            19

<210> SEQ ID NO 395
<211> LENGTH: 19
<212> TYPE: RNA
<213> ORGANISM: Artificial Sequence
<220> FEATURE:
<223> OTHER INFORMATION: Synthetic

<400> SEQUENCE: 395
aagaugccuu guucacuga                                            19

<210> SEQ ID NO 396
<211> LENGTH: 19
```

```
<212> TYPE: RNA
<213> ORGANISM: Artificial Sequence
<220> FEATURE:
<223> OTHER INFORMATION: Synthetic

<400> SEQUENCE: 396
uaagaugccu uguucacug                                              19

<210> SEQ ID NO 397
<211> LENGTH: 18
<212> TYPE: RNA
<213> ORGANISM: Artificial Sequence
<220> FEATURE:
<223> OTHER INFORMATION: Synthetic

<400> SEQUENCE: 397
ugccuuguuc acugaguu                                               18

<210> SEQ ID NO 398
<211> LENGTH: 18
<212> TYPE: RNA
<213> ORGANISM: Artificial Sequence
<220> FEATURE:
<223> OTHER INFORMATION: Synthetic

<400> SEQUENCE: 398
augccuuguu cacgagu                                                18

<210> SEQ ID NO 399
<211> LENGTH: 18
<212> TYPE: RNA
<213> ORGANISM: Artificial Sequence
<220> FEATURE:
<223> OTHER INFORMATION: Synthetic

<400> SEQUENCE: 399
gaugccuugu ucacugag                                               18

<210> SEQ ID NO 400
<211> LENGTH: 18
<212> TYPE: RNA
<213> ORGANISM: Artificial Sequence
<220> FEATURE:
<223> OTHER INFORMATION: Synthetic

<400> SEQUENCE: 400
agaugccuug uucacuga                                               18

<210> SEQ ID NO 401
<211> LENGTH: 24
<212> TYPE: RNA
<213> ORGANISM: Artificial Sequence
<220> FEATURE:
<223> OTHER INFORMATION: Synthetic

<400> SEQUENCE: 401
caagauuuac uggguucuu cacg                                         24

<210> SEQ ID NO 402
<211> LENGTH: 24
<212> TYPE: RNA
<213> ORGANISM: Artificial Sequence
<220> FEATURE:
<223> OTHER INFORMATION: Synthetic

<400> SEQUENCE: 402
```
gcaagauuua cugggguucu ucac 24

<210> SEQ ID NO 403
<211> LENGTH: 24
<212> TYPE: RNA
<213> ORGANISM: Artificial Sequence
<220> FEATURE:
<223> OTHER INFORMATION: Synthetic

<400> SEQUENCE: 403
ugcaagauuu acuggguuc uuca 24

<210> SEQ ID NO 404
<211> LENGTH: 24
<212> TYPE: RNA
<213> ORGANISM: Artificial Sequence
<220> FEATURE:
<223> OTHER INFORMATION: Synthetic

<400> SEQUENCE: 404
cugcaagauu uacuggggu cuuc 24

<210> SEQ ID NO 405
<211> LENGTH: 24
<212> TYPE: RNA
<213> ORGANISM: Artificial Sequence
<220> FEATURE:
<223> OTHER INFORMATION: Synthetic

<400> SEQUENCE: 405
acugcaagau uuacugggu ucuu 24

<210> SEQ ID NO 406
<211> LENGTH: 24
<212> TYPE: RNA
<213> ORGANISM: Artificial Sequence
<220> FEATURE:
<223> OTHER INFORMATION: Synthetic

<400> SEQUENCE: 406
uacugcaaga uuuacugggg uucu 24

<210> SEQ ID NO 407
<211> LENGTH: 24
<212> TYPE: RNA
<213> ORGANISM: Artificial Sequence
<220> FEATURE:
<223> OTHER INFORMATION: Synthetic

<400> SEQUENCE: 407
auacugcaag auuuacuggg guuc 24

<210> SEQ ID NO 408
<211> LENGTH: 24
<212> TYPE: RNA
<213> ORGANISM: Artificial Sequence
<220> FEATURE:
<223> OTHER INFORMATION: Synthetic

<400> SEQUENCE: 408
aauacugcaa gauuuacugg gguu 24

<210> SEQ ID NO 409
<211> LENGTH: 24
<212> TYPE: RNA
<213> ORGANISM: Artificial Sequence

```
<220> FEATURE:
<223> OTHER INFORMATION: Synthetic

<400> SEQUENCE: 409
caauacugca agauuuacug gggu                                          24

<210> SEQ ID NO 410
<211> LENGTH: 23
<212> TYPE: RNA
<213> ORGANISM: Artificial Sequence
<220> FEATURE:
<223> OTHER INFORMATION: Synthetic

<400> SEQUENCE: 410
aagauuuacu gggguucuuc acg                                           23

<210> SEQ ID NO 411
<211> LENGTH: 23
<212> TYPE: RNA
<213> ORGANISM: Artificial Sequence
<220> FEATURE:
<223> OTHER INFORMATION: Synthetic

<400> SEQUENCE: 411
caagauuuac uggguucuu cac                                            23

<210> SEQ ID NO 412
<211> LENGTH: 23
<212> TYPE: RNA
<213> ORGANISM: Artificial Sequence
<220> FEATURE:
<223> OTHER INFORMATION: Synthetic

<400> SEQUENCE: 412
gcaagauuua cuggguucu uca                                            23

<210> SEQ ID NO 413
<211> LENGTH: 23
<212> TYPE: RNA
<213> ORGANISM: Artificial Sequence
<220> FEATURE:
<223> OTHER INFORMATION: Synthetic

<400> SEQUENCE: 413
ugcaagauuu acuggguuc uuc                                            23

<210> SEQ ID NO 414
<211> LENGTH: 23
<212> TYPE: RNA
<213> ORGANISM: Artificial Sequence
<220> FEATURE:
<223> OTHER INFORMATION: Synthetic

<400> SEQUENCE: 414
cugcaagauu uacuggggu cuu                                            23

<210> SEQ ID NO 415
<211> LENGTH: 23
<212> TYPE: RNA
<213> ORGANISM: Artificial Sequence
<220> FEATURE:
<223> OTHER INFORMATION: Synthetic

<400> SEQUENCE: 415
acugcaagau uuacugggg u ucu                                          23
```

```
<210> SEQ ID NO 416
<211> LENGTH: 23
<212> TYPE: RNA
<213> ORGANISM: Artificial Sequence
<220> FEATURE:
<223> OTHER INFORMATION: Synthetic

<400> SEQUENCE: 416
uacugcaaga uuuacuggggg uuc                                              23

<210> SEQ ID NO 417
<211> LENGTH: 23
<212> TYPE: RNA
<213> ORGANISM: Artificial Sequence
<220> FEATURE:
<223> OTHER INFORMATION: Synthetic

<400> SEQUENCE: 417
auacugcaag auuuacuggg guu                                               23

<210> SEQ ID NO 418
<211> LENGTH: 23
<212> TYPE: RNA
<213> ORGANISM: Artificial Sequence
<220> FEATURE:
<223> OTHER INFORMATION: Synthetic

<400> SEQUENCE: 418
aauacugcaa gauuuacugg ggu                                               23

<210> SEQ ID NO 419
<211> LENGTH: 22
<212> TYPE: RNA
<213> ORGANISM: Artificial Sequence
<220> FEATURE:
<223> OTHER INFORMATION: Synthetic

<400> SEQUENCE: 419
agauuuacug ggguucuuca cg                                                22

<210> SEQ ID NO 420
<211> LENGTH: 22
<212> TYPE: RNA
<213> ORGANISM: Artificial Sequence
<220> FEATURE:
<223> OTHER INFORMATION: Synthetic

<400> SEQUENCE: 420
aagauuuacu ggguucuuc ac                                                 22

<210> SEQ ID NO 421
<211> LENGTH: 22
<212> TYPE: RNA
<213> ORGANISM: Artificial Sequence
<220> FEATURE:
<223> OTHER INFORMATION: Synthetic

<400> SEQUENCE: 421
caagauuuac uggguucuu ca                                                 22

<210> SEQ ID NO 422
<211> LENGTH: 22
<212> TYPE: RNA
<213> ORGANISM: Artificial Sequence
<220> FEATURE:
<223> OTHER INFORMATION: Synthetic
```

```
<400> SEQUENCE: 422
gcaagauuua cugggguucu uc                                              22

<210> SEQ ID NO 423
<211> LENGTH: 22
<212> TYPE: RNA
<213> ORGANISM: Artificial Sequence
<220> FEATURE:
<223> OTHER INFORMATION: Synthetic

<400> SEQUENCE: 423
ugcaagauuu acuggguuc uu                                               22

<210> SEQ ID NO 424
<211> LENGTH: 22
<212> TYPE: RNA
<213> ORGANISM: Artificial Sequence
<220> FEATURE:
<223> OTHER INFORMATION: Synthetic

<400> SEQUENCE: 424
cugcaagauu uacugggguu cu                                              22

<210> SEQ ID NO 425
<211> LENGTH: 22
<212> TYPE: RNA
<213> ORGANISM: Artificial Sequence
<220> FEATURE:
<223> OTHER INFORMATION: Synthetic

<400> SEQUENCE: 425
acugcaagau uuacugggu uc                                               22

<210> SEQ ID NO 426
<211> LENGTH: 22
<212> TYPE: RNA
<213> ORGANISM: Artificial Sequence
<220> FEATURE:
<223> OTHER INFORMATION: Synthetic

<400> SEQUENCE: 426
uacugcaaga uuuacugggg uu                                              22

<210> SEQ ID NO 427
<211> LENGTH: 22
<212> TYPE: RNA
<213> ORGANISM: Artificial Sequence
<220> FEATURE:
<223> OTHER INFORMATION: Synthetic

<400> SEQUENCE: 427
auacugcaag auuuacuggg gu                                              22

<210> SEQ ID NO 428
<211> LENGTH: 21
<212> TYPE: RNA
<213> ORGANISM: Artificial Sequence
<220> FEATURE:
<223> OTHER INFORMATION: Synthetic

<400> SEQUENCE: 428
gauuuacugg gguucuucac g                                               21

<210> SEQ ID NO 429
```

```
<211> LENGTH: 21
<212> TYPE: RNA
<213> ORGANISM: Artificial Sequence
<220> FEATURE:
<223> OTHER INFORMATION: Synthetic

<400> SEQUENCE: 429
agauuuacug ggguucuuca c                                          21

<210> SEQ ID NO 430
<211> LENGTH: 21
<212> TYPE: RNA
<213> ORGANISM: Artificial Sequence
<220> FEATURE:
<223> OTHER INFORMATION: Synthetic

<400> SEQUENCE: 430
aagauuuacu gggguucuuc a                                          21

<210> SEQ ID NO 431
<211> LENGTH: 21
<212> TYPE: RNA
<213> ORGANISM: Artificial Sequence
<220> FEATURE:
<223> OTHER INFORMATION: Synthetic

<400> SEQUENCE: 431
caagauuuac ugggguucuu c                                          21

<210> SEQ ID NO 432
<211> LENGTH: 21
<212> TYPE: RNA
<213> ORGANISM: Artificial Sequence
<220> FEATURE:
<223> OTHER INFORMATION: Synthetic

<400> SEQUENCE: 432
gcaagauuua cugggguucu u                                          21

<210> SEQ ID NO 433
<211> LENGTH: 21
<212> TYPE: RNA
<213> ORGANISM: Artificial Sequence
<220> FEATURE:
<223> OTHER INFORMATION: Synthetic

<400> SEQUENCE: 433
ugcaagauuu acugggguuc u                                          21

<210> SEQ ID NO 434
<211> LENGTH: 21
<212> TYPE: RNA
<213> ORGANISM: Artificial Sequence
<220> FEATURE:
<223> OTHER INFORMATION: Synthetic

<400> SEQUENCE: 434
cugcaagauu uacugggguu c                                          21

<210> SEQ ID NO 435
<211> LENGTH: 21
<212> TYPE: RNA
<213> ORGANISM: Artificial Sequence
<220> FEATURE:
<223> OTHER INFORMATION: Synthetic

<400> SEQUENCE: 435
```
acugcaagau uuacuggggu u                                        21

<210> SEQ ID NO 436
<211> LENGTH: 21
<212> TYPE: RNA
<213> ORGANISM: Artificial Sequence
<220> FEATURE:
<223> OTHER INFORMATION: Synthetic

<400> SEQUENCE: 436
uacugcaaga uuuacugggg u                                        21

<210> SEQ ID NO 437
<211> LENGTH: 20
<212> TYPE: RNA
<213> ORGANISM: Artificial Sequence
<220> FEATURE:
<223> OTHER INFORMATION: Synthetic

<400> SEQUENCE: 437
auuuacuggg guucuucacg                                          20

<210> SEQ ID NO 438
<211> LENGTH: 20
<212> TYPE: RNA
<213> ORGANISM: Artificial Sequence
<220> FEATURE:
<223> OTHER INFORMATION: Synthetic

<400> SEQUENCE: 438
gauuuacugg gguucuucac                                          20

<210> SEQ ID NO 439
<211> LENGTH: 20
<212> TYPE: RNA
<213> ORGANISM: Artificial Sequence
<220> FEATURE:
<223> OTHER INFORMATION: Synthetic

<400> SEQUENCE: 439
agauuuacug ggguucuuca                                          20

<210> SEQ ID NO 440
<211> LENGTH: 20
<212> TYPE: RNA
<213> ORGANISM: Artificial Sequence
<220> FEATURE:
<223> OTHER INFORMATION: Synthetic

<400> SEQUENCE: 440
aagauuuacu gggguucuuc                                          20

<210> SEQ ID NO 441
<211> LENGTH: 20
<212> TYPE: RNA
<213> ORGANISM: Artificial Sequence
<220> FEATURE:
<223> OTHER INFORMATION: Synthetic

<400> SEQUENCE: 441
caagauuuac uggggguucuu                                         20

<210> SEQ ID NO 442
<211> LENGTH: 20
<212> TYPE: RNA

```
<213> ORGANISM: Artificial Sequence
<220> FEATURE:
<223> OTHER INFORMATION: Synthetic

<400> SEQUENCE: 442
gcaagauuua cugggguucu                                                    20

<210> SEQ ID NO 443
<211> LENGTH: 20
<212> TYPE: RNA
<213> ORGANISM: Artificial Sequence
<220> FEATURE:
<223> OTHER INFORMATION: Synthetic

<400> SEQUENCE: 443
ugcaagauuu acuggggguuc                                                   20

<210> SEQ ID NO 444
<211> LENGTH: 20
<212> TYPE: RNA
<213> ORGANISM: Artificial Sequence
<220> FEATURE:
<223> OTHER INFORMATION: Synthetic

<400> SEQUENCE: 444
cugcaagauu uacuggggguu                                                   20

<210> SEQ ID NO 445
<211> LENGTH: 20
<212> TYPE: RNA
<213> ORGANISM: Artificial Sequence
<220> FEATURE:
<223> OTHER INFORMATION: Synthetic

<400> SEQUENCE: 445
acugcaagau uuacugggu                                                     20

<210> SEQ ID NO 446
<211> LENGTH: 19
<212> TYPE: RNA
<213> ORGANISM: Artificial Sequence
<220> FEATURE:
<223> OTHER INFORMATION: Synthetic

<400> SEQUENCE: 446
uuuacugggg uucuucacg                                                     19

<210> SEQ ID NO 447
<211> LENGTH: 19
<212> TYPE: RNA
<213> ORGANISM: Artificial Sequence
<220> FEATURE:
<223> OTHER INFORMATION: Synthetic

<400> SEQUENCE: 447
auuuacuggg guucuucac                                                     19

<210> SEQ ID NO 448
<211> LENGTH: 19
<212> TYPE: RNA
<213> ORGANISM: Artificial Sequence
<220> FEATURE:
<223> OTHER INFORMATION: Synthetic

<400> SEQUENCE: 448
gauuuacugg gguucuuca                                                     19
```

<210> SEQ ID NO 449
<211> LENGTH: 19
<212> TYPE: RNA
<213> ORGANISM: Artificial Sequence
<220> FEATURE:
<223> OTHER INFORMATION: Synthetic

<400> SEQUENCE: 449
agauuuacug ggguucuuc                                                  19

<210> SEQ ID NO 450
<211> LENGTH: 19
<212> TYPE: RNA
<213> ORGANISM: Artificial Sequence
<220> FEATURE:
<223> OTHER INFORMATION: Synthetic

<400> SEQUENCE: 450
aagauuuacu gggguucuu                                                  19

<210> SEQ ID NO 451
<211> LENGTH: 19
<212> TYPE: RNA
<213> ORGANISM: Artificial Sequence
<220> FEATURE:
<223> OTHER INFORMATION: Synthetic

<400> SEQUENCE: 451
caagauuuac uggggguucu                                                 19

<210> SEQ ID NO 452
<211> LENGTH: 19
<212> TYPE: RNA
<213> ORGANISM: Artificial Sequence
<220> FEATURE:
<223> OTHER INFORMATION: Synthetic

<400> SEQUENCE: 452
gcaagauuua cugggguuc                                                  19

<210> SEQ ID NO 453
<211> LENGTH: 19
<212> TYPE: RNA
<213> ORGANISM: Artificial Sequence
<220> FEATURE:
<223> OTHER INFORMATION: Synthetic

<400> SEQUENCE: 453
ugcaagauuu acuggggguu                                                 19

<210> SEQ ID NO 454
<211> LENGTH: 19
<212> TYPE: RNA
<213> ORGANISM: Artificial Sequence
<220> FEATURE:
<223> OTHER INFORMATION: Synthetic

<400> SEQUENCE: 454
cugcaagauu uacuggggu                                                  19

<210> SEQ ID NO 455
<211> LENGTH: 18
<212> TYPE: RNA
<213> ORGANISM: Artificial Sequence
<220> FEATURE:

<223> OTHER INFORMATION: Synthetic

<400> SEQUENCE: 455
uuacuggggu ucuucacg                                        18

<210> SEQ ID NO 456
<211> LENGTH: 18
<212> TYPE: RNA
<213> ORGANISM: Artificial Sequence
<220> FEATURE:
<223> OTHER INFORMATION: Synthetic

<400> SEQUENCE: 456
uuuacugggg uucuucac                                        18

<210> SEQ ID NO 457
<211> LENGTH: 18
<212> TYPE: RNA
<213> ORGANISM: Artificial Sequence
<220> FEATURE:
<223> OTHER INFORMATION: Synthetic

<400> SEQUENCE: 457
auuuacuggg guucuuca                                        18

<210> SEQ ID NO 458
<211> LENGTH: 18
<212> TYPE: RNA
<213> ORGANISM: Artificial Sequence
<220> FEATURE:
<223> OTHER INFORMATION: Synthetic

<400> SEQUENCE: 458
gauuuacugg gguucuuc                                        18

<210> SEQ ID NO 459
<211> LENGTH: 18
<212> TYPE: RNA
<213> ORGANISM: Artificial Sequence
<220> FEATURE:
<223> OTHER INFORMATION: Synthetic

<400> SEQUENCE: 459
agauuuacug ggguucuu                                        18

<210> SEQ ID NO 460
<211> LENGTH: 18
<212> TYPE: RNA
<213> ORGANISM: Artificial Sequence
<220> FEATURE:
<223> OTHER INFORMATION: Synthetic

<400> SEQUENCE: 460
aagauuuacu gggguucu                                        18

<210> SEQ ID NO 461
<211> LENGTH: 18
<212> TYPE: RNA
<213> ORGANISM: Artificial Sequence
<220> FEATURE:
<223> OTHER INFORMATION: Synthetic

<400> SEQUENCE: 461
caagauuuac uggggguuc                                       18

```
<210> SEQ ID NO 462
<211> LENGTH: 18
<212> TYPE: RNA
<213> ORGANISM: Artificial Sequence
<220> FEATURE:
<223> OTHER INFORMATION: Synthetic

<400> SEQUENCE: 462
gcaagauuua cugggguu                                                 18

<210> SEQ ID NO 463
<211> LENGTH: 18
<212> TYPE: RNA
<213> ORGANISM: Artificial Sequence
<220> FEATURE:
<223> OTHER INFORMATION: Synthetic

<400> SEQUENCE: 463
ugcaagauuu acuggggu                                                 18

<210> SEQ ID NO 464
<211> LENGTH: 24
<212> TYPE: RNA
<213> ORGANISM: Artificial Sequence
<220> FEATURE:
<223> OTHER INFORMATION: Synthetic

<400> SEQUENCE: 464
caagguuuac aggaguucuu cacg                                          24

<210> SEQ ID NO 465
<211> LENGTH: 24
<212> TYPE: RNA
<213> ORGANISM: Artificial Sequence
<220> FEATURE:
<223> OTHER INFORMATION: Synthetic

<400> SEQUENCE: 465
gcaagguuua cuggaguucu ucac                                          24

<210> SEQ ID NO 466
<211> LENGTH: 24
<212> TYPE: RNA
<213> ORGANISM: Artificial Sequence
<220> FEATURE:
<223> OTHER INFORMATION: Synthetic

<400> SEQUENCE: 466
ggcaagguuu acuggaguuc uuca                                          24

<210> SEQ ID NO 467
<211> LENGTH: 24
<212> TYPE: RNA
<213> ORGANISM: Artificial Sequence
<220> FEATURE:
<223> OTHER INFORMATION: Synthetic

<400> SEQUENCE: 467
cggcaagguu uacuggaguu cuuc                                          24

<210> SEQ ID NO 468
<211> LENGTH: 24
<212> TYPE: RNA
<213> ORGANISM: Artificial Sequence
<220> FEATURE:
<223> OTHER INFORMATION: Synthetic
```

-continued

<400> SEQUENCE: 468
acggcaaggu uuacuggagu ucuu                                           24

<210> SEQ ID NO 469
<211> LENGTH: 24
<212> TYPE: RNA
<213> ORGANISM: Artificial Sequence
<220> FEATURE:
<223> OTHER INFORMATION: Synthetic

<400> SEQUENCE: 469
aacggcaagg uuuacuggag uucu                                           24

<210> SEQ ID NO 470
<211> LENGTH: 24
<212> TYPE: RNA
<213> ORGANISM: Artificial Sequence
<220> FEATURE:
<223> OTHER INFORMATION: Synthetic

<400> SEQUENCE: 470
aaacggcaag guuuacugga guuc                                           24

<210> SEQ ID NO 471
<211> LENGTH: 24
<212> TYPE: RNA
<213> ORGANISM: Artificial Sequence
<220> FEATURE:
<223> OTHER INFORMATION: Synthetic

<400> SEQUENCE: 471
aaaacggcaa gguuuacugg aguu                                           24

<210> SEQ ID NO 472
<211> LENGTH: 24
<212> TYPE: RNA
<213> ORGANISM: Artificial Sequence
<220> FEATURE:
<223> OTHER INFORMATION: Synthetic

<400> SEQUENCE: 472
caaaacggca agguuuacug gagu                                           24

<210> SEQ ID NO 473
<211> LENGTH: 23
<212> TYPE: RNA
<213> ORGANISM: Artificial Sequence
<220> FEATURE:
<223> OTHER INFORMATION: Synthetic

<400> SEQUENCE: 473
aagguuuaca ggaguucuuc acg                                            23

<210> SEQ ID NO 474
<211> LENGTH: 23
<212> TYPE: RNA
<213> ORGANISM: Artificial Sequence
<220> FEATURE:
<223> OTHER INFORMATION: Synthetic

<400> SEQUENCE: 474
caagguuuac uggaguucuu cac                                            23

<210> SEQ ID NO 475
<211> LENGTH: 23

```
<212> TYPE: RNA
<213> ORGANISM: Artificial Sequence
<220> FEATURE:
<223> OTHER INFORMATION: Synthetic

<400> SEQUENCE: 475
gcaagguuua cuggaguucu uca                                              23

<210> SEQ ID NO 476
<211> LENGTH: 23
<212> TYPE: RNA
<213> ORGANISM: Artificial Sequence
<220> FEATURE:
<223> OTHER INFORMATION: Synthetic

<400> SEQUENCE: 476
ggcaagguuu acuggaguuc uuc                                              23

<210> SEQ ID NO 477
<211> LENGTH: 23
<212> TYPE: RNA
<213> ORGANISM: Artificial Sequence
<220> FEATURE:
<223> OTHER INFORMATION: Synthetic

<400> SEQUENCE: 477
cggcaagguu uacuggaguu cuu                                              23

<210> SEQ ID NO 478
<211> LENGTH: 23
<212> TYPE: RNA
<213> ORGANISM: Artificial Sequence
<220> FEATURE:
<223> OTHER INFORMATION: Synthetic

<400> SEQUENCE: 478
acggcaaggu uuacuggagu ucu                                              23

<210> SEQ ID NO 479
<211> LENGTH: 23
<212> TYPE: RNA
<213> ORGANISM: Artificial Sequence
<220> FEATURE:
<223> OTHER INFORMATION: Synthetic

<400> SEQUENCE: 479
aacggcaagg uuuacuggag uuc                                              23

<210> SEQ ID NO 480
<211> LENGTH: 23
<212> TYPE: RNA
<213> ORGANISM: Artificial Sequence
<220> FEATURE:
<223> OTHER INFORMATION: Synthetic

<400> SEQUENCE: 480
aaacggcaag guuuacugga guu                                              23

<210> SEQ ID NO 481
<211> LENGTH: 23
<212> TYPE: RNA
<213> ORGANISM: Artificial Sequence
<220> FEATURE:
<223> OTHER INFORMATION: Synthetic

<400> SEQUENCE: 481
```

```
aaaacggcaa gguuuacugg agu                                           23

<210> SEQ ID NO 482
<211> LENGTH: 22
<212> TYPE: RNA
<213> ORGANISM: Artificial Sequence
<220> FEATURE:
<223> OTHER INFORMATION: Synthetic

<400> SEQUENCE: 482
agguuuacag gaguucuuca cg                                            22

<210> SEQ ID NO 483
<211> LENGTH: 22
<212> TYPE: RNA
<213> ORGANISM: Artificial Sequence
<220> FEATURE:
<223> OTHER INFORMATION: Synthetic

<400> SEQUENCE: 483
aagguuuacu ggaguucuuc ac                                            22

<210> SEQ ID NO 484
<211> LENGTH: 22
<212> TYPE: RNA
<213> ORGANISM: Artificial Sequence
<220> FEATURE:
<223> OTHER INFORMATION: Synthetic

<400> SEQUENCE: 484
caagguuuac uggaguucuu ca                                            22

<210> SEQ ID NO 485
<211> LENGTH: 22
<212> TYPE: RNA
<213> ORGANISM: Artificial Sequence
<220> FEATURE:
<223> OTHER INFORMATION: Synthetic

<400> SEQUENCE: 485
gcaagguuua cuggaguucu uc                                            22

<210> SEQ ID NO 486
<211> LENGTH: 22
<212> TYPE: RNA
<213> ORGANISM: Artificial Sequence
<220> FEATURE:
<223> OTHER INFORMATION: Synthetic

<400> SEQUENCE: 486
ggcaagguuu acuggaguuc uu                                            22

<210> SEQ ID NO 487
<211> LENGTH: 22
<212> TYPE: RNA
<213> ORGANISM: Artificial Sequence
<220> FEATURE:
<223> OTHER INFORMATION: Synthetic

<400> SEQUENCE: 487
cggcaagguu uacuggaguu cu                                            22

<210> SEQ ID NO 488
<211> LENGTH: 22
<212> TYPE: RNA
<213> ORGANISM: Artificial Sequence
```

```
<220> FEATURE:
<223> OTHER INFORMATION: Synthetic

<400> SEQUENCE: 488
acggcaaggu uuacuggagu uc                                              22

<210> SEQ ID NO 489
<211> LENGTH: 22
<212> TYPE: RNA
<213> ORGANISM: Artificial Sequence
<220> FEATURE:
<223> OTHER INFORMATION: Synthetic

<400> SEQUENCE: 489
aacggcaagg uuuacuggag uu                                              22

<210> SEQ ID NO 490
<211> LENGTH: 22
<212> TYPE: RNA
<213> ORGANISM: Artificial Sequence
<220> FEATURE:
<223> OTHER INFORMATION: Synthetic

<400> SEQUENCE: 490
aaacggcaag guuuacugga gu                                              22

<210> SEQ ID NO 491
<211> LENGTH: 21
<212> TYPE: RNA
<213> ORGANISM: Artificial Sequence
<220> FEATURE:
<223> OTHER INFORMATION: Synthetic

<400> SEQUENCE: 491
gguuuacagg aguucuucac g                                               21

<210> SEQ ID NO 492
<211> LENGTH: 21
<212> TYPE: RNA
<213> ORGANISM: Artificial Sequence
<220> FEATURE:
<223> OTHER INFORMATION: Synthetic

<400> SEQUENCE: 492
agguuuacug gaguucuuca c                                               21

<210> SEQ ID NO 493
<211> LENGTH: 21
<212> TYPE: RNA
<213> ORGANISM: Artificial Sequence
<220> FEATURE:
<223> OTHER INFORMATION: Synthetic

<400> SEQUENCE: 493
aagguuuacu ggaguucuuc a                                               21

<210> SEQ ID NO 494
<211> LENGTH: 21
<212> TYPE: RNA
<213> ORGANISM: Artificial Sequence
<220> FEATURE:
<223> OTHER INFORMATION: Synthetic

<400> SEQUENCE: 494
caagguuuac uggaguucuu c                                               21
```

```
<210> SEQ ID NO 495
<211> LENGTH: 21
<212> TYPE: RNA
<213> ORGANISM: Artificial Sequence
<220> FEATURE:
<223> OTHER INFORMATION: Synthetic

<400> SEQUENCE: 495
gcaagguuua cuggaguucu u                                              21

<210> SEQ ID NO 496
<211> LENGTH: 21
<212> TYPE: RNA
<213> ORGANISM: Artificial Sequence
<220> FEATURE:
<223> OTHER INFORMATION: Synthetic

<400> SEQUENCE: 496
ggcaagguuu acuggaguuc u                                              21

<210> SEQ ID NO 497
<211> LENGTH: 21
<212> TYPE: RNA
<213> ORGANISM: Artificial Sequence
<220> FEATURE:
<223> OTHER INFORMATION: Synthetic

<400> SEQUENCE: 497
cggcaagguu uacuggaguu c                                              21

<210> SEQ ID NO 498
<211> LENGTH: 21
<212> TYPE: RNA
<213> ORGANISM: Artificial Sequence
<220> FEATURE:
<223> OTHER INFORMATION: Synthetic

<400> SEQUENCE: 498
acggcaaggu uuacuggagu u                                              21

<210> SEQ ID NO 499
<211> LENGTH: 21
<212> TYPE: RNA
<213> ORGANISM: Artificial Sequence
<220> FEATURE:
<223> OTHER INFORMATION: Synthetic

<400> SEQUENCE: 499
aacggcaagg uuuacuggag u                                              21

<210> SEQ ID NO 500
<211> LENGTH: 20
<212> TYPE: RNA
<213> ORGANISM: Artificial Sequence
<220> FEATURE:
<223> OTHER INFORMATION: Synthetic

<400> SEQUENCE: 500
guuuacagga guucuucacg                                                20

<210> SEQ ID NO 501
<211> LENGTH: 20
<212> TYPE: RNA
<213> ORGANISM: Artificial Sequence
<220> FEATURE:
<223> OTHER INFORMATION: Synthetic
```

```
<400> SEQUENCE: 501
gguuuacugg aguucuuca                                               20

<210> SEQ ID NO 502
<211> LENGTH: 20
<212> TYPE: RNA
<213> ORGANISM: Artificial Sequence
<220> FEATURE:
<223> OTHER INFORMATION: Synthetic

<400> SEQUENCE: 502
agguuuacug gaguucuuca                                              20

<210> SEQ ID NO 503
<211> LENGTH: 20
<212> TYPE: RNA
<213> ORGANISM: Artificial Sequence
<220> FEATURE:
<223> OTHER INFORMATION: Synthetic

<400> SEQUENCE: 503
aagguuuacu ggaguucuuc                                              20

<210> SEQ ID NO 504
<211> LENGTH: 20
<212> TYPE: RNA
<213> ORGANISM: Artificial Sequence
<220> FEATURE:
<223> OTHER INFORMATION: Synthetic

<400> SEQUENCE: 504
caagguuuac uggaguucuu                                              20

<210> SEQ ID NO 505
<211> LENGTH: 20
<212> TYPE: RNA
<213> ORGANISM: Artificial Sequence
<220> FEATURE:
<223> OTHER INFORMATION: Synthetic

<400> SEQUENCE: 505
gcaagguuua cuggaguucu                                              20

<210> SEQ ID NO 506
<211> LENGTH: 20
<212> TYPE: RNA
<213> ORGANISM: Artificial Sequence
<220> FEATURE:
<223> OTHER INFORMATION: Synthetic

<400> SEQUENCE: 506
ggcaagguuu acuggaguuc                                              20

<210> SEQ ID NO 507
<211> LENGTH: 20
<212> TYPE: RNA
<213> ORGANISM: Artificial Sequence
<220> FEATURE:
<223> OTHER INFORMATION: Synthetic

<400> SEQUENCE: 507
cggcaagguu uacuggaguu                                              20

<210> SEQ ID NO 508
```

```
<211> LENGTH: 20
<212> TYPE: RNA
<213> ORGANISM: Artificial Sequence
<220> FEATURE:
<223> OTHER INFORMATION: Synthetic

<400> SEQUENCE: 508
acggcaaggu uuacuggagu                                                    20

<210> SEQ ID NO 509
<211> LENGTH: 19
<212> TYPE: RNA
<213> ORGANISM: Artificial Sequence
<220> FEATURE:
<223> OTHER INFORMATION: Synthetic

<400> SEQUENCE: 509
uuuacaggag uucuucacg                                                     19

<210> SEQ ID NO 510
<211> LENGTH: 19
<212> TYPE: RNA
<213> ORGANISM: Artificial Sequence
<220> FEATURE:
<223> OTHER INFORMATION: Synthetic

<400> SEQUENCE: 510
guuuacugga guucuucac                                                     19

<210> SEQ ID NO 511
<211> LENGTH: 19
<212> TYPE: RNA
<213> ORGANISM: Artificial Sequence
<220> FEATURE:
<223> OTHER INFORMATION: Synthetic

<400> SEQUENCE: 511
gguuuacugg aguucuuca                                                     19

<210> SEQ ID NO 512
<211> LENGTH: 19
<212> TYPE: RNA
<213> ORGANISM: Artificial Sequence
<220> FEATURE:
<223> OTHER INFORMATION: Synthetic

<400> SEQUENCE: 512
agguuuacug gaguucuuc                                                     19

<210> SEQ ID NO 513
<211> LENGTH: 19
<212> TYPE: RNA
<213> ORGANISM: Artificial Sequence
<220> FEATURE:
<223> OTHER INFORMATION: Synthetic

<400> SEQUENCE: 513
aagguuuacu ggaguucuu                                                     19

<210> SEQ ID NO 514
<211> LENGTH: 19
<212> TYPE: RNA
<213> ORGANISM: Artificial Sequence
<220> FEATURE:
<223> OTHER INFORMATION: Synthetic

<400> SEQUENCE: 514
```
caagguuuac uggaguucu                                          19

<210> SEQ ID NO 515
<211> LENGTH: 19
<212> TYPE: RNA
<213> ORGANISM: Artificial Sequence
<220> FEATURE:
<223> OTHER INFORMATION: Synthetic

<400> SEQUENCE: 515
gcaagguuua cuggaguuc                                          19

<210> SEQ ID NO 516
<211> LENGTH: 19
<212> TYPE: RNA
<213> ORGANISM: Artificial Sequence
<220> FEATURE:
<223> OTHER INFORMATION: Synthetic

<400> SEQUENCE: 516
ggcaagguuu acuggaguu                                          19

<210> SEQ ID NO 517
<211> LENGTH: 19
<212> TYPE: RNA
<213> ORGANISM: Artificial Sequence
<220> FEATURE:
<223> OTHER INFORMATION: Synthetic

<400> SEQUENCE: 517
cggcaagguu uacuggagu                                          19

<210> SEQ ID NO 518
<211> LENGTH: 18
<212> TYPE: RNA
<213> ORGANISM: Artificial Sequence
<220> FEATURE:
<223> OTHER INFORMATION: Synthetic

<400> SEQUENCE: 518
uuacaggagu ucuucacg                                           18

<210> SEQ ID NO 519
<211> LENGTH: 18
<212> TYPE: RNA
<213> ORGANISM: Artificial Sequence
<220> FEATURE:
<223> OTHER INFORMATION: Synthetic

<400> SEQUENCE: 519
uuuacuggag uucuucac                                           18

<210> SEQ ID NO 520
<211> LENGTH: 18
<212> TYPE: RNA
<213> ORGANISM: Artificial Sequence
<220> FEATURE:
<223> OTHER INFORMATION: Synthetic

<400> SEQUENCE: 520
guuuacugga guucuuca                                           18

<210> SEQ ID NO 521
<211> LENGTH: 18
<212> TYPE: RNA

<213> ORGANISM: Artificial Sequence
<220> FEATURE:
<223> OTHER INFORMATION: Synthetic

<400> SEQUENCE: 521
gguuuacugg aguucuuc                                              18

<210> SEQ ID NO 522
<211> LENGTH: 18
<212> TYPE: RNA
<213> ORGANISM: Artificial Sequence
<220> FEATURE:
<223> OTHER INFORMATION: Synthetic

<400> SEQUENCE: 522
agguuuacug gaguucuu                                              18

<210> SEQ ID NO 523
<211> LENGTH: 18
<212> TYPE: RNA
<213> ORGANISM: Artificial Sequence
<220> FEATURE:
<223> OTHER INFORMATION: Synthetic

<400> SEQUENCE: 523
aagguuuacu ggaguucu                                              18

<210> SEQ ID NO 524
<211> LENGTH: 18
<212> TYPE: RNA
<213> ORGANISM: Artificial Sequence
<220> FEATURE:
<223> OTHER INFORMATION: Synthetic

<400> SEQUENCE: 524
caagguuuac uggaguuc                                              18

<210> SEQ ID NO 525
<211> LENGTH: 18
<212> TYPE: RNA
<213> ORGANISM: Artificial Sequence
<220> FEATURE:
<223> OTHER INFORMATION: Synthetic

<400> SEQUENCE: 525
gcaagguuua cuggaguu                                              18

<210> SEQ ID NO 526
<211> LENGTH: 18
<212> TYPE: RNA
<213> ORGANISM: Artificial Sequence
<220> FEATURE:
<223> OTHER INFORMATION: Synthetic

<400> SEQUENCE: 526
ggcaagguuu acuggagu                                              18

<210> SEQ ID NO 527
<211> LENGTH: 24
<212> TYPE: RNA
<213> ORGANISM: Artificial Sequence
<220> FEATURE:
<223> OTHER INFORMATION: Synthetic

<400> SEQUENCE: 527
caguacuguc uucacuguca gcug                                       24

<210> SEQ ID NO 528
<211> LENGTH: 24
<212> TYPE: RNA
<213> ORGANISM: Artificial Sequence
<220> FEATURE:
<223> OTHER INFORMATION: Synthetic

<400> SEQUENCE: 528
acaguacugu cuucacuguc agcu                                              24

<210> SEQ ID NO 529
<211> LENGTH: 24
<212> TYPE: RNA
<213> ORGANISM: Artificial Sequence
<220> FEATURE:
<223> OTHER INFORMATION: Synthetic

<400> SEQUENCE: 529
uacaguacug ucuucacugu cagc                                              24

<210> SEQ ID NO 530
<211> LENGTH: 24
<212> TYPE: RNA
<213> ORGANISM: Artificial Sequence
<220> FEATURE:
<223> OTHER INFORMATION: Synthetic

<400> SEQUENCE: 530
ucuucgucac ugccuucauu uucu                                              24

<210> SEQ ID NO 531
<211> LENGTH: 24
<212> TYPE: RNA
<213> ORGANISM: Artificial Sequence
<220> FEATURE:
<223> OTHER INFORMATION: Synthetic

<400> SEQUENCE: 531
caucaguuuc aaugucuucg ucac                                              24

<210> SEQ ID NO 532
<211> LENGTH: 24
<212> TYPE: RNA
<213> ORGANISM: Artificial Sequence
<220> FEATURE:
<223> OTHER INFORMATION: Synthetic

<400> SEQUENCE: 532
acaucaguuu caaugucuuc guca                                              24

<210> SEQ ID NO 533
<211> LENGTH: 23
<212> TYPE: RNA
<213> ORGANISM: Artificial Sequence
<220> FEATURE:
<223> OTHER INFORMATION: Synthetic

<400> SEQUENCE: 533
aguacugucu ucacgucag cug                                                23

<210> SEQ ID NO 534
<211> LENGTH: 23
<212> TYPE: RNA
<213> ORGANISM: Artificial Sequence
<220> FEATURE:

<223> OTHER INFORMATION: Synthetic

<400> SEQUENCE: 534
caguacuguc uucacuguca gcu                                              23

<210> SEQ ID NO 535
<211> LENGTH: 23
<212> TYPE: RNA
<213> ORGANISM: Artificial Sequence
<220> FEATURE:
<223> OTHER INFORMATION: Synthetic

<400> SEQUENCE: 535
acaguacugu cuucacuguc agc                                              23

<210> SEQ ID NO 536
<211> LENGTH: 23
<212> TYPE: RNA
<213> ORGANISM: Artificial Sequence
<220> FEATURE:
<223> OTHER INFORMATION: Synthetic

<400> SEQUENCE: 536
cuucgucacu gccuucauuu ucu                                              23

<210> SEQ ID NO 537
<211> LENGTH: 23
<212> TYPE: RNA
<213> ORGANISM: Artificial Sequence
<220> FEATURE:
<223> OTHER INFORMATION: Synthetic

<400> SEQUENCE: 537
ucuucgucac ugccuucauu uuc                                              23

<210> SEQ ID NO 538
<211> LENGTH: 23
<212> TYPE: RNA
<213> ORGANISM: Artificial Sequence
<220> FEATURE:
<223> OTHER INFORMATION: Synthetic

<400> SEQUENCE: 538
aucaguuuca augucuucgu cac                                              23

<210> SEQ ID NO 539
<211> LENGTH: 23
<212> TYPE: RNA
<213> ORGANISM: Artificial Sequence
<220> FEATURE:
<223> OTHER INFORMATION: Synthetic

<400> SEQUENCE: 539
caucaguuuc aaugucuucg uca                                              23

<210> SEQ ID NO 540
<211> LENGTH: 23
<212> TYPE: RNA
<213> ORGANISM: Artificial Sequence
<220> FEATURE:
<223> OTHER INFORMATION: Synthetic

<400> SEQUENCE: 540
acaucaguuu caaugucuuc guc                                              23

```
<210> SEQ ID NO 541
<211> LENGTH: 23
<212> TYPE: RNA
<213> ORGANISM: Artificial Sequence
<220> FEATURE:
<223> OTHER INFORMATION: Synthetic

<400> SEQUENCE: 541
aacucacugc uguauugaug agg                                              23

<210> SEQ ID NO 542
<211> LENGTH: 22
<212> TYPE: RNA
<213> ORGANISM: Artificial Sequence
<220> FEATURE:
<223> OTHER INFORMATION: Synthetic

<400> SEQUENCE: 542
guacugucuu cacugucagc ug                                               22

<210> SEQ ID NO 543
<211> LENGTH: 22
<212> TYPE: RNA
<213> ORGANISM: Artificial Sequence
<220> FEATURE:
<223> OTHER INFORMATION: Synthetic

<400> SEQUENCE: 543
aguacugucu ucacugucag cu                                               22

<210> SEQ ID NO 544
<211> LENGTH: 22
<212> TYPE: RNA
<213> ORGANISM: Artificial Sequence
<220> FEATURE:
<223> OTHER INFORMATION: Synthetic

<400> SEQUENCE: 544
caguacuguc uucacuguca gc                                               22

<210> SEQ ID NO 545
<211> LENGTH: 22
<212> TYPE: RNA
<213> ORGANISM: Artificial Sequence
<220> FEATURE:
<223> OTHER INFORMATION: Synthetic

<400> SEQUENCE: 545
uucgucacug ccuucauuuu cu                                               22

<210> SEQ ID NO 546
<211> LENGTH: 22
<212> TYPE: RNA
<213> ORGANISM: Artificial Sequence
<220> FEATURE:
<223> OTHER INFORMATION: Synthetic

<400> SEQUENCE: 546
cuucgucacu gccuucauuu uc                                               22

<210> SEQ ID NO 547
<211> LENGTH: 22
<212> TYPE: RNA
<213> ORGANISM: Artificial Sequence
<220> FEATURE:
<223> OTHER INFORMATION: Synthetic
```

<400> SEQUENCE: 547
ucuucgucac ugccuucauu uu                                                22

<210> SEQ ID NO 548
<211> LENGTH: 22
<212> TYPE: DNA
<213> ORGANISM: Artificial Sequence
<220> FEATURE:
<223> OTHER INFORMATION: Synthetic

<400> SEQUENCE: 548
ucaguuucaa ugucuucguc ac                                                22

<210> SEQ ID NO 549
<211> LENGTH: 22
<212> TYPE: RNA
<213> ORGANISM: Artificial Sequence
<220> FEATURE:
<223> OTHER INFORMATION: Synthetic

<400> SEQUENCE: 549
aucaguuuca augucuucgu ca                                                22

<210> SEQ ID NO 550
<211> LENGTH: 22
<212> TYPE: RNA
<213> ORGANISM: Artificial Sequence
<220> FEATURE:
<223> OTHER INFORMATION: Synthetic

<400> SEQUENCE: 550
caucaguuuc aaugucuucg uc                                                22

<210> SEQ ID NO 551
<211> LENGTH: 22
<212> TYPE: RNA
<213> ORGANISM: Artificial Sequence
<220> FEATURE:
<223> OTHER INFORMATION: Synthetic

<400> SEQUENCE: 551
acaucaguuu caaugucuuc gu                                                22

<210> SEQ ID NO 552
<211> LENGTH: 22
<212> TYPE: RNA
<213> ORGANISM: Artificial Sequence
<220> FEATURE:
<223> OTHER INFORMATION: Synthetic

<400> SEQUENCE: 552
acucacugcu guauugauga gg                                                22

<210> SEQ ID NO 553
<211> LENGTH: 22
<212> TYPE: RNA
<213> ORGANISM: Artificial Sequence
<220> FEATURE:
<223> OTHER INFORMATION: Synthetic

<400> SEQUENCE: 553
aacucacugc uguauugaug ag                                                22

<210> SEQ ID NO 554
<211> LENGTH: 21

```
<212> TYPE: RNA
<213> ORGANISM: Artificial Sequence
<220> FEATURE:
<223> OTHER INFORMATION: Synthetic

<400> SEQUENCE: 554
uacugucuuc acugucagcu g                                              21

<210> SEQ ID NO 555
<211> LENGTH: 21
<212> TYPE: RNA
<213> ORGANISM: Artificial Sequence
<220> FEATURE:
<223> OTHER INFORMATION: Synthetic

<400> SEQUENCE: 555
guacugucuu cacugucagc u                                              21

<210> SEQ ID NO 556
<211> LENGTH: 21
<212> TYPE: RNA
<213> ORGANISM: Artificial Sequence
<220> FEATURE:
<223> OTHER INFORMATION: Synthetic

<400> SEQUENCE: 556
aguacugucu ucacugucag c                                              21

<210> SEQ ID NO 557
<211> LENGTH: 21
<212> TYPE: RNA
<213> ORGANISM: Artificial Sequence
<220> FEATURE:
<223> OTHER INFORMATION: Synthetic

<400> SEQUENCE: 557
ucgucacugc cuucauuuuc u                                              21

<210> SEQ ID NO 558
<211> LENGTH: 21
<212> TYPE: RNA
<213> ORGANISM: Artificial Sequence
<220> FEATURE:
<223> OTHER INFORMATION: Synthetic

<400> SEQUENCE: 558
uucgucacug ccuucauuuu c                                              21

<210> SEQ ID NO 559
<211> LENGTH: 21
<212> TYPE: RNA
<213> ORGANISM: Artificial Sequence
<220> FEATURE:
<223> OTHER INFORMATION: Synthetic

<400> SEQUENCE: 559
cuucgucacu gccuucauuu u                                              21

<210> SEQ ID NO 560
<211> LENGTH: 21
<212> TYPE: RNA
<213> ORGANISM: Artificial Sequence
<220> FEATURE:
<223> OTHER INFORMATION: Synthetic

<400> SEQUENCE: 560
```
ucuucgucac ugccuucauu u                                              21

<210> SEQ ID NO 561
<211> LENGTH: 21
<212> TYPE: RNA
<213> ORGANISM: Artificial Sequence
<220> FEATURE:
<223> OTHER INFORMATION: Synthetic

<400> SEQUENCE: 561
caguuucaau gucuucguca c                                              21

<210> SEQ ID NO 562
<211> LENGTH: 21
<212> TYPE: RNA
<213> ORGANISM: Artificial Sequence
<220> FEATURE:
<223> OTHER INFORMATION: Synthetic

<400> SEQUENCE: 562
ucaguuucaa ugucuucguc a                                              21

<210> SEQ ID NO 563
<211> LENGTH: 21
<212> TYPE: RNA
<213> ORGANISM: Artificial Sequence
<220> FEATURE:
<223> OTHER INFORMATION: Synthetic

<400> SEQUENCE: 563
aucaguuuca augucuucgu c                                              21

<210> SEQ ID NO 564
<211> LENGTH: 21
<212> TYPE: RNA
<213> ORGANISM: Artificial Sequence
<220> FEATURE:
<223> OTHER INFORMATION: Synthetic

<400> SEQUENCE: 564
caucaguuuc aaugucuucg u                                              21

<210> SEQ ID NO 565
<211> LENGTH: 21
<212> TYPE: RNA
<213> ORGANISM: Artificial Sequence
<220> FEATURE:
<223> OTHER INFORMATION: Synthetic

<400> SEQUENCE: 565
acaucaguuu caaugucuuc g                                              21

<210> SEQ ID NO 566
<211> LENGTH: 21
<212> TYPE: RNA
<213> ORGANISM: Artificial Sequence
<220> FEATURE:
<223> OTHER INFORMATION: Synthetic

<400> SEQUENCE: 566
cucacugcug uauugaugag g                                              21

<210> SEQ ID NO 567
<211> LENGTH: 21
<212> TYPE: RNA
<213> ORGANISM: Artificial Sequence -continued
<220> FEATURE:
<223> OTHER INFORMATION: Synthetic

<400> SEQUENCE: 567
acucacugcu guauugauga g                                              21

<210> SEQ ID NO 568
<211> LENGTH: 21
<212> TYPE: RNA
<213> ORGANISM: Artificial Sequence
<220> FEATURE:
<223> OTHER INFORMATION: Synthetic

<400> SEQUENCE: 568
aacucacugc uguauugaug a                                              21

<210> SEQ ID NO 569
<211> LENGTH: 20
<212> TYPE: RNA
<213> ORGANISM: Artificial Sequence
<220> FEATURE:
<223> OTHER INFORMATION: Synthetic

<400> SEQUENCE: 569
acugucuuca cugucagcug                                                20

<210> SEQ ID NO 570
<211> LENGTH: 20
<212> TYPE: RNA
<213> ORGANISM: Artificial Sequence
<220> FEATURE:
<223> OTHER INFORMATION: Synthetic

<400> SEQUENCE: 570
uacugucuuc acugucagcu                                                20

<210> SEQ ID NO 571
<211> LENGTH: 20
<212> TYPE: RNA
<213> ORGANISM: Artificial Sequence
<220> FEATURE:
<223> OTHER INFORMATION: Synthetic

<400> SEQUENCE: 571
guacugucuu cacugucagc                                                20

<210> SEQ ID NO 572
<211> LENGTH: 20
<212> TYPE: RNA
<213> ORGANISM: Artificial Sequence
<220> FEATURE:
<223> OTHER INFORMATION: Synthetic

<400> SEQUENCE: 572
cgucacugcc uucauuuucu                                                20

<210> SEQ ID NO 573
<211> LENGTH: 20
<212> TYPE: RNA
<213> ORGANISM: Artificial Sequence
<220> FEATURE:
<223> OTHER INFORMATION: Synthetic

<400> SEQUENCE: 573
ucgucacugc cuucauuuuc                                                20

<210> SEQ ID NO 574
<211> LENGTH: 20
<212> TYPE: RNA
<213> ORGANISM: Artificial Sequence
<220> FEATURE:
<223> OTHER INFORMATION: Synthetic

<400> SEQUENCE: 574
uucgucacug ccuucauuuu                                          20

<210> SEQ ID NO 575
<211> LENGTH: 20
<212> TYPE: RNA
<213> ORGANISM: Artificial Sequence
<220> FEATURE:
<223> OTHER INFORMATION: Synthetic

<400> SEQUENCE: 575
cuucgucacu gccuucauuu                                          20

<210> SEQ ID NO 576
<211> LENGTH: 20
<212> TYPE: RNA
<213> ORGANISM: Artificial Sequence
<220> FEATURE:
<223> OTHER INFORMATION: Synthetic

<400> SEQUENCE: 576
ucuucgucac ugccuucauu                                          20

<210> SEQ ID NO 577
<211> LENGTH: 20
<212> TYPE: RNA
<213> ORGANISM: Artificial Sequence
<220> FEATURE:
<223> OTHER INFORMATION: Synthetic

<400> SEQUENCE: 577
aguuucaaug ucuucgucac                                          20

<210> SEQ ID NO 578
<211> LENGTH: 20
<212> TYPE: RNA
<213> ORGANISM: Artificial Sequence
<220> FEATURE:
<223> OTHER INFORMATION: Synthetic

<400> SEQUENCE: 578
caguuucaau gucuucguca                                          20

<210> SEQ ID NO 579
<211> LENGTH: 20
<212> TYPE: RNA
<213> ORGANISM: Artificial Sequence
<220> FEATURE:
<223> OTHER INFORMATION: Synthetic

<400> SEQUENCE: 579
ucaguuucaa ugucuucguc                                          20

<210> SEQ ID NO 580
<211> LENGTH: 20
<212> TYPE: RNA
<213> ORGANISM: Artificial Sequence
<220> FEATURE:
<223> OTHER INFORMATION: Synthetic

```
<400> SEQUENCE: 580
aucaguuuca augucuucgu                                            20

<210> SEQ ID NO 581
<211> LENGTH: 19
<212> TYPE: RNA
<213> ORGANISM: Artificial Sequence
<220> FEATURE:
<223> OTHER INFORMATION: Synthetic

<400> SEQUENCE: 581
aucaguuuca augucuucg                                             19

<210> SEQ ID NO 582
<211> LENGTH: 20
<212> TYPE: RNA
<213> ORGANISM: Artificial Sequence
<220> FEATURE:
<223> OTHER INFORMATION: Synthetic

<400> SEQUENCE: 582
acaucaguuu caaugucuuc                                            20

<210> SEQ ID NO 583
<211> LENGTH: 20
<212> TYPE: RNA
<213> ORGANISM: Artificial Sequence
<220> FEATURE:
<223> OTHER INFORMATION: Synthetic

<400> SEQUENCE: 583
ucacugcugu auugaugagg                                            20

<210> SEQ ID NO 584
<211> LENGTH: 20
<212> TYPE: RNA
<213> ORGANISM: Artificial Sequence
<220> FEATURE:
<223> OTHER INFORMATION: Synthetic

<400> SEQUENCE: 584
cucacugcug uauugaugag                                            20

<210> SEQ ID NO 585
<211> LENGTH: 20
<212> TYPE: RNA
<213> ORGANISM: Artificial Sequence
<220> FEATURE:
<223> OTHER INFORMATION: Synthetic

<400> SEQUENCE: 585
acucacugcu guauugauga                                            20

<210> SEQ ID NO 586
<211> LENGTH: 20
<212> TYPE: RNA
<213> ORGANISM: Artificial Sequence
<220> FEATURE:
<223> OTHER INFORMATION: Synthetic

<400> SEQUENCE: 586
aacucacugc uguauugaug                                            20

<210> SEQ ID NO 587
```

```
<211> LENGTH: 19
<212> TYPE: RNA
<213> ORGANISM: Artificial Sequence
<220> FEATURE:
<223> OTHER INFORMATION: Synthetic

<400> SEQUENCE: 587
cugucuucac ugucagcug                                                  19

<210> SEQ ID NO 588
<211> LENGTH: 19
<212> TYPE: RNA
<213> ORGANISM: Artificial Sequence
<220> FEATURE:
<223> OTHER INFORMATION: Synthetic

<400> SEQUENCE: 588
acugucuuca cugucagcu                                                  19

<210> SEQ ID NO 589
<211> LENGTH: 19
<212> TYPE: RNA
<213> ORGANISM: Artificial Sequence
<220> FEATURE:
<223> OTHER INFORMATION: Synthetic

<400> SEQUENCE: 589
uacugucuuc acugucagc                                                  19

<210> SEQ ID NO 590
<211> LENGTH: 19
<212> TYPE: RNA
<213> ORGANISM: Artificial Sequence
<220> FEATURE:
<223> OTHER INFORMATION: Synthetic

<400> SEQUENCE: 590
gucacugccu ucauuuucu                                                  19

<210> SEQ ID NO 591
<211> LENGTH: 19
<212> TYPE: RNA
<213> ORGANISM: Artificial Sequence
<220> FEATURE:
<223> OTHER INFORMATION: Synthetic

<400> SEQUENCE: 591
cgucacugcc uucauuuuc                                                  19

<210> SEQ ID NO 592
<211> LENGTH: 19
<212> TYPE: RNA
<213> ORGANISM: Artificial Sequence
<220> FEATURE:
<223> OTHER INFORMATION: Synthetic

<400> SEQUENCE: 592
ucgucacugc cuucauuuu                                                  19

<210> SEQ ID NO 593
<211> LENGTH: 19
<212> TYPE: RNA
<213> ORGANISM: Artificial Sequence
<220> FEATURE:
<223> OTHER INFORMATION: Synthetic

<400> SEQUENCE: 593
```
uucgucacug ccuucauuu                                               19

<210> SEQ ID NO 594
<211> LENGTH: 19
<212> TYPE: RNA
<213> ORGANISM: Artificial Sequence
<220> FEATURE:
<223> OTHER INFORMATION: Synthetic

<400> SEQUENCE: 594
cuucgucacu gccuucauu                                               19

<210> SEQ ID NO 595
<211> LENGTH: 19
<212> TYPE: RNA
<213> ORGANISM: Artificial Sequence
<220> FEATURE:
<223> OTHER INFORMATION: Synthetic

<400> SEQUENCE: 595
ucuucgucac ugccuucau                                               19

<210> SEQ ID NO 596
<211> LENGTH: 19
<212> TYPE: RNA
<213> ORGANISM: Artificial Sequence
<220> FEATURE:
<223> OTHER INFORMATION: Synthetic

<400> SEQUENCE: 596
cacugcugua uugaugagg                                               19

<210> SEQ ID NO 597
<211> LENGTH: 19
<212> TYPE: RNA
<213> ORGANISM: Artificial Sequence
<220> FEATURE:
<223> OTHER INFORMATION: Synthetic

<400> SEQUENCE: 597
ucacugcugu auugaugag                                               19

<210> SEQ ID NO 598
<211> LENGTH: 19
<212> TYPE: RNA
<213> ORGANISM: Artificial Sequence
<220> FEATURE:
<223> OTHER INFORMATION: Synthetic

<400> SEQUENCE: 598
cucacugcug uauugauga                                               19

<210> SEQ ID NO 599
<211> LENGTH: 19
<212> TYPE: RNA
<213> ORGANISM: Artificial Sequence
<220> FEATURE:
<223> OTHER INFORMATION: Synthetic

<400> SEQUENCE: 599
acucacugcu guauugaug                                               19

<210> SEQ ID NO 600
<211> LENGTH: 19
<212> TYPE: RNA

```
<213> ORGANISM: Artificial Sequence
<220> FEATURE:
<223> OTHER INFORMATION: Synthetic

<400> SEQUENCE: 600
aacucacugc uguauugau                                                    19

<210> SEQ ID NO 601
<211> LENGTH: 18
<212> TYPE: RNA
<213> ORGANISM: Artificial Sequence
<220> FEATURE:
<223> OTHER INFORMATION: Synthetic

<400> SEQUENCE: 601
cuucacuguc agcuguga                                                     18

<210> SEQ ID NO 602
<211> LENGTH: 18
<212> TYPE: RNA
<213> ORGANISM: Artificial Sequence
<220> FEATURE:
<223> OTHER INFORMATION: Synthetic

<400> SEQUENCE: 602 ugcuucacu gucagcug                                                      18

<210> SEQ ID NO 603
<211> LENGTH: 18
<212> TYPE: RNA
<213> ORGANISM: Artificial Sequence
<220> FEATURE:
<223> OTHER INFORMATION: Synthetic

<400> SEQUENCE: 603
cugucuucac ugucagcu                                                     18

<210> SEQ ID NO 604
<211> LENGTH: 18
<212> TYPE: RNA
<213> ORGANISM: Artificial Sequence
<220> FEATURE:
<223> OTHER INFORMATION: Synthetic

<400> SEQUENCE: 604
acugucuuca cugucagc                                                     18

<210> SEQ ID NO 605
<211> LENGTH: 18
<212> TYPE: RNA
<213> ORGANISM: Artificial Sequence
<220> FEATURE:
<223> OTHER INFORMATION: Synthetic

<400> SEQUENCE: 605
ucuucgucac ugccuuca                                                     18

<210> SEQ ID NO 606
<211> LENGTH: 18
<212> TYPE: RNA
<213> ORGANISM: Artificial Sequence
<220> FEATURE:
<223> OTHER INFORMATION: Synthetic

<400> SEQUENCE: 606
acugcuguau ugaugagg                                                     18
```

```
<210> SEQ ID NO 607
<211> LENGTH: 18
<212> TYPE: RNA
<213> ORGANISM: Artificial Sequence
<220> FEATURE:
<223> OTHER INFORMATION: Synthetic

<400> SEQUENCE: 607
cacugcugua uugaugag                                                 18

<210> SEQ ID NO 608
<211> LENGTH: 18
<212> TYPE: RNA
<213> ORGANISM: Artificial Sequence
<220> FEATURE:
<223> OTHER INFORMATION: Synthetic

<400> SEQUENCE: 608
ucacugcugu auugauga                                                 18

<210> SEQ ID NO 609
<211> LENGTH: 18
<212> TYPE: RNA
<213> ORGANISM: Artificial Sequence
<220> FEATURE:
<223> OTHER INFORMATION: Synthetic

<400> SEQUENCE: 609
cucacugcug uauugaug                                                 18

<210> SEQ ID NO 610
<211> LENGTH: 18
<212> TYPE: RNA
<213> ORGANISM: Artificial Sequence
<220> FEATURE:
<223> OTHER INFORMATION: Synthetic

<400> SEQUENCE: 610
acucacugcu guauugau                                                 18

<210> SEQ ID NO 611
<211> LENGTH: 18
<212> TYPE: RNA
<213> ORGANISM: Artificial Sequence
<220> FEATURE:
<223> OTHER INFORMATION: Synthetic

<400> SEQUENCE: 611
aacucacugc uguauuga                                                 18

<210> SEQ ID NO 612
<211> LENGTH: 24
<212> TYPE: RNA
<213> ORGANISM: Artificial Sequence
<220> FEATURE:
<223> OTHER INFORMATION: Synthetic

<400> SEQUENCE: 612
accuaaccac uguacaaaag auuu                                          24

<210> SEQ ID NO 613
<211> LENGTH: 24
<212> TYPE: RNA
<213> ORGANISM: Artificial Sequence
<220> FEATURE:
```

<223> OTHER INFORMATION: Synthetic

<400> SEQUENCE: 613
uaccuaacca cuguacaaaa gauu 24

<210> SEQ ID NO 614
<211> LENGTH: 24
<212> TYPE: RNA
<213> ORGANISM: Artificial Sequence
<220> FEATURE:
<223> OTHER INFORMATION: Synthetic

<400> SEQUENCE: 614
cuaccuaacc acuguacaaa agau 24

<210> SEQ ID NO 615
<211> LENGTH: 24
<212> TYPE: RNA
<213> ORGANISM: Artificial Sequence
<220> FEATURE:
<223> OTHER INFORMATION: Synthetic

<400> SEQUENCE: 615
ccuaccuaac cacuguacaa aaga 24

<210> SEQ ID NO 616
<211> LENGTH: 24
<212> TYPE: RNA
<213> ORGANISM: Artificial Sequence
<220> FEATURE:
<223> OTHER INFORMATION: Synthetic

<400> SEQUENCE: 616
accuaccuaa ccacuguaca aaag 24

<210> SEQ ID NO 617
<211> LENGTH: 23
<212> TYPE: RNA
<213> ORGANISM: Artificial Sequence
<220> FEATURE:
<223> OTHER INFORMATION: Synthetic

<400> SEQUENCE: 617
accuaaccac uguacaaaag auu 23

<210> SEQ ID NO 618
<211> LENGTH: 23
<212> TYPE: RNA
<213> ORGANISM: Artificial Sequence
<220> FEATURE:
<223> OTHER INFORMATION: Synthetic

<400> SEQUENCE: 618
uaccuaacca cuguacaaaa gau 23

<210> SEQ ID NO 619
<211> LENGTH: 23
<212> TYPE: RNA
<213> ORGANISM: Artificial Sequence
<220> FEATURE:
<223> OTHER INFORMATION: Synthetic

<400> SEQUENCE: 619
cuaccuaacc acuguacaaa aga 23

-continued

<210> SEQ ID NO 620
<211> LENGTH: 23
<212> TYPE: RNA
<213> ORGANISM: Artificial Sequence
<220> FEATURE:
<223> OTHER INFORMATION: Synthetic

<400> SEQUENCE: 620
ccuaccuaac cacuguacaa aag                                        23

<210> SEQ ID NO 621
<211> LENGTH: 23
<212> TYPE: RNA
<213> ORGANISM: Artificial Sequence
<220> FEATURE:
<223> OTHER INFORMATION: Synthetic

<400> SEQUENCE: 621
accuaccuaa ccacuguaca aaa                                        23

<210> SEQ ID NO 622
<211> LENGTH: 22
<212> TYPE: RNA
<213> ORGANISM: Artificial Sequence
<220> FEATURE:
<223> OTHER INFORMATION: Synthetic

<400> SEQUENCE: 622
accuaaccac uguacaaaag au                                         22

<210> SEQ ID NO 623
<211> LENGTH: 22
<212> TYPE: RNA
<213> ORGANISM: Artificial Sequence
<220> FEATURE:
<223> OTHER INFORMATION: Synthetic

<400> SEQUENCE: 623
uaccuaacca cuguacaaaa ga                                         22

<210> SEQ ID NO 624
<211> LENGTH: 22
<212> TYPE: RNA
<213> ORGANISM: Artificial Sequence
<220> FEATURE:
<223> OTHER INFORMATION: Synthetic

<400> SEQUENCE: 624
cuaccuaacc acuguacaaa ag                                         22

<210> SEQ ID NO 625
<211> LENGTH: 22
<212> TYPE: RNA
<213> ORGANISM: Artificial Sequence
<220> FEATURE:
<223> OTHER INFORMATION: Synthetic

<400> SEQUENCE: 625
ccuaccuaac cacuguacaa aa                                         22

<210> SEQ ID NO 626
<211> LENGTH: 22
<212> TYPE: RNA
<213> ORGANISM: Artificial Sequence
<220> FEATURE:
<223> OTHER INFORMATION: Synthetic

<400> SEQUENCE: 626
accuaccuaa ccacuguaca aa                                            22

<210> SEQ ID NO 627
<211> LENGTH: 22
<212> TYPE: RNA
<213> ORGANISM: Artificial Sequence
<220> FEATURE:
<223> OTHER INFORMATION: Synthetic

<400> SEQUENCE: 627
uguacaaaag auuucaccau ag                                            22

<210> SEQ ID NO 628
<211> LENGTH: 21
<212> TYPE: RNA
<213> ORGANISM: Artificial Sequence
<220> FEATURE:
<223> OTHER INFORMATION: Synthetic

<400> SEQUENCE: 628
accuaaccac uguacaaaag a                                             21

<210> SEQ ID NO 629
<211> LENGTH: 21
<212> TYPE: RNA
<213> ORGANISM: Artificial Sequence
<220> FEATURE:
<223> OTHER INFORMATION: Synthetic

<400> SEQUENCE: 629
uaccuaacca cuguacaaaa g                                             21

<210> SEQ ID NO 630
<211> LENGTH: 21
<212> TYPE: RNA
<213> ORGANISM: Artificial Sequence
<220> FEATURE:
<223> OTHER INFORMATION: Synthetic

<400> SEQUENCE: 630
cuaccuaacc acuguacaaa a                                             21

<210> SEQ ID NO 631
<211> LENGTH: 21
<212> TYPE: RNA
<213> ORGANISM: Artificial Sequence
<220> FEATURE:
<223> OTHER INFORMATION: Synthetic

<400> SEQUENCE: 631
ccuaccuaac cacuguacaa a                                             21

<210> SEQ ID NO 632
<211> LENGTH: 21
<212> TYPE: RNA
<213> ORGANISM: Artificial Sequence
<220> FEATURE:
<223> OTHER INFORMATION: Synthetic

<400> SEQUENCE: 632
accuaccuaa ccacuguaca a                                             21

<210> SEQ ID NO 633
<211> LENGTH: 21

```
<212> TYPE: RNA
<213> ORGANISM: Artificial Sequence
<220> FEATURE:
<223> OTHER INFORMATION: Synthetic

<400> SEQUENCE: 633
guacaaaaga uuucaccaua g                                              21

<210> SEQ ID NO 634
<211> LENGTH: 21
<212> TYPE: RNA
<213> ORGANISM: Artificial Sequence
<220> FEATURE:
<223> OTHER INFORMATION: Synthetic

<400> SEQUENCE: 634
uguacaaaag auuucaccau a                                              21

<210> SEQ ID NO 635
<211> LENGTH: 20
<212> TYPE: RNA
<213> ORGANISM: Artificial Sequence
<220> FEATURE:
<223> OTHER INFORMATION: Synthetic

<400> SEQUENCE: 635
accuaaccac uguacaaaag                                                20

<210> SEQ ID NO 636
<211> LENGTH: 20
<212> TYPE: RNA
<213> ORGANISM: Artificial Sequence
<220> FEATURE:
<223> OTHER INFORMATION: Synthetic

<400> SEQUENCE: 636
uaccuaacca cuguacaaaa                                                20

<210> SEQ ID NO 637
<211> LENGTH: 20
<212> TYPE: RNA
<213> ORGANISM: Artificial Sequence
<220> FEATURE:
<223> OTHER INFORMATION: Synthetic

<400> SEQUENCE: 637
cuaccuaacc acuguacaaa                                                20

<210> SEQ ID NO 638
<211> LENGTH: 20
<212> TYPE: RNA
<213> ORGANISM: Artificial Sequence
<220> FEATURE:
<223> OTHER INFORMATION: Synthetic

<400> SEQUENCE: 638
ccuaccuaac cacuguacaa                                                20

<210> SEQ ID NO 639
<211> LENGTH: 20
<212> TYPE: RNA
<213> ORGANISM: Artificial Sequence
<220> FEATURE:
<223> OTHER INFORMATION: Synthetic

<400> SEQUENCE: 639
```
accuaccuaa ccacuguaca                                      20

<210> SEQ ID NO 640
<211> LENGTH: 20
<212> TYPE: RNA
<213> ORGANISM: Artificial Sequence
<220> FEATURE:
<223> OTHER INFORMATION: Synthetic

<400> SEQUENCE: 640
uacaaaagau uucaccauag                                      20

<210> SEQ ID NO 641
<211> LENGTH: 20
<212> TYPE: RNA
<213> ORGANISM: Artificial Sequence
<220> FEATURE:
<223> OTHER INFORMATION: Synthetic

<400> SEQUENCE: 641
guacaaaaga uuucaccaua                                      20

<210> SEQ ID NO 642
<211> LENGTH: 20
<212> TYPE: RNA
<213> ORGANISM: Artificial Sequence
<220> FEATURE:
<223> OTHER INFORMATION: Synthetic

<400> SEQUENCE: 642
uguacaaaag auuucaccau                                      20

<210> SEQ ID NO 643
<211> LENGTH: 19
<212> TYPE: RNA
<213> ORGANISM: Artificial Sequence
<220> FEATURE:
<223> OTHER INFORMATION: Synthetic

<400> SEQUENCE: 643
accuaaccac uguacaaaa                                       19

<210> SEQ ID NO 644
<211> LENGTH: 19
<212> TYPE: RNA
<213> ORGANISM: Artificial Sequence
<220> FEATURE:
<223> OTHER INFORMATION: Synthetic

<400> SEQUENCE: 644
uaccuaacca cuguacaaa                                       19

<210> SEQ ID NO 645
<211> LENGTH: 19
<212> TYPE: RNA
<213> ORGANISM: Artificial Sequence
<220> FEATURE:
<223> OTHER INFORMATION: Synthetic

<400> SEQUENCE: 645
cuaccuaacc acuguacaa                                       19

<210> SEQ ID NO 646
<211> LENGTH: 19
<212> TYPE: RNA
<213> ORGANISM: Artificial Sequence

```
<220> FEATURE:
<223> OTHER INFORMATION: Synthetic

<400> SEQUENCE: 646
ccuaccuaac cacuguaca                                                    19

<210> SEQ ID NO 647
<211> LENGTH: 19
<212> TYPE: RNA
<213> ORGANISM: Artificial Sequence
<220> FEATURE:
<223> OTHER INFORMATION: Synthetic

<400> SEQUENCE: 647
accuaccuaa ccacuguac                                                    19

<210> SEQ ID NO 648
<211> LENGTH: 19
<212> TYPE: RNA
<213> ORGANISM: Artificial Sequence
<220> FEATURE:
<223> OTHER INFORMATION: Synthetic

<400> SEQUENCE: 648
acaaaagauu ucaccauag                                                    19

<210> SEQ ID NO 649
<211> LENGTH: 19
<212> TYPE: RNA
<213> ORGANISM: Artificial Sequence
<220> FEATURE:
<223> OTHER INFORMATION: Synthetic

<400> SEQUENCE: 649
uacaaaagau uucaccaua                                                    19

<210> SEQ ID NO 650
<211> LENGTH: 19
<212> TYPE: RNA
<213> ORGANISM: Artificial Sequence
<220> FEATURE:
<223> OTHER INFORMATION: Synthetic

<400> SEQUENCE: 650
guacaaaaga uuucaccau                                                    19

<210> SEQ ID NO 651
<211> LENGTH: 19
<212> TYPE: RNA
<213> ORGANISM: Artificial Sequence
<220> FEATURE:
<223> OTHER INFORMATION: Synthetic

<400> SEQUENCE: 651
uguacaaaag auuucacca                                                    19

<210> SEQ ID NO 652
<211> LENGTH: 18
<212> TYPE: RNA
<213> ORGANISM: Artificial Sequence
<220> FEATURE:
<223> OTHER INFORMATION: Synthetic

<400> SEQUENCE: 652
accuaaccac uguacaaa                                                     18
```

```
<210> SEQ ID NO 653
<211> LENGTH: 18
<212> TYPE: RNA
<213> ORGANISM: Artificial Sequence
<220> FEATURE:
<223> OTHER INFORMATION: Synthetic

<400> SEQUENCE: 653
uaccuaacca cuguacaa                                                 18

<210> SEQ ID NO 654
<211> LENGTH: 18
<212> TYPE: RNA
<213> ORGANISM: Artificial Sequence
<220> FEATURE:
<223> OTHER INFORMATION: Synthetic

<400> SEQUENCE: 654
cuaccuaacc acuguaca                                                 18

<210> SEQ ID NO 655
<211> LENGTH: 18
<212> TYPE: RNA
<213> ORGANISM: Artificial Sequence
<220> FEATURE:
<223> OTHER INFORMATION: Synthetic

<400> SEQUENCE: 655
ccuaccuaac cacuguac                                                 18

<210> SEQ ID NO 656
<211> LENGTH: 18
<212> TYPE: RNA
<213> ORGANISM: Artificial Sequence
<220> FEATURE:
<223> OTHER INFORMATION: Synthetic

<400> SEQUENCE: 656
accuaccuaa ccacugua                                                 18

<210> SEQ ID NO 657
<211> LENGTH: 18
<212> TYPE: RNA
<213> ORGANISM: Artificial Sequence
<220> FEATURE:
<223> OTHER INFORMATION: Synthetic

<400> SEQUENCE: 657
caaaagauuu caccauag                                                 18

<210> SEQ ID NO 658
<211> LENGTH: 18
<212> TYPE: RNA
<213> ORGANISM: Artificial Sequence
<220> FEATURE:
<223> OTHER INFORMATION: Synthetic

<400> SEQUENCE: 658
acaaaagauu ucaccaua                                                 18

<210> SEQ ID NO 659
<211> LENGTH: 18
<212> TYPE: RNA
<213> ORGANISM: Artificial Sequence
<220> FEATURE:
<223> OTHER INFORMATION: Synthetic
```

```
<400> SEQUENCE: 659
uacaaaagau uucaccau                                                 18

<210> SEQ ID NO 660
<211> LENGTH: 18
<212> TYPE: RNA
<213> ORGANISM: Artificial Sequence
<220> FEATURE:
<223> OTHER INFORMATION: Synthetic

<400> SEQUENCE: 660
guacaaaaga uuucacca                                                 18

<210> SEQ ID NO 661
<211> LENGTH: 18
<212> TYPE: RNA
<213> ORGANISM: Artificial Sequence
<220> FEATURE:
<223> OTHER INFORMATION: Synthetic

<400> SEQUENCE: 661
uguacaaaag auuucacc                                                 18

<210> SEQ ID NO 662
<211> LENGTH: 22
<212> TYPE: RNA
<213> ORGANISM: Artificial Sequence
<220> FEATURE:
<223> OTHER INFORMATION: Synthetic

<400> SEQUENCE: 662
cagaaacuaa acaggaagaa aa                                            22

<210> SEQ ID NO 663
<211> LENGTH: 22
<212> TYPE: RNA
<213> ORGANISM: Artificial Sequence
<220> FEATURE:
<223> OTHER INFORMATION: Synthetic

<400> SEQUENCE: 663
ccagaaacua aacaggaaga aa                                            22

<210> SEQ ID NO 664
<211> LENGTH: 21
<212> TYPE: RNA
<213> ORGANISM: Artificial Sequence
<220> FEATURE:
<223> OTHER INFORMATION: Synthetic

<400> SEQUENCE: 664
ccagaaacua aacaggaaga a                                             21

<210> SEQ ID NO 665
<211> LENGTH: 20
<212> TYPE: RNA
<213> ORGANISM: Artificial Sequence
<220> FEATURE:
<223> OTHER INFORMATION: Synthetic

<400> SEQUENCE: 665
cagaaacuaa acaggaagaa                                               20

<210> SEQ ID NO 666
```

```
<211> LENGTH: 20
<212> TYPE: RNA
<213> ORGANISM: Artificial Sequence
<220> FEATURE:
<223> OTHER INFORMATION: Synthetic

<400> SEQUENCE: 666
ccagaaacua aacaggaaga                                                    20

<210> SEQ ID NO 667
<211> LENGTH: 19
<212> TYPE: RNA
<213> ORGANISM: Artificial Sequence
<220> FEATURE:
<223> OTHER INFORMATION: Synthetic

<400> SEQUENCE: 667
cagaaacuaa acaggaaga                                                     19

<210> SEQ ID NO 668
<211> LENGTH: 19
<212> TYPE: RNA
<213> ORGANISM: Artificial Sequence
<220> FEATURE:
<223> OTHER INFORMATION: Synthetic

<400> SEQUENCE: 668
ccagaaacua aacaggaag                                                     19

<210> SEQ ID NO 669
<211> LENGTH: 18
<212> TYPE: RNA
<213> ORGANISM: Artificial Sequence
<220> FEATURE:
<223> OTHER INFORMATION: Synthetic

<400> SEQUENCE: 669
ccagaaacua aacaggaa                                                      18

<210> SEQ ID NO 670
<211> LENGTH: 21
<212> TYPE: RNA
<213> ORGANISM: Artificial Sequence
<220> FEATURE:
<223> OTHER INFORMATION: Synthetic

<400> SEQUENCE: 670
acuccacuca ugauuccaaa g                                                  21

<210> SEQ ID NO 671
<211> LENGTH: 20
<212> TYPE: RNA
<213> ORGANISM: Artificial Sequence
<220> FEATURE:
<223> OTHER INFORMATION: Synthetic

<400> SEQUENCE: 671
acuccacuca ugauuccaaa                                                    20

<210> SEQ ID NO 672
<211> LENGTH: 19
<212> TYPE: RNA
<213> ORGANISM: Artificial Sequence
<220> FEATURE:
<223> OTHER INFORMATION: Synthetic

<400> SEQUENCE: 672
```

```
acuccacuca ugauuccaa                                                    19

<210> SEQ ID NO 673
<211> LENGTH: 18
<212> TYPE: RNA
<213> ORGANISM: Artificial Sequence
<220> FEATURE:
<223> OTHER INFORMATION: Synthetic

<400> SEQUENCE: 673
cuccacucau gauuccaa                                                     18

<210> SEQ ID NO 674
<211> LENGTH: 20
<212> TYPE: RNA
<213> ORGANISM: Artificial Sequence
<220> FEATURE:
<223> OTHER INFORMATION: Synthetic

<400> SEQUENCE: 674
cuccacucau gauuccaaag                                                   20

<210> SEQ ID NO 675
<211> LENGTH: 20
<212> TYPE: RNA
<213> ORGANISM: Artificial Sequence
<220> FEATURE:
<223> OTHER INFORMATION: Synthetic

<400> SEQUENCE: 675
uacuccacuc augauuccaa                                                   20

<210> SEQ ID NO 676
<211> LENGTH: 20
<212> TYPE: RNA
<213> ORGANISM: Artificial Sequence
<220> FEATURE:
<223> OTHER INFORMATION: Synthetic

<400> SEQUENCE: 676
auacuccacu caugauucca                                                   20

<210> SEQ ID NO 677
<211> LENGTH: 20
<212> TYPE: RNA
<213> ORGANISM: Artificial Sequence
<220> FEATURE:
<223> OTHER INFORMATION: Synthetic

<400> SEQUENCE: 677
aauacuccac ucaugauucc                                                   20

<210> SEQ ID NO 678
<211> LENGTH: 19
<212> TYPE: RNA
<213> ORGANISM: Artificial Sequence
<220> FEATURE:
<223> OTHER INFORMATION: Synthetic

<400> SEQUENCE: 678
uccacucaug auuccaaag                                                    19

<210> SEQ ID NO 679
<211> LENGTH: 19
<212> TYPE: RNA
```

```
<213> ORGANISM: Artificial Sequence
<220> FEATURE:
<223> OTHER INFORMATION: Synthetic

<400> SEQUENCE: 679
cuccacucau gauuccaaa                                                    19

<210> SEQ ID NO 680
<211> LENGTH: 19
<212> TYPE: RNA
<213> ORGANISM: Artificial Sequence
<220> FEATURE:
<223> OTHER INFORMATION: Synthetic

<400> SEQUENCE: 680
uacuccacuc augauucca                                                    19

<210> SEQ ID NO 681
<211> LENGTH: 19
<212> TYPE: RNA
<213> ORGANISM: Artificial Sequence
<220> FEATURE:
<223> OTHER INFORMATION: Synthetic

<400> SEQUENCE: 681
auacuccacu caugauucc                                                    19

<210> SEQ ID NO 682
<211> LENGTH: 18
<212> TYPE: RNA
<213> ORGANISM: Artificial Sequence
<220> FEATURE:
<223> OTHER INFORMATION: Synthetic

<400> SEQUENCE: 682
acuccacuca ugauucca                                                     18

<210> SEQ ID NO 683
<211> LENGTH: 18
<212> TYPE: RNA
<213> ORGANISM: Artificial Sequence
<220> FEATURE:
<223> OTHER INFORMATION: Synthetic

<400> SEQUENCE: 683
uacuccacuc augauucc                                                     18

<210> SEQ ID NO 684
<211> LENGTH: 20
<212> TYPE: RNA
<213> ORGANISM: Artificial Sequence
<220> FEATURE:
<223> OTHER INFORMATION: Synthetic

<400> SEQUENCE: 684
ugaaugccca cugugccugg                                                   20

<210> SEQ ID NO 685
<211> LENGTH: 20
<212> TYPE: RNA
<213> ORGANISM: Artificial Sequence
<220> FEATURE:
<223> OTHER INFORMATION: Synthetic

<400> SEQUENCE: 685
augaaugccc acugugccug                                                   20
```

<210> SEQ ID NO 686
<211> LENGTH: 20
<212> TYPE: RNA
<213> ORGANISM: Artificial Sequence
<220> FEATURE:
<223> OTHER INFORMATION: Synthetic

<400> SEQUENCE: 686
caugaaugcc cacugugccu                                               20

<210> SEQ ID NO 687
<211> LENGTH: 20
<212> TYPE: RNA
<213> ORGANISM: Artificial Sequence
<220> FEATURE:
<223> OTHER INFORMATION: Synthetic

<400> SEQUENCE: 687
ccaugaaugc ccacugugcc                                               20

<210> SEQ ID NO 688
<211> LENGTH: 19
<212> TYPE: RNA
<213> ORGANISM: Artificial Sequence
<220> FEATURE:
<223> OTHER INFORMATION: Synthetic

<400> SEQUENCE: 688
gaaugcccac ugugccugg                                                19

<210> SEQ ID NO 689
<211> LENGTH: 19
<212> TYPE: RNA
<213> ORGANISM: Artificial Sequence
<220> FEATURE:
<223> OTHER INFORMATION: Synthetic

<400> SEQUENCE: 689
ugaaugccca cugugccug                                                19

<210> SEQ ID NO 690
<211> LENGTH: 19
<212> TYPE: RNA
<213> ORGANISM: Artificial Sequence
<220> FEATURE:
<223> OTHER INFORMATION: Synthetic

<400> SEQUENCE: 690
augaaugccc acugugccu                                                19

<210> SEQ ID NO 691
<211> LENGTH: 19
<212> TYPE: RNA
<213> ORGANISM: Artificial Sequence
<220> FEATURE:
<223> OTHER INFORMATION: Synthetic

<400> SEQUENCE: 691
caugaaugcc cacugugcc                                                19

<210> SEQ ID NO 692
<211> LENGTH: 19
<212> TYPE: RNA
<213> ORGANISM: Artificial Sequence
<220> FEATURE:

<223> OTHER INFORMATION: Synthetic

<400> SEQUENCE: 692
ccaugaaugc ccacugugc                                           19

<210> SEQ ID NO 693
<211> LENGTH: 18
<212> TYPE: RNA
<213> ORGANISM: Artificial Sequence
<220> FEATURE:
<223> OTHER INFORMATION: Synthetic

<400> SEQUENCE: 693
aaugcccacu gugccugg                                            18

<210> SEQ ID NO 694
<211> LENGTH: 18
<212> TYPE: RNA
<213> ORGANISM: Artificial Sequence
<220> FEATURE:
<223> OTHER INFORMATION: Synthetic

<400> SEQUENCE: 694
gaaugcccac ugugccug                                            18

<210> SEQ ID NO 695
<211> LENGTH: 18
<212> TYPE: RNA
<213> ORGANISM: Artificial Sequence
<220> FEATURE:
<223> OTHER INFORMATION: Synthetic

<400> SEQUENCE: 695
ugaaugccca cugugccu                                            18

<210> SEQ ID NO 696
<211> LENGTH: 18
<212> TYPE: RNA
<213> ORGANISM: Artificial Sequence
<220> FEATURE:
<223> OTHER INFORMATION: Synthetic

<400> SEQUENCE: 696
augaaugccc acugugcc                                            18

<210> SEQ ID NO 697
<211> LENGTH: 18
<212> TYPE: RNA
<213> ORGANISM: Artificial Sequence
<220> FEATURE:
<223> OTHER INFORMATION: Synthetic

<400> SEQUENCE: 697
caugaaugcc cacugugc                                            18

<210> SEQ ID NO 698
<211> LENGTH: 18
<212> TYPE: RNA
<213> ORGANISM: Artificial Sequence
<220> FEATURE:
<223> OTHER INFORMATION: Synthetic

<400> SEQUENCE: 698
ccaugaaugc ccacugug                                            18

```
<210> SEQ ID NO 699
<211> LENGTH: 22
<212> TYPE: RNA
<213> ORGANISM: Artificial Sequence
<220> FEATURE:
<223> OTHER INFORMATION: Synthetic

<400> SEQUENCE: 699
cuaugagaca cauaccugaa ua                                              22

<210> SEQ ID NO 700
<211> LENGTH: 22
<212> TYPE: RNA
<213> ORGANISM: Artificial Sequence
<220> FEATURE:
<223> OTHER INFORMATION: Synthetic

<400> SEQUENCE: 700
gcuaugagac acauaccuga au                                              22

<210> SEQ ID NO 701
<211> LENGTH: 22
<212> TYPE: RNA
<213> ORGANISM: Artificial Sequence
<220> FEATURE:
<223> OTHER INFORMATION: Synthetic

<400> SEQUENCE: 701
agcuaugaga cacauaccug aa                                              22

<210> SEQ ID NO 702
<211> LENGTH: 22
<212> TYPE: RNA
<213> ORGANISM: Artificial Sequence
<220> FEATURE:
<223> OTHER INFORMATION: Synthetic

<400> SEQUENCE: 702
cagcuaugag acacauaccu ga                                              22

<210> SEQ ID NO 703
<211> LENGTH: 22
<212> TYPE: RNA
<213> ORGANISM: Artificial Sequence
<220> FEATURE:
<223> OTHER INFORMATION: Synthetic

<400> SEQUENCE: 703
acagcuauga gacacauacc ug                                              22

<210> SEQ ID NO 704
<211> LENGTH: 22
<212> TYPE: RNA
<213> ORGANISM: Artificial Sequence
<220> FEATURE:
<223> OTHER INFORMATION: Synthetic

<400> SEQUENCE: 704
gacagcuaug agacacauac cu                                              22

<210> SEQ ID NO 705
<211> LENGTH: 22
<212> TYPE: RNA
<213> ORGANISM: Artificial Sequence
<220> FEATURE:
<223> OTHER INFORMATION: Synthetic
```

```
<400> SEQUENCE: 705
ugacagcuau gagacacaua cc                                              22

<210> SEQ ID NO 706
<211> LENGTH: 21
<212> TYPE: RNA
<213> ORGANISM: Artificial Sequence
<220> FEATURE:
<223> OTHER INFORMATION: Synthetic

<400> SEQUENCE: 706
uaugagacac auaccugaau a                                               21

<210> SEQ ID NO 707
<211> LENGTH: 21
<212> TYPE: RNA
<213> ORGANISM: Artificial Sequence
<220> FEATURE:
<223> OTHER INFORMATION: Synthetic

<400> SEQUENCE: 707
cuaugagaca cauaccugaa u                                               21

<210> SEQ ID NO 708
<211> LENGTH: 21
<212> TYPE: RNA
<213> ORGANISM: Artificial Sequence
<220> FEATURE:
<223> OTHER INFORMATION: Synthetic

<400> SEQUENCE: 708
gcuaugagac acauaccuga a                                               21

<210> SEQ ID NO 709
<211> LENGTH: 21
<212> TYPE: RNA
<213> ORGANISM: Artificial Sequence
<220> FEATURE:
<223> OTHER INFORMATION: Synthetic

<400> SEQUENCE: 709
agcuaugaga cacauaccug a                                               21

<210> SEQ ID NO 710
<211> LENGTH: 21
<212> TYPE: RNA
<213> ORGANISM: Artificial Sequence
<220> FEATURE:
<223> OTHER INFORMATION: Synthetic

<400> SEQUENCE: 710
cagcuaugag acacauaccu g                                               21

<210> SEQ ID NO 711
<211> LENGTH: 21
<212> TYPE: RNA
<213> ORGANISM: Artificial Sequence
<220> FEATURE:
<223> OTHER INFORMATION: Synthetic

<400> SEQUENCE: 711
acagcuauga gacacauacc u                                               21

<210> SEQ ID NO 712
<211> LENGTH: 20
```

```
<212> TYPE: RNA
<213> ORGANISM: Artificial Sequence
<220> FEATURE:
<223> OTHER INFORMATION: Synthetic

<400> SEQUENCE: 712
augagacaca uaccugaaua                                               20

<210> SEQ ID NO 713
<211> LENGTH: 20
<212> TYPE: RNA
<213> ORGANISM: Artificial Sequence
<220> FEATURE:
<223> OTHER INFORMATION: Synthetic

<400> SEQUENCE: 713
uaugagacac auaccugaau                                               20

<210> SEQ ID NO 714
<211> LENGTH: 20
<212> TYPE: RNA
<213> ORGANISM: Artificial Sequence
<220> FEATURE:
<223> OTHER INFORMATION: Synthetic

<400> SEQUENCE: 714
cuaugagaca cauaccugaa                                               20

<210> SEQ ID NO 715
<211> LENGTH: 20
<212> TYPE: RNA
<213> ORGANISM: Artificial Sequence
<220> FEATURE:
<223> OTHER INFORMATION: Synthetic

<400> SEQUENCE: 715
gcuaugagac acauaccuga                                               20

<210> SEQ ID NO 716
<211> LENGTH: 20
<212> TYPE: RNA
<213> ORGANISM: Artificial Sequence
<220> FEATURE:
<223> OTHER INFORMATION: Synthetic

<400> SEQUENCE: 716
agcuaugaga cacauaccug                                               20

<210> SEQ ID NO 717
<211> LENGTH: 20
<212> TYPE: RNA
<213> ORGANISM: Artificial Sequence
<220> FEATURE:
<223> OTHER INFORMATION: Synthetic

<400> SEQUENCE: 717
cagcuaugag acacauaccu                                               20

<210> SEQ ID NO 718
<211> LENGTH: 20
<212> TYPE: RNA
<213> ORGANISM: Artificial Sequence
<220> FEATURE:
<223> OTHER INFORMATION: Synthetic

<400> SEQUENCE: 718
```
acagcuauga gacacauacc                                                        20

<210> SEQ ID NO 719
<211> LENGTH: 19
<212> TYPE: RNA
<213> ORGANISM: Artificial Sequence
<220> FEATURE:
<223> OTHER INFORMATION: Synthetic

<400> SEQUENCE: 719
ugagacacau accugaaua                                                         19

<210> SEQ ID NO 720
<211> LENGTH: 19
<212> TYPE: RNA
<213> ORGANISM: Artificial Sequence
<220> FEATURE:
<223> OTHER INFORMATION: Synthetic

<400> SEQUENCE: 720
uaugagacac auaccugaa                                                         19

<210> SEQ ID NO 721
<211> LENGTH: 19
<212> TYPE: RNA
<213> ORGANISM: Artificial Sequence
<220> FEATURE:
<223> OTHER INFORMATION: Synthetic

<400> SEQUENCE: 721
cuaugagaca cauaccuga                                                         19

<210> SEQ ID NO 722
<211> LENGTH: 19
<212> TYPE: RNA
<213> ORGANISM: Artificial Sequence
<220> FEATURE:
<223> OTHER INFORMATION: Synthetic

<400> SEQUENCE: 722
gcuaugagac acauaccug                                                         19

<210> SEQ ID NO 723
<211> LENGTH: 19
<212> TYPE: RNA
<213> ORGANISM: Artificial Sequence
<220> FEATURE:
<223> OTHER INFORMATION: Synthetic

<400> SEQUENCE: 723
agcuaugaga cacauaccu                                                         19

<210> SEQ ID NO 724
<211> LENGTH: 19
<212> TYPE: RNA
<213> ORGANISM: Artificial Sequence
<220> FEATURE:
<223> OTHER INFORMATION: Synthetic

<400> SEQUENCE: 724
cagcuaugag acacauacc                                                         19

<210> SEQ ID NO 725
<211> LENGTH: 18
<212> TYPE: RNA
<213> ORGANISM: Artificial Sequence

```
<220> FEATURE:
<223> OTHER INFORMATION: Synthetic

<400> SEQUENCE: 725
cuaugagaca cauaccug                                                 18

<210> SEQ ID NO 726
<211> LENGTH: 18
<212> TYPE: RNA
<213> ORGANISM: Artificial Sequence
<220> FEATURE:
<223> OTHER INFORMATION: Synthetic

<400> SEQUENCE: 726
gcuaugagac acauaccu                                                 18

<210> SEQ ID NO 727
<211> LENGTH: 18
<212> TYPE: RNA
<213> ORGANISM: Artificial Sequence
<220> FEATURE:
<223> OTHER INFORMATION: Synthetic

<400> SEQUENCE: 727
agcuaugaga cacauacc                                                 18

<210> SEQ ID NO 728
<211> LENGTH: 13
<212> TYPE: RNA
<213> ORGANISM: Artificial Sequence
<220> FEATURE:
<223> OTHER INFORMATION: Synthetic

<400> SEQUENCE: 728
cacauaccug aau                                                      13

<210> SEQ ID NO 729
<211> LENGTH: 24
<212> TYPE: RNA
<213> ORGANISM: Artificial Sequence
<220> FEATURE:
<223> OTHER INFORMATION: Synthetic

<400> SEQUENCE: 729
ugagcugagu caagcggagc uggc                                          24

<210> SEQ ID NO 730
<211> LENGTH: 23
<212> TYPE: RNA
<213> ORGANISM: Artificial Sequence
<220> FEATURE:
<223> OTHER INFORMATION: Synthetic

<400> SEQUENCE: 730
gggaacugac cggugagcug agu                                           23

<210> SEQ ID NO 731
<211> LENGTH: 22
<212> TYPE: RNA
<213> ORGANISM: Artificial Sequence
<220> FEATURE:
<223> OTHER INFORMATION: Synthetic

<400> SEQUENCE: 731
accggugagc ugagucaagc gg                                            22
```

```
<210> SEQ ID NO 732
<211> LENGTH: 22
<212> TYPE: RNA
<213> ORGANISM: Artificial Sequence
<220> FEATURE:
<223> OTHER INFORMATION: Synthetic

<400> SEQUENCE: 732
gaccggugag cugagucaag cg                                              22

<210> SEQ ID NO 733
<211> LENGTH: 22
<212> TYPE: RNA
<213> ORGANISM: Artificial Sequence
<220> FEATURE:
<223> OTHER INFORMATION: Synthetic

<400> SEQUENCE: 733
ugaccgguga gcugagucaa gc                                              22

<210> SEQ ID NO 734
<211> LENGTH: 22
<212> TYPE: RNA
<213> ORGANISM: Artificial Sequence
<220> FEATURE:
<223> OTHER INFORMATION: Synthetic

<400> SEQUENCE: 734
cugaccggug agcugaguca ag                                              22

<210> SEQ ID NO 735
<211> LENGTH: 22
<212> TYPE: RNA
<213> ORGANISM: Artificial Sequence
<220> FEATURE:
<223> OTHER INFORMATION: Synthetic

<400> SEQUENCE: 735
acugaccggu gagcugaguc aa                                              22

<210> SEQ ID NO 736
<211> LENGTH: 22
<212> TYPE: RNA
<213> ORGANISM: Artificial Sequence
<220> FEATURE:
<223> OTHER INFORMATION: Synthetic

<400> SEQUENCE: 736
aacugaccgg ugagcugagu ca                                              22

<210> SEQ ID NO 737
<211> LENGTH: 22
<212> TYPE: RNA
<213> ORGANISM: Artificial Sequence
<220> FEATURE:
<223> OTHER INFORMATION: Synthetic

<400> SEQUENCE: 737
gaacugaccg gugagcugag uc                                              22

<210> SEQ ID NO 738
<211> LENGTH: 22
<212> TYPE: RNA
<213> ORGANISM: Artificial Sequence
<220> FEATURE:
<223> OTHER INFORMATION: Synthetic
```

-continued

<400> SEQUENCE: 738
ggaacugacc ggugagcuga gu                                             22

<210> SEQ ID NO 739
<211> LENGTH: 22
<212> TYPE: RNA
<213> ORGANISM: Artificial Sequence
<220> FEATURE:
<223> OTHER INFORMATION: Synthetic

<400> SEQUENCE: 739
gggaacugac cggugagcug ag                                             22

<210> SEQ ID NO 740
<211> LENGTH: 21
<212> TYPE: RNA
<213> ORGANISM: Artificial Sequence
<220> FEATURE:
<223> OTHER INFORMATION: Synthetic

<400> SEQUENCE: 740
accggugagc ugagucaagc g                                              21

<210> SEQ ID NO 741
<211> LENGTH: 21
<212> TYPE: RNA
<213> ORGANISM: Artificial Sequence
<220> FEATURE:
<223> OTHER INFORMATION: Synthetic

<400> SEQUENCE: 741
gaccggugag cugagucaag c                                              21

<210> SEQ ID NO 742
<211> LENGTH: 21
<212> TYPE: RNA
<213> ORGANISM: Artificial Sequence
<220> FEATURE:
<223> OTHER INFORMATION: Synthetic

<400> SEQUENCE: 742
ugaccgguga gcugagucaa g                                              21

<210> SEQ ID NO 743
<211> LENGTH: 21
<212> TYPE: RNA
<213> ORGANISM: Artificial Sequence
<220> FEATURE:
<223> OTHER INFORMATION: Synthetic

<400> SEQUENCE: 743
cugaccggug agcugaguca a                                              21

<210> SEQ ID NO 744
<211> LENGTH: 21
<212> TYPE: RNA
<213> ORGANISM: Artificial Sequence
<220> FEATURE:
<223> OTHER INFORMATION: Synthetic

<400> SEQUENCE: 744
acugaccggu gagcugaguc a                                              21

<210> SEQ ID NO 745

```
<211> LENGTH: 21
<212> TYPE: RNA
<213> ORGANISM: Artificial Sequence
<220> FEATURE:
<223> OTHER INFORMATION: Synthetic

<400> SEQUENCE: 745
aacugaccgg ugagcugagu c                                               21

<210> SEQ ID NO 746
<211> LENGTH: 21
<212> TYPE: RNA
<213> ORGANISM: Artificial Sequence
<220> FEATURE:
<223> OTHER INFORMATION: Synthetic

<400> SEQUENCE: 746
gaacugaccg gugagcugag u                                               21

<210> SEQ ID NO 747
<211> LENGTH: 21
<212> TYPE: RNA
<213> ORGANISM: Artificial Sequence
<220> FEATURE:
<223> OTHER INFORMATION: Synthetic

<400> SEQUENCE: 747
ggaacugacc ggugagcuga g                                               21

<210> SEQ ID NO 748
<211> LENGTH: 21
<212> TYPE: RNA
<213> ORGANISM: Artificial Sequence
<220> FEATURE:
<223> OTHER INFORMATION: Synthetic

<400> SEQUENCE: 748
gggaacugac cggugagcug a                                               21

<210> SEQ ID NO 749
<211> LENGTH: 20
<212> TYPE: RNA
<213> ORGANISM: Artificial Sequence
<220> FEATURE:
<223> OTHER INFORMATION: Synthetic

<400> SEQUENCE: 749
accggugagc ugagucaagc                                                 20

<210> SEQ ID NO 750
<211> LENGTH: 20
<212> TYPE: RNA
<213> ORGANISM: Artificial Sequence
<220> FEATURE:
<223> OTHER INFORMATION: Synthetic

<400> SEQUENCE: 750
gaccggugag cugagucaag                                                 20

<210> SEQ ID NO 751
<211> LENGTH: 20
<212> TYPE: RNA
<213> ORGANISM: Artificial Sequence
<220> FEATURE:
<223> OTHER INFORMATION: Synthetic

<400> SEQUENCE: 751
```
ugaccgguga gcugagucaa                                                         20

<210> SEQ ID NO 752
<211> LENGTH: 20
<212> TYPE: RNA
<213> ORGANISM: Artificial Sequence
<220> FEATURE:
<223> OTHER INFORMATION: Synthetic

<400> SEQUENCE: 752
cugaccggug agcugaguca                                                         20

<210> SEQ ID NO 753
<211> LENGTH: 20
<212> TYPE: RNA
<213> ORGANISM: Artificial Sequence
<220> FEATURE:
<223> OTHER INFORMATION: Synthetic

<400> SEQUENCE: 753
acugaccggu gagcugaguc                                                         20

<210> SEQ ID NO 754
<211> LENGTH: 20
<212> TYPE: RNA
<213> ORGANISM: Artificial Sequence
<220> FEATURE:
<223> OTHER INFORMATION: Synthetic

<400> SEQUENCE: 754
aacugaccgg ugagcugagu                                                         20

<210> SEQ ID NO 755
<211> LENGTH: 20
<212> TYPE: RNA
<213> ORGANISM: Artificial Sequence
<220> FEATURE:
<223> OTHER INFORMATION: Synthetic

<400> SEQUENCE: 755
gaacugaccg gugagcugag                                                         20

<210> SEQ ID NO 756
<211> LENGTH: 20
<212> TYPE: RNA
<213> ORGANISM: Artificial Sequence
<220> FEATURE:
<223> OTHER INFORMATION: Synthetic

<400> SEQUENCE: 756
ggaacugacc ggugagcuga                                                         20

<210> SEQ ID NO 757
<211> LENGTH: 20
<212> TYPE: RNA
<213> ORGANISM: Artificial Sequence
<220> FEATURE:
<223> OTHER INFORMATION: Synthetic

<400> SEQUENCE: 757
gggaacugac cggugagcug                                                         20

<210> SEQ ID NO 758
<211> LENGTH: 19
<212> TYPE: RNA

```
<213> ORGANISM: Artificial Sequence
<220> FEATURE:
<223> OTHER INFORMATION: Synthetic

<400> SEQUENCE: 758
accggugagc ugagucaag                                                    19

<210> SEQ ID NO 759
<211> LENGTH: 19
<212> TYPE: RNA
<213> ORGANISM: Artificial Sequence
<220> FEATURE:
<223> OTHER INFORMATION: Synthetic

<400> SEQUENCE: 759
gaccggugag cugagucaa                                                    19

<210> SEQ ID NO 760
<211> LENGTH: 19
<212> TYPE: RNA
<213> ORGANISM: Artificial Sequence
<220> FEATURE:
<223> OTHER INFORMATION: Synthetic

<400> SEQUENCE: 760
ugaccgguga gcugaguca                                                    19

<210> SEQ ID NO 761
<211> LENGTH: 19
<212> TYPE: RNA
<213> ORGANISM: Artificial Sequence
<220> FEATURE:
<223> OTHER INFORMATION: Synthetic

<400> SEQUENCE: 761
cugaccggug agcugaguc                                                    19

<210> SEQ ID NO 762
<211> LENGTH: 19
<212> TYPE: RNA
<213> ORGANISM: Artificial Sequence
<220> FEATURE:
<223> OTHER INFORMATION: Synthetic

<400> SEQUENCE: 762
acugaccggu gagcugagu                                                    19

<210> SEQ ID NO 763
<211> LENGTH: 19
<212> TYPE: RNA
<213> ORGANISM: Artificial Sequence
<220> FEATURE:
<223> OTHER INFORMATION: Synthetic

<400> SEQUENCE: 763
aacugaccgg ugagcugag                                                    19

<210> SEQ ID NO 764
<211> LENGTH: 19
<212> TYPE: RNA
<213> ORGANISM: Artificial Sequence
<220> FEATURE:
<223> OTHER INFORMATION: Synthetic

<400> SEQUENCE: 764
gaacugaccg gugagcuga                                                    19
```

<210> SEQ ID NO 765
<211> LENGTH: 19
<212> TYPE: RNA
<213> ORGANISM: Artificial Sequence
<220> FEATURE:
<223> OTHER INFORMATION: Synthetic

<400> SEQUENCE: 765
ggaacugacc ggugagcug                                                    19

<210> SEQ ID NO 766
<211> LENGTH: 19
<212> TYPE: RNA
<213> ORGANISM: Artificial Sequence
<220> FEATURE:
<223> OTHER INFORMATION: Synthetic

<400> SEQUENCE: 766
gggaacugac cggugagcu                                                    19

<210> SEQ ID NO 767
<211> LENGTH: 18
<212> TYPE: RNA
<213> ORGANISM: Artificial Sequence
<220> FEATURE:
<223> OTHER INFORMATION: Synthetic

<400> SEQUENCE: 767
accggugagc ugagucaa                                                     18

<210> SEQ ID NO 768
<211> LENGTH: 18
<212> TYPE: RNA
<213> ORGANISM: Artificial Sequence
<220> FEATURE:
<223> OTHER INFORMATION: Synthetic

<400> SEQUENCE: 768
gaccggugag cugaguca                                                     18

<210> SEQ ID NO 769
<211> LENGTH: 18
<212> TYPE: RNA
<213> ORGANISM: Artificial Sequence
<220> FEATURE:
<223> OTHER INFORMATION: Synthetic

<400> SEQUENCE: 769
ugaccgguga gcugaguc                                                     18

<210> SEQ ID NO 770
<211> LENGTH: 18
<212> TYPE: RNA
<213> ORGANISM: Artificial Sequence
<220> FEATURE:
<223> OTHER INFORMATION: Synthetic

<400> SEQUENCE: 770
cugaccggug agcugagu                                                     18

<210> SEQ ID NO 771
<211> LENGTH: 18
<212> TYPE: RNA
<213> ORGANISM: Artificial Sequence
<220> FEATURE:

<223> OTHER INFORMATION: Synthetic

<400> SEQUENCE: 771
acugaccggu gagcugag                                                        18

<210> SEQ ID NO 772
<211> LENGTH: 18
<212> TYPE: RNA
<213> ORGANISM: Artificial Sequence
<220> FEATURE:
<223> OTHER INFORMATION: Synthetic

<400> SEQUENCE: 772
aacugaccgg ugagcuga                                                        18

<210> SEQ ID NO 773
<211> LENGTH: 18
<212> TYPE: RNA
<213> ORGANISM: Artificial Sequence
<220> FEATURE:
<223> OTHER INFORMATION: Synthetic

<400> SEQUENCE: 773
gaacugaccg gugagcug                                                        18

<210> SEQ ID NO 774
<211> LENGTH: 18
<212> TYPE: RNA
<213> ORGANISM: Artificial Sequence
<220> FEATURE:
<223> OTHER INFORMATION: Synthetic

<400> SEQUENCE: 774
ggaacugacc ggugagcu                                                        18

<210> SEQ ID NO 775
<211> LENGTH: 18
<212> TYPE: RNA
<213> ORGANISM: Artificial Sequence
<220> FEATURE:
<223> OTHER INFORMATION: Synthetic

<400> SEQUENCE: 775
gggaacugac cggugagc                                                        18

<210> SEQ ID NO 776
<211> LENGTH: 17
<212> TYPE: RNA
<213> ORGANISM: Artificial Sequence
<220> FEATURE:
<223> OTHER INFORMATION: Synthetic

<400> SEQUENCE: 776
accggugagc ugaguca                                                         17

<210> SEQ ID NO 777
<211> LENGTH: 17
<212> TYPE: RNA
<213> ORGANISM: Artificial Sequence
<220> FEATURE:
<223> OTHER INFORMATION: Synthetic

<400> SEQUENCE: 777
gaccggugag cugaguc                                                         17

<210> SEQ ID NO 778
<211> LENGTH: 17
<212> TYPE: RNA
<213> ORGANISM: Artificial Sequence
<220> FEATURE:
<223> OTHER INFORMATION: Synthetic

<400> SEQUENCE: 778
ugaccgguga gcugagu                                                    17

<210> SEQ ID NO 779
<211> LENGTH: 17
<212> TYPE: RNA
<213> ORGANISM: Artificial Sequence
<220> FEATURE:
<223> OTHER INFORMATION: Synthetic

<400> SEQUENCE: 779
cugaccggug agcugag                                                    17

<210> SEQ ID NO 780
<211> LENGTH: 17
<212> TYPE: RNA
<213> ORGANISM: Artificial Sequence
<220> FEATURE:
<223> OTHER INFORMATION: Synthetic

<400> SEQUENCE: 780
acugaccggu gagcuga                                                    17

<210> SEQ ID NO 781
<211> LENGTH: 17
<212> TYPE: DNA
<213> ORGANISM: Artificial Sequence
<220> FEATURE:
<223> OTHER INFORMATION: Synthetic

<400> SEQUENCE: 781
aacugaccgg ugagcug                                                    17

<210> SEQ ID NO 782
<211> LENGTH: 17
<212> TYPE: RNA
<213> ORGANISM: Artificial Sequence
<220> FEATURE:
<223> OTHER INFORMATION: Synthetic

<400> SEQUENCE: 782
gaacugaccg gugagcu                                                    17

<210> SEQ ID NO 783
<211> LENGTH: 17
<212> TYPE: RNA
<213> ORGANISM: Artificial Sequence
<220> FEATURE:
<223> OTHER INFORMATION: Synthetic

<400> SEQUENCE: 783
ggaacugacc ggugagc                                                    17

<210> SEQ ID NO 784
<211> LENGTH: 17
<212> TYPE: RNA
<213> ORGANISM: Artificial Sequence
<220> FEATURE:
<223> OTHER INFORMATION: Synthetic

```
<400> SEQUENCE: 784
gggaacugac cggugag                                              17

<210> SEQ ID NO 785
<211> LENGTH: 16
<212> TYPE: RNA
<213> ORGANISM: Artificial Sequence
<220> FEATURE:
<223> OTHER INFORMATION: Synthetic

<400> SEQUENCE: 785
accggugagc ugaguc                                               16

<210> SEQ ID NO 786
<211> LENGTH: 16
<212> TYPE: RNA
<213> ORGANISM: Artificial Sequence
<220> FEATURE:
<223> OTHER INFORMATION: Synthetic

<400> SEQUENCE: 786
gaccggugag cugagu                                               16

<210> SEQ ID NO 787
<211> LENGTH: 16
<212> TYPE: RNA
<213> ORGANISM: Artificial Sequence
<220> FEATURE:
<223> OTHER INFORMATION: Synthetic

<400> SEQUENCE: 787
ugaccgguga gcugag                                               16

<210> SEQ ID NO 788
<211> LENGTH: 16
<212> TYPE: RNA
<213> ORGANISM: Artificial Sequence
<220> FEATURE:
<223> OTHER INFORMATION: Synthetic

<400> SEQUENCE: 788
cugaccggug agcuga                                               16

<210> SEQ ID NO 789
<211> LENGTH: 16
<212> TYPE: RNA
<213> ORGANISM: Artificial Sequence
<220> FEATURE:
<223> OTHER INFORMATION: Synthetic

<400> SEQUENCE: 789
acugaccggu gagcug                                               16

<210> SEQ ID NO 790
<211> LENGTH: 16
<212> TYPE: RNA
<213> ORGANISM: Artificial Sequence
<220> FEATURE:
<223> OTHER INFORMATION: Synthetic

<400> SEQUENCE: 790
aacugaccgg ugagcu                                               16

<210> SEQ ID NO 791
<211> LENGTH: 16
```

```
<212> TYPE: RNA
<213> ORGANISM: Artificial Sequence
<220> FEATURE:
<223> OTHER INFORMATION: Synthetic

<400> SEQUENCE: 791
gaacugaccg gugagc                                                    16

<210> SEQ ID NO 792
<211> LENGTH: 16
<212> TYPE: RNA
<213> ORGANISM: Artificial Sequence
<220> FEATURE:
<223> OTHER INFORMATION: Synthetic

<400> SEQUENCE: 792
ggaacugacc ggugag                                                    16

<210> SEQ ID NO 793
<211> LENGTH: 16
<212> TYPE: RNA
<213> ORGANISM: Artificial Sequence
<220> FEATURE:
<223> OTHER INFORMATION: Synthetic

<400> SEQUENCE: 793
gggaacugac cgguga                                                    16

<210> SEQ ID NO 794
<211> LENGTH: 15
<212> TYPE: RNA
<213> ORGANISM: Artificial Sequence
<220> FEATURE:
<223> OTHER INFORMATION: Synthetic

<400> SEQUENCE: 794
accggugagc ugagu                                                     15

<210> SEQ ID NO 795
<211> LENGTH: 15
<212> TYPE: RNA
<213> ORGANISM: Artificial Sequence
<220> FEATURE:
<223> OTHER INFORMATION: Synthetic

<400> SEQUENCE: 795
gaccggugag cugag                                                     15

<210> SEQ ID NO 796
<211> LENGTH: 15
<212> TYPE: RNA
<213> ORGANISM: Artificial Sequence
<220> FEATURE:
<223> OTHER INFORMATION: Synthetic

<400> SEQUENCE: 796
ugaccgguga gcuga                                                     15

<210> SEQ ID NO 797
<211> LENGTH: 15
<212> TYPE: RNA
<213> ORGANISM: Artificial Sequence
<220> FEATURE:
<223> OTHER INFORMATION: Synthetic

<400> SEQUENCE: 797
```
cugaccggug agcug                                                          15

<210> SEQ ID NO 798
<211> LENGTH: 15
<212> TYPE: RNA
<213> ORGANISM: Artificial Sequence
<220> FEATURE:
<223> OTHER INFORMATION: Synthetic

<400> SEQUENCE: 798
acugaccggu gagcu                                                          15

<210> SEQ ID NO 799
<211> LENGTH: 15
<212> TYPE: RNA
<213> ORGANISM: Artificial Sequence
<220> FEATURE:
<223> OTHER INFORMATION: Synthetic

<400> SEQUENCE: 799
aacugaccgg ugagc                                                          15

<210> SEQ ID NO 800
<211> LENGTH: 15
<212> TYPE: RNA
<213> ORGANISM: Artificial Sequence
<220> FEATURE:
<223> OTHER INFORMATION: Synthetic

<400> SEQUENCE: 800
gaacugaccg gugag                                                          15

<210> SEQ ID NO 801
<211> LENGTH: 15
<212> TYPE: RNA
<213> ORGANISM: Artificial Sequence
<220> FEATURE:
<223> OTHER INFORMATION: Synthetic

<400> SEQUENCE: 801
ggaacugacc gguga                                                          15

<210> SEQ ID NO 802
<211> LENGTH: 15
<212> TYPE: RNA
<213> ORGANISM: Artificial Sequence
<220> FEATURE:
<223> OTHER INFORMATION: Synthetic

<400> SEQUENCE: 802
gggaacugac cggug                                                          15

<210> SEQ ID NO 803
<211> LENGTH: 24
<212> TYPE: RNA
<213> ORGANISM: Artificial Sequence
<220> FEATURE:
<223> OTHER INFORMATION: Synthetic

<400> SEQUENCE: 803
uaaccugagg gguuggagag aggc                                                24

<210> SEQ ID NO 804
<211> LENGTH: 24
<212> TYPE: RNA
<213> ORGANISM: Artificial Sequence

```
<220> FEATURE:
<223> OTHER INFORMATION: Synthetic

<400> SEQUENCE: 804
uggauguuca gguaaccuga gggg                                              24

<210> SEQ ID NO 805
<211> LENGTH: 24
<212> TYPE: RNA
<213> ORGANISM: Artificial Sequence
<220> FEATURE:
<223> OTHER INFORMATION: Synthetic

<400> SEQUENCE: 805
cuggauguuc agguaaccug aggg                                              24

<210> SEQ ID NO 806
<211> LENGTH: 23
<212> TYPE: RNA
<213> ORGANISM: Artificial Sequence
<220> FEATURE:
<223> OTHER INFORMATION: Synthetic

<400> SEQUENCE: 806
aaccugaggg guuggagaga ggc                                               23

<210> SEQ ID NO 807
<211> LENGTH: 23
<212> TYPE: RNA
<213> ORGANISM: Artificial Sequence
<220> FEATURE:
<223> OTHER INFORMATION: Synthetic

<400> SEQUENCE: 807
cuggauguuc agguaaccug agg                                               23

<210> SEQ ID NO 808
<211> LENGTH: 22
<212> TYPE: RNA
<213> ORGANISM: Artificial Sequence
<220> FEATURE:
<223> OTHER INFORMATION: Synthetic

<400> SEQUENCE: 808
accugagggg uuggagagag gc                                                22

<210> SEQ ID NO 809
<211> LENGTH: 22
<212> TYPE: RNA
<213> ORGANISM: Artificial Sequence
<220> FEATURE:
<223> OTHER INFORMATION: Synthetic

<400> SEQUENCE: 809
cuggauguuc agguaaccug ag                                                22

<210> SEQ ID NO 810
<211> LENGTH: 21
<212> TYPE: RNA
<213> ORGANISM: Artificial Sequence
<220> FEATURE:
<223> OTHER INFORMATION: Synthetic

<400> SEQUENCE: 810
cuggauguuc agguaaccug a                                                 21
```

<210> SEQ ID NO 811
<211> LENGTH: 20
<212> TYPE: RNA
<213> ORGANISM: Artificial Sequence
<220> FEATURE:
<223> OTHER INFORMATION: Synthetic

<400> SEQUENCE: 811
cuggauguuc agguaaccug                                               20

<210> SEQ ID NO 812
<211> LENGTH: 19
<212> TYPE: RNA
<213> ORGANISM: Artificial Sequence
<220> FEATURE:
<223> OTHER INFORMATION: Synthetic

<400> SEQUENCE: 812
cuggauguuc agguaaccu                                                19

<210> SEQ ID NO 813
<211> LENGTH: 18
<212> TYPE: RNA
<213> ORGANISM: Artificial Sequence
<220> FEATURE:
<223> OTHER INFORMATION: Synthetic

<400> SEQUENCE: 813
uggauguuca gguaaccu                                                 18

<210> SEQ ID NO 814
<211> LENGTH: 24
<212> TYPE: RNA
<213> ORGANISM: Artificial Sequence
<220> FEATURE:
<223> OTHER INFORMATION: Synthetic

<400> SEQUENCE: 814
ugcgacaucu ugacuugcag acgu                                          24

<210> SEQ ID NO 815
<211> LENGTH: 23
<212> TYPE: RNA
<213> ORGANISM: Artificial Sequence
<220> FEATURE:
<223> OTHER INFORMATION: Synthetic

<400> SEQUENCE: 815
gcgacaucuu gacuugcaga cgu                                           23

<210> SEQ ID NO 816
<211> LENGTH: 22
<212> TYPE: RNA
<213> ORGANISM: Artificial Sequence
<220> FEATURE:
<223> OTHER INFORMATION: Synthetic

<400> SEQUENCE: 816
cgacaucuug acuugcagac gu                                            22

<210> SEQ ID NO 817
<211> LENGTH: 21
<212> TYPE: RNA
<213> ORGANISM: Artificial Sequence
<220> FEATURE:
<223> OTHER INFORMATION: Synthetic

<400> SEQUENCE: 817
gacaucuuga cuugcagacg u                                                  21

<210> SEQ ID NO 818
<211> LENGTH: 20
<212> TYPE: RNA
<213> ORGANISM: Artificial Sequence
<220> FEATURE:
<223> OTHER INFORMATION: Synthetic

<400> SEQUENCE: 818
acaucuugac uugcagacgu                                                    20

<210> SEQ ID NO 819
<211> LENGTH: 19
<212> TYPE: RNA
<213> ORGANISM: Artificial Sequence
<220> FEATURE:
<223> OTHER INFORMATION: Synthetic

<400> SEQUENCE: 819
caucuugacu ugcagacgu                                                     19

<210> SEQ ID NO 820
<211> LENGTH: 24
<212> TYPE: RNA
<213> ORGANISM: Artificial Sequence
<220> FEATURE:
<223> OTHER INFORMATION: Synthetic

<400> SEQUENCE: 820
gggugcgaca ucuugacuug caga                                               24

<210> SEQ ID NO 821
<211> LENGTH: 23
<212> TYPE: RNA
<213> ORGANISM: Artificial Sequence
<220> FEATURE:
<223> OTHER INFORMATION: Synthetic

<400> SEQUENCE: 821
ggugcgacau cuugacuugc aga                                                23

<210> SEQ ID NO 822
<211> LENGTH: 22
<212> TYPE: RNA
<213> ORGANISM: Artificial Sequence
<220> FEATURE:
<223> OTHER INFORMATION: Synthetic

<400> SEQUENCE: 822
gugcgacauc uugacuugca ga                                                 22

<210> SEQ ID NO 823
<211> LENGTH: 21
<212> TYPE: RNA
<213> ORGANISM: Artificial Sequence
<220> FEATURE:
<223> OTHER INFORMATION: Synthetic

<400> SEQUENCE: 823
ugcgacaucu ugacuugcag a                                                  21

<210> SEQ ID NO 824

```
<211> LENGTH: 20
<212> TYPE: RNA
<213> ORGANISM: Artificial Sequence
<220> FEATURE:
<223> OTHER INFORMATION: Synthetic

<400> SEQUENCE: 824
gcgacaucuu gacuugcaga                                              20

<210> SEQ ID NO 825
<211> LENGTH: 24
<212> TYPE: RNA
<213> ORGANISM: Artificial Sequence
<220> FEATURE:
<223> OTHER INFORMATION: Synthetic

<400> SEQUENCE: 825
gcucaccucg cucccucccg augu                                         24

<210> SEQ ID NO 826
<211> LENGTH: 23
<212> TYPE: RNA
<213> ORGANISM: Artificial Sequence
<220> FEATURE:
<223> OTHER INFORMATION: Synthetic

<400> SEQUENCE: 826
gcucaccucg cucccucccg aug                                          23

<210> SEQ ID NO 827
<211> LENGTH: 22
<212> TYPE: RNA
<213> ORGANISM: Artificial Sequence
<220> FEATURE:
<223> OTHER INFORMATION: Synthetic

<400> SEQUENCE: 827
gcucaccucg cucccucccg au                                           22

<210> SEQ ID NO 828
<211> LENGTH: 21
<212> TYPE: RNA
<213> ORGANISM: Artificial Sequence
<220> FEATURE:
<223> OTHER INFORMATION: Synthetic

<400> SEQUENCE: 828
gcucaccucg cucccucccg a                                            21

<210> SEQ ID NO 829
<211> LENGTH: 20
<212> TYPE: RNA
<213> ORGANISM: Artificial Sequence
<220> FEATURE:
<223> OTHER INFORMATION: Synthetic

<400> SEQUENCE: 829
gcucaccucg cucccucccg                                              20

<210> SEQ ID NO 830
<211> LENGTH: 19
<212> TYPE: RNA
<213> ORGANISM: Artificial Sequence
<220> FEATURE:
<223> OTHER INFORMATION: Synthetic

<400> SEQUENCE: 830
```

```
gcucaccucg cuccccucc                                          19

<210> SEQ ID NO 831
<211> LENGTH: 24
<212> TYPE: RNA
<213> ORGANISM: Artificial Sequence
<220> FEATURE:
<223> OTHER INFORMATION: Synthetic

<400> SEQUENCE: 831
cucaccucgc uccccuccga uguc                                    24

<210> SEQ ID NO 832
<211> LENGTH: 23
<212> TYPE: RNA
<213> ORGANISM: Artificial Sequence
<220> FEATURE:
<223> OTHER INFORMATION: Synthetic

<400> SEQUENCE: 832
cucaccucgc uccccuccga ugu                                     23

<210> SEQ ID NO 833
<211> LENGTH: 22
<212> TYPE: RNA
<213> ORGANISM: Artificial Sequence
<220> FEATURE:
<223> OTHER INFORMATION: Synthetic

<400> SEQUENCE: 833
cucaccucgc uccccuccga ug                                      22

<210> SEQ ID NO 834
<211> LENGTH: 21
<212> TYPE: RNA
<213> ORGANISM: Artificial Sequence
<220> FEATURE:
<223> OTHER INFORMATION: Synthetic

<400> SEQUENCE: 834
cucaccucgc uccccuccga u                                       21

<210> SEQ ID NO 835
<211> LENGTH: 20
<212> TYPE: RNA
<213> ORGANISM: Artificial Sequence
<220> FEATURE:
<223> OTHER INFORMATION: Synthetic

<400> SEQUENCE: 835
cucaccucgc uccccuccga                                         20

<210> SEQ ID NO 836
<211> LENGTH: 19
<212> TYPE: RNA
<213> ORGANISM: Artificial Sequence
<220> FEATURE:
<223> OTHER INFORMATION: Synthetic

<400> SEQUENCE: 836
cucaccucgc uccccuccg                                          19

<210> SEQ ID NO 837
<211> LENGTH: 23
<212> TYPE: RNA
```

```
<213> ORGANISM: Artificial Sequence
<220> FEATURE:
<223> OTHER INFORMATION: Synthetic

<400> SEQUENCE: 837
ucaccucgcu ccccuccaug ucc                                              23

<210> SEQ ID NO 838
<211> LENGTH: 22
<212> TYPE: RNA
<213> ORGANISM: Artificial Sequence
<220> FEATURE:
<223> OTHER INFORMATION: Synthetic

<400> SEQUENCE: 838
ucaccucgcu ccccuccaug uc                                               22

<210> SEQ ID NO 839
<211> LENGTH: 21
<212> TYPE: RNA
<213> ORGANISM: Artificial Sequence
<220> FEATURE:
<223> OTHER INFORMATION: Synthetic

<400> SEQUENCE: 839
ucaccucgcu ccccuccaug u                                                21

<210> SEQ ID NO 840
<211> LENGTH: 20
<212> TYPE: RNA
<213> ORGANISM: Artificial Sequence
<220> FEATURE:
<223> OTHER INFORMATION: Synthetic

<400> SEQUENCE: 840
ucaccucgcu ccccuccaug                                                  20

<210> SEQ ID NO 841
<211> LENGTH: 19
<212> TYPE: RNA
<213> ORGANISM: Artificial Sequence
<220> FEATURE:
<223> OTHER INFORMATION: Synthetic

<400> SEQUENCE: 841
ucaccucgcu ccccuccau                                                   19

<210> SEQ ID NO 842
<211> LENGTH: 18
<212> TYPE: RNA
<213> ORGANISM: Artificial Sequence
<220> FEATURE:
<223> OTHER INFORMATION: Synthetic

<400> SEQUENCE: 842
ucaccucgcu ccccucca                                                    18

<210> SEQ ID NO 843
<211> LENGTH: 24
<212> TYPE: RNA
<213> ORGANISM: Artificial Sequence
<220> FEATURE:
<223> OTHER INFORMATION: Synthetic

<400> SEQUENCE: 843
caccucgcuc ccuccgaug ucca                                              24
```

<210> SEQ ID NO 844
<211> LENGTH: 23
<212> TYPE: RNA
<213> ORGANISM: Artificial Sequence
<220> FEATURE:
<223> OTHER INFORMATION: Synthetic

<400> SEQUENCE: 844
caccucgcuc cccuccgaug ucc            23

<210> SEQ ID NO 845
<211> LENGTH: 22
<212> TYPE: RNA
<213> ORGANISM: Artificial Sequence
<220> FEATURE:
<223> OTHER INFORMATION: Synthetic

<400> SEQUENCE: 845
caccucgcuc cccuccgaug uc             22

<210> SEQ ID NO 846
<211> LENGTH: 21
<212> TYPE: RNA
<213> ORGANISM: Artificial Sequence
<220> FEATURE:
<223> OTHER INFORMATION: Synthetic

<400> SEQUENCE: 846
caccucgcuc cccuccgaug u              21

<210> SEQ ID NO 847
<211> LENGTH: 20
<212> TYPE: RNA
<213> ORGANISM: Artificial Sequence
<220> FEATURE:
<223> OTHER INFORMATION: Synthetic

<400> SEQUENCE: 847
caccucgcuc cccuccgaug                20

<210> SEQ ID NO 848
<211> LENGTH: 23
<212> TYPE: RNA
<213> ORGANISM: Artificial Sequence
<220> FEATURE:
<223> OTHER INFORMATION: Synthetic

<400> SEQUENCE: 848
accucgcucc ccuccauguc cac            23

<210> SEQ ID NO 849
<211> LENGTH: 22
<212> TYPE: RNA
<213> ORGANISM: Artificial Sequence
<220> FEATURE:
<223> OTHER INFORMATION: Synthetic

<400> SEQUENCE: 849
accucgcucc ccuccauguc ca             22

<210> SEQ ID NO 850
<211> LENGTH: 21
<212> TYPE: RNA
<213> ORGANISM: Artificial Sequence
<220> FEATURE:

```
<223> OTHER INFORMATION: Synthetic

<400> SEQUENCE: 850
accucgcucc cuccauguc c                                              21

<210> SEQ ID NO 851
<211> LENGTH: 20
<212> TYPE: RNA
<213> ORGANISM: Artificial Sequence
<220> FEATURE:
<223> OTHER INFORMATION: Synthetic

<400> SEQUENCE: 851
accucgcucc cuccauguc                                                20

<210> SEQ ID NO 852
<211> LENGTH: 19
<212> TYPE: RNA
<213> ORGANISM: Artificial Sequence
<220> FEATURE:
<223> OTHER INFORMATION: Synthetic

<400> SEQUENCE: 852
accucgcucc ccuccaugu                                                19

<210> SEQ ID NO 853
<211> LENGTH: 24
<212> TYPE: RNA
<213> ORGANISM: Artificial Sequence
<220> FEATURE:
<223> OTHER INFORMATION: Synthetic

<400> SEQUENCE: 853
ccucgcuccc cuccgauguc cacg                                          24

<210> SEQ ID NO 854
<211> LENGTH: 23
<212> TYPE: RNA
<213> ORGANISM: Artificial Sequence
<220> FEATURE:
<223> OTHER INFORMATION: Synthetic

<400> SEQUENCE: 854
ccucgcuccc cuccgauguc cac                                           23

<210> SEQ ID NO 855
<211> LENGTH: 22
<212> TYPE: RNA
<213> ORGANISM: Artificial Sequence
<220> FEATURE:
<223> OTHER INFORMATION: Synthetic

<400> SEQUENCE: 855
ccucgcuccc cuccgauguc ca                                            22

<210> SEQ ID NO 856
<211> LENGTH: 21
<212> TYPE: RNA
<213> ORGANISM: Artificial Sequence
<220> FEATURE:
<223> OTHER INFORMATION: Synthetic

<400> SEQUENCE: 856
ccucgcuccc cuccgauguc c                                             21
```

```
<210> SEQ ID NO 857
<211> LENGTH: 20
<212> TYPE: RNA
<213> ORGANISM: Artificial Sequence
<220> FEATURE:
<223> OTHER INFORMATION: Synthetic

<400> SEQUENCE: 857
ccucgcuccc cuccgauguc                                              20

<210> SEQ ID NO 858
<211> LENGTH: 24
<212> TYPE: RNA
<213> ORGANISM: Artificial Sequence
<220> FEATURE:
<223> OTHER INFORMATION: Synthetic

<400> SEQUENCE: 858
aucauaaauu ucuuaauaac uaca                                         24

<210> SEQ ID NO 859
<211> LENGTH: 23
<212> TYPE: RNA
<213> ORGANISM: Artificial Sequence
<220> FEATURE:
<223> OTHER INFORMATION: Synthetic

<400> SEQUENCE: 859
ucauaaauuu cuuaauaacu aca                                          23

<210> SEQ ID NO 860
<211> LENGTH: 22
<212> TYPE: RNA
<213> ORGANISM: Artificial Sequence
<220> FEATURE:
<223> OTHER INFORMATION: Synthetic

<400> SEQUENCE: 860
cauaaauuuc uuaauaacua ca                                           22

<210> SEQ ID NO 861
<211> LENGTH: 21
<212> TYPE: RNA
<213> ORGANISM: Artificial Sequence
<220> FEATURE:
<223> OTHER INFORMATION: Synthetic

<400> SEQUENCE: 861
auaaauuucu uaauaacuac a                                            21

<210> SEQ ID NO 862
<211> LENGTH: 20
<212> TYPE: RNA
<213> ORGANISM: Artificial Sequence
<220> FEATURE:
<223> OTHER INFORMATION: Synthetic

<400> SEQUENCE: 862
uaaauuucuu aauaacuaca                                              20

<210> SEQ ID NO 863
<211> LENGTH: 19
<212> TYPE: RNA
<213> ORGANISM: Artificial Sequence
<220> FEATURE:
<223> OTHER INFORMATION: Synthetic
```

<400> SEQUENCE: 863
aaauuucuua auaacuaca							19

<210> SEQ ID NO 864
<211> LENGTH: 24
<212> TYPE: RNA
<213> ORGANISM: Artificial Sequence
<220> FEATURE:
<223> OTHER INFORMATION: Synthetic

<400> SEQUENCE: 864
aaucauaaau uucuuaauaa cuac						24

<210> SEQ ID NO 865
<211> LENGTH: 23
<212> TYPE: RNA
<213> ORGANISM: Artificial Sequence
<220> FEATURE:
<223> OTHER INFORMATION: Synthetic

<400> SEQUENCE: 865
aucauaaauu ucuuaauaac uac						23

<210> SEQ ID NO 866
<211> LENGTH: 22
<212> TYPE: RNA
<213> ORGANISM: Artificial Sequence
<220> FEATURE:
<223> OTHER INFORMATION: Synthetic

<400> SEQUENCE: 866
ucauaaauuu cuuaauaacu ac						22

<210> SEQ ID NO 867
<211> LENGTH: 21
<212> TYPE: RNA
<213> ORGANISM: Artificial Sequence
<220> FEATURE:
<223> OTHER INFORMATION: Synthetic

<400> SEQUENCE: 867
cauaaauuuc uuaauaacua c							21

<210> SEQ ID NO 868
<211> LENGTH: 20
<212> TYPE: RNA
<213> ORGANISM: Artificial Sequence
<220> FEATURE:
<223> OTHER INFORMATION: Synthetic

<400> SEQUENCE: 868
auaaauuucu uaauaacuac						20

<210> SEQ ID NO 869
<211> LENGTH: 19
<212> TYPE: RNA
<213> ORGANISM: Artificial Sequence
<220> FEATURE:
<223> OTHER INFORMATION: Synthetic

<400> SEQUENCE: 869
uaaauuucuu aauaacuac						19

<210> SEQ ID NO 870
<211> LENGTH: 24

```
<212> TYPE: RNA
<213> ORGANISM: Artificial Sequence
<220> FEATURE:
<223> OTHER INFORMATION: Synthetic

<400> SEQUENCE: 870
gaaucauaaa uuucuuaaua acua                                              24

<210> SEQ ID NO 871
<211> LENGTH: 23
<212> TYPE: RNA
<213> ORGANISM: Artificial Sequence
<220> FEATURE:
<223> OTHER INFORMATION: Synthetic

<400> SEQUENCE: 871
aaucauaaau uucuuaauaa cua                                               23

<210> SEQ ID NO 872
<211> LENGTH: 22
<212> TYPE: RNA
<213> ORGANISM: Artificial Sequence
<220> FEATURE:
<223> OTHER INFORMATION: Synthetic

<400> SEQUENCE: 872
aucauaaauu ucuuaauaac ua                                                22

<210> SEQ ID NO 873
<211> LENGTH: 21
<212> TYPE: RNA
<213> ORGANISM: Artificial Sequence
<220> FEATURE:
<223> OTHER INFORMATION: Synthetic

<400> SEQUENCE: 873
ucauaaauuu cuuaauaacu a                                                 21

<210> SEQ ID NO 874
<211> LENGTH: 20
<212> TYPE: RNA
<213> ORGANISM: Artificial Sequence
<220> FEATURE:
<223> OTHER INFORMATION: Synthetic

<400> SEQUENCE: 874
cauaaauuuc uuaauaacua                                                   20

<210> SEQ ID NO 875
<211> LENGTH: 19
<212> TYPE: RNA
<213> ORGANISM: Artificial Sequence
<220> FEATURE:
<223> OTHER INFORMATION: Synthetic

<400> SEQUENCE: 875
auaaauuucu uaauaacua                                                    19

<210> SEQ ID NO 876
<211> LENGTH: 24
<212> TYPE: RNA
<213> ORGANISM: Artificial Sequence
<220> FEATURE:
<223> OTHER INFORMATION: Synthetic

<400> SEQUENCE: 876
```
ugaaacauaa auuucuuaau aacu 24

<210> SEQ ID NO 877
<211> LENGTH: 23
<212> TYPE: RNA
<213> ORGANISM: Artificial Sequence
<220> FEATURE:
<223> OTHER INFORMATION: Synthetic

<400> SEQUENCE: 877
gaaacauaaa uuucuuaaua acu 23

<210> SEQ ID NO 878
<211> LENGTH: 22
<212> TYPE: RNA
<213> ORGANISM: Artificial Sequence
<220> FEATURE:
<223> OTHER INFORMATION: Synthetic

<400> SEQUENCE: 878
aaacauaaau uucuuaauaa cu 22

<210> SEQ ID NO 879
<211> LENGTH: 21
<212> TYPE: RNA
<213> ORGANISM: Artificial Sequence
<220> FEATURE:
<223> OTHER INFORMATION: Synthetic

<400> SEQUENCE: 879
aacauaaauu ucuuaauaac u 21

<210> SEQ ID NO 880
<211> LENGTH: 20
<212> TYPE: RNA
<213> ORGANISM: Artificial Sequence
<220> FEATURE:
<223> OTHER INFORMATION: Synthetic

<400> SEQUENCE: 880
acauaaauuu cuuaauaacu 20

<210> SEQ ID NO 881
<211> LENGTH: 19
<212> TYPE: RNA
<213> ORGANISM: Artificial Sequence
<220> FEATURE:
<223> OTHER INFORMATION: Synthetic

<400> SEQUENCE: 881
cauaaauuuc uuaauaacu 19

<210> SEQ ID NO 882
<211> LENGTH: 24
<212> TYPE: RNA
<213> ORGANISM: Artificial Sequence
<220> FEATURE:
<223> OTHER INFORMATION: Synthetic

<400> SEQUENCE: 882
cugaaucaua aauucuuaa uaac 24

<210> SEQ ID NO 883
<211> LENGTH: 23
<212> TYPE: RNA
<213> ORGANISM: Artificial Sequence

```
<220> FEATURE:
<223> OTHER INFORMATION: Synthetic

<400> SEQUENCE: 883
ugaaucauaa auuucuuaau aac                                              23

<210> SEQ ID NO 884
<211> LENGTH: 22
<212> TYPE: RNA
<213> ORGANISM: Artificial Sequence
<220> FEATURE:
<223> OTHER INFORMATION: Synthetic

<400> SEQUENCE: 884
gaaucauaaa uuucuuaaua ac                                               22

<210> SEQ ID NO 885
<211> LENGTH: 21
<212> TYPE: RNA
<213> ORGANISM: Artificial Sequence
<220> FEATURE:
<223> OTHER INFORMATION: Synthetic

<400> SEQUENCE: 885
aaucauaaau uucuuaauaa c                                                21

<210> SEQ ID NO 886
<211> LENGTH: 20
<212> TYPE: RNA
<213> ORGANISM: Artificial Sequence
<220> FEATURE:
<223> OTHER INFORMATION: Synthetic

<400> SEQUENCE: 886
aucauaaauu ucuuaauaac                                                  20

<210> SEQ ID NO 887
<211> LENGTH: 18
<212> TYPE: RNA
<213> ORGANISM: Artificial Sequence
<220> FEATURE:
<223> OTHER INFORMATION: Synthetic

<400> SEQUENCE: 887
cauaaauuuc uuaauaac                                                    18

<210> SEQ ID NO 888
<211> LENGTH: 24
<212> TYPE: RNA
<213> ORGANISM: Artificial Sequence
<220> FEATURE:
<223> OTHER INFORMATION: Synthetic

<400> SEQUENCE: 888
ucuccaccug ucccauucug auuu                                             24

<210> SEQ ID NO 889
<211> LENGTH: 23
<212> TYPE: RNA
<213> ORGANISM: Artificial Sequence
<220> FEATURE:
<223> OTHER INFORMATION: Synthetic

<400> SEQUENCE: 889
ucuccaccug ucccauucug auu                                              23
```

<210> SEQ ID NO 890
<211> LENGTH: 22
<212> TYPE: RNA
<213> ORGANISM: Artificial Sequence
<220> FEATURE:
<223> OTHER INFORMATION: Synthetic

<400> SEQUENCE: 890
ucuccaccug ucccauucug au                                          22

<210> SEQ ID NO 891
<211> LENGTH: 21
<212> TYPE: RNA
<213> ORGANISM: Artificial Sequence
<220> FEATURE:
<223> OTHER INFORMATION: Synthetic

<400> SEQUENCE: 891
ucuccaccug ucccauucug a                                           21

<210> SEQ ID NO 892
<211> LENGTH: 20
<212> TYPE: RNA
<213> ORGANISM: Artificial Sequence
<220> FEATURE:
<223> OTHER INFORMATION: Synthetic

<400> SEQUENCE: 892
cuccaccugu cccauucuga                                             20

<210> SEQ ID NO 893
<211> LENGTH: 19
<212> TYPE: RNA
<213> ORGANISM: Artificial Sequence
<220> FEATURE:
<223> OTHER INFORMATION: Synthetic

<400> SEQUENCE: 893 uccaccguc ccauucuga                                               19

<210> SEQ ID NO 894
<211> LENGTH: 24
<212> TYPE: RNA
<213> ORGANISM: Artificial Sequence
<220> FEATURE:
<223> OTHER INFORMATION: Synthetic

<400> SEQUENCE: 894
acuuucucca ccugucccau ucug                                        24

<210> SEQ ID NO 895
<211> LENGTH: 23
<212> TYPE: RNA
<213> ORGANISM: Artificial Sequence
<220> FEATURE:
<223> OTHER INFORMATION: Synthetic

<400> SEQUENCE: 895
acuuucucca ccugucccau ucu                                         23

<210> SEQ ID NO 896
<211> LENGTH: 22
<212> TYPE: RNA
<213> ORGANISM: Artificial Sequence
<220> FEATURE:
<223> OTHER INFORMATION: Synthetic

```
<400> SEQUENCE: 896 acuucucca ccugucccau uc                                              22

<210> SEQ ID NO 897
<211> LENGTH: 21
<212> TYPE: RNA
<213> ORGANISM: Artificial Sequence
<220> FEATURE:
<223> OTHER INFORMATION: Synthetic

<400> SEQUENCE: 897 acuucucca ccugucccau u                                               21

<210> SEQ ID NO 898
<211> LENGTH: 20
<212> TYPE: RNA
<213> ORGANISM: Artificial Sequence
<220> FEATURE:
<223> OTHER INFORMATION: Synthetic

<400> SEQUENCE: 898 acuucucca ccugucccau                                                 20

<210> SEQ ID NO 899
<211> LENGTH: 19
<212> TYPE: RNA
<213> ORGANISM: Artificial Sequence
<220> FEATURE:
<223> OTHER INFORMATION: Synthetic

<400> SEQUENCE: 899 acuucucca ccuguccca                                                  19

<210> SEQ ID NO 900
<211> LENGTH: 20
<212> TYPE: RNA
<213> ORGANISM: Artificial Sequence
<220> FEATURE:
<223> OTHER INFORMATION: Synthetic

<400> SEQUENCE: 900
uuucaucuuc aaauuuuuca                                                20

<210> SEQ ID NO 901
<211> LENGTH: 24
<212> TYPE: RNA
<213> ORGANISM: Artificial Sequence
<220> FEATURE:
<223> OTHER INFORMATION: Synthetic

<400> SEQUENCE: 901
ccuuguaaug gaaauuuuca ucuu                                           24

<210> SEQ ID NO 902
<211> LENGTH: 23
<212> TYPE: RNA
<213> ORGANISM: Artificial Sequence
<220> FEATURE:
<223> OTHER INFORMATION: Synthetic

<400> SEQUENCE: 902
ccuuguaaug gaaauuuuca ucu                                            23

<210> SEQ ID NO 903
```

```
<211> LENGTH: 22
<212> TYPE: RNA
<213> ORGANISM: Artificial Sequence
<220> FEATURE:
<223> OTHER INFORMATION: Synthetic

<400> SEQUENCE: 903
ccuuguaaug gaaauuuuca uc                                              22

<210> SEQ ID NO 904
<211> LENGTH: 21
<212> TYPE: RNA
<213> ORGANISM: Artificial Sequence
<220> FEATURE:
<223> OTHER INFORMATION: Synthetic

<400> SEQUENCE: 904
ccuuguaaug gaaauuuuca u                                               21

<210> SEQ ID NO 905
<211> LENGTH: 20
<212> TYPE: RNA
<213> ORGANISM: Artificial Sequence
<220> FEATURE:
<223> OTHER INFORMATION: Synthetic

<400> SEQUENCE: 905
ccuuguaaug gaaauuuuca                                                 20

<210> SEQ ID NO 906
<211> LENGTH: 19
<212> TYPE: RNA
<213> ORGANISM: Artificial Sequence
<220> FEATURE:
<223> OTHER INFORMATION: Synthetic

<400> SEQUENCE: 906
ccuuguaaug gaaauuuuc                                                  19

<210> SEQ ID NO 907
<211> LENGTH: 23
<212> TYPE: RNA
<213> ORGANISM: Artificial Sequence
<220> FEATURE:
<223> OTHER INFORMATION: Synthetic

<400> SEQUENCE: 907
accuuguaau ggaaauuuuc auc                                             23

<210> SEQ ID NO 908
<211> LENGTH: 22
<212> TYPE: RNA
<213> ORGANISM: Artificial Sequence
<220> FEATURE:
<223> OTHER INFORMATION: Synthetic

<400> SEQUENCE: 908
accuuguaau ggaaauuuuc au                                              22

<210> SEQ ID NO 909
<211> LENGTH: 21
<212> TYPE: RNA
<213> ORGANISM: Artificial Sequence
<220> FEATURE:
<223> OTHER INFORMATION: Synthetic

<400> SEQUENCE: 909
```
accuuguaau ggaaauuuuc a                                          21

<210> SEQ ID NO 910
<211> LENGTH: 20
<212> TYPE: RNA
<213> ORGANISM: Artificial Sequence
<220> FEATURE:
<223> OTHER INFORMATION: Synthetic

<400> SEQUENCE: 910
accuuguaau ggaaauuuuc                                            20

<210> SEQ ID NO 911
<211> LENGTH: 19
<212> TYPE: RNA
<213> ORGANISM: Artificial Sequence
<220> FEATURE:
<223> OTHER INFORMATION: Synthetic

<400> SEQUENCE: 911
accuuguaau ggaaauuuu                                             19

<210> SEQ ID NO 912
<211> LENGTH: 18
<212> TYPE: RNA
<213> ORGANISM: Artificial Sequence
<220> FEATURE:
<223> OTHER INFORMATION: Synthetic

<400> SEQUENCE: 912
accuuguaau ggaaauuu                                              18

<210> SEQ ID NO 913
<211> LENGTH: 24
<212> TYPE: RNA
<213> ORGANISM: Artificial Sequence
<220> FEATURE:
<223> OTHER INFORMATION: Synthetic

<400> SEQUENCE: 913
uaccuuguaa uggaaauuuu cauc                                       24

<210> SEQ ID NO 914
<211> LENGTH: 23
<212> TYPE: RNA
<213> ORGANISM: Artificial Sequence
<220> FEATURE:
<223> OTHER INFORMATION: Synthetic

<400> SEQUENCE: 914
uaccuuguaa uggaaauuuu cau                                        23

<210> SEQ ID NO 915
<211> LENGTH: 22
<212> TYPE: RNA
<213> ORGANISM: Artificial Sequence
<220> FEATURE:
<223> OTHER INFORMATION: Synthetic

<400> SEQUENCE: 915
uaccuuguaa uggaaauuuu ca                                         22

<210> SEQ ID NO 916
<211> LENGTH: 21
<212> TYPE: RNA

```
<213> ORGANISM: Artificial Sequence
<220> FEATURE:
<223> OTHER INFORMATION: Synthetic

<400> SEQUENCE: 916
uaccuuguaa uggaaauuuu c                                              21

<210> SEQ ID NO 917
<211> LENGTH: 20
<212> TYPE: RNA
<213> ORGANISM: Artificial Sequence
<220> FEATURE:
<223> OTHER INFORMATION: Synthetic

<400> SEQUENCE: 917
uaccuuguaa uggaaauuuu                                                20

<210> SEQ ID NO 918
<211> LENGTH: 19
<212> TYPE: RNA
<213> ORGANISM: Artificial Sequence
<220> FEATURE:
<223> OTHER INFORMATION: Synthetic

<400> SEQUENCE: 918
uaccuuguaa uggaaauuu                                                 19

<210> SEQ ID NO 919
<211> LENGTH: 22
<212> TYPE: RNA
<213> ORGANISM: Artificial Sequence
<220> FEATURE:
<223> OTHER INFORMATION: Synthetic

<400> SEQUENCE: 919
caucuuucga agccacugga ug                                             22

<210> SEQ ID NO 920
<211> LENGTH: 21
<212> TYPE: RNA
<213> ORGANISM: Artificial Sequence
<220> FEATURE:
<223> OTHER INFORMATION: Synthetic

<400> SEQUENCE: 920
aucuuucgaa gccacuggau g                                              21

<210> SEQ ID NO 921
<211> LENGTH: 20
<212> TYPE: RNA
<213> ORGANISM: Artificial Sequence
<220> FEATURE:
<223> OTHER INFORMATION: Synthetic

<400> SEQUENCE: 921
ucuuucgaag ccacuggaug                                                20

<210> SEQ ID NO 922
<211> LENGTH: 22
<212> TYPE: RNA
<213> ORGANISM: Artificial Sequence
<220> FEATURE:
<223> OTHER INFORMATION: Synthetic

<400> SEQUENCE: 922
cugcuccagg ugacaauucu cc                                             22
```

<210> SEQ ID NO 923
<211> LENGTH: 21
<212> TYPE: RNA
<213> ORGANISM: Artificial Sequence
<220> FEATURE:
<223> OTHER INFORMATION: Synthetic

<400> SEQUENCE: 923
ugcuccaggu gacaauucuc c                                              21

<210> SEQ ID NO 924
<211> LENGTH: 20
<212> TYPE: RNA
<213> ORGANISM: Artificial Sequence
<220> FEATURE:
<223> OTHER INFORMATION: Synthetic

<400> SEQUENCE: 924
ugcuccaggu gacaauucuc                                                20

<210> SEQ ID NO 925
<211> LENGTH: 19
<212> TYPE: RNA
<213> ORGANISM: Artificial Sequence
<220> FEATURE:
<223> OTHER INFORMATION: Synthetic

<400> SEQUENCE: 925
gcuccaggug acaauucuc                                                 19

<210> SEQ ID NO 926
<211> LENGTH: 18
<212> TYPE: RNA
<213> ORGANISM: Artificial Sequence
<220> FEATURE:
<223> OTHER INFORMATION: Synthetic

<400> SEQUENCE: 926
cuccagguga caauucuc                                                  18

<210> SEQ ID NO 927
<211> LENGTH: 22
<212> TYPE: RNA
<213> ORGANISM: Artificial Sequence
<220> FEATURE:
<223> OTHER INFORMATION: Synthetic

<400> SEQUENCE: 927
accuuaaccu gucgcugcuc ca                                             22

<210> SEQ ID NO 928
<211> LENGTH: 22
<212> TYPE: RNA
<213> ORGANISM: Artificial Sequence
<220> FEATURE:
<223> OTHER INFORMATION: Synthetic

<400> SEQUENCE: 928
uaccuuaacc ugucgcugcu cc                                             22

<210> SEQ ID NO 929
<211> LENGTH: 22
<212> TYPE: RNA
<213> ORGANISM: Artificial Sequence
<220> FEATURE:

<223> OTHER INFORMATION: Synthetic

<400> SEQUENCE: 929
ucaccuuaac cugucgcugc uc                                            22

<210> SEQ ID NO 930
<211> LENGTH: 22
<212> TYPE: RNA
<213> ORGANISM: Artificial Sequence
<220> FEATURE:
<223> OTHER INFORMATION: Synthetic

<400> SEQUENCE: 930
uucaccuuaa ccugucgcug cu                                            22

<210> SEQ ID NO 931
<211> LENGTH: 21
<212> TYPE: RNA
<213> ORGANISM: Artificial Sequence
<220> FEATURE:
<223> OTHER INFORMATION: Synthetic

<400> SEQUENCE: 931
accuuaaccu gucgcugcuc c                                             21

<210> SEQ ID NO 932
<211> LENGTH: 21
<212> TYPE: RNA
<213> ORGANISM: Artificial Sequence
<220> FEATURE:
<223> OTHER INFORMATION: Synthetic

<400> SEQUENCE: 932
caccuuaacc ugucgcugcu c                                             21

<210> SEQ ID NO 933
<211> LENGTH: 21
<212> TYPE: RNA
<213> ORGANISM: Artificial Sequence
<220> FEATURE:
<223> OTHER INFORMATION: Synthetic

<400> SEQUENCE: 933
ucaccuuaac cugucgcugc u                                             21

<210> SEQ ID NO 934
<211> LENGTH: 21
<212> TYPE: RNA
<213> ORGANISM: Artificial Sequence
<220> FEATURE:
<223> OTHER INFORMATION: Synthetic

<400> SEQUENCE: 934
uucaccuuaa ccugucgcug c                                             21

<210> SEQ ID NO 935
<211> LENGTH: 21
<212> TYPE: RNA
<213> ORGANISM: Artificial Sequence
<220> FEATURE:
<223> OTHER INFORMATION: Synthetic

<400> SEQUENCE: 935
auucaccuua accugucgcu g                                             21

```
<210> SEQ ID NO 936
<211> LENGTH: 21
<212> TYPE: RNA
<213> ORGANISM: Artificial Sequence
<220> FEATURE:
<223> OTHER INFORMATION: Synthetic

<400> SEQUENCE: 936
aauucaccuu aaccugucgc u                                              21

<210> SEQ ID NO 937
<211> LENGTH: 20
<212> TYPE: RNA
<213> ORGANISM: Artificial Sequence
<220> FEATURE:
<223> OTHER INFORMATION: Synthetic

<400> SEQUENCE: 937
accuuaaccu gucgcugcuc                                                20

<210> SEQ ID NO 938
<211> LENGTH: 20
<212> TYPE: RNA
<213> ORGANISM: Artificial Sequence
<220> FEATURE:
<223> OTHER INFORMATION: Synthetic

<400> SEQUENCE: 938
caccuuaacc ugucgcugcu                                                20

<210> SEQ ID NO 939
<211> LENGTH: 20
<212> TYPE: RNA
<213> ORGANISM: Artificial Sequence
<220> FEATURE:
<223> OTHER INFORMATION: Synthetic

<400> SEQUENCE: 939
ucaccuuaac cugucgcugc                                                20

<210> SEQ ID NO 940
<211> LENGTH: 20
<212> TYPE: RNA
<213> ORGANISM: Artificial Sequence
<220> FEATURE:
<223> OTHER INFORMATION: Synthetic

<400> SEQUENCE: 940
uucaccuuaa ccugucgcug                                                20

<210> SEQ ID NO 941
<211> LENGTH: 20
<212> TYPE: RNA
<213> ORGANISM: Artificial Sequence
<220> FEATURE:
<223> OTHER INFORMATION: Synthetic

<400> SEQUENCE: 941
auucaccuua accugucgcu                                                20

<210> SEQ ID NO 942
<211> LENGTH: 20
<212> TYPE: RNA
<213> ORGANISM: Artificial Sequence
<220> FEATURE:
<223> OTHER INFORMATION: Synthetic
```

<400> SEQUENCE: 942
aauucaccuu aaccugucgc					20

<210> SEQ ID NO 943
<211> LENGTH: 19
<212> TYPE: RNA
<213> ORGANISM: Artificial Sequence
<220> FEATURE:
<223> OTHER INFORMATION: Synthetic

<400> SEQUENCE: 943
accuuaaccu gucgcugcu					19

<210> SEQ ID NO 944
<211> LENGTH: 19
<212> TYPE: RNA
<213> ORGANISM: Artificial Sequence
<220> FEATURE:
<223> OTHER INFORMATION: Synthetic

<400> SEQUENCE: 944
caccuuaacc ugucgcugc					19

<210> SEQ ID NO 945
<211> LENGTH: 19
<212> TYPE: RNA
<213> ORGANISM: Artificial Sequence
<220> FEATURE:
<223> OTHER INFORMATION: Synthetic

<400> SEQUENCE: 945
ucaccuuaac cugucgcug					19

<210> SEQ ID NO 946
<211> LENGTH: 19
<212> TYPE: RNA
<213> ORGANISM: Artificial Sequence
<220> FEATURE:
<223> OTHER INFORMATION: Synthetic

<400> SEQUENCE: 946
uucaccuuaa ccugucgcu					19

<210> SEQ ID NO 947
<211> LENGTH: 19
<212> TYPE: RNA
<213> ORGANISM: Artificial Sequence
<220> FEATURE:
<223> OTHER INFORMATION: Synthetic

<400> SEQUENCE: 947
auucaccuua accugucgc					19

<210> SEQ ID NO 948
<211> LENGTH: 19
<212> TYPE: RNA
<213> ORGANISM: Artificial Sequence
<220> FEATURE:
<223> OTHER INFORMATION: Synthetic

<400> SEQUENCE: 948
aauucaccuu aaccugucg					19

<210> SEQ ID NO 949
<211> LENGTH: 18

-continued

```
<212> TYPE: RNA
<213> ORGANISM: Artificial Sequence
<220> FEATURE:
<223> OTHER INFORMATION: Synthetic

<400> SEQUENCE: 949
accuuaaccu gucgcugc                                                 18

<210> SEQ ID NO 950
<211> LENGTH: 18
<212> TYPE: RNA
<213> ORGANISM: Artificial Sequence
<220> FEATURE:
<223> OTHER INFORMATION: Synthetic

<400> SEQUENCE: 950
caccuuaacc ugucgcug                                                 18

<210> SEQ ID NO 951
<211> LENGTH: 18
<212> TYPE: RNA
<213> ORGANISM: Artificial Sequence
<220> FEATURE:
<223> OTHER INFORMATION: Synthetic

<400> SEQUENCE: 951
ucaccuuaac cugucgcu                                                 18

<210> SEQ ID NO 952
<211> LENGTH: 18
<212> TYPE: RNA
<213> ORGANISM: Artificial Sequence
<220> FEATURE:
<223> OTHER INFORMATION: Synthetic

<400> SEQUENCE: 952
uucaccuuaa ccugucgc                                                 18

<210> SEQ ID NO 953
<211> LENGTH: 18
<212> TYPE: RNA
<213> ORGANISM: Artificial Sequence
<220> FEATURE:
<223> OTHER INFORMATION: Synthetic

<400> SEQUENCE: 953
auucaccuua accgucg                                                  18

<210> SEQ ID NO 954
<211> LENGTH: 22
<212> TYPE: RNA
<213> ORGANISM: Artificial Sequence
<220> FEATURE:
<223> OTHER INFORMATION: Synthetic

<400> SEQUENCE: 954 ggcuggguggc ggcuggguggc gg                                          22

<210> SEQ ID NO 955
<211> LENGTH: 23
<212> TYPE: RNA
<213> ORGANISM: Artificial Sequence
<220> FEATURE:
<223> OTHER INFORMATION: Synthetic

<400> SEQUENCE: 955
```

| | | |
|---|---|---|
| uggcuggugg cggcuggugg cgg | | 23 |

<210> SEQ ID NO 956
<211> LENGTH: 22
<212> TYPE: RNA
<213> ORGANISM: Artificial Sequence
<220> FEATURE:
<223> OTHER INFORMATION: Synthetic

<400> SEQUENCE: 956

| | | |
|---|---|---|
| ggcugguggc ggcugguggc gg | | 22 |

<210> SEQ ID NO 957
<211> LENGTH: 21
<212> TYPE: RNA
<213> ORGANISM: Artificial Sequence
<220> FEATURE:
<223> OTHER INFORMATION: Synthetic

<400> SEQUENCE: 957

| | | |
|---|---|---|
| gcugguggcg gcugguggcg g | | 21 |

<210> SEQ ID NO 958
<211> LENGTH: 20
<212> TYPE: RNA
<213> ORGANISM: Artificial Sequence
<220> FEATURE:
<223> OTHER INFORMATION: Synthetic

<400> SEQUENCE: 958

| | | |
|---|---|---|
| cugguggcgg cugguggcgg | | 20 |

<210> SEQ ID NO 959
<211> LENGTH: 19
<212> TYPE: RNA
<213> ORGANISM: Artificial Sequence
<220> FEATURE:
<223> OTHER INFORMATION: Synthetic

<400> SEQUENCE: 959

| | | |
|---|---|---|
| ugguggcggc ugguggcgg | | 19 |

<210> SEQ ID NO 960
<211> LENGTH: 24
<212> TYPE: RNA
<213> ORGANISM: Artificial Sequence
<220> FEATURE:
<223> OTHER INFORMATION: Synthetic

<400> SEQUENCE: 960

| | | |
|---|---|---|
| cuggguccag uggcuggugg cggc | | 24 |

<210> SEQ ID NO 961
<211> LENGTH: 23
<212> TYPE: RNA
<213> ORGANISM: Artificial Sequence
<220> FEATURE:
<223> OTHER INFORMATION: Synthetic

<400> SEQUENCE: 961

| | | |
|---|---|---|
| uggguccagu ggcugguggc ggc | | 23 |

<210> SEQ ID NO 962
<211> LENGTH: 22
<212> TYPE: RNA
<213> ORGANISM: Artificial Sequence -continued
<220> FEATURE:
<223> OTHER INFORMATION: Synthetic

<400> SEQUENCE: 962
ggguccagug gcugguggcg gc                                              22

<210> SEQ ID NO 963
<211> LENGTH: 21
<212> TYPE: RNA
<213> ORGANISM: Artificial Sequence
<220> FEATURE:
<223> OTHER INFORMATION: Synthetic

<400> SEQUENCE: 963
gguccagugg cugguggcgg c                                               21

<210> SEQ ID NO 964
<211> LENGTH: 20
<212> TYPE: RNA
<213> ORGANISM: Artificial Sequence
<220> FEATURE:
<223> OTHER INFORMATION: Synthetic

<400> SEQUENCE: 964
guccaguggc ugguggcggc                                                 20

<210> SEQ ID NO 965
<211> LENGTH: 19
<212> TYPE: RNA
<213> ORGANISM: Artificial Sequence
<220> FEATURE:
<223> OTHER INFORMATION: Synthetic

<400> SEQUENCE: 965
uccaguggcu gguggcggc                                                  19

<210> SEQ ID NO 966
<211> LENGTH: 24
<212> TYPE: RNA
<213> ORGANISM: Artificial Sequence
<220> FEATURE:
<223> OTHER INFORMATION: Synthetic

<400> SEQUENCE: 966 ggcuggguggc ggcugguggc ggcc                                           24

<210> SEQ ID NO 967
<211> LENGTH: 23
<212> TYPE: RNA
<213> ORGANISM: Artificial Sequence
<220> FEATURE:
<223> OTHER INFORMATION: Synthetic

<400> SEQUENCE: 967
gcugguggcg gcugguggcg gcc                                             23

<210> SEQ ID NO 968
<211> LENGTH: 22
<212> TYPE: RNA
<213> ORGANISM: Artificial Sequence
<220> FEATURE:
<223> OTHER INFORMATION: Synthetic

<400> SEQUENCE: 968
cugguggcgg cugguggcgg cc                                              22

```
<210> SEQ ID NO 969
<211> LENGTH: 21
<212> TYPE: RNA
<213> ORGANISM: Artificial Sequence
<220> FEATURE:
<223> OTHER INFORMATION: Synthetic

<400> SEQUENCE: 969
ugguggcggc ugguggcggc c                                              21

<210> SEQ ID NO 970
<211> LENGTH: 20
<212> TYPE: RNA
<213> ORGANISM: Artificial Sequence
<220> FEATURE:
<223> OTHER INFORMATION: Synthetic

<400> SEQUENCE: 970
gguggcggcu gguggcggcc                                                20

<210> SEQ ID NO 971
<211> LENGTH: 19
<212> TYPE: RNA
<213> ORGANISM: Artificial Sequence
<220> FEATURE:
<223> OTHER INFORMATION: Synthetic

<400> SEQUENCE: 971
guggcggcug guggcggcc                                                 19

<210> SEQ ID NO 972
<211> LENGTH: 24
<212> TYPE: RNA
<213> ORGANISM: Artificial Sequence
<220> FEATURE:
<223> OTHER INFORMATION: Synthetic

<400> SEQUENCE: 972
gcugguggcg gcugguggcg gcca                                           24

<210> SEQ ID NO 973
<211> LENGTH: 23
<212> TYPE: RNA
<213> ORGANISM: Artificial Sequence
<220> FEATURE:
<223> OTHER INFORMATION: Synthetic

<400> SEQUENCE: 973
cugguggcgg cugguggcgg cca                                            23

<210> SEQ ID NO 974
<211> LENGTH: 22
<212> TYPE: RNA
<213> ORGANISM: Artificial Sequence
<220> FEATURE:
<223> OTHER INFORMATION: Synthetic

<400> SEQUENCE: 974
ugguggcggc ugguggcggc ca                                             22

<210> SEQ ID NO 975
<211> LENGTH: 21
<212> TYPE: RNA
<213> ORGANISM: Artificial Sequence
<220> FEATURE:
<223> OTHER INFORMATION: Synthetic
```

-continued

<400> SEQUENCE: 975
gguggcggcu gguggcggcc a                                            21

<210> SEQ ID NO 976
<211> LENGTH: 20
<212> TYPE: RNA
<213> ORGANISM: Artificial Sequence
<220> FEATURE:
<223> OTHER INFORMATION: Synthetic

<400> SEQUENCE: 976
guggcggcug guggcggcca                                              20

<210> SEQ ID NO 977
<211> LENGTH: 19
<212> TYPE: RNA
<213> ORGANISM: Artificial Sequence
<220> FEATURE:
<223> OTHER INFORMATION: Synthetic

<400> SEQUENCE: 977
uggcggcugg uggcggcca                                               19

<210> SEQ ID NO 978
<211> LENGTH: 24
<212> TYPE: RNA
<213> ORGANISM: Artificial Sequence
<220> FEATURE:
<223> OTHER INFORMATION: Synthetic

<400> SEQUENCE: 978
cugguggcgg cugguggcgg ccag                                         24

<210> SEQ ID NO 979
<211> LENGTH: 23
<212> TYPE: RNA
<213> ORGANISM: Artificial Sequence
<220> FEATURE:
<223> OTHER INFORMATION: Synthetic

<400> SEQUENCE: 979
ugguggcggc ugguggcggc cag                                          23

<210> SEQ ID NO 980
<211> LENGTH: 22
<212> TYPE: RNA
<213> ORGANISM: Artificial Sequence
<220> FEATURE:
<223> OTHER INFORMATION: Synthetic

<400> SEQUENCE: 980
gguggcggcu gguggcggcc ag                                           22

<210> SEQ ID NO 981
<211> LENGTH: 21
<212> TYPE: RNA
<213> ORGANISM: Artificial Sequence
<220> FEATURE:
<223> OTHER INFORMATION: Synthetic

<400> SEQUENCE: 981
guggcggcug guggcggcca g                                            21

<210> SEQ ID NO 982

```
<211> LENGTH: 20
<212> TYPE: RNA
<213> ORGANISM: Artificial Sequence
<220> FEATURE:
<223> OTHER INFORMATION: Synthetic

<400> SEQUENCE: 982
uggcggcugg uggcggccag                                                   20

<210> SEQ ID NO 983
<211> LENGTH: 19
<212> TYPE: RNA
<213> ORGANISM: Artificial Sequence
<220> FEATURE:
<223> OTHER INFORMATION: Synthetic

<400> SEQUENCE: 983
ggcggcuggu ggcggccag                                                    19

<210> SEQ ID NO 984
<211> LENGTH: 24
<212> TYPE: RNA
<213> ORGANISM: Artificial Sequence
<220> FEATURE:
<223> OTHER INFORMATION: Synthetic

<400> SEQUENCE: 984
ugguggcggc ugguggcggc cagg                                              24

<210> SEQ ID NO 985
<211> LENGTH: 23
<212> TYPE: RNA
<213> ORGANISM: Artificial Sequence
<220> FEATURE:
<223> OTHER INFORMATION: Synthetic

<400> SEQUENCE: 985
gguggcggcu gguggcggcc agg                                               23

<210> SEQ ID NO 986
<211> LENGTH: 22
<212> TYPE: RNA
<213> ORGANISM: Artificial Sequence
<220> FEATURE:
<223> OTHER INFORMATION: Synthetic

<400> SEQUENCE: 986
guggcggcug guggcggcca gg                                                22

<210> SEQ ID NO 987
<211> LENGTH: 21
<212> TYPE: RNA
<213> ORGANISM: Artificial Sequence
<220> FEATURE:
<223> OTHER INFORMATION: Synthetic

<400> SEQUENCE: 987
uggcggcugg uggcggccag g                                                 21

<210> SEQ ID NO 988
<211> LENGTH: 20
<212> TYPE: RNA
<213> ORGANISM: Artificial Sequence
<220> FEATURE:
<223> OTHER INFORMATION: Synthetic

<400> SEQUENCE: 988
```

```
ggcggcuggu ggcggccagg                                              20

<210> SEQ ID NO 989
<211> LENGTH: 19
<212> TYPE: RNA
<213> ORGANISM: Artificial Sequence
<220> FEATURE:
<223> OTHER INFORMATION: Synthetic

<400> SEQUENCE: 989
gcggcuggug gcggccagg                                               19

<210> SEQ ID NO 990
<211> LENGTH: 24
<212> TYPE: RNA
<213> ORGANISM: Artificial Sequence
<220> FEATURE:
<223> OTHER INFORMATION: Synthetic

<400> SEQUENCE: 990
gguggcggcu gguggcggcc aggc                                         24

<210> SEQ ID NO 991
<211> LENGTH: 23
<212> TYPE: RNA
<213> ORGANISM: Artificial Sequence
<220> FEATURE:
<223> OTHER INFORMATION: Synthetic

<400> SEQUENCE: 991
guggcggcug guggcggcca ggc                                          23

<210> SEQ ID NO 992
<211> LENGTH: 22
<212> TYPE: RNA
<213> ORGANISM: Artificial Sequence
<220> FEATURE:
<223> OTHER INFORMATION: Synthetic

<400> SEQUENCE: 992
uggcggcugg uggcggccag gc                                           22

<210> SEQ ID NO 993
<211> LENGTH: 21
<212> TYPE: RNA
<213> ORGANISM: Artificial Sequence
<220> FEATURE:
<223> OTHER INFORMATION: Synthetic

<400> SEQUENCE: 993
ggcggcuggu ggcggccagg c                                            21

<210> SEQ ID NO 994
<211> LENGTH: 20
<212> TYPE: RNA
<213> ORGANISM: Artificial Sequence
<220> FEATURE:
<223> OTHER INFORMATION: Synthetic

<400> SEQUENCE: 994
gcggcuggug gcggccaggc                                              20

<210> SEQ ID NO 995
<211> LENGTH: 19
<212> TYPE: RNA
```

```
<213> ORGANISM: Artificial Sequence
<220> FEATURE:
<223> OTHER INFORMATION: Synthetic

<400> SEQUENCE: 995
cggcuggugg cggccaggc                                                    19

<210> SEQ ID NO 996
<211> LENGTH: 24
<212> TYPE: RNA
<213> ORGANISM: Artificial Sequence
<220> FEATURE:
<223> OTHER INFORMATION: Synthetic

<400> SEQUENCE: 996
acccuggguc caguggcugg uggc                                              24

<210> SEQ ID NO 997
<211> LENGTH: 23
<212> TYPE: RNA
<213> ORGANISM: Artificial Sequence
<220> FEATURE:
<223> OTHER INFORMATION: Synthetic

<400> SEQUENCE: 997
cccugggucc aguggcuggu ggc                                               23

<210> SEQ ID NO 998
<211> LENGTH: 22
<212> TYPE: RNA
<213> ORGANISM: Artificial Sequence
<220> FEATURE:
<223> OTHER INFORMATION: Synthetic

<400> SEQUENCE: 998
ccugggucca guggcuggug gc                                                22

<210> SEQ ID NO 999
<211> LENGTH: 21
<212> TYPE: RNA
<213> ORGANISM: Artificial Sequence
<220> FEATURE:
<223> OTHER INFORMATION: Synthetic

<400> SEQUENCE: 999
cuggguccag uggcuggugg c                                                 21

<210> SEQ ID NO 1000
<211> LENGTH: 20
<212> TYPE: RNA
<213> ORGANISM: Artificial Sequence
<220> FEATURE:
<223> OTHER INFORMATION: Synthetic

<400> SEQUENCE: 1000
uggguccagu ggcugguggc                                                   20

<210> SEQ ID NO 1001
<211> LENGTH: 24
<212> TYPE: RNA
<213> ORGANISM: Artificial Sequence
<220> FEATURE:
<223> OTHER INFORMATION: Synthetic

<400> SEQUENCE: 1001
gacccugggu ccaguggcug gugg                                              24
```

<210> SEQ ID NO 1002
<211> LENGTH: 23
<212> TYPE: RNA
<213> ORGANISM: Artificial Sequence
<220> FEATURE:
<223> OTHER INFORMATION: Synthetic

<400> SEQUENCE: 1002
acccuggguc caguggcugg ugg                                          23

<210> SEQ ID NO 1003
<211> LENGTH: 22
<212> TYPE: RNA
<213> ORGANISM: Artificial Sequence
<220> FEATURE:
<223> OTHER INFORMATION: Synthetic

<400> SEQUENCE: 1003
cccuggaucc aguggcuggu gg                                           22

<210> SEQ ID NO 1004
<211> LENGTH: 21
<212> TYPE: RNA
<213> ORGANISM: Artificial Sequence
<220> FEATURE:
<223> OTHER INFORMATION: Synthetic

<400> SEQUENCE: 1004
ccuggaucca guggcuggug g                                            21

<210> SEQ ID NO 1005
<211> LENGTH: 20
<212> TYPE: RNA
<213> ORGANISM: Artificial Sequence
<220> FEATURE:
<223> OTHER INFORMATION: Synthetic

<400> SEQUENCE: 1005 cuggaccag uggcuggugg                                               20

<210> SEQ ID NO 1006
<211> LENGTH: 24
<212> TYPE: RNA
<213> ORGANISM: Artificial Sequence
<220> FEATURE:
<223> OTHER INFORMATION: Synthetic

<400> SEQUENCE: 1006
agacccuggg uccaguggcu ggug                                         24

<210> SEQ ID NO 1007
<211> LENGTH: 23
<212> TYPE: RNA
<213> ORGANISM: Artificial Sequence
<220> FEATURE:
<223> OTHER INFORMATION: Synthetic

<400> SEQUENCE: 1007
gacccugggu ccaguggcug gug                                          23

<210> SEQ ID NO 1008
<211> LENGTH: 22
<212> TYPE: RNA
<213> ORGANISM: Artificial Sequence
<220> FEATURE:

<223> OTHER INFORMATION: Synthetic

<400> SEQUENCE: 1008
acccuggguc caguggcugg ug                                    22

<210> SEQ ID NO 1009
<211> LENGTH: 21
<212> TYPE: RNA
<213> ORGANISM: Artificial Sequence
<220> FEATURE:
<223> OTHER INFORMATION: Synthetic

<400> SEQUENCE: 1009
cccugggucc aguggcuggu g                                     21

<210> SEQ ID NO 1010
<211> LENGTH: 20
<212> TYPE: RNA
<213> ORGANISM: Artificial Sequence
<220> FEATURE:
<223> OTHER INFORMATION: Synthetic

<400> SEQUENCE: 1010
ccugggucca guggcuggug                                       20

<210> SEQ ID NO 1011
<211> LENGTH: 24
<212> TYPE: RNA
<213> ORGANISM: Artificial Sequence
<220> FEATURE:
<223> OTHER INFORMATION: Synthetic

<400> SEQUENCE: 1011
cgggcaauug uggagacccu gggu                                  24

<210> SEQ ID NO 1012
<211> LENGTH: 23
<212> TYPE: RNA
<213> ORGANISM: Artificial Sequence
<220> FEATURE:
<223> OTHER INFORMATION: Synthetic

<400> SEQUENCE: 1012
gggcaauugu ggagacccug ggu                                   23

<210> SEQ ID NO 1013
<211> LENGTH: 22
<212> TYPE: RNA
<213> ORGANISM: Artificial Sequence
<220> FEATURE:
<223> OTHER INFORMATION: Synthetic

<400> SEQUENCE: 1013
ggcaauugug gagacccugg gu                                    22

<210> SEQ ID NO 1014
<211> LENGTH: 21
<212> TYPE: RNA
<213> ORGANISM: Artificial Sequence
<220> FEATURE:
<223> OTHER INFORMATION: Synthetic

<400> SEQUENCE: 1014
gcaauugugg agacccuggg u                                     21

```
<210> SEQ ID NO 1015
<211> LENGTH: 20
<212> TYPE: RNA
<213> ORGANISM: Artificial Sequence
<220> FEATURE:
<223> OTHER INFORMATION: Synthetic

<400> SEQUENCE: 1015
caauugugga gacccugggu                                                   20

<210> SEQ ID NO 1016
<211> LENGTH: 24
<212> TYPE: RNA
<213> ORGANISM: Artificial Sequence
<220> FEATURE:
<223> OTHER INFORMATION: Synthetic

<400> SEQUENCE: 1016
ucgggcaauu guggagaccc uggg                                              24

<210> SEQ ID NO 1017
<211> LENGTH: 23
<212> TYPE: RNA
<213> ORGANISM: Artificial Sequence
<220> FEATURE:
<223> OTHER INFORMATION: Synthetic

<400> SEQUENCE: 1017
cgggcaauug uggagacccu ggg                                               23

<210> SEQ ID NO 1018
<211> LENGTH: 22
<212> TYPE: RNA
<213> ORGANISM: Artificial Sequence
<220> FEATURE:
<223> OTHER INFORMATION: Synthetic

<400> SEQUENCE: 1018
gggcaauugu ggagacccug gg                                                22

<210> SEQ ID NO 1019
<211> LENGTH: 21
<212> TYPE: RNA
<213> ORGANISM: Artificial Sequence
<220> FEATURE:
<223> OTHER INFORMATION: Synthetic

<400> SEQUENCE: 1019
ggcaauugug gagacccugg g                                                 21

<210> SEQ ID NO 1020
<211> LENGTH: 20
<212> TYPE: RNA
<213> ORGANISM: Artificial Sequence
<220> FEATURE:
<223> OTHER INFORMATION: Synthetic

<400> SEQUENCE: 1020 gcaaugugg agacccuggg                                                    20

<210> SEQ ID NO 1021
<211> LENGTH: 24
<212> TYPE: RNA
<213> ORGANISM: Artificial Sequence
<220> FEATURE:
<223> OTHER INFORMATION: Synthetic
```

```
<400> SEQUENCE: 1021
gugcucgggc aauuguggag accc                                    24

<210> SEQ ID NO 1022
<211> LENGTH: 23
<212> TYPE: RNA
<213> ORGANISM: Artificial Sequence
<220> FEATURE:
<223> OTHER INFORMATION: Synthetic

<400> SEQUENCE: 1022
ugcucgggca auuguggaga ccc                                     23

<210> SEQ ID NO 1023
<211> LENGTH: 22
<212> TYPE: RNA
<213> ORGANISM: Artificial Sequence
<220> FEATURE:
<223> OTHER INFORMATION: Synthetic

<400> SEQUENCE: 1023
gcucgggcaa uuguggagac cc                                      22

<210> SEQ ID NO 1024
<211> LENGTH: 21
<212> TYPE: RNA
<213> ORGANISM: Artificial Sequence
<220> FEATURE:
<223> OTHER INFORMATION: Synthetic

<400> SEQUENCE: 1024
cucgggcaau uguggagacc c                                       21

<210> SEQ ID NO 1025
<211> LENGTH: 20
<212> TYPE: RNA
<213> ORGANISM: Artificial Sequence
<220> FEATURE:
<223> OTHER INFORMATION: Synthetic

<400> SEQUENCE: 1025
ucgggcaauu guggagaccc                                         20

<210> SEQ ID NO 1026
<211> LENGTH: 24
<212> TYPE: RNA
<213> ORGANISM: Artificial Sequence
<220> FEATURE:
<223> OTHER INFORMATION: Synthetic

<400> SEQUENCE: 1026
caagugcucg ggcaauugug gaga                                    24

<210> SEQ ID NO 1027
<211> LENGTH: 23
<212> TYPE: RNA
<213> ORGANISM: Artificial Sequence
<220> FEATURE:
<223> OTHER INFORMATION: Synthetic

<400> SEQUENCE: 1027
aagugcucgg gcaauugugg aga                                     23

<210> SEQ ID NO 1028
<211> LENGTH: 22
```

```
<212> TYPE: RNA
<213> ORGANISM: Artificial Sequence
<220> FEATURE:
<223> OTHER INFORMATION: Synthetic

<400> SEQUENCE: 1028
agugcucggg caauugugga ga                                            22

<210> SEQ ID NO 1029
<211> LENGTH: 21
<212> TYPE: RNA
<213> ORGANISM: Artificial Sequence
<220> FEATURE:
<223> OTHER INFORMATION: Synthetic

<400> SEQUENCE: 1029
gugcucgggc aauguggag a                                              21

<210> SEQ ID NO 1030
<211> LENGTH: 20
<212> TYPE: RNA
<213> ORGANISM: Artificial Sequence
<220> FEATURE:
<223> OTHER INFORMATION: Synthetic

<400> SEQUENCE: 1030
ugcucgggca auuguggaga                                               20

<210> SEQ ID NO 1031
<211> LENGTH: 24
<212> TYPE: RNA
<213> ORGANISM: Artificial Sequence
<220> FEATURE:
<223> OTHER INFORMATION: Synthetic

<400> SEQUENCE: 1031
ccaagugcuc gggcaauugu ggag                                          24

<210> SEQ ID NO 1032
<211> LENGTH: 23
<212> TYPE: RNA
<213> ORGANISM: Artificial Sequence
<220> FEATURE:
<223> OTHER INFORMATION: Synthetic

<400> SEQUENCE: 1032
caagugcucg ggcaauugug gag                                           23

<210> SEQ ID NO 1033
<211> LENGTH: 22
<212> TYPE: RNA
<213> ORGANISM: Artificial Sequence
<220> FEATURE:
<223> OTHER INFORMATION: Synthetic

<400> SEQUENCE: 1033
aagugcucgg gcaauugugg ag                                            22

<210> SEQ ID NO 1034
<211> LENGTH: 21
<212> TYPE: RNA
<213> ORGANISM: Artificial Sequence
<220> FEATURE:
<223> OTHER INFORMATION: Synthetic

<400> SEQUENCE: 1034
```
agugcucggg caauugugga g                                          21

<210> SEQ ID NO 1035
<211> LENGTH: 20
<212> TYPE: RNA
<213> ORGANISM: Artificial Sequence
<220> FEATURE:
<223> OTHER INFORMATION: Synthetic

<400> SEQUENCE: 1035
gugcucgggc aauguggag                                             20

<210> SEQ ID NO 1036
<211> LENGTH: 24
<212> TYPE: RNA
<213> ORGANISM: Artificial Sequence
<220> FEATURE:
<223> OTHER INFORMATION: Synthetic

<400> SEQUENCE: 1036
ugauuccaag ugcucgggca auug                                       24

<210> SEQ ID NO 1037
<211> LENGTH: 23
<212> TYPE: RNA
<213> ORGANISM: Artificial Sequence
<220> FEATURE:
<223> OTHER INFORMATION: Synthetic

<400> SEQUENCE: 1037
gauuccaagu gcucgggcaa uug                                        23

<210> SEQ ID NO 1038
<211> LENGTH: 22
<212> TYPE: RNA
<213> ORGANISM: Artificial Sequence
<220> FEATURE:
<223> OTHER INFORMATION: Synthetic

<400> SEQUENCE: 1038
auuccaagug cucgggcaau ug                                         22

<210> SEQ ID NO 1039
<211> LENGTH: 21
<212> TYPE: RNA
<213> ORGANISM: Artificial Sequence
<220> FEATURE:
<223> OTHER INFORMATION: Synthetic

<400> SEQUENCE: 1039
uuccaagugc ucgggcaauu g                                          21

<210> SEQ ID NO 1040
<211> LENGTH: 20
<212> TYPE: RNA
<213> ORGANISM: Artificial Sequence
<220> FEATURE:
<223> OTHER INFORMATION: Synthetic

<400> SEQUENCE: 1040
uccaagugcu cgggcaauug                                            20

<210> SEQ ID NO 1041
<211> LENGTH: 19
<212> TYPE: RNA
<213> ORGANISM: Artificial Sequence

```
<220> FEATURE:
<223> OTHER INFORMATION: Synthetic

<400> SEQUENCE: 1041
ccaagugcuc gggcaauug                                                  19

<210> SEQ ID NO 1042
<211> LENGTH: 24
<212> TYPE: RNA
<213> ORGANISM: Artificial Sequence
<220> FEATURE:
<223> OTHER INFORMATION: Synthetic

<400> SEQUENCE: 1042
cugauuccaa gugcucgggc aauu                                            24

<210> SEQ ID NO 1043
<211> LENGTH: 23
<212> TYPE: RNA
<213> ORGANISM: Artificial Sequence
<220> FEATURE:
<223> OTHER INFORMATION: Synthetic

<400> SEQUENCE: 1043
cugauuccaa gugcucgggc aau                                             23

<210> SEQ ID NO 1044
<211> LENGTH: 22
<212> TYPE: RNA
<213> ORGANISM: Artificial Sequence
<220> FEATURE:
<223> OTHER INFORMATION: Synthetic

<400> SEQUENCE: 1044
cugauuccaa gugcucgggc aa                                              22

<210> SEQ ID NO 1045
<211> LENGTH: 21
<212> TYPE: RNA
<213> ORGANISM: Artificial Sequence
<220> FEATURE:
<223> OTHER INFORMATION: Synthetic

<400> SEQUENCE: 1045
cugauuccaa gugcucgggc a                                               21

<210> SEQ ID NO 1046
<211> LENGTH: 20
<212> TYPE: RNA
<213> ORGANISM: Artificial Sequence
<220> FEATURE:
<223> OTHER INFORMATION: Synthetic

<400> SEQUENCE: 1046
cugauuccaa gugcucgggc                                                 20

<210> SEQ ID NO 1047
<211> LENGTH: 19
<212> TYPE: RNA
<213> ORGANISM: Artificial Sequence
<220> FEATURE:
<223> OTHER INFORMATION: Synthetic

<400> SEQUENCE: 1047
cugauuccaa gugcucggg                                                  19
```

<210> SEQ ID NO 1048
<211> LENGTH: 24
<212> TYPE: RNA
<213> ORGANISM: Artificial Sequence
<220> FEATURE:
<223> OTHER INFORMATION: Synthetic

<400> SEQUENCE: 1048
acugauucca agugcucggg caau                                              24

<210> SEQ ID NO 1049
<211> LENGTH: 23
<212> TYPE: RNA
<213> ORGANISM: Artificial Sequence
<220> FEATURE:
<223> OTHER INFORMATION: Synthetic

<400> SEQUENCE: 1049
acugauucca agugcucggg caa                                               23

<210> SEQ ID NO 1050
<211> LENGTH: 22
<212> TYPE: RNA
<213> ORGANISM: Artificial Sequence
<220> FEATURE:
<223> OTHER INFORMATION: Synthetic

<400> SEQUENCE: 1050
acugauucca agugcucggg ca                                                22

<210> SEQ ID NO 1051
<211> LENGTH: 21
<212> TYPE: RNA
<213> ORGANISM: Artificial Sequence
<220> FEATURE:
<223> OTHER INFORMATION: Synthetic

<400> SEQUENCE: 1051
acugauucca agugcucggg c                                                 21

<210> SEQ ID NO 1052
<211> LENGTH: 20
<212> TYPE: RNA
<213> ORGANISM: Artificial Sequence
<220> FEATURE:
<223> OTHER INFORMATION: Synthetic

<400> SEQUENCE: 1052
acugauucca agugcucggg                                                   20

<210> SEQ ID NO 1053
<211> LENGTH: 19
<212> TYPE: RNA
<213> ORGANISM: Artificial Sequence
<220> FEATURE:
<223> OTHER INFORMATION: Synthetic

<400> SEQUENCE: 1053
acugauucca agugcucgg                                                    19

<210> SEQ ID NO 1054
<211> LENGTH: 24
<212> TYPE: RNA
<213> ORGANISM: Artificial Sequence
<220> FEATURE:
<223> OTHER INFORMATION: Synthetic

```
<400> SEQUENCE: 1054
uacugauucc aagugcucgg gcaa                                          24

<210> SEQ ID NO 1055
<211> LENGTH: 23
<212> TYPE: RNA
<213> ORGANISM: Artificial Sequence
<220> FEATURE:
<223> OTHER INFORMATION: Synthetic

<400> SEQUENCE: 1055
uacugauucc aagugcucgg gca                                           23

<210> SEQ ID NO 1056
<211> LENGTH: 22
<212> TYPE: RNA
<213> ORGANISM: Artificial Sequence
<220> FEATURE:
<223> OTHER INFORMATION: Synthetic

<400> SEQUENCE: 1056
uacugauucc aagugcucgg gc                                            22

<210> SEQ ID NO 1057
<211> LENGTH: 21
<212> TYPE: RNA
<213> ORGANISM: Artificial Sequence
<220> FEATURE:
<223> OTHER INFORMATION: Synthetic

<400> SEQUENCE: 1057
uacugauucc aagugcucgg g                                             21

<210> SEQ ID NO 1058
<211> LENGTH: 20
<212> TYPE: RNA
<213> ORGANISM: Artificial Sequence
<220> FEATURE:
<223> OTHER INFORMATION: Synthetic

<400> SEQUENCE: 1058
uacugauucc aagugcucgg                                               20

<210> SEQ ID NO 1059
<211> LENGTH: 19
<212> TYPE: RNA
<213> ORGANISM: Artificial Sequence
<220> FEATURE:
<223> OTHER INFORMATION: Synthetic

<400> SEQUENCE: 1059
uacugauucc aagugcucg                                                19

<210> SEQ ID NO 1060
<211> LENGTH: 24
<212> TYPE: RNA
<213> ORGANISM: Artificial Sequence
<220> FEATURE:
<223> OTHER INFORMATION: Synthetic

<400> SEQUENCE: 1060
uuacugauuc caagugcucg ggca                                          24

<210> SEQ ID NO 1061
```

```
<211> LENGTH: 23
<212> TYPE: RNA
<213> ORGANISM: Artificial Sequence
<220> FEATURE:
<223> OTHER INFORMATION: Synthetic

<400> SEQUENCE: 1061
uuacugauuc caagugcucg ggc                                              23

<210> SEQ ID NO 1062
<211> LENGTH: 22
<212> TYPE: RNA
<213> ORGANISM: Artificial Sequence
<220> FEATURE:
<223> OTHER INFORMATION: Synthetic

<400> SEQUENCE: 1062
uuacugauuc caagugcucg gg                                               22

<210> SEQ ID NO 1063
<211> LENGTH: 21
<212> TYPE: RNA
<213> ORGANISM: Artificial Sequence
<220> FEATURE:
<223> OTHER INFORMATION: Synthetic

<400> SEQUENCE: 1063
uuacugauuc caagugcucg g                                                21

<210> SEQ ID NO 1064
<211> LENGTH: 20
<212> TYPE: RNA
<213> ORGANISM: Artificial Sequence
<220> FEATURE:
<223> OTHER INFORMATION: Synthetic

<400> SEQUENCE: 1064
uuacugauuc caagugcucg                                                  20

<210> SEQ ID NO 1065
<211> LENGTH: 19
<212> TYPE: RNA
<213> ORGANISM: Artificial Sequence
<220> FEATURE:
<223> OTHER INFORMATION: Synthetic

<400> SEQUENCE: 1065
uuacugauuc caagugcuc                                                   19

<210> SEQ ID NO 1066
<211> LENGTH: 24
<212> TYPE: RNA
<213> ORGANISM: Artificial Sequence
<220> FEATURE:
<223> OTHER INFORMATION: Synthetic

<400> SEQUENCE: 1066
cuuacugauu ccaagugcuc gggc                                             24

<210> SEQ ID NO 1067
<211> LENGTH: 23
<212> TYPE: RNA
<213> ORGANISM: Artificial Sequence
<220> FEATURE:
<223> OTHER INFORMATION: Synthetic

<400> SEQUENCE: 1067
```

| | |
|---|---|
| cuuacugauu ccaagugcuc ggg | 23 |

<210> SEQ ID NO 1068
<211> LENGTH: 22
<212> TYPE: RNA
<213> ORGANISM: Artificial Sequence
<220> FEATURE:
<223> OTHER INFORMATION: Synthetic

<400> SEQUENCE: 1068

| | |
|---|---|
| cuuacugauu ccaagugcuc gg | 22 |

<210> SEQ ID NO 1069
<211> LENGTH: 21
<212> TYPE: RNA
<213> ORGANISM: Artificial Sequence
<220> FEATURE:
<223> OTHER INFORMATION: Synthetic

<400> SEQUENCE: 1069

| | |
|---|---|
| cuuacugauu ccaagugcuc g | 21 |

<210> SEQ ID NO 1070
<211> LENGTH: 20
<212> TYPE: RNA
<213> ORGANISM: Artificial Sequence
<220> FEATURE:
<223> OTHER INFORMATION: Synthetic

<400> SEQUENCE: 1070

| | |
|---|---|
| cuuacugauu ccaagugcuc | 20 |

<210> SEQ ID NO 1071
<211> LENGTH: 19
<212> TYPE: RNA
<213> ORGANISM: Artificial Sequence
<220> FEATURE:
<223> OTHER INFORMATION: Synthetic

<400> SEQUENCE: 1071

| | |
|---|---|
| cuuacugauu ccaagugcu | 19 |

<210> SEQ ID NO 1072
<211> LENGTH: 24
<212> TYPE: RNA
<213> ORGANISM: Artificial Sequence
<220> FEATURE:
<223> OTHER INFORMATION: Synthetic

<400> SEQUENCE: 1072

| | |
|---|---|
| ccuuacugau uccaagugcu cggg | 24 |

<210> SEQ ID NO 1073
<211> LENGTH: 23
<212> TYPE: RNA
<213> ORGANISM: Artificial Sequence
<220> FEATURE:
<223> OTHER INFORMATION: Synthetic

<400> SEQUENCE: 1073

| | |
|---|---|
| ccuuacugau uccaagugcu cgg | 23 |

<210> SEQ ID NO 1074
<211> LENGTH: 22
<212> TYPE: RNA

```
<213> ORGANISM: Artificial Sequence
<220> FEATURE:
<223> OTHER INFORMATION: Synthetic

<400> SEQUENCE: 1074
ccuuacugau uccaagugcu cg                                              22

<210> SEQ ID NO 1075
<211> LENGTH: 21
<212> TYPE: RNA
<213> ORGANISM: Artificial Sequence
<220> FEATURE:
<223> OTHER INFORMATION: Synthetic

<400> SEQUENCE: 1075
ccuuacugau uccaagugcu c                                               21

<210> SEQ ID NO 1076
<211> LENGTH: 20
<212> TYPE: RNA
<213> ORGANISM: Artificial Sequence
<220> FEATURE:
<223> OTHER INFORMATION: Synthetic

<400> SEQUENCE: 1076
ccuuacugau uccaagugcu                                                 20

<210> SEQ ID NO 1077
<211> LENGTH: 19
<212> TYPE: RNA
<213> ORGANISM: Artificial Sequence
<220> FEATURE:
<223> OTHER INFORMATION: Synthetic

<400> SEQUENCE: 1077
ccuuacugau uccaagugc                                                  19

<210> SEQ ID NO 1078
<211> LENGTH: 24
<212> TYPE: RNA
<213> ORGANISM: Artificial Sequence
<220> FEATURE:
<223> OTHER INFORMATION: Synthetic

<400> SEQUENCE: 1078
accuuacuga uuccaagugc ucgg                                            24

<210> SEQ ID NO 1079
<211> LENGTH: 23
<212> TYPE: RNA
<213> ORGANISM: Artificial Sequence
<220> FEATURE:
<223> OTHER INFORMATION: Synthetic

<400> SEQUENCE: 1079
accuuacuga uuccaagugc ucg                                             23

<210> SEQ ID NO 1080
<211> LENGTH: 22
<212> TYPE: RNA
<213> ORGANISM: Artificial Sequence
<220> FEATURE:
<223> OTHER INFORMATION: Synthetic

<400> SEQUENCE: 1080
accuuacuga uuccaagugc uc                                              22
```

<210> SEQ ID NO 1081
<211> LENGTH: 21
<212> TYPE: RNA
<213> ORGANISM: Artificial Sequence
<220> FEATURE:
<223> OTHER INFORMATION: Synthetic

<400> SEQUENCE: 1081
accuuacuga uuccaagugc u                                              21

<210> SEQ ID NO 1082
<211> LENGTH: 20
<212> TYPE: RNA
<213> ORGANISM: Artificial Sequence
<220> FEATURE:
<223> OTHER INFORMATION: Synthetic

<400> SEQUENCE: 1082
accuuacuga uuccaagugc                                                20

<210> SEQ ID NO 1083
<211> LENGTH: 19
<212> TYPE: RNA
<213> ORGANISM: Artificial Sequence
<220> FEATURE:
<223> OTHER INFORMATION: Synthetic

<400> SEQUENCE: 1083
accuuacuga uuccaagug                                                 19

<210> SEQ ID NO 1084
<211> LENGTH: 24
<212> TYPE: RNA
<213> ORGANISM: Artificial Sequence
<220> FEATURE:
<223> OTHER INFORMATION: Synthetic

<400> SEQUENCE: 1084
aaccuuacug auuccaagug cucg                                           24

<210> SEQ ID NO 1085
<211> LENGTH: 23
<212> TYPE: RNA
<213> ORGANISM: Artificial Sequence
<220> FEATURE:
<223> OTHER INFORMATION: Synthetic

<400> SEQUENCE: 1085
aaccuuacug auuccaagug cuc                                            23

<210> SEQ ID NO 1086
<211> LENGTH: 22
<212> TYPE: RNA
<213> ORGANISM: Artificial Sequence
<220> FEATURE:
<223> OTHER INFORMATION: Synthetic

<400> SEQUENCE: 1086
aaccuuacug auuccaagug cu                                             22

<210> SEQ ID NO 1087
<211> LENGTH: 21
<212> TYPE: RNA
<213> ORGANISM: Artificial Sequence
<220> FEATURE:

<223> OTHER INFORMATION: Synthetic

<400> SEQUENCE: 1087
aaccuuacug auuccaagug c     21

<210> SEQ ID NO 1088
<211> LENGTH: 20
<212> TYPE: RNA
<213> ORGANISM: Artificial Sequence
<220> FEATURE:
<223> OTHER INFORMATION: Synthetic

<400> SEQUENCE: 1088
aaccuuacug auuccaagug     20

<210> SEQ ID NO 1089
<211> LENGTH: 19
<212> TYPE: RNA
<213> ORGANISM: Artificial Sequence
<220> FEATURE:
<223> OTHER INFORMATION: Synthetic

<400> SEQUENCE: 1089
aaccuuacug auuccaagu     19

<210> SEQ ID NO 1090
<211> LENGTH: 115
<212> TYPE: DNA
<213> ORGANISM: Artificial Sequence
<220> FEATURE:
<223> OTHER INFORMATION: mGluR1-flop exon

<400> SEQUENCE: 1090
aaatccagta aacctggcag tgttaaaact gaacgagcag ggcttttgga caaattgaaa     60
aacaaatggt ggtacgacag agggcgagtg cggcagcggg ggaggtgact ccaag     115

<210> SEQ ID NO 1091
<211> LENGTH: 115
<212> TYPE: DNA
<213> ORGANISM: Artificial Sequence
<220> FEATURE:
<223> OTHER INFORMATION: mGluR2-flop exon

<400> SEQUENCE: 1091
aaatgcggtt aacctcgcag tactaaaact gaatgaacaa ggcctgttgg acaaattgaa     60
aaacaaatgg tggtacgaca aaggagagtg cggcagcggg ggaggtgatt ccaag     115

<210> SEQ ID NO 1092
<211> LENGTH: 115
<212> TYPE: DNA
<213> ORGANISM: Artificial Sequence
<220> FEATURE:
<223> OTHER INFORMATION: mGluR3-flop exon

<400> SEQUENCE: 1092
aaatgctgtt aacctggcag tattaaaact gaatgagcaa ggcctcttgg acaaattgaa     60
aaacaaatgg tggtacgaca aaggagagtg cggcagcggg ggcggtgact ccaag     115

<210> SEQ ID NO 1093
<211> LENGTH: 115
<212> TYPE: DNA
<213> ORGANISM: Artificial Sequence
<220> FEATURE:
<223> OTHER INFORMATION: mGluR4-flop exon

<400> SEQUENCE: 1093
aaatgctgtt aacctcgcag ttttaaaact gaatgaacaa ggcctcttgg acaaattgaa    60
aaacaaatgg tggtacgaca aggagaatg tggcagcggg ggaggtgact ccaag          115

<210> SEQ ID NO 1094
<211> LENGTH: 115
<212> TYPE: DNA
<213> ORGANISM: Artificial Sequence
<220> FEATURE:
<223> OTHER INFORMATION: mGluR1-flip exon

<400> SEQUENCE: 1094
aggtcccgta aacctagcgg ttttgaaact cagtgagcaa ggcgtcttag acaagctgaa    60
aagcaaatgg tggtacgata aaggggaatg tggaagcaag gactccggaa gtaag         115

<210> SEQ ID NO 1095
<211> LENGTH: 115
<212> TYPE: DNA
<213> ORGANISM: Artificial Sequence
<220> FEATURE:
<223> OTHER INFORMATION: mGluR2-flip exon

<400> SEQUENCE: 1095
aaccccagta aatcttgcag tattgaaact cagtgagcaa ggcgtcttag acaagctgaa    60
aaacaaatgg tggtacgata aaggtgaatg tggagccaag gactcgggaa gtaag         115

<210> SEQ ID NO 1096
<211> LENGTH: 115
<212> TYPE: DNA
<213> ORGANISM: Artificial Sequence
<220> FEATURE:
<223> OTHER INFORMATION: mGluR3-flip exon

<400> SEQUENCE: 1096
aacgcctgta aaccttgcag tattgaaact cagtgaacaa ggcatcttag acaagctgaa    60
aaacaaatgg tggtacgata aggggaatg tggagccaag gactccggga gtaag          115

<210> SEQ ID NO 1097
<211> LENGTH: 115
<212> TYPE: DNA
<213> ORGANISM: Artificial Sequence
<220> FEATURE:
<223> OTHER INFORMATION: mGluR4-flip exon

<400> SEQUENCE: 1097
aactcctgta aaccttgccg ttttgaaact cagtgaggca ggcgtcttag acaagctgaa    60
aaacaaatgg tggtacgata aaggtgaatg tggacccaag gactcgggaa gcaag         115

<210> SEQ ID NO 1098
<211> LENGTH: 83
<212> TYPE: DNA
<213> ORGANISM: Artificial Sequence
<220> FEATURE:
<223> OTHER INFORMATION: mGluR4-flip with exon skipped

<400> SEQUENCE: 1098
gaagaactcc tgtaaaacctt gccgttttga aagataaagg tgaatgtgga cccaaggact    60
cgggaagcaa ggtcagtcgg tgc                                            83

<210> SEQ ID NO 1099

```
<211> LENGTH: 83
<212> TYPE: DNA
<213> ORGANISM: Artificial Sequence
<220> FEATURE:
<223> OTHER INFORMATION: mGluR1-flip with exon skipped

<400> SEQUENCE: 1099
gaagaggtcc cgtaaaccta gcggttttga aagataaagg ggaatgtgga agcaaggact      60
ccggaagtaa ggtcagtcac ctg                                             83

<210> SEQ ID NO 1100
<211> LENGTH: 83
<212> TYPE: DNA
<213> ORGANISM: Artificial Sequence
<220> FEATURE:
<223> OTHER INFORMATION: mGluR2-flip with exon skipped

<400> SEQUENCE: 1100
gaagaacccc agtaaatctt gcagtattga aagataaagg tgaatgtgga gccaaggact      60
cgggaagtaa ggtcagttgc tgc                                             83

<210> SEQ ID NO 1101
<211> LENGTH: 83
<212> TYPE: DNA
<213> ORGANISM: Artificial Sequence
<220> FEATURE:
<223> OTHER INFORMATION: mGluR3-flip with exon skipped

<400> SEQUENCE: 1101
gaagaacgcc tgtaaacctt gcagtattga aagataaggg ggaatgtgga gccaaggact      60
ccgggagtaa ggtcagtcgc tga                                             83

<210> SEQ ID NO 1102
<211> LENGTH: 23
<212> TYPE: RNA
<213> ORGANISM: Artificial Sequence
<220> FEATURE:
<223> OTHER INFORMATION: Antisense oligonucleotide

<400> SEQUENCE: 1102 auuccccuu acaccucggu ucc                                              23

<210> SEQ ID NO 1103
<211> LENGTH: 22
<212> TYPE: RNA
<213> ORGANISM: Artificial Sequence
<220> FEATURE:
<223> OTHER INFORMATION: Antisense oligonucleotide

<400> SEQUENCE: 1103
aggcccucau uccagucagc ga                                              22

<210> SEQ ID NO 1104
<211> LENGTH: 20
<212> TYPE: RNA
<213> ORGANISM: Artificial Sequence
<220> FEATURE:
<223> OTHER INFORMATION: Antisense oligonucleotide

<400> SEQUENCE: 1104
acauuuggaa cgucauaacu                                                 20

<210> SEQ ID NO 1105
<211> LENGTH: 23
```

```
<212> TYPE: RNA
<213> ORGANISM: Artificial Sequence
<220> FEATURE:
<223> OTHER INFORMATION: Antisense oligonucleotide

<400> SEQUENCE: 1105
cccccuuaca ccucgguucc uga                                          23

<210> SEQ ID NO 1106
<211> LENGTH: 70
<212> TYPE: DNA
<213> ORGANISM: Artificial Sequence
<220> FEATURE:
<223> OTHER INFORMATION: GluR2 skip exon 15 sequence

<400> SEQUENCE: 1106
tgaagaaccc cagtaaatct tgcagtattg tgtggagcca aggactcggg aagtaaggtc    60
agttgctgca                                                          70

<210> SEQ ID NO 1107
<211> LENGTH: 25
<212> TYPE: RNA
<213> ORGANISM: Artificial Sequence
<220> FEATURE:
<223> OTHER INFORMATION: Synthetic

<400> SEQUENCE: 1107
acuucuuggg gucauuuaga acguc                                         25

<210> SEQ ID NO 1108
<211> LENGTH: 16
<212> TYPE: RNA
<213> ORGANISM: Artificial Sequence
<220> FEATURE:
<223> OTHER INFORMATION: Synthetic

<400> SEQUENCE: 1108
acaccucggu uccuga                                                   16

<210> SEQ ID NO 1109
<211> LENGTH: 22
<212> TYPE: RNA
<213> ORGANISM: Artificial Sequence
<220> FEATURE:
<223> OTHER INFORMATION: Synthetic

<400> SEQUENCE: 1109
ccuucauucc agucaacgac gu                                            22

<210> SEQ ID NO 1110
<211> LENGTH: 21
<212> TYPE: RNA
<213> ORGANISM: Artificial Sequence
<220> FEATURE:
<223> OTHER INFORMATION: Synthetic

<400> SEQUENCE: 1110
ccuucauucc agucaacgac g                                             21

<210> SEQ ID NO 1111
<211> LENGTH: 23
<212> TYPE: RNA
<213> ORGANISM: Artificial Sequence
<220> FEATURE:
<223> OTHER INFORMATION: Synthetic
```

```
<400> SEQUENCE: 1111
ggggucauuu agaacgucau aac                                          23

<210> SEQ ID NO 1112
<211> LENGTH: 20
<212> TYPE: RNA
<213> ORGANISM: Artificial Sequence
<220> FEATURE:
<223> OTHER INFORMATION: Synthetic

<400> SEQUENCE: 1112
ggggucauuu agaacgucau                                              20

<210> SEQ ID NO 1113
<211> LENGTH: 19
<212> TYPE: RNA
<213> ORGANISM: Artificial Sequence
<220> FEATURE:
<223> OTHER INFORMATION: Synthetic

<400> SEQUENCE: 1113
ccuucauucc agucaacga                                               19
```